(12) United States Patent
Tse et al.

(10) Patent No.: US 12,251,178 B2
(45) Date of Patent: Mar. 18, 2025

(54) SURGICAL PLATFORM WITH MOTORIZED ARMS FOR ADJUSTABLE ARM SUPPORTS

(71) Applicant: Auris Health, Inc., Redwood City, CA (US)

(72) Inventors: Allison Tiffany Tse, San Francisco, CA (US); Christian de Jesus Ruiz, Redwood City, CA (US); Yoichiro Dan, Los Altos, CA (US); Nicholas J. Eyre, Sunnyvale, CA (US); Sven Wehrmann, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 578 days.

(21) Appl. No.: 17/545,999

(22) Filed: Dec. 8, 2021

(65) Prior Publication Data
US 2022/0096179 A1    Mar. 31, 2022

Related U.S. Application Data

(63) Continuation of application No. 16/796,053, filed on Feb. 20, 2020, now Pat. No. 11,202,683.
(Continued)

(51) Int. Cl.
| | |
|---|---|
| *A61B 34/30* | (2016.01) |
| *A61G 13/08* | (2006.01) |
| *A61G 13/10* | (2006.01) |
| *B25J 5/04* | (2006.01) |
| *B25J 9/00* | (2006.01) |
| *B25J 9/04* | (2006.01) |
| *B25J 9/10* | (2006.01) |
| *B25J 17/02* | (2006.01) |
| *B25J 19/00* | (2006.01) |

(Continued)

(52) U.S. Cl.
CPC .............. *A61B 34/30* (2016.02); *A61G 13/08* (2013.01); *A61G 13/101* (2013.01); *B25J 5/04* (2013.01); *B25J 9/0009* (2013.01); *B25J 9/046* (2013.01); *B25J 9/102* (2013.01); *B25J 17/025* (2013.01); *B25J 19/0004* (2013.01); *A61B 2034/301* (2016.02); *A61B 2034/302* (2016.02); *A61B 2034/303* (2016.02); *A61B 2090/3764* (2016.02); *A61B 2090/508* (2016.02)

(58) Field of Classification Search
CPC .............. A61B 34/30; A61B 2034/301; A61B 2090/508; B25J 19/0004; B25J 5/04; B25J 9/0009; B25J 9/102
See application file for complete search history.

(56) References Cited

U.S. PATENT DOCUMENTS

| | | |
|---|---|---|
| 3,997,926 A | 12/1976 | England |
| 4,878,494 A | 11/1989 | Phillips et al. |

(Continued)

FOREIGN PATENT DOCUMENTS

| | | |
|---|---|---|
| GB | 810956 | 3/1959 |
| WO | WO 10/068005 | 6/2010 |

*Primary Examiner* — Lynsey C Eiseman
*Assistant Examiner* — Skylar Lindsey Christianson
(74) *Attorney, Agent, or Firm* — Frost Brown Todd LLP

(57) ABSTRACT

A robotic medical system can include a motorized arm that is supported by a column of the system. The robotic arm can be operated by rotating a link of the motorized arm by actuating an actuator to drive rotation of a rotary joint. A brake can then be applied to the rotary joint to stop rotation of the link. The arm can also include an arbor that can be actuated to increase a torsional stiffness of the rotary joint.

7 Claims, 62 Drawing Sheets

Related U.S. Application Data

(60) Provisional application No. 62/809,197, filed on Feb. 22, 2019.

(51) Int. Cl.
*A61B 90/00* (2016.01)
*A61B 90/50* (2016.01)

(56) References Cited

U.S. PATENT DOCUMENTS

| | | | |
|---|---|---|---|
| 5,013,018 A | 5/1991 | Sicek | |
| 5,160,106 A | 11/1992 | Monick | |
| 5,405,604 A | 4/1995 | Has et al. | |
| 5,555,897 A | 9/1996 | Lathrop, Jr. et al. | |
| 5,571,072 A | 11/1996 | Kronner | |
| 5,631,973 A | 5/1997 | Green | |
| 5,696,837 A | 12/1997 | Green | |
| 5,762,458 A | 6/1998 | Wang et al. | |
| 5,792,135 A | 8/1998 | Madhani et al. | |
| 5,797,900 A | 8/1998 | Madhani et al. | |
| 5,807,377 A | 8/1998 | Madhani et al. | |
| 5,808,665 A | 9/1998 | Green | |
| 5,814,038 A | 9/1998 | Jensen et al. | |
| 5,859,934 A | 1/1999 | Green | |
| 5,926,875 A | 7/1999 | Okamoto et al. | |
| 5,944,476 A | 8/1999 | Bacchi et al. | |
| 5,976,122 A | 11/1999 | Madhani et al. | |
| 6,132,368 A | 10/2000 | Cooper | |
| 6,170,102 B1 | 1/2001 | Kreuzer | |
| 6,202,230 B1 | 3/2001 | Borders | |
| 6,223,100 B1 | 4/2001 | Green | |
| 6,259,806 B1 | 7/2001 | Green | |
| 6,309,397 B1 | 10/2001 | Julian et al. | |
| 6,331,181 B1 | 12/2001 | Tierney et al. | |
| 6,346,072 B1 | 2/2002 | Cooper | |
| 6,364,888 B1 | 4/2002 | Niemeyer et al. | |
| 6,371,952 B1 | 4/2002 | Madhani et al. | |
| 6,394,998 B1 | 5/2002 | Wallace et al. | |
| 6,398,726 B1 | 6/2002 | Ramans et al. | |
| 6,424,885 B1 | 7/2002 | Niemeyer et al. | |
| 6,459,926 B1 | 10/2002 | Nowlin et al. | |
| 6,468,265 B1 | 10/2002 | Evans et al. | |
| 6,491,701 B2 | 12/2002 | Tierney et al. | |
| 6,493,608 B1 | 12/2002 | Niemeyer | |
| 6,522,906 B1 | 2/2003 | Salisbury, Jr. et al. | |
| 6,574,355 B2 | 6/2003 | Green | |
| 6,620,173 B2 | 9/2003 | Gerbi et al. | |
| 6,620,174 B2 | 9/2003 | Jensen et al. | |
| 6,640,363 B1 | 11/2003 | Pattee et al. | |
| 6,659,939 B2 | 12/2003 | Moll et al. | |
| 6,671,581 B2 | 12/2003 | Niemeyer et al. | |
| 6,676,669 B2 | 1/2004 | Charles et al. | |
| 6,684,129 B2 | 1/2004 | Salisbury, Jr. et al. | |
| 6,714,839 B2 | 3/2004 | Salisbury, Jr. et al. | |
| 6,720,988 B1 | 4/2004 | Gere et al. | |
| 6,731,988 B1 | 5/2004 | Green | |
| 6,764,445 B2 | 7/2004 | Ramans et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,788,018 B1 | 9/2004 | Blumenkranz | |
| 6,788,999 B2 | 9/2004 | Green | |
| 6,799,065 B1 | 9/2004 | Niemeyer | |
| 6,804,581 B2 | 10/2004 | Wang | |
| 6,837,883 B2 | 1/2005 | Moll et al. | |
| 6,850,817 B1 | 2/2005 | Green | |
| 6,852,107 B2 | 2/2005 | Wang et al. | |
| 6,858,003 B2 | 2/2005 | Evans et al. | |
| 6,866,671 B2 | 3/2005 | Tierney et al. | |
| 6,936,042 B2 | 8/2005 | Wallace et al. | |
| 6,951,535 B2 | 10/2005 | Ghodoussi et al. | |
| 6,963,792 B1 | 11/2005 | Green | |
| 6,991,627 B2 | 1/2006 | Madhani et al. | |
| 6,999,852 B2 | 2/2006 | Green | |
| 7,006,895 B2 | 2/2006 | Green | |
| 7,025,761 B2 | 4/2006 | Wang et al. |
| 7,048,745 B2 | 5/2006 | Tierney et al. |
| 7,074,179 B2 | 7/2006 | Wang et al. |
| 7,087,049 B2 | 8/2006 | Nowlin et al. |
| 7,107,090 B2 | 9/2006 | Salisbury, Jr. et al. |
| 7,107,124 B2 | 9/2006 | Green |
| 7,125,403 B2 | 10/2006 | Julian et al. |
| 7,155,315 B2 | 12/2006 | Niemeyer et al. |
| 7,248,944 B2 | 7/2007 | Green |
| 7,250,028 B2 | 7/2007 | Julian et al. |
| 7,277,120 B2 | 10/2007 | Gere et al. |
| 7,316,681 B2 | 1/2008 | Madhani et al. |
| 7,333,642 B2 | 2/2008 | Green |
| 7,357,774 B2 | 4/2008 | Cooper |
| 7,413,565 B2 | 8/2008 | Wang et al. |
| 7,524,320 B2 | 4/2009 | Tierney et al. |
| 7,555,191 B1 | 6/2009 | Moore |
| 7,574,250 B2 | 8/2009 | Niemeyer |
| 7,594,912 B2 | 9/2009 | Cooper et al. |
| 7,682,357 B2 | 3/2010 | Ghodoussi et al. |
| 7,699,855 B2 | 3/2010 | Anderson et al. |
| 7,722,599 B2 | 5/2010 | Julian et al. |
| 7,725,214 B2 | 5/2010 | Diolaiti |
| 7,727,244 B2 | 6/2010 | Orban, III et al. |
| 7,752,920 B2 | 7/2010 | Larkin et al. |
| 7,763,015 B2 | 7/2010 | Cooper et al. |
| 7,780,651 B2 | 8/2010 | Madhani et al. |
| 7,806,891 B2 | 10/2010 | Nowlin et al. |
| 7,819,885 B2 | 10/2010 | Cooper |
| 7,865,266 B2 | 1/2011 | Moll et al. |
| 7,890,211 B2 | 2/2011 | Green |
| 7,930,065 B2 | 4/2011 | Larkin et al. |
| 7,942,868 B2 | 5/2011 | Cooper |
| 7,955,322 B2 | 6/2011 | Devengenzo et al. |
| 7,963,913 B2 | 6/2011 | Devengenzo et al. |
| 7,967,813 B2 | 6/2011 | Cooper et al. |
| 8,004,229 B2 | 6/2011 | Nowlin et al. |
| 7,979,157 B2 | 7/2011 | Anvari |
| 7,996,110 B2 | 8/2011 | Lipow et al. |
| 8,029,516 B2 | 10/2011 | Mohr et al. |
| 8,057,385 B2 | 11/2011 | Cooper et al. |
| 8,062,211 B2 | 11/2011 | Duval et al. |
| 8,062,288 B2 | 11/2011 | Cooper et al. |
| 8,068,649 B2 | 11/2011 | Green |
| 8,083,667 B2 | 12/2011 | Cooper et al. |
| 8,100,133 B2 | 1/2012 | Mintz et al. |
| 8,105,235 B2 | 1/2012 | Ramans et al. |
| 8,105,338 B2 | 1/2012 | Anderson et al. |
| 8,123,740 B2 | 2/2012 | Madhani et al. |
| 8,142,420 B2 | 3/2012 | Schena |
| 8,142,447 B2 | 3/2012 | Tierney et al. |
| 8,182,415 B2 | 5/2012 | Larkin et al. |
| 8,182,469 B2 | 5/2012 | Anderson et al. |
| 8,182,470 B2 | 5/2012 | Devengenzo et al. |
| 8,182,476 B2 | 5/2012 | Julian et al. |
| 8,202,278 B2 | 6/2012 | Orban, III et al. |
| 8,206,406 B2 | 6/2012 | Orban, III et al. |
| 8,216,250 B2 | 7/2012 | Orban, III et al. |
| 8,230,863 B2 | 7/2012 | Ravikumar et al. |
| 8,256,319 B2 | 9/2012 | Cooper et al. |
| 8,271,130 B2 | 9/2012 | Hourtash |
| 8,343,096 B2 | 1/2013 | Kirschenman et al. |
| 8,343,141 B2 | 1/2013 | Madhani et al. |
| 8,348,931 B2 | 1/2013 | Cooper et al. |
| 8,375,808 B2 | 2/2013 | Blumenkranz et al. |
| 8,377,045 B2 | 2/2013 | Schena |
| 8,377,046 B2 | 2/2013 | Cooper et al. |
| 8,400,094 B2 | 3/2013 | Schena |
| 8,414,598 B2 | 4/2013 | Brock et al. |
| 8,419,717 B2 | 4/2013 | Diolaiti et al. |
| 8,425,404 B2 | 4/2013 | Wilson et al. |
| 8,463,439 B2 | 6/2013 | Blumenkranz et al. |
| 8,465,474 B2 | 6/2013 | Blumenkranz et al. |
| 8,469,945 B2 | 6/2013 | Schena |
| 8,469,947 B2 | 6/2013 | Devengenzo et al. |
| 8,489,235 B2 | 7/2013 | Moll et al. |
| 8,491,574 B2 | 7/2013 | Blumenkranz et al. |
| 8,496,647 B2 | 7/2013 | Blumenkranz et al. |
| 8,504,204 B2 | 8/2013 | Owens, Jr. |

(56) References Cited

U.S. PATENT DOCUMENTS

| | | |
|---|---|---|
| 8,506,556 B2 | 8/2013 | Schena |
| 8,512,353 B2 | 8/2013 | Rosielle et al. |
| 8,515,576 B2 | 8/2013 | Lipow et al. |
| 8,517,933 B2 | 8/2013 | Mohr |
| 8,526,737 B2 | 9/2013 | Green |
| 8,527,094 B2 | 9/2013 | Kumar et al. |
| 8,529,582 B2 | 9/2013 | Devengenzo et al. |
| 8,541,970 B2 | 9/2013 | Nowlin et al. |
| 8,551,076 B2 | 10/2013 | Duval et al. |
| 8,551,116 B2 | 10/2013 | Julian et al. |
| 8,561,473 B2 | 10/2013 | Blumenkranz et al. |
| 8,562,594 B2 | 10/2013 | Cooper et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,613,230 B2 | 12/2013 | Blumenkranz et al. |
| 8,620,473 B2 | 12/2013 | Diolaiti et al. |
| 8,621,939 B2 | 1/2014 | Blumenkranz et al. |
| 8,624,537 B2 | 1/2014 | Nowlin et al. |
| 8,628,518 B2 | 1/2014 | Blumenkranz et al. |
| 8,641,698 B2 | 2/2014 | Sanchez et al. |
| 8,641,700 B2 | 2/2014 | Devengenzo et al. |
| 8,666,544 B2 | 3/2014 | Moll et al. |
| 8,672,833 B2 | 3/2014 | Cooper et al. |
| 8,672,922 B2 | 3/2014 | Loh et al. |
| 8,679,099 B2 | 3/2014 | Cooper et al. |
| 8,709,000 B2 | 4/2014 | Madhani et al. |
| 8,740,885 B2 | 6/2014 | Larkin et al. |
| 8,746,252 B2 | 6/2014 | Mcgrogan et al. |
| 8,749,189 B2 | 6/2014 | Nowlin et al. |
| 8,749,190 B2 | 6/2014 | Nowlin et al. |
| 8,758,352 B2 | 6/2014 | Tierney et al. |
| 8,768,516 B2 | 7/2014 | Diolaiti et al. |
| 8,771,180 B2 | 7/2014 | Mohr |
| 8,784,435 B2 | 7/2014 | Cooper et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,852,208 B2 | 10/2014 | Gomez et al. |
| 8,864,652 B2 | 10/2014 | Diolaiti et al. |
| 8,864,752 B2 | 10/2014 | Diolaiti et al. |
| 8,870,900 B2 | 10/2014 | Julian et al. |
| 8,888,764 B2 | 11/2014 | Devengenzo et al. |
| 8,894,634 B2 | 11/2014 | Devengenzo et al. |
| 8,903,546 B2 | 12/2014 | Diolaiti et al. |
| 8,911,429 B2 | 12/2014 | Olds et al. |
| 8,914,150 B2 | 12/2014 | Moll et al. |
| 8,918,211 B2 | 12/2014 | Diolaiti et al. |
| 8,944,070 B2 | 2/2015 | Guthart et al. |
| 8,945,095 B2 | 2/2015 | Blumenkranz et al. |
| 8,945,148 B2 | 2/2015 | Solomon et al. |
| 8,960,622 B2 | 2/2015 | von Pechmann et al. |
| 8,968,333 B2 | 3/2015 | Yu et al. |
| 8,971,597 B2 | 3/2015 | Zhao et al. |
| 8,986,196 B2 | 3/2015 | Larkin et al. |
| 8,998,799 B2 | 4/2015 | Orban, III et al. |
| 8,998,930 B2 | 4/2015 | Orban, III et al. |
| 9,023,060 B2 | 5/2015 | Cooper et al. |
| 9,039,681 B2 | 5/2015 | Wang et al. |
| 9,039,685 B2 | 5/2015 | Larkin et al. |
| 9,050,119 B2 | 6/2015 | Devengenzo et al. |
| 9,055,962 B2 | 6/2015 | Blumenkranz et al. |
| 9,060,678 B2 | 6/2015 | Larkin et al. |
| 9,060,793 B2 | 6/2015 | Larkin et al. |
| 9,066,739 B2 | 6/2015 | Larkin et al. |
| 9,068,628 B2 | 6/2015 | Solomon et al. |
| 9,084,623 B2 | 7/2015 | Gomez et al. |
| 9,084,624 B2 | 7/2015 | Larkin et al. |
| 9,089,256 B2 | 7/2015 | Tognaccini et al. |
| 9,096,033 B2 | 8/2015 | Holop et al. |
| 9,101,380 B2 | 8/2015 | Larkin et al. |
| 9,101,397 B2 | 8/2015 | Plowe et al. |
| 9,107,683 B2 | 8/2015 | Houtash |
| 9,119,654 B2 | 9/2015 | Ramans et al. |
| 9,125,679 B2 | 9/2015 | Larkin et al. |
| 9,138,129 B2 | 9/2015 | Diolaiti et al. |
| 9,173,547 B2 | 11/2015 | Duvall et al. |
| 9,192,448 B2 | 11/2015 | Blumenkranz et al. |
| 9,215,967 B2 | 12/2015 | Cooper et al. |
| 9,232,984 B2 | 1/2016 | Guthart et al. |
| 9,241,769 B2 | 1/2016 | Larkin et al. |
| 9,259,276 B2 | 2/2016 | Mintz et al. |
| 9,259,280 B2 | 2/2016 | Au et al. |
| 9,259,281 B2 | 2/2016 | Griffiths et al. |
| 9,261,172 B2 | 2/2016 | Solomon et al. |
| 9,271,798 B2 | 3/2016 | Kumar et al. |
| 9,272,416 B2 | 3/2016 | Hourtash et al. |
| 9,283,049 B2 | 3/2016 | Diolaiti et al. |
| 9,295,525 B2 | 3/2016 | Hingwe et al. |
| 9,296,104 B2 | 3/2016 | Swamp et al. |
| 9,301,807 B2 | 4/2016 | Duval et al. |
| 9,320,416 B2 | 4/2016 | Cooper et al. |
| 9,320,568 B2 | 4/2016 | Orban, III et al. |
| 9,333,042 B2 | 5/2016 | Diolaiti et al. |
| 9,339,347 B2 | 5/2016 | Blumenkranz et al. |
| 9,345,387 B2 | 5/2016 | Larkin |
| 9,345,544 B2 | 5/2016 | Hourtash et al. |
| 9,352,849 B2 | 5/2016 | McCollough et al. |
| 9,375,284 B2 | 6/2016 | Hourtash |
| 9,381,067 B2 | 7/2016 | Julian et al. |
| 9,415,510 B2 | 8/2016 | Hourtash et al. |
| 9,417,621 B2 | 8/2016 | Diolaiti et al. |
| 9,439,732 B2 | 9/2016 | Devengenzo et al. |
| 9,468,501 B2 | 10/2016 | Hourtash et al. |
| 9,469,034 B2 | 10/2016 | Diolaiti et al. |
| 9,480,533 B2 | 11/2016 | Devengenzo et al. |
| 9,486,288 B2 | 11/2016 | Devengenzo et al. |
| 9,492,235 B2 | 11/2016 | Hourtash et al. |
| 9,492,927 B2 | 11/2016 | Diolaiti et al. |
| 9,504,527 B2 | 11/2016 | Smaby et al. |
| 9,504,604 B2 | 11/2016 | Alvarez |
| 9,510,734 B2 | 12/2016 | Cooper et al. |
| 9,510,915 B2 | 12/2016 | Madhani et al. |
| 9,516,996 B2 | 12/2016 | Diolaiti et al. |
| 9,517,106 B2 | 12/2016 | Hourtash et al. |
| 9,526,583 B2 | 12/2016 | Larkin et al. |
| 9,549,663 B2 | 1/2017 | Larkin |
| 9,554,859 B2 | 1/2017 | Nowlin et al. |
| 9,554,865 B2 | 1/2017 | Olds et al. |
| 9,561,083 B2 | 2/2017 | Yu et al. |
| 9,585,726 B2 | 3/2017 | Au et al. |
| 9,610,689 B2 | 4/2017 | Swamp et al. |
| 9,615,889 B2 | 4/2017 | Jensen |
| 9,622,826 B2 | 4/2017 | Diolaiti et al. |
| 9,622,827 B2 | 4/2017 | Yu et al. |
| 9,629,520 B2 | 4/2017 | Diolaiti et al. |
| 9,636,000 B2 | 5/2017 | Mohr |
| 9,636,184 B2 | 5/2017 | Lee et al. |
| 9,636,186 B2 | 5/2017 | Kumar et al. |
| 9,649,172 B2 | 5/2017 | Blumenkranz et al. |
| 9,666,101 B2 | 5/2017 | Kumar et al. |
| 9,675,421 B2 | 6/2017 | Hourtash et al. |
| 9,675,422 B2 | 6/2017 | Hourtash et al. |
| 9,687,310 B2 | 6/2017 | Nowlin et al. |
| 9,713,499 B2 | 7/2017 | Bar et al. |
| 9,713,509 B2 | 7/2017 | Schuh et al. |
| 9,717,563 B2 | 8/2017 | Tognaccini et al. |
| 9,718,190 B2 | 8/2017 | Larkin et al. |
| 9,724,163 B2 | 8/2017 | Orban |
| 9,724,169 B2 | 8/2017 | Mohr et al. |
| 9,727,963 B2 | 8/2017 | Mintz et al. |
| 9,737,371 B2 | 8/2017 | Romo |
| 9,737,373 B2 | 8/2017 | Schuh |
| 9,744,335 B2 | 8/2017 | Jiang |
| 9,757,149 B2 | 9/2017 | Cooper et al. |
| 9,757,203 B2 | 9/2017 | Hourtash et al. |
| 9,763,741 B2 | 9/2017 | Alvarez et al. |
| 9,782,230 B2 | 10/2017 | Smaby et al. |
| 9,786,203 B2 | 10/2017 | Wang et al. |
| 9,788,909 B2 | 10/2017 | Larkin et al. |
| 9,788,910 B2 | 10/2017 | Schuh |
| 9,789,608 B2 | 10/2017 | Itkowitz et al. |
| 9,795,453 B2 | 10/2017 | Tierney et al. |
| 9,795,454 B2 | 10/2017 | Seeber et al. |

(56) References Cited

U.S. PATENT DOCUMENTS

| | | |
|---|---|---|
| 9,797,484 B2 | 10/2017 | Solomon et al. |
| 9,801,526 B2 | 10/2017 | Larkin et al. |
| 9,801,654 B2 | 10/2017 | Gomez et al. |
| 9,801,690 B2 | 10/2017 | Larkin et al. |
| 9,803,727 B2 | 10/2017 | Solomon et al. |
| 9,820,819 B2 | 11/2017 | Olson |
| 9,844,411 B2 | 12/2017 | Schena |
| 9,844,412 B2 | 12/2017 | Bogusky et al. |
| 9,844,415 B2 | 12/2017 | Hourtash |
| 9,850,924 B2 | 12/2017 | Vogtherr et al. |
| 9,855,102 B2 | 1/2018 | Blumenkranz et al. |
| 9,861,447 B2 | 1/2018 | Hourtash et al. |
| 9,867,635 B2 | 1/2018 | Alvarez et al. |
| 9,867,671 B2 | 1/2018 | Kumar et al. |
| 9,883,914 B2 | 2/2018 | Larkin et al. |
| 9,883,920 B2 | 2/2018 | Blumenkranz et al. |
| 9,901,408 B2 | 2/2018 | Larkin |
| 9,907,458 B2 | 3/2018 | Schena |
| 9,907,619 B2 | 3/2018 | Hourtash et al. |
| 9,918,681 B2 | 3/2018 | Wallace et al. |
| 9,931,025 B1 | 4/2018 | Graetzel et al. |
| 9,931,172 B2 | 4/2018 | Hourtash et al. |
| 9,943,375 B2 | 4/2018 | Blumenkranz et al. |
| 9,949,620 B2 | 4/2018 | Duval et al. |
| 9,949,749 B2 | 4/2018 | Noonan et al. |
| 9,949,799 B2 | 4/2018 | Hingwe et al. |
| 9,949,801 B2 | 4/2018 | Hourtash et al. |
| 9,949,802 B2 | 4/2018 | Cooper |
| 9,952,107 B2 | 4/2018 | Blumenkranz et al. |
| 9,955,986 B2 | 5/2018 | Shah |
| 9,955,996 B2 | 5/2018 | Mcgrogan et al. |
| 9,956,044 B2 | 5/2018 | Gomez et al. |
| 9,962,066 B2 | 5/2018 | Rogers et al. |
| 9,962,228 B2 | 5/2018 | Schuh et al. |
| 9,980,630 B2 | 5/2018 | Larkin et al. |
| 9,980,785 B2 | 5/2018 | Schuh |
| 9,993,313 B2 | 6/2018 | Schuh et al. |
| 9,999,476 B2 | 6/2018 | Griffiths |
| 10,008,017 B2 | 6/2018 | Itkowitz et al. |
| 10,016,900 B1 | 7/2018 | Meyer et al. |
| 10,022,192 B1 | 7/2018 | Ummalaneni |
| 10,029,367 B2 | 7/2018 | Hourtash |
| 10,052,167 B2 | 8/2018 | Au et al. |
| 10,071,479 B2 | 9/2018 | Swamp et al. |
| 10,080,576 B2 | 9/2018 | Romo et al. |
| 10,085,809 B2 | 10/2018 | Blumenkranz et al. |
| 10,117,714 B2 | 11/2018 | Nowlin et al. |
| 10,123,844 B2 | 11/2018 | Nowlin et al. |
| 10,136,959 B2 | 11/2018 | Mintz et al. |
| 10,137,575 B2 | 11/2018 | Itkowitz et al. |
| 10,145,747 B1 | 12/2018 | Lin et al. |
| 10,149,720 B2 | 12/2018 | Romo |
| 10,149,729 B2 | 12/2018 | Smaby et al. |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,182,876 B2 | 1/2019 | Devengenzo et al. |
| 10,188,472 B2 | 1/2019 | Diolaiti et al. |
| 10,194,997 B2 | 2/2019 | Hourtash et al. |
| 10,194,998 B2 | 2/2019 | Nowlin et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,251,715 B2 | 4/2019 | Hourtash et al. |
| 10,258,416 B2 | 4/2019 | Mintz et al. |
| 10,271,909 B2 | 4/2019 | Guthart et al. |
| 10,271,915 B2 | 4/2019 | Diolaiti et al. |
| 10,282,881 B2 | 5/2019 | Itkowitz et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,335,242 B2 | 7/2019 | Devengenzo et al. |
| 10,342,625 B2 | 7/2019 | Loh et al. |
| 10,363,107 B2 | 7/2019 | Blumenkranz et al. |
| 10,368,952 B2 | 8/2019 | Tognaccini et al. |
| 10,383,765 B2 | 8/2019 | Alvarez et al. |
| 10,390,896 B2 | 8/2019 | Blumenkranz et al. |
| 10,398,518 B2 | 9/2019 | Yu et al. |
| 10,398,520 B2 | 9/2019 | Larkin et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,433,919 B2 | 10/2019 | Guthart et al. |
| 10,434,660 B2 | 10/2019 | Meyer |
| 10,448,813 B2 | 10/2019 | Cooper et al. |
| 10,449,011 B2 | 10/2019 | Cooper et al. |
| 10,456,166 B2 | 10/2019 | Cooper et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,512,513 B2 | 12/2019 | Nowlin et al. |
| 10,512,514 B2 | 12/2019 | Nowlin et al. |
| 10,513,031 B2 | 12/2019 | Hourtash |
| 10,517,692 B2 | 12/2019 | Eyre et al. |
| 10,524,866 B2 | 1/2020 | Srinivasan |
| 10,537,358 B2 | 1/2020 | Mcgrogan et al. |
| 10,537,994 B2 | 1/2020 | Diolaiti et al. |
| 10,539,478 B2 | 1/2020 | Lin |
| 10,543,048 B2 | 1/2020 | Noonan et al. |
| 10,555,778 B2 | 2/2020 | Ummalaneni et al. |
| 10,595,948 B2 | 3/2020 | Solomon |
| 10,617,480 B2 | 4/2020 | Brisson |
| 10,620,066 B2 | 4/2020 | Blumenkranz et al. |
| 10,624,672 B2 | 4/2020 | Gomez et al. |
| 10,631,949 B2 | 4/2020 | Schuh et al. |
| 10,639,109 B2 | 5/2020 | Bovay et al. |
| 10,646,292 B2 | 5/2020 | Solomon |
| 10,682,191 B2 | 6/2020 | Hourtash et al. |
| 10,687,908 B2 | 6/2020 | Hourtash et al. |
| 10,695,136 B2 | 6/2020 | Larkin |
| 10,730,187 B2 | 8/2020 | Larkin et al. |
| 10,737,394 B2 | 8/2020 | Itkowitz et al. |
| 10,743,953 B2 | 8/2020 | Smaby et al. |
| 10,772,689 B2 | 9/2020 | Gomez et al. |
| 10,773,388 B2 | 9/2020 | Larkin et al. |
| 10,806,524 B2 | 10/2020 | Blumenkranz et al. |
| 10,828,774 B2 | 11/2020 | Diolaiti et al. |
| 10,856,946 B2 | 12/2020 | Solomon et al. |
| 10,869,730 B2 | 12/2020 | Holop et al. |
| 10,905,502 B2 | 2/2021 | Blumenkranz et al. |
| 10,905,507 B2 | 2/2021 | Smaby et al. |
| 10,918,449 B2 | 2/2021 | Solomon et al. |
| 2002/0042620 A1 | 4/2002 | Julian et al. |
| 2002/0058929 A1 | 5/2002 | Green |
| 2002/0091374 A1 | 7/2002 | Cooper et al. |
| 2002/0162926 A1 | 11/2002 | Nguyen |
| 2002/0165524 A1 | 11/2002 | Sanchez et al. |
| 2002/0170116 A1 | 11/2002 | Borders |
| 2003/0191455 A1 | 10/2003 | Sanchez et al. |
| 2004/0039485 A1 | 2/2004 | Niemeyer et al. |
| 2004/0054355 A1 | 3/2004 | Gerbi et al. |
| 2004/0243147 A1 | 12/2004 | Lipow |
| 2004/0261179 A1 | 12/2004 | Blumenkranz |
| 2005/0027397 A1 | 2/2005 | Niemeyer et al. |
| 2005/0107808 A1 | 5/2005 | Evans et al. |
| 2005/0222554 A1 | 10/2005 | Wallace et al. |
| 2006/0069383 A1 | 3/2006 | Bogaerts |
| 2006/0149418 A1 | 7/2006 | Anvari |
| 2007/0038083 A1 | 2/2007 | Srinivasan et al. |
| 2007/0142824 A1 | 6/2007 | Devengenzo et al. |
| 2007/0285508 A1 | 12/2007 | Gere et al. |
| 2008/0039867 A1 | 2/2008 | Feussner |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065100 A1 | 3/2008 | Larkin |
| 2008/0065101 A1 | 3/2008 | Larkin |
| 2008/0065104 A1 | 3/2008 | Larkin et al. |
| 2008/0065106 A1 | 3/2008 | Larkin |

(56) References Cited

U.S. PATENT DOCUMENTS

| | | |
|---|---|---|
| 2008/0071288 A1 | 3/2008 | Larkin |
| 2008/0167750 A1 | 7/2008 | Stahler |
| 2008/0255585 A1 | 10/2008 | Gerbi et al. |
| 2009/0012534 A1 | 1/2009 | Madhani et al. |
| 2009/0030429 A1 | 1/2009 | Madhani et al. |
| 2009/0192523 A1 | 7/2009 | Larkin et al. |
| 2009/0326553 A1 | 12/2009 | Mustufa et al. |
| 2010/0185211 A1 | 7/2010 | Herman |
| 2010/0198232 A1 | 8/2010 | Diolaiti |
| 2010/0204713 A1 | 8/2010 | Ruiz |
| 2010/0286712 A1 | 11/2010 | Won |
| 2010/0313679 A1 | 12/2010 | Larkin et al. |
| 2011/0066161 A1 | 3/2011 | Cooper |
| 2011/0257786 A1 | 10/2011 | Caron |
| 2011/0282357 A1 | 11/2011 | Rogers et al. |
| 2012/0143212 A1 | 6/2012 | Madhani et al. |
| 2012/0266379 A1 | 10/2012 | Hushek |
| 2013/0053866 A1 | 2/2013 | Leung et al. |
| 2013/0096576 A1 | 5/2013 | Cooper |
| 2013/0131695 A1 | 5/2013 | Scarfogliero et al. |
| 2013/0255425 A1 | 10/2013 | Schena |
| 2013/0282024 A1 | 10/2013 | Blumenkranz et al. |
| 2013/0338679 A1 | 12/2013 | Rosielle et al. |
| 2014/0107627 A1 | 4/2014 | Blumenkranz et al. |
| 2014/0107666 A1 | 4/2014 | Madhani et al. |
| 2014/0142591 A1 | 5/2014 | Alvarez et al. |
| 2014/0180309 A1 | 6/2014 | Seeber et al. |
| 2014/0180310 A1 | 6/2014 | Blumenkranz et al. |
| 2014/0188132 A1 | 7/2014 | Kang |
| 2014/0249546 A1 | 9/2014 | Shvartsberg et al. |
| 2014/0316430 A1 | 10/2014 | Hourtash |
| 2014/0357984 A1 | 12/2014 | Wallace et al. |
| 2014/0364870 A1 | 12/2014 | Alvarez et al. |
| 2015/0038981 A1 | 2/2015 | Kilroy et al. |
| 2015/0164598 A1 | 6/2015 | Blumenkranz et al. |
| 2015/0239082 A1 | 8/2015 | Krouglicof |
| 2015/0335389 A1 | 11/2015 | Greenberg |
| 2016/0001038 A1 | 1/2016 | Romo et al. |
| 2016/0100900 A1 | 4/2016 | Madhani et al. |
| 2016/0157942 A1 | 6/2016 | Gombert |
| 2016/0157945 A1 | 6/2016 | Madhani et al. |
| 2016/0270865 A1 | 9/2016 | Landey et al. |
| 2016/0287279 A1 | 10/2016 | Bovay et al. |
| 2016/0346052 A1 | 12/2016 | Rosielle et al. |
| 2016/0374767 A1 | 12/2016 | Diolaiti et al. |
| 2016/0374771 A1 | 12/2016 | Mirbagheri |
| 2017/0007337 A1 | 1/2017 | Dan |
| 2017/0045807 A1 | 2/2017 | Ye |
| 2017/0071692 A1 | 3/2017 | Taylor et al. |
| 2017/0071693 A1 | 3/2017 | Taylor et al. |
| 2017/0095301 A1 | 4/2017 | Brisson |
| 2017/0119481 A1 | 5/2017 | Romo |
| 2017/0135771 A1 | 5/2017 | Auld et al. |
| 2017/0202627 A1 | 7/2017 | Sramek et al. |
| 2017/0209073 A1 | 7/2017 | Sramek et al. |
| 2017/0209217 A1 | 7/2017 | Jensen |
| 2017/0210012 A1 | 7/2017 | Larkin et al. |
| 2017/0215976 A1 | 8/2017 | Nowlin et al. |
| 2017/0258534 A1 | 9/2017 | Hourtash et al. |
| 2017/0290631 A1 | 10/2017 | Lee et al. |
| 2017/0304021 A1 | 10/2017 | Hathaway |
| 2017/0325906 A1 | 11/2017 | Piecuch et al. |
| 2017/0340353 A1 | 11/2017 | Ahluwalia et al. |
| 2017/0340396 A1 | 11/2017 | Romo et al. |
| 2017/0354318 A1 | 12/2017 | Rogers et al. |
| 2018/0025666 A1 | 1/2018 | Ho et al. |
| 2018/0065252 A1 | 3/2018 | Tabandeh |
| 2018/0078439 A1 | 3/2018 | Cagle et al. |
| 2018/0078440 A1 | 3/2018 | Koenig et al. |
| 2018/0079090 A1 | 3/2018 | Koenig et al. |
| 2018/0116735 A1 | 5/2018 | Tierney et al. |
| 2018/0116758 A1 | 5/2018 | Schlosser |
| 2018/0116760 A1 | 5/2018 | Blumenkranz et al. |
| 2018/0177470 A1 | 6/2018 | Suga |
| 2018/0185110 A1 | 7/2018 | Kumar et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0289445 A1 | 10/2018 | Krinninger |
| 2018/0296285 A1 | 10/2018 | Simi et al. |
| 2018/0297206 A1 | 10/2018 | Larkin et al. |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2018/0369035 A1 | 12/2018 | Bhimavarapu |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0090967 A1 | 3/2019 | Guthart et al. |
| 2019/0110839 A1 | 4/2019 | Rafii-Tari et al. |
| 2019/0110847 A1 | 4/2019 | Diolaiti et al. |
| 2019/0151148 A1 | 4/2019 | Alvarez et al. |
| 2019/0167366 A1 | 6/2019 | Ummalaneni |
| 2019/0167369 A1 | 6/2019 | Devengenzo et al. |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0192240 A1 | 6/2019 | Mintz et al. |
| 2019/0201152 A1 | 7/2019 | Diolaiti et al. |
| 2019/0213770 A1 | 7/2019 | Itkowitz et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0255359 A1 | 8/2019 | Benali |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0282313 A1 | 9/2019 | Devengenzo et al. |
| 2019/0282315 A1 | 9/2019 | Loh et al. |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298463 A1 | 10/2019 | Tognaccini et al. |
| 2019/0298465 A1 | 10/2019 | Chin |
| 2019/0328213 A1 | 10/2019 | Landey et al. |
| 2019/0336229 A1 | 11/2019 | Blumenkranz et al. |
| 2019/0336238 A1 | 11/2019 | Yu |
| 2019/0343595 A1 | 11/2019 | Blumenkranz et al. |
| 2019/0365201 A1 | 12/2019 | Noonan et al. |
| 2019/0365202 A1 | 12/2019 | Larkin et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374293 A1 | 12/2019 | Larkin et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000317 A1 | 1/2020 | Cooper et al. |
| 2020/0000490 A1 | 1/2020 | Mcgrogan et al. |
| 2020/0000530 A1 | 1/2020 | DeFonzo |
| 2020/0000533 A1 | 1/2020 | Schuh |
| 2020/0015919 A1 | 1/2020 | Cooper et al. |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0060777 A1 | 2/2020 | Nowlin et al. |
| 2020/0061813 A1 | 2/2020 | Hourtash |
| 2020/0085516 A1 | 3/2020 | DeFonzo |

(56) References Cited

U.S. PATENT DOCUMENTS

| | | |
|---|---|---|
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0106937 A1 | 4/2020 | Cooper et al. |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0240861 A1 | 7/2020 | Blumenkranz et al. |
| 2020/0246096 A1 | 8/2020 | Gomez et al. |
| 2020/0261172 A1 | 8/2020 | Romo |
| 2020/0268459 A1 | 8/2020 | Noonan et al. |
| 2020/0268465 A1 | 8/2020 | Mcgrogan et al. |
| 2020/0281787 A1 | 9/2020 | Ruiz |
| 2020/0289213 A1 | 9/2020 | Swamp et al. |
| 2020/0331147 A1 | 10/2020 | Larkin et al. |
| 2020/0368915 A1 | 11/2020 | Itkowitz et al. |

SURGICAL PLATFORM WITH MOTORIZED ARMS FOR ADJUSTABLE ARM SUPPORTS

CROSS-REFERENCE TO RELATED APPLICATIONS

This application is a continuation of U.S. patent application Ser. No. 16/796,053, filed Feb. 20, 2020, now issued as U.S. Pat. No. 11,202,683, which claims priority to U.S. Provisional Patent Application No. 62/809,197, filed Feb. 22, 2019, all of which are incorporated by reference herein in their entirety and for all purposes. Any and all applications for which a foreign or domestic priority claim is identified in the Application Data Sheet as filed with the present application are hereby incorporated by reference under 37 CFR 1.57.

BACKGROUND

Field

This description generally relates to medical systems, and particularly to surgical or medical platforms, tables, or beds with motorized arms for adjustable robotic arm supports.

Description

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. Recently, physicians have started using robotic arms to help perform surgical procedures. For instance, physicians use robotic arms to control surgical instruments inside a patient. However, existing medical systems including robotic arms have a high capital cost and are typically specialized to perform limited types of surgical procedures. Thus, physicians or their assistants may need to obtain multiple robotic arm systems to accommodate a range of surgical procedures. Manually reconfiguring a robotic arm system for each surgical procedure is also time-consuming and physically demanding for the physicians.

SUMMARY

A surgical or medical robotics system with robotic arms is configurable to perform a variety of surgical or medical procedures. In a first aspect, a motorized arm for a robotic medical system includes a shoulder coupled to a column by a translational joint configured to allow translation of the shoulder along a longitudinal axis of the column, wherein the column is coupled to a table, a first link extending between a first proximal end and a first distal end, wherein the first proximal end is coupled to the shoulder by a first rotary joint configured to permit rotation of the first link relative to the shoulder, and a second link extending between a second proximal end and a second distal end, wherein the second proximal end is coupled to the first distal end by a second rotary joint, and wherein the second distal end is coupled to an arm support configured to support one or more robotic arms.

The motorized arm can include one or more of the following features in any combination: (a) wherein the translational joint, the first rotary joint, and the second rotary joint are configured to allow the arm support to transition from a stowed position below a surface of the table to a deployed position above the surface of the table; (b) wherein the second distal end of the second link is coupled to the arm support by a third rotary joint that is configured to allow the arm support to rotate relative to the second link; (c) a translation mechanism positioned at the second distal end of the second link, the translation mechanism configured to allow the arm support to translate along a translation axis relative to the second link; (d) wherein the first link comprises a first actuator positioned in the first proximal end of the first link and configured to drive rotation of the first link relative to the shoulder, and a first arbor positioned in the first proximal end of the first link configured to increase torsional stiffness of the first rotary joint; (e) wherein the first arbor comprises a hydraulic arbor; (f) wherein the first actuator is positioned on a first lateral side of the first proximal end of the first link, and the first arbor is positioned on a second lateral side of the first proximal end of the first link; (g) wherein the second link comprises a second actuator positioned in the second proximal end of the second link and configured to drive rotation of the second link relative to the first link, and a second arbor positioned in the second proximal end of the second link configured to increase torsional stiffness of the second rotary joint; (h) wherein the second distal end of the second link is coupled to the arm support by a third rotary joint that is configured to allow the arm support to rotate relative to the second link, and wherein the second link further comprises a third actuator positioned in the second distal end of the second link and configured to drive rotation of the adjustable arm support relative to the second link, and a third arbor positioned in the second distal end of the second link configured to increase torsional stiffness of the third rotary joint; and/or (i) wherein the second arbor and the third arbor each comprise hydraulic arbors, and wherein the second arbor and the third arbor are actuated by a single actuation mechanism positioned within the second link.

In another aspect, a motorized arm for a robotic medical system includes a shoulder coupled to a column supporting a table, wherein the table is configured to support a patient during a medical procedure, a first link extending between a first proximal end and a first distal end, the first proximal end coupled to the shoulder by a first rotary joint configured to permit rotation of the first link relative to the shoulder, a first joint actuation mechanism positioned in the first proximal end of the first link and configured to drive rotation of the first link relative to the shoulder, and a first torsional stiffness mechanism positioned in the first proximal end of the first link and configured to, upon actuation of the first torsional stiffness mechanism, increase torsional stiffness of the first rotary joint.

In some embodiments, the motorized arm includes one or more of the following features in any combination: (a) wherein the first joint actuation mechanism comprises a motor; (b) wherein the first joint actuation mechanism comprises a harmonic drive; (c) wherein the first joint torsional stiffness mechanism comprises an arbor; (d) wherein the arbor comprises a hydraulic arbor; (e) wherein the first joint actuation mechanism is positioned on a first lateral side of the first proximal end of the first link and the first torsional stiffness mechanism is positioned on a second lateral side of the first proximal end of the first link; (f) an adjustable arm support coupled to the first distal end of the first link by a second rotary joint, the adjustable arm support configured to support one or more robotic arms; (g) wherein rotation of the second rotary joint is mechanically constrained to rotation of the first rotary joint such that an upper surface of adjustable arm support remains substantially parallel to a support surface supporting the table during rotation of the motorized arm; (h) a second link extending between a second proximal end and a second distal end, the second proximal end coupled to the first distal end of the first link by a second rotary joint configured to permit rotation of the second link relative to the first link, a second joint actuation mechanism positioned in the second proximal end of the second link and configured to drive rotation of the second link relative to the first link, and a second torsional stiffness mechanism positioned in the second proximal end of the second link and configured to, upon actuation of the second torsional stiffness mechanism, increase torsional stiffness of the second rotary joint; (i) wherein the second joint actuation mechanism comprises a motor; (j) wherein the second joint actuation mechanism comprises a harmonic drive; (k) wherein the second torsional stiffness mechanism comprises an arbor; (l) wherein the arbor comprises a hydraulic arbor; (m) wherein the first joint actuation mechanism and the second joint actuation mechanism are positioned on a first lateral side of the first and second links, and the first torsional stiffness mechanism and the second torsional stiffness mechanism are positioned on a second lateral side of the first and second links; (n) wherein the first joint actuation mechanism and the second torsional stiffness mechanism are positioned on a first lateral side of the motorized arm, and the first torsional stiffness mechanism and the second joint actuation mechanism are positioned on a second lateral side of the motorized arm; (o) an adjustable arm support coupled to the second distal end of the second link by a third rotary joint, the adjustable arm support configured to support one or more robotic arms, a third joint actuation mechanism positioned in the second distal end of the second link and configured to drive rotation of the third rotary joint, and a third torsional stiffness mechanism positioned in the second distal end of the second link and configured to, upon actuation of the third torsional stiffness mechanism, increase torsional stiffness of the third rotary joint; (p) wherein the second torsional stiffness mechanism and the third torsional stiffness mechanism are each actuated by a single actuation mechanism positioned in the second link; and/or (q) wherein the shoulder is coupled to the column by a translational joint configured to allow translation of the shoulder along a longitudinal axis of the column.

In another aspect, a method for positioning a motorized arm of a robotic medical system includes rotating a link of the motorized arm by actuating an actuator to drive rotation of a rotary joint, applying a brake to the joint to stop rotation of the link, and actuating an arbor to increase a torsional stiffness of the rotary joint.

The method may include one or more of the following features in any combination: (a) wherein the actuator comprises a gearbox; (b) wherein the arbor comprises a hydraulic arbor; (c) translating the motorized arm in a vertical direction; (d) wherein translating the motorized arm comprises translating a shoulder of the motorized arm along a column supporting a table of the robotic medical system, wherein a proximal end of the link is coupled to the shoulder; (e) performing a robotic medical procedure using at least one robotic arm positioned on adjustable arm support coupled to a distal end of the motorized arm; and/or (f) translating the arm support along an axis of the arm support relative to the motorized arm.

BRIEF DESCRIPTION OF THE DRAWINGS

FIG. 23A illustrates the motorized arm in a first configuration, and FIG. 23B illustrates the motorized arm in a second configuration.

FIG. 23C illustrates the motorized arm in a first configuration, and FIG. 23D illustrates the motorized arm in a second configuration.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. System Overview

Figure 1:
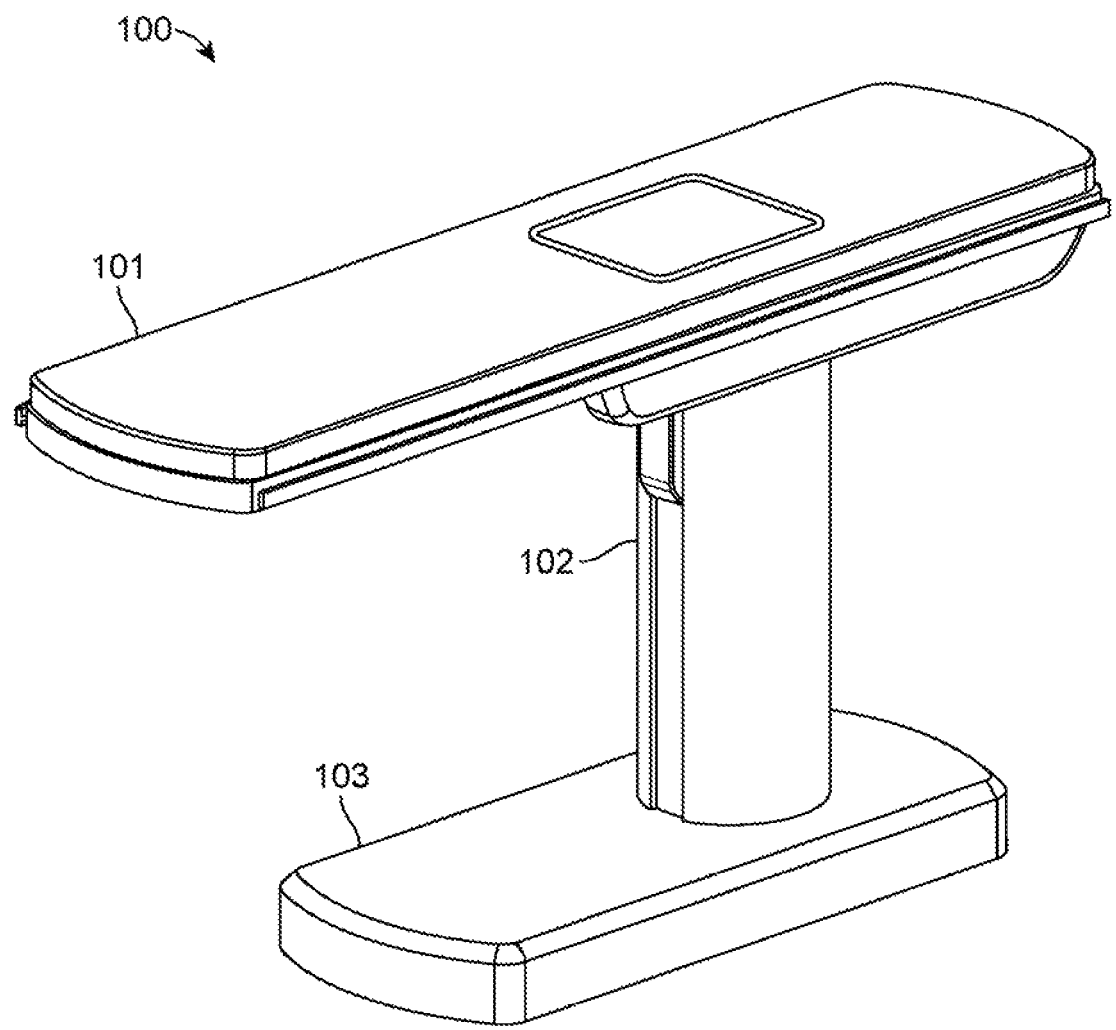
FIG. 1 is an isometric view of a surgical robotics system according to an embodiment.

FIG. 1 is an isometric view of a surgical robotics system 100 according to an embodiment. A user, e.g., a physician or assistant, uses the surgical robotics system 100 to perform robotically assisted surgery on a patient. The surgical robotics system 100 includes a table 101, column 102, and base 103 physically coupled together. Although not shown in FIG. 1, the table 101, column 102, and/or base 103 may house, connect to, or use electronics, fluidics, pneumatics, aspiration, or other electrical and mechanical components that support the function of the surgical robotics system 100.

The table 101 provides support for a patient undergoing surgery using the surgical robotics system 100. Generally, the table 101 is parallel to the ground, though the table 101 may change its orientation and configuration to facilitate a variety of surgical procedures. The table 101 is further described with reference to FIGS. 2A-I in Section II. Table The column 102 is coupled to the table 101 on one end and coupled to the base 103 on the other end. Generally, the column 102 is cylindrically shaped to accommodate column rings coupled to the column 102, which are further described with reference to FIGS. 5A-E in Section V. Column Ring, however the column 102 may have other shapes such as oval or rectangular. The column 102 is further described with reference to FIGS. 3A-B in Section III. Column.

The base 103 is parallel to the ground and provides support for the column 102 and the table 101. The base 103 may include wheels, treads, or other means of positioning or transporting the surgical robotics system 100. The base 103 is further described with reference to FIGS. 8A-E in Section VIII. Base.

Alternative views and embodiments of the surgical robotics system 100 including the above-mentioned components are further illustrated and described at least in U.S. Provisional Application No. 62/162,486 filed May 15, 2015 and U.S. Provisional Application No. 62/162,467 filed May 15, 2015.

Figure 2A:
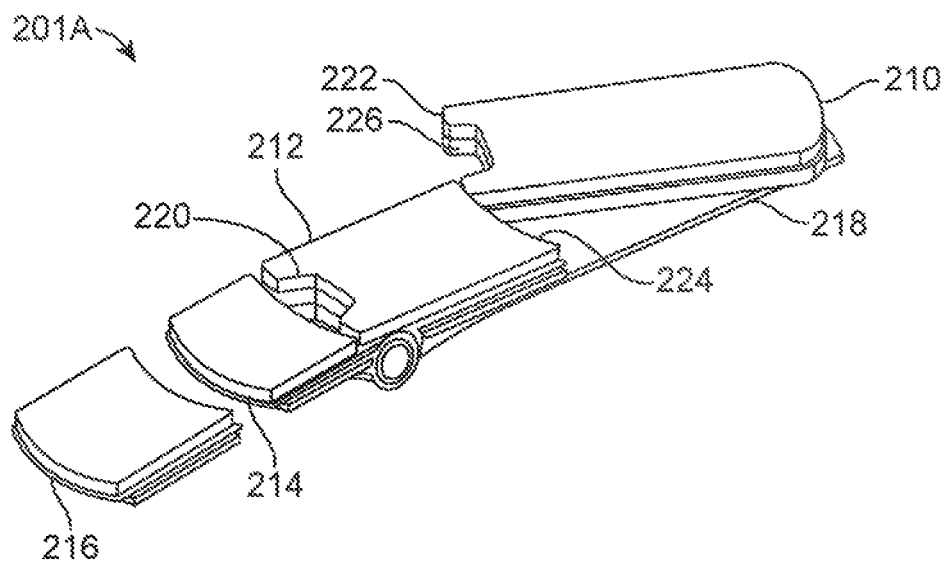
FIG. 2A is an isometric view of a table of the surgical robotics system according to one embodiment.

FIG. 2A is an isometric view of a table 201A of the surgical robotics system 100 according to one embodiment. The table 201A is an embodiment of the table 101 in FIG. 1. The table 201A includes a set of one or more segments. Generally, a user changes the configuration of the table 201A by configuring the set of segments. The surgical robotics system 100 may also configure the segments automatically, for example, by using a motor to reposition a segment of the set of segments. An example set of segments is shown in FIG. 2A, and includes a swivel segment 210, center segment 212, foldable segment 214, detachable segment 216, and table base 218. The swivel segment 210, center segment 212, and foldable segment 214 are coupled to the table base 218. FIG. 2A shows the detachable segment 216 separated from the table base 218, though the detachable segment 216 may also be coupled to the table base 218. In various implementations, additional or fewer segments may be used.

An advantage of configuring the set of segments of the table 201A is that a configured table 201A may provide greater access to a patient on the table 201A. For instance, the surgical robotics system 100 performs a surgical procedure on the patient that requires access to the groin area of the patient. When a patient is laying face-up on a typical surgical bed, there is more access to the patient's head, arms, and legs than to the patient's groin area. Since the groin area is located toward the center of the patient's body, the legs often obstruct access to the groin area. The detachable segment 216 is detachable from the table 201A. The table 201A without the detachable segment 216 provides greater access to the groin area of a patient lying on the table 201A with the patient's head toward the side of the table 201A with the swivel segment 210. In particular, removing the detachable segment 216 opens more space, for example, to insert a surgical instrument into the groin area. If additional space is required to access the groin area, the foldable segment 214 may be folded down, away from the patient (further described in FIG. 2H). The center segment 212 includes a cutout section 220, which also provides greater access to the groin area.

The swivel segment 210 pivots laterally relative to the table 201A. The swivel segment 210 includes an arcuate edge 222 and the center segment 212 also includes in arcuate edge 224. Due to the arcuate edges, there is minimal gap between the swivel segment 210 and the center segment 212 as the swivel segment 210 pivots away from or toward the table 201A. A configuration of the table 201A with the swivel segment 210 pivoted away from the table 201A provides greater access to the groin area because the other segments of the table 201A are not obstructing the groin area. An example of this configuration is further described with respect to FIGS. 7C-D in Section VII. A. Lower Body Surgery. Additionally, the swivel segment 210 also includes a cutout section 226, which provides yet greater access to the groin area.

Figure 2B:
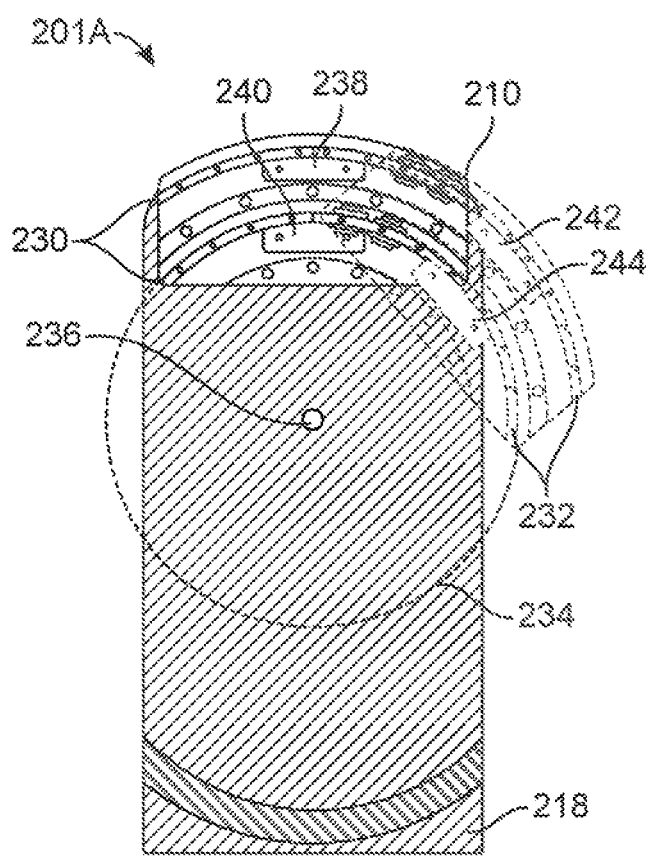
FIG. 2B is a top view of the table according to one embodiment.

FIG. 2B is a top view of the table 201A according to one embodiment. Specifically, FIG. 2B shows the table base 218 with a partial cutaway view and a portion of the swivel segment 210. Components inside the swivel segment 210 are exposed for purposes of illustration. The table base 218 includes double curved rails 230, that is, two curved linear rails (also referred to as a first bearing subassembly). The swivel segment 210 also includes double curved rails 232 (also referred to as a second bearing subassembly). The first bearing assembly coupled to the second bearing assembly may be referred to as a bearing mechanism. The double curved rails 230 of the table base 218 engage with the double curved rails 232 of the swivel segment 210. Both double curved rails are concentric to a virtual circle 234. The swivel segment 210 pivots about an axis passing through a point 236 at the center of the virtual circle 234 perpendicular to the plane of the table base 218. The double curved rails 230 of the table base 218 include a first carriage 238 and a second carriage 240. Similarly, the double curved rails 232 of the swivel segment 210 include a first carriage 242 and a second carriage 244. The carriages provide structural support and negate moment loads, which enables the double curved rails to support high cantilevered loads up to at least 500 pounds. For instance, pivoting a patient away from the table 201A generates a high cantilevered load on the double curved rails supporting the patient's weight. The table base 218 and swivel segment 210 may include additional load-sharing components such as rollers, cam followers, and bearings. In some embodiments, the swivel segment 210 and table base 218 each include a single curved rail instead of double curved rails. Further, each curved rail may include additional or fewer carriages.

Figure 2C:
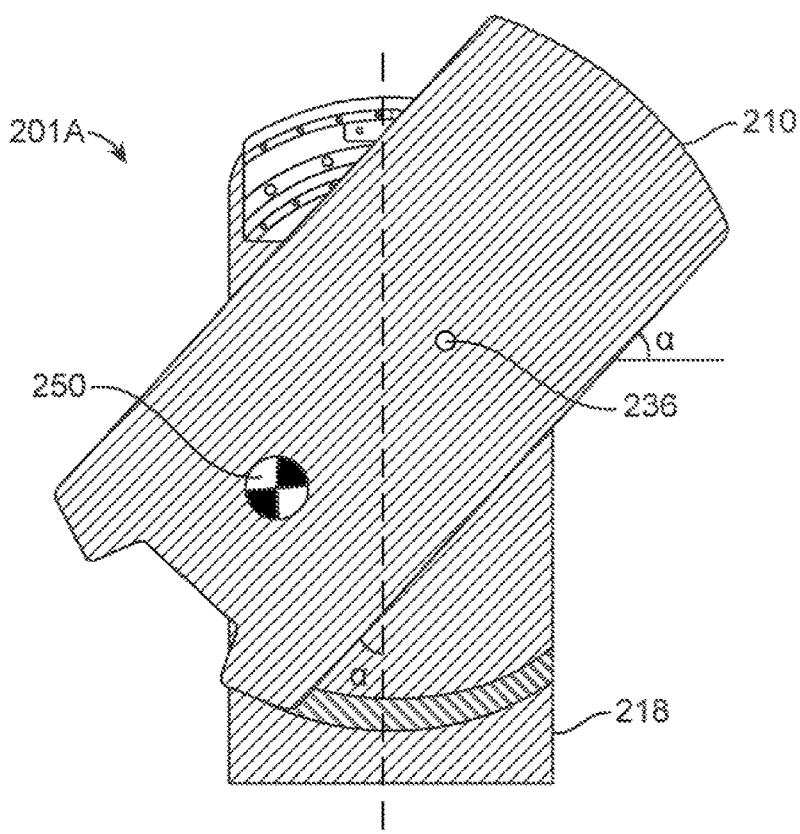
FIG. 2C is a top view of a swivel segment of a table according to one embodiment.
Figure 2D:
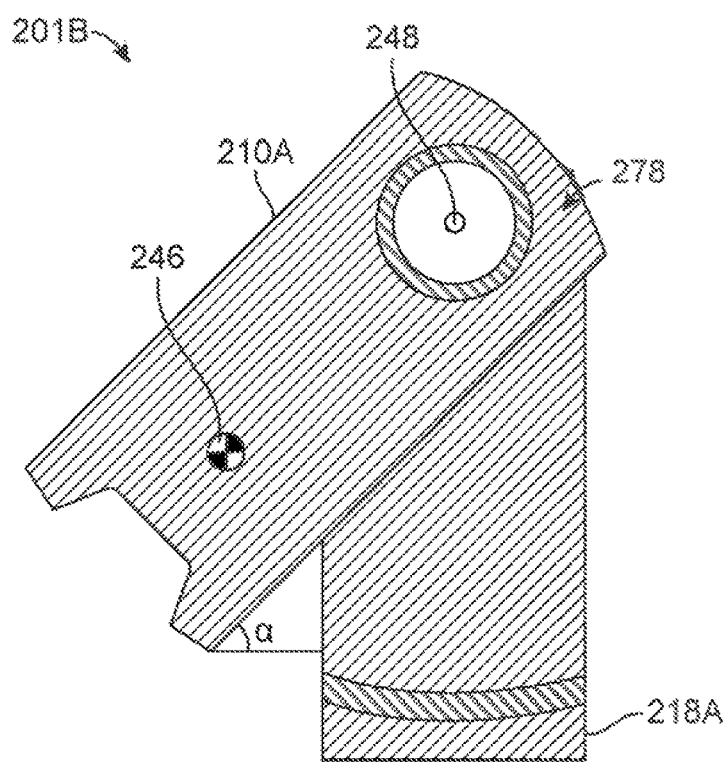
FIG. 2D is a top view of a swivel segment of the table according to one embodiment.

FIG. 2C is a top view of the swivel segment 210 of the table 201A according to one embodiment. The center of mass 250 illustrates the center of mass of the swivel segment 210 and a patient (not shown) lying on the swivel segment 210. The swivel segment 210 is pivoted at an angle .alpha. about the axis 236. Compared to the center of mass 246 shown in FIG. 2D, the center of mass 250 is closer toward the table base 218 (corresponding to table base 218B in FIG. 2D), even though the swivel segments in both FIG. 2C and FIG. 2D are each pivoted at the same angle .alpha. Keeping the center of mass 250 close toward the table 218 helps the swivel segment 210 support greater cantilever loads-due to the patient-without tipping over the surgical robotics system. In some embodiments, the swivel segment 210 may be rotated up to an angle of 30 degrees or 45 degrees relative to table base 218, while keeping the center of mass of the swivel segment 210 above the table 201A.

FIG. 2D is a top view of a swivel segment 210A of a table 201B according to one embodiment. Specifically, the table 201B includes a table base 218A and a swivel segment 210A. The table 201B does not include double curved rails, but instead includes a swivel mechanism 278 that is further described below with reference to FIGS. 2E-G. The center of mass 246 illustrates the center of mass of the swivel segment 210A and a patient (not shown) lying on the swivel segment 210A. The swivel segment 210A is pivoted at an angle .alpha. about an axis 248. Accordingly, the center of mass 246 is positioned off of the table base 218A.

Figure 2E:
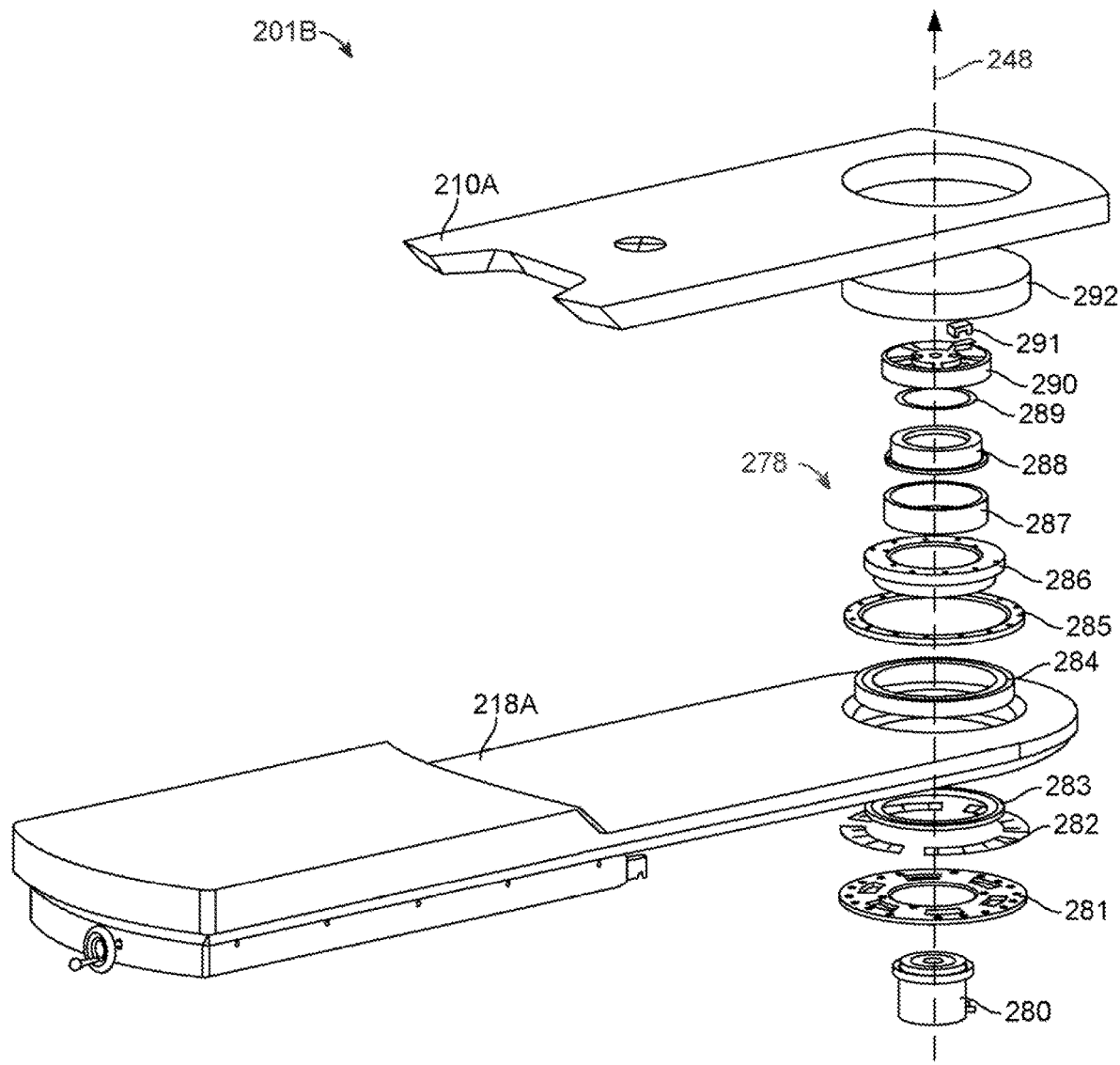
FIG. 2E is an isometric exploded view of components of a swivel mechanism according to one embodiment.

FIG. 2E is an isometric exploded view of components of a swivel mechanism 278 (which can also be referred to as a bearing mechanism) of the table 201B according to one embodiment. The swivel mechanism 278 includes a first bearing subassembly coupled to a second bearing subassembly. In particular, the swivel mechanism 278 includes a harmonic drive motor 280, static plate 281, shim 282, inner bearing race 283, bearing 284, outer bearing race cleat 285, inner bearing race support 286, static ring 287, motor housing mount 288, encoder strip 289, drive plate 290, encoder sensor 291, and swivel insert 292. The motor housing mount 288 is stationary relative to the table base 218A. The harmonic drive motor 280 rotates the swivel segment 210A about the axis 248. The first bearing subassembly includes the components described above that are coupled to the table base 218A. The second bearing subassembly includes the components described above that are coupled to the swivel segment 210A.

Figure 2F:
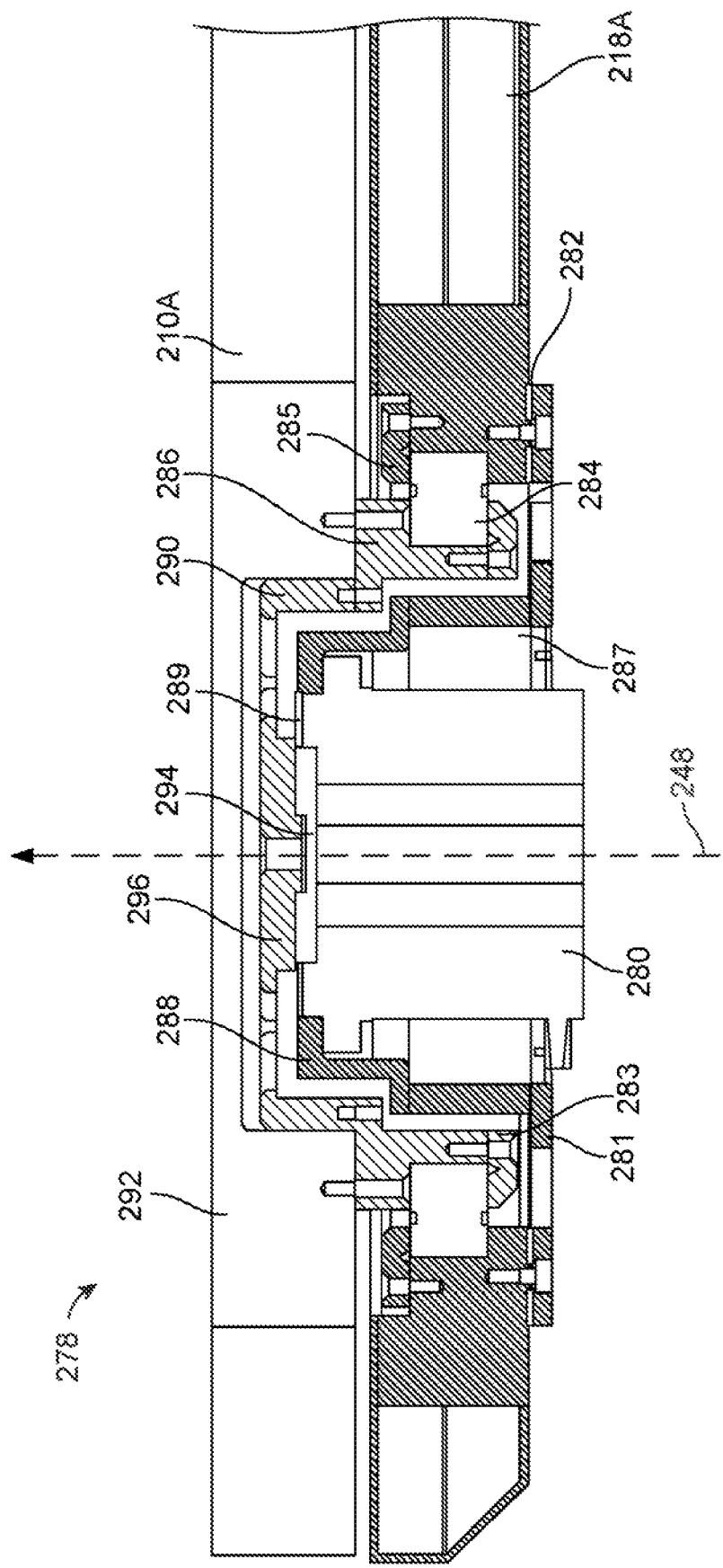
FIG. 2F is a cross-sectional view of the swivel mechanism shown in FIG. 2E according to one embodiment.

FIG. 2F is a cross-sectional view of the swivel mechanism 278 shown in FIG. 2E according to one embodiment. The harmonic drive motor 280 is coupled to the motor housing mount 288. The motor housing mount 288 is coupled to the static ring 287 and the static plate 281. The static plate 281 is coupled to the table base 218A using the shim 282 such that the harmonic drive motor 280 is also stationary relative to the table base 218A.

The harmonic drive motor 280 includes a driving axle 294 coupled to a driving face 296 such that the driving axle 294 and driving face 296 rotate together. The driving face 296 is coupled to the drive plate 290. The drive plate 290 is coupled to the inner bearing race support 286. The inner bearing race support 286 is coupled to the swivel insert 292 and the inner bearing race cleat 283. The inner bearing race support 286 is movably coupled to the table base 218A by the bearing 284 (e.g., a cross roller bearing). The swivel insert 292 is coupled to the swivel segment 210A such that rotating the driving axle 294 and driving face 296 causes the swivel segment 210A to rotate in the same direction. Though not shown in FIG. 2F, the swivel mechanism 278 may include additional components between the static plate 281 and the inner bearing race cleat 283 to provide additional stability, e.g., in the form of a physical hard stop. Further, though not shown in FIG. 2F, the encoder sensor 291 is coupled to the motor housing mount 288 by the encoder strip 289. The encoder sensor 291 records information about the rotation of the swivel segment 210A, e.g., the position of the swivel segment 210A up to an accuracy of 0.1 degrees at 0.01 degree resolution. FIG. 2F shows several screws (or bolts) that are used to couple components of the swivel mechanism, though it should be noted that the components may be coupled using other methods, e.g., welding, press fit, gluing, etc.

The swivel mechanism 278 allows the harmonic drive motor 280 to rotate the swivel segment 210A with precise control, while supporting a load of up to 500 pounds, e.g., from a patient lying on the swivel segment 210A. In particular, the harmonic drive motor 280 may rotate the swivel segment 210A up to a rotational velocity of 10 degrees per second, and up to 45 degrees in either direction about the axis 248. Further, the swivel segment 210A is rotated such that the maximum velocity of the center of mass of the patient is 100 millimeters per second, and the time to the maximum velocity is 0.5 seconds. In some embodiments, one of the bearings of the swivel mechanism is a cross roller bearing—e.g., with ball bearings with a bearing friction coefficient of approximately 0.0025—that helps further provide stability to allow the precise rotation of the swivel segment 210A, while maintaining cantilever loads from the patient's weight. The harmonic drive motor 280 can generate up to 33 Newton meters of torque to rotate the swivel segment 210A with the weight of the patient. In some embodiments, the harmonic drive motor 280 includes an internal brake with a holding torque of at least 40 Newton meters.

Figure 2G:
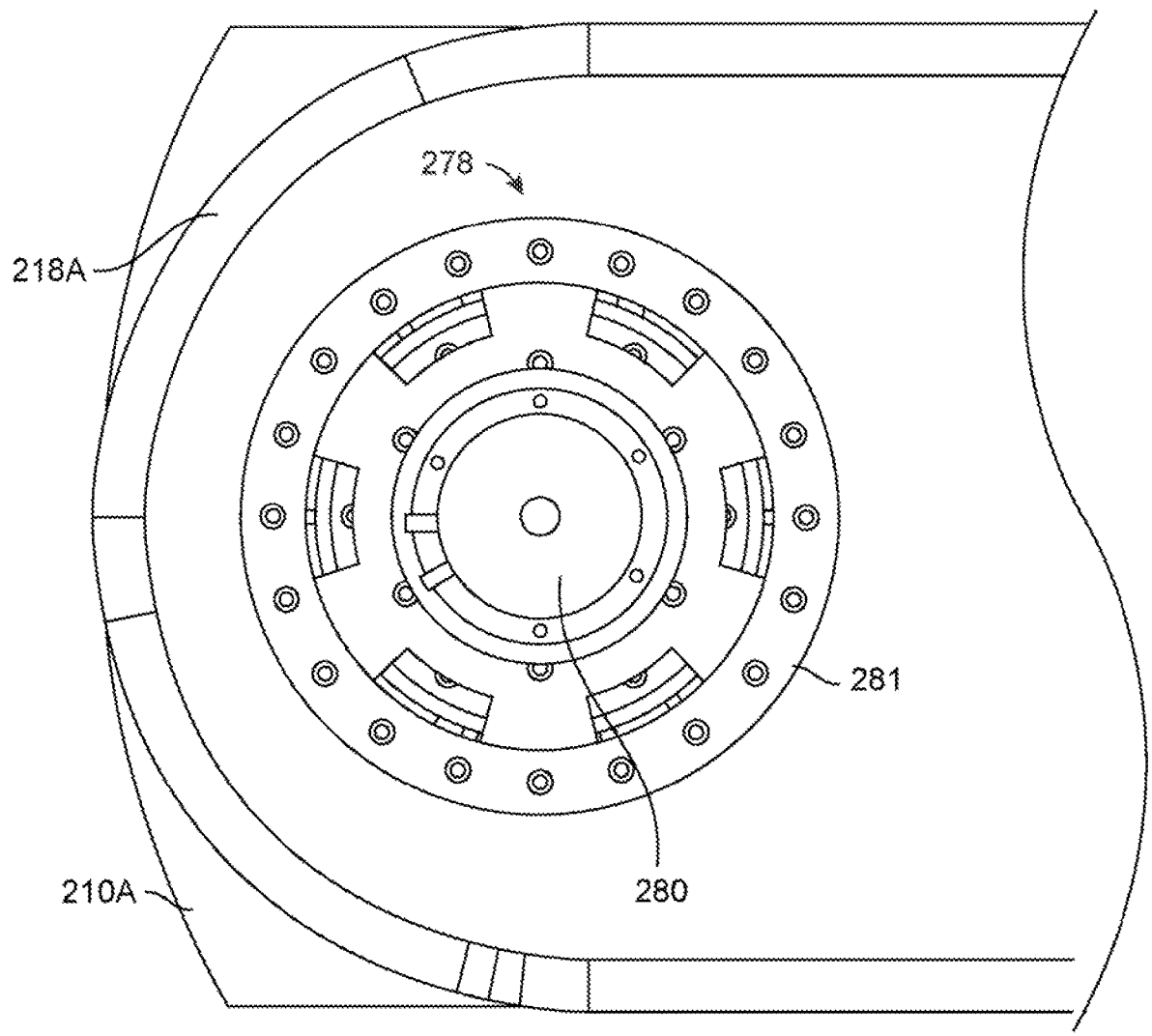
FIG. 2G is a bottom view of the swivel mechanism shown in FIG. 2E according to one embodiment.

FIG. 2G is a bottom view of the swivel mechanism shown in FIG. 2E according to one embodiment. The harmonic drive motor 280 is exposed such that electrical wires, e.g., from a column of the surgical robotics system, may be coupled to the harmonic drive motor 280 to provide control signals to the harmonic drive motor 280.

Figure 2H:
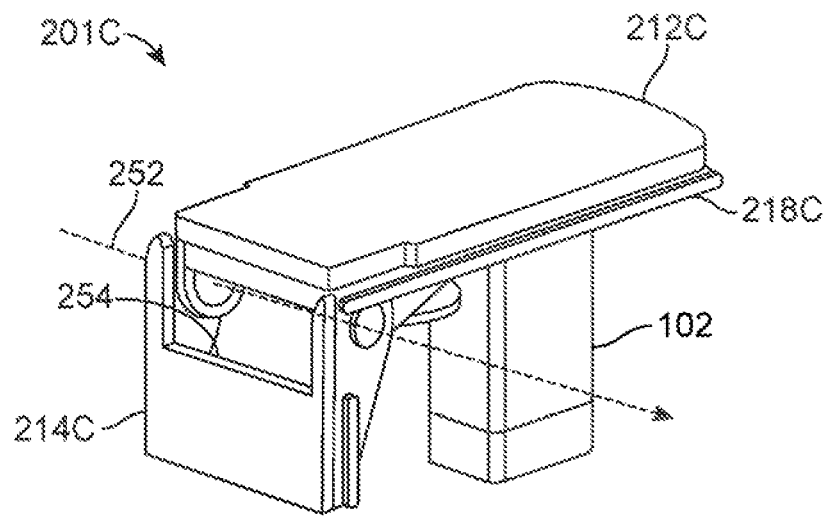
FIG. 2H is an isometric view of a folding segment of the table according to one embodiment.

FIG. 2H is an isometric view of a foldable segment 214C of a table 201C according to one embodiment. The table 201C is an embodiment of table 201A in FIG. 2A. The table 201C also includes a center segment 212C coupled to a table base 218C. The foldable segment 214C rotates using bearings about an axis 252 parallel to the table base 218C. The foldable segment 214C is rotated such that the foldable segment 214C is orthogonal to the table base 218C and the center segment 212C. In other embodiments, the foldable segment 214C may be rotated to other angles relative to the table base 218C and the center segment 212C. The foldable segment 214C includes a cutout section 254, for example, to provide greater access to a patient lying on the table 201C. In other embodiments, the foldable segment 214C does not include a cutout section.

Figure 2I:
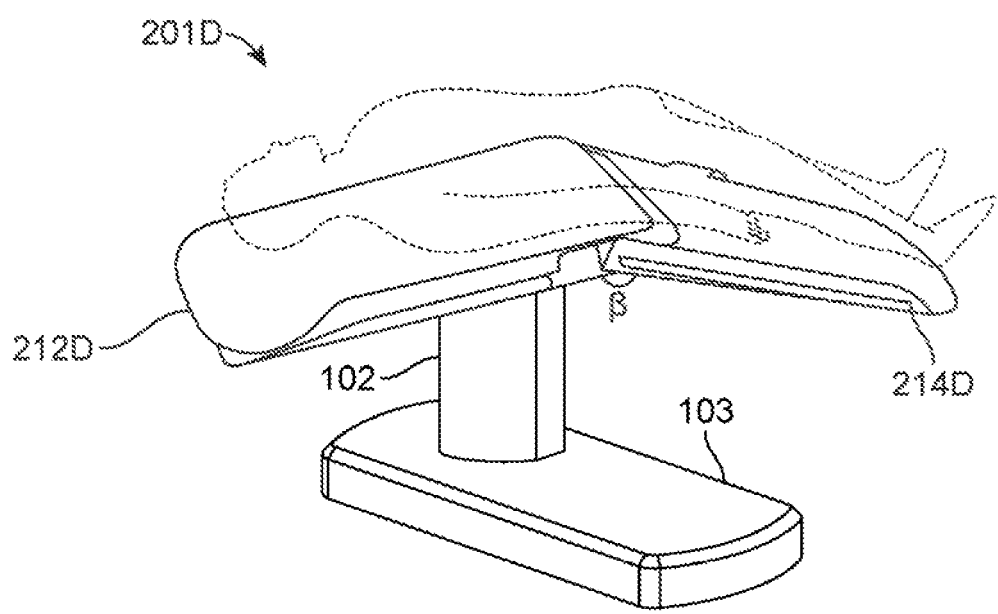
FIG. 2I is another isometric view of a folding segment of the table according to one embodiment.

FIG. 2I is another isometric view of a foldable segment 214D of a table 201D according to one embodiment. The table 201D is an embodiment of table 201A in FIG. 2A. The foldable segment 214D is rotated such that the foldable segment 214D and the table base 218D is positioned at an angle 3 relative to each other. The table 201D includes a mechanism for the foldable segment 214D and the center segment 212D to maintain the rotated position while supporting the weight of a patient on the table 201D. For example, the mechanism is a friction brake at the joint of the foldable segment 214D and the center segment 212D that holds the two segments at the angle .beta. Alternatively, the foldable segment 214D rotates about the center segment 212D using a shaft and the mechanism is a clutch that locks the shaft, and thus keeps the two segments at a fixed position. Though not shown in FIG. 2I, the table 201D may include motors or other actuators to automatically rotate and lock the foldable segment 214D to a certain angle relative to the center segment 212D. Rotating the foldable segment 214D is advantageous, for example, because the corresponding configuration of the table 201D provides greater access to the area around the abdomen of a patient lying on the table 201D.

Figure 2J:
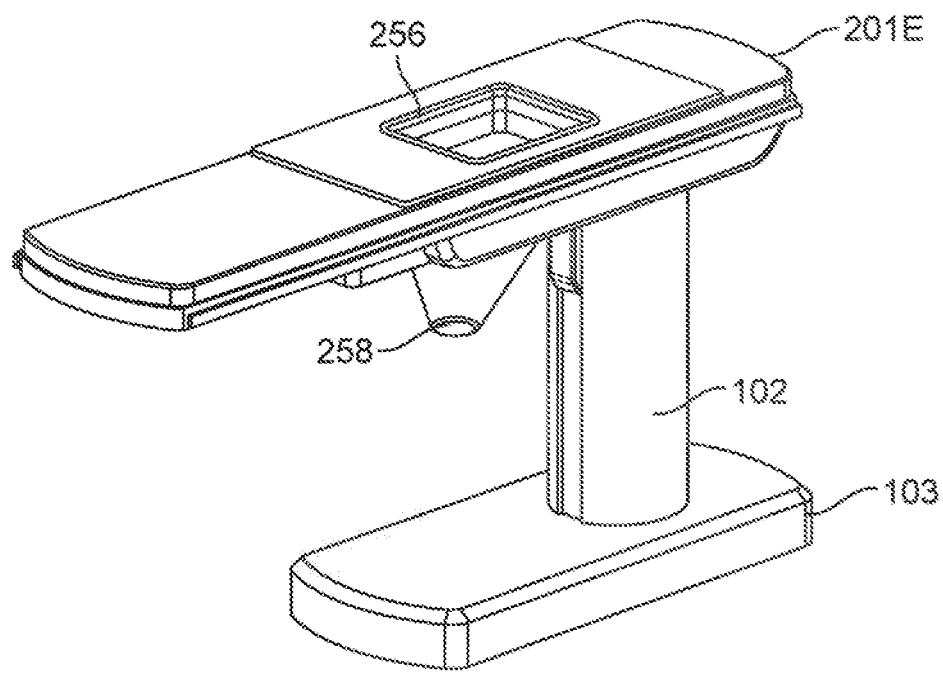
FIG. 2J is an isometric view of a trapdoor of the table according to one embodiment.

FIG. 2J is an isometric view of a trapdoor 256 of a table 201E according to one embodiment. The table 201E is an embodiment of table 201A in FIG. 2A. Specifically, the table 201E includes the trapdoor 256 and a drainage component 258 positioned below the trapdoor 256. The trapdoor 256 and drainage component 258 collect waste materials such as fluid (e.g., urine), debris (e.g., feces) that are secreted or released by a patient lying on the table during a surgical procedure. A container (not shown) may be positioned below the drainage component 258 to collect and store the waste materials. The trapdoor 256 and drainage component 258 are advantageous because they prevent waste materials from soiling or de-sterilizing equipment such as other components of the surgical robotic system 100 or other surgical tools in an operating room with the surgical robotic system 100.

Figure 2K:
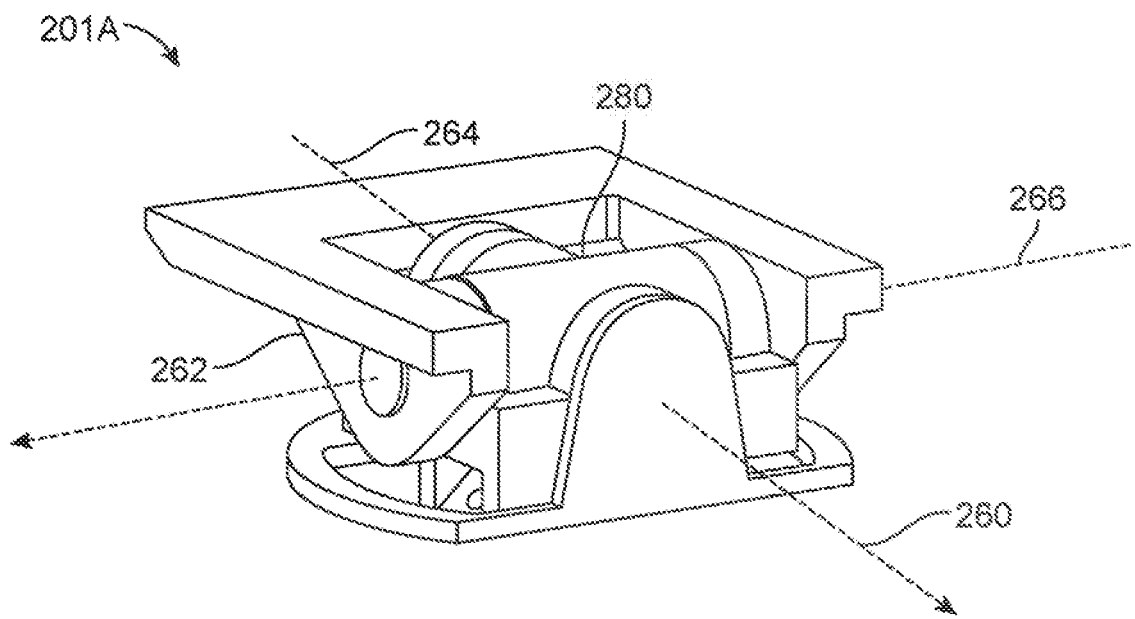
FIG. 2K is an isometric view of pivots of the table according to one embodiment.

FIG. 2K is an isometric view of pivots of the table 201A according to one embodiment. Specifically, the table 201A includes a first pivot 260 and a second pivot 262. The table 201A rotates about a first axis 264. A user, e.g., a physician, may rotate the table 201A about the first axis 264 or the second axis 266 manually or assisted by the surgical robotics system 100. The surgical robotics system 100 may also rotate the table 201A automatically, for example, by using control signals to operate a motor coupled to the first pivot 260 or the second pivot 262. The motor 280 is coupled to the first pivot 260. Rotation of the table 201A may provide greater access to certain areas of a patient lying on the table 201A during a surgical procedure. Specifically, the table 201A is configured to orient a patient lying on the table 201A in a Trendelenburg position by rotating about the first axis 264. Rotation of the table 201A is further described in FIGS. 2L-M.

Figure 2L:
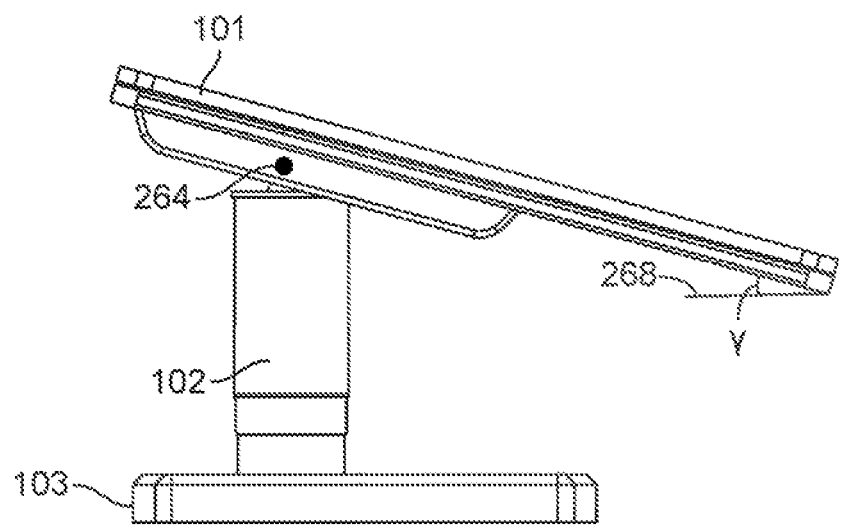
FIG. 2L is a side view of the table rotated about an axis of pitch according to one embodiment.

FIG. 2L is a side view of the table 201A rotated about the axis of pitch 264 according to one embodiment. Specifically, the table 201A is rotated to an angle .gamma. relative to a plane 268 parallel to the ground.

Figure 2M:
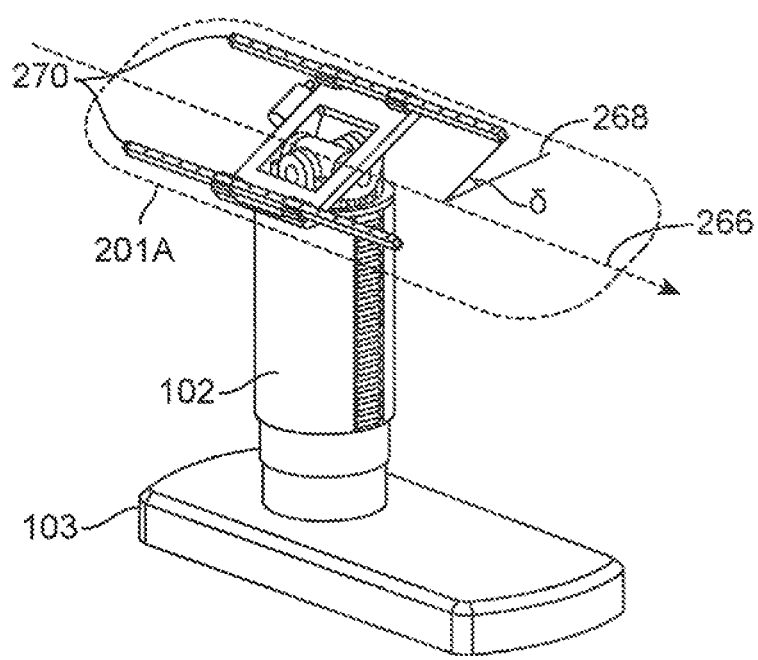
FIG. 2M is an isometric view of the table rotated about an axis of row according to one embodiment.

FIG. 2M is an isometric view of the table 201A rotated about the axis of row 266 according to one embodiment. Specifically, the table 201A is rotated to an angle .delta. relative to the plane 268 parallel to the ground. The table 201A is illustrated as transparent to expose components underneath the table 201A. The table includes a set of rails 270. The table 201A may translate laterally along an axis 266 parallel to the set of rails 270. The surgical robotics system 100 translates the table 201A laterally using, for example, a motor or other means of actuation (not shown). A user of the surgical robotics system 100 may also manually translate the table 201A, or with assistance from the surgical robotics system 100.

Alternative views and embodiments of the table 201A including the above-mentioned components are further illustrated and described at least in U.S. Provisional Application No. 62/235,394 filed Sep. 30, 2015.

III. Column

Figure 3A:
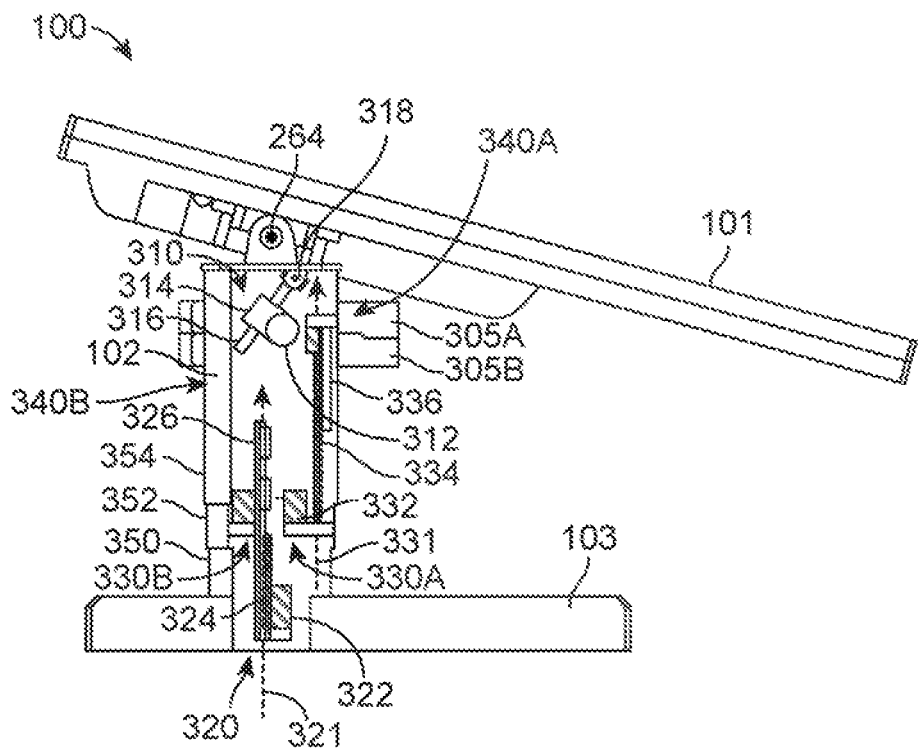
FIG. 3A is a side cutaway view of a column of the surgical robotics system according to one embodiment.

FIG. 3A is a side cutaway view of the column 102 of the surgical robotics system 100 according to one embodiment. The column 102 includes electrical and mechanical and other types of components to perform functions of the surgical robotics system 100. The column 102 includes a pitch rotation mechanism 310, column telescoping mechanism 320, ring telescoping mechanisms 330A and 330B, and ring rotation mechanisms 340A and 340B. The ring rotation mechanisms 340A and 340B are further described in FIG. 3B.

The surgical robotics system 100 rotates the table 101 about the axis of pitch 264 (also illustrated previously in FIGS. 2K-L) using the pitch rotation mechanism 310. The pitch rotation mechanism 310 includes a pitch rotation motor 312, right angle gearbox 314, pitch rotation lead screw 316, and pitch rotation bracket 318. The pitch rotation motor 312 is coupled to the right angle gearbox 314. The pitch rotation motor 312 is orthogonal to the pitch rotation lead screw 316. The pitch rotation lead screw 316 is movably coupled to the pitch rotation bracket 318. The right angle gearbox 314 is coupled to the pitch rotation lead screw 316. Output rotation of the pitch rotation motor 312 causes translational motion of the pitch rotation lead screw along an axis 311. Accordingly, translational motion of the pitch rotation lead screw 318 causes the table 101 to rotate about the axis of pitch 264.

The surgical robotics system 100 translates the table vertically using the column telescoping mechanism 320. The column telescoping mechanism 320 includes a column telescoping motor 322, column telescoping lead screw 324, and column telescoping rail 326. The column telescoping motor 322 is coupled to the column telescoping lead screw 324. The column telescoping motor 322 and the column telescoping lead screw 324 are stationary relative to the base 103. The column telescoping lead screw 324 is engaged with the column telescoping rail 326. Output rotation of the column telescoping motor 322 causes the column telescoping rail 326 to translate along a vertical axis 321 along the column telescoping lead screw 324. As the column telescoping rail 326 translates in the positive direction along the vertical axis 321, the height of the column 102 and the table 101 increases.

The column 102 also includes a lower column segment 350, middle column segment 352, and upper column segment 354. The lower column segment 350 is coupled to the base 103 and stationary relative to the base 103. The middle column segment 352 is movably coupled to the lower column segment 350. The upper column segment 354 is movably coupled to the middle column segment 352. In other embodiments, a column 102 may include additional or fewer column segments.

The upper column segment 354 and/or the middle column segment 352 also translate along the vertical axis 321 to extend the height of the column 102. Similarly, as the column telescoping rail 326 translates in the negative direction along the vertical axis 321, the height of the column 102 and the table 101 decreases. Further, the upper column segment 354 and/or the middle column segment 352 also translate along the vertical axis 321, collapsing over the lower column segment 350. A table 101 with adjustable height is advantageous because the table 101 facilitates a variety of surgical procedures. Specifically, one surgical procedure requires a patient lying on the table 101 to be positioned at a height lower than the height of a patient lying on the table 101 for a different surgical procedure. In some embodiments, the column telescoping mechanism 320 uses other means of actuation such as hydraulics or pneumatics instead of—or in addition to—motors.

The surgical robotics system 100 translates column rings 305A and 305B vertically using the ring telescoping mechanisms 330A and 330B. The ring telescoping mechanism 330A includes a ring telescoping motor 332, ring telescoping lead screw 334, and ring telescoping rail 336. Column rings are further described with reference to FIGS. 5A-E in Section V. Column Ring. Column rings 305A and 305B are movably coupled to the column 102 and translate along a vertical axis 331. Generally, a column 102 includes a ring telescoping mechanism for each column ring of the column 102. Specifically, the column 102 includes ring telescoping mechanism 330A and second ring telescoping mechanism 330B. The ring telescoping motor 332 is coupled to the ring telescoping lead screw 334. The ring telescoping motor 332 and the ring telescoping lead screw 334 are stationary relative to the base 103. The ring telescoping lead screw 334 is engaged with the ring telescoping rail 336. The ring telescoping rail 336 is coupled to the column ring 305A. Output rotation of the ring telescoping motor 332 causes the ring telescoping rail 336 to translate along the vertical axis 331 and along the ring telescoping lead screw 334. As the ring telescoping rail 336 translates in the positive direction or negative direction along the vertical axis 331, the height of a corresponding column ring increases or decreases, respectively.

Figure 3B:
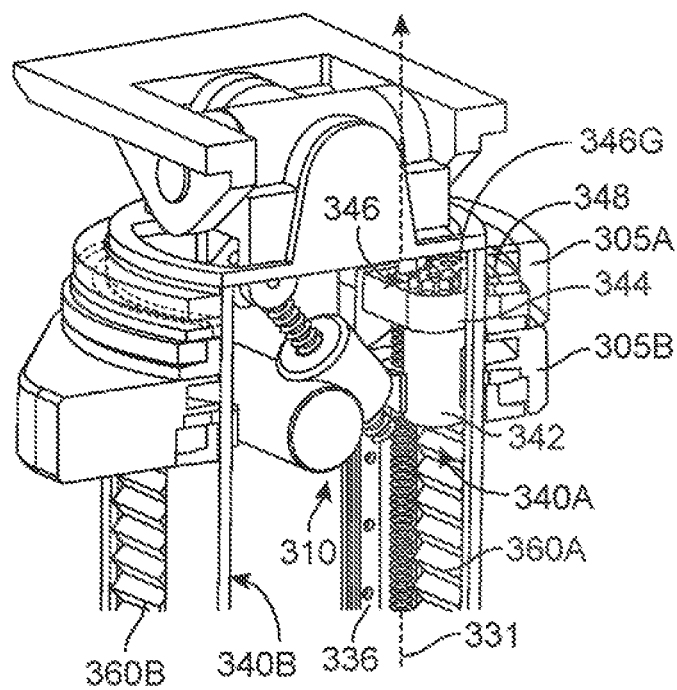
FIG. 3B is an isometric cutaway view of the column according to one embodiment.

FIG. 3B is an isometric cutaway view of the column 102 according to one embodiment. The column 102 includes a first accordion panel 360A and a second accordion panel 360B. The accordion panels 360A and 360B extend or fold as the surgical robotics system 100 translates column rings 305A and 305B in the positive direction or negative direction along the vertical axis 331, respectively. The accordion panels 360A and 360B are advantageous because they protect electrical and mechanical and other types of components inside the column 102 (e.g., the pitch rotation mechanism 310, column telescoping mechanism 320, ring telescoping mechanisms 330A and 330B, and ring rotation mechanisms 340A and 340B) from becoming soiled or de-sterilized by fluid waste and other hazards. FIG. 3B shows an isometric view of the ring rotation mechanism 340A, while the ring rotation mechanism 340B is obscured by the column 102.

The surgical robotics system 100 rotates column rings 305A and 305B using the ring rotation mechanisms 340A and 340B, respectively. The ring telescoping rail 336 is coupled to the ring rotation motor 342 by a ring rotation bracket 344. The ring rotation motor 342 is coupled to a set of gears 346. The set of gears 346 includes a driving gear 346G. The driving gear 346G is engaged with a column ring rail 348 of the column ring 305A. Output rotation of the ring rotation motor 342 causes the set of gears 346 and the driving gear 346G to rotate. Accordingly, the rotation of the driving gear 346G causes the column ring 305A to rotate about a vertical axis 341 concentric to the column 102. The column 102 includes another ring rotation mechanism 340B corresponding to the column ring 305B. Generally, both ring rotation mechanisms 340A and 340B and column rings 305A and 305B will be substantially the same, however in other implementations they may be constructed using different mechanisms.

Figure 3C:
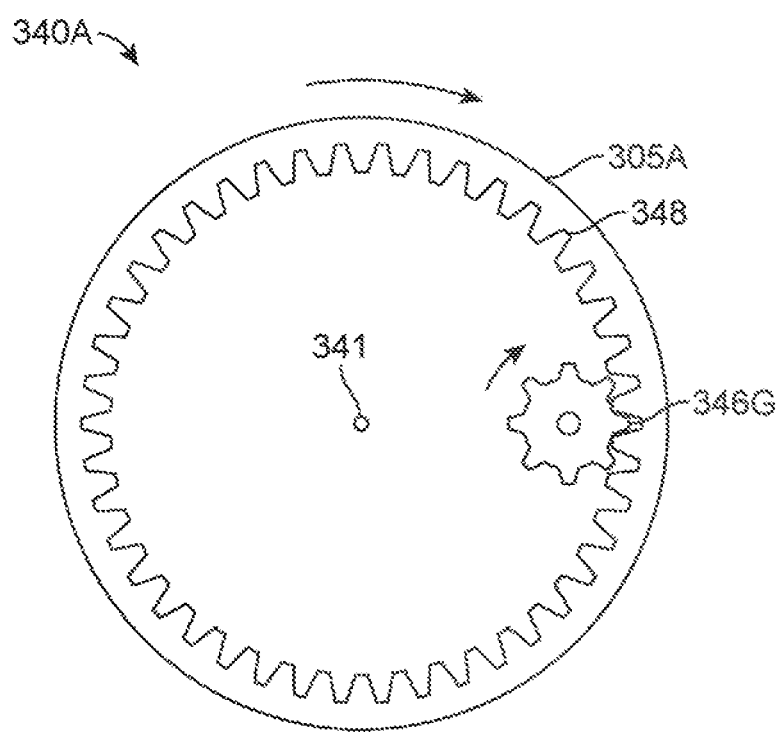
FIG. 3C is a top view of the column according to one embodiment.

FIG. 3C is a top view of the ring rotation mechanism 340A according to one embodiment. For purposes of clarity, FIG. 3C only shows the driving gear 346G, the column ring 305A, and the column ring rail 348 of the ring rotation mechanism 340A. In an example use case, the surgical robotics system 100 rotates the driving gear 346G clockwise to rotate the column ring rail 348—and thus, the column ring 305A—clockwise about the vertical axis 341.

Alternative views and embodiments of the column 103 including the above-mentioned components are further illustrated and described at least in U.S. Provisional Application No. 62/162,486 filed May 15, 2015 and U.S. Provisional Application No. 62/162,467 filed May 15, 2015.

IV. Column-Mounted Robotic Arms

Figure 4A:
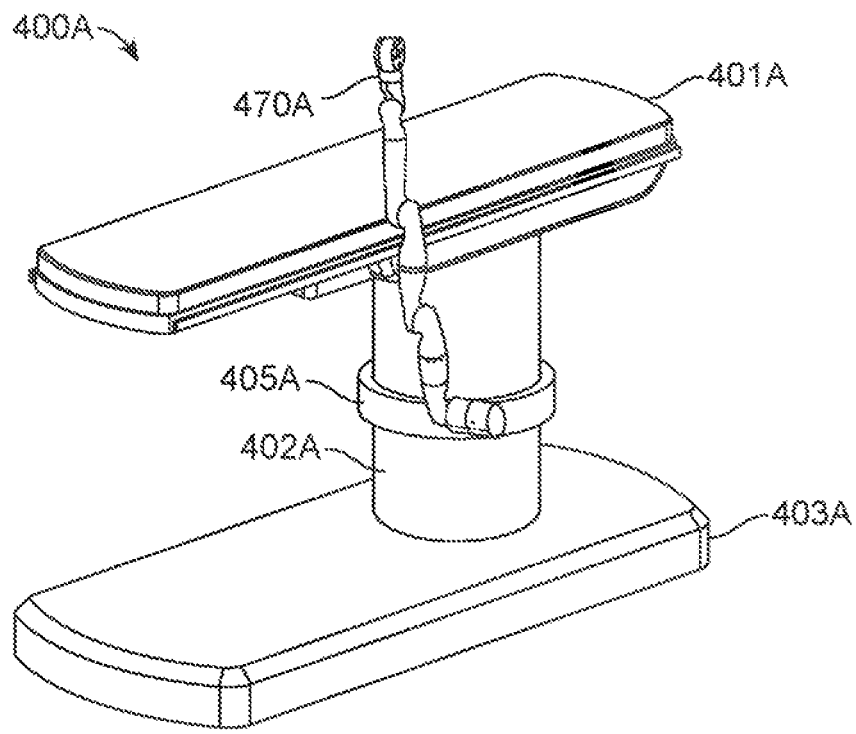
FIG. 4A is an isometric view of a surgical robotics system with a column-mounted robotic arm according to one embodiment.

FIG. 4A is an isometric view of a surgical robotics system 400A with a column-mounted robotic arm 470A according to one embodiment. The surgical robotics system 400A includes a set of robotic arms, a set of column rings, table 401A, column 402A, and base 403A. The surgical robotics system 400A is an embodiment of the surgical robotics system 100 shown in FIG. 1. Generally, the set of robotics arms includes one or more robotic arms, such as robotic arm 470A, where the robotic arms are coupled to one or more column rings, such as column ring 405A. Column rings are described in more detail with respect to FIGS. 5A-E in Section V. Column Ring below. Robotic arms are described in more detail with respect to FIGS. 6A-C in Section VI. Robotic Arm below. Column rings 405A are movably coupled to the column 402A. Thus, a robotic arm 470A attached to a column 405A may be referred to as a column-mounted robotic arm 470A. As introduced above, the surgical robotics system 400A uses robotic arms 470A to perform surgical procedures on a patient lying on the table 401A.

Figure 4B:
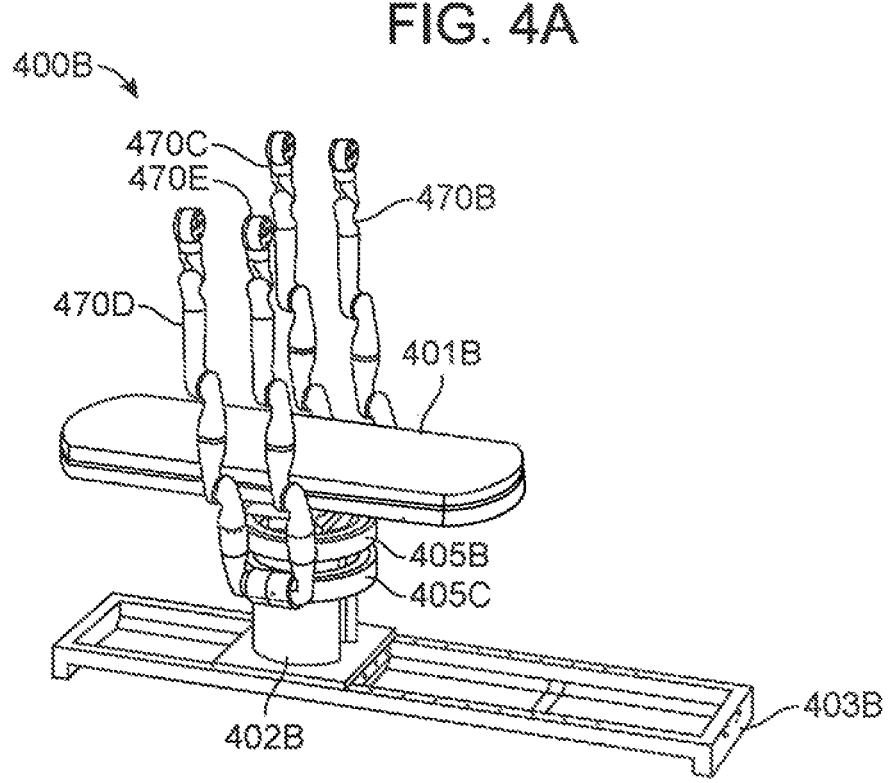
FIG. 4B is an isometric view of a surgical robotics system with column-mounted robotic arms according to one embodiment.

FIG. 4B is an isometric view of a surgical robotics system 400B with column-mounted robotic arms according to one embodiment. The surgical robotics system 400B is an embodiment of the surgical robotics system 400A shown in FIG. 4A. The surgical robotics system 400B includes multiple robotic arms, i.e., a first robotic arm 470B, second robotic arm 470C, third robotic arm 470D, and fourth robotic arm 470E, as well as multiple column rings, i.e., a first column ring 405B and second column ring 405C. In other embodiments, the surgical robotics system 400B may include additional or fewer robotic arms and/or column rings. Further, the robotic arms may be coupled to column rings in various configurations. For example, three robotic arms may be coupled to a column ring. Additionally, the surgical robotics system 400B may include three column rings each coupled to two robotic arms.

Alternative views and embodiments of the surgical robotics system 400B including the above-mentioned components with column-mounted robotic arms are further illustrated and described at least in U.S. Provisional Application No. 62/162,486 filed May 15, 2015 and U.S. Provisional Application No. 62/162,467 filed May 15, 2015.

V. Column Ring

Figure 5A:
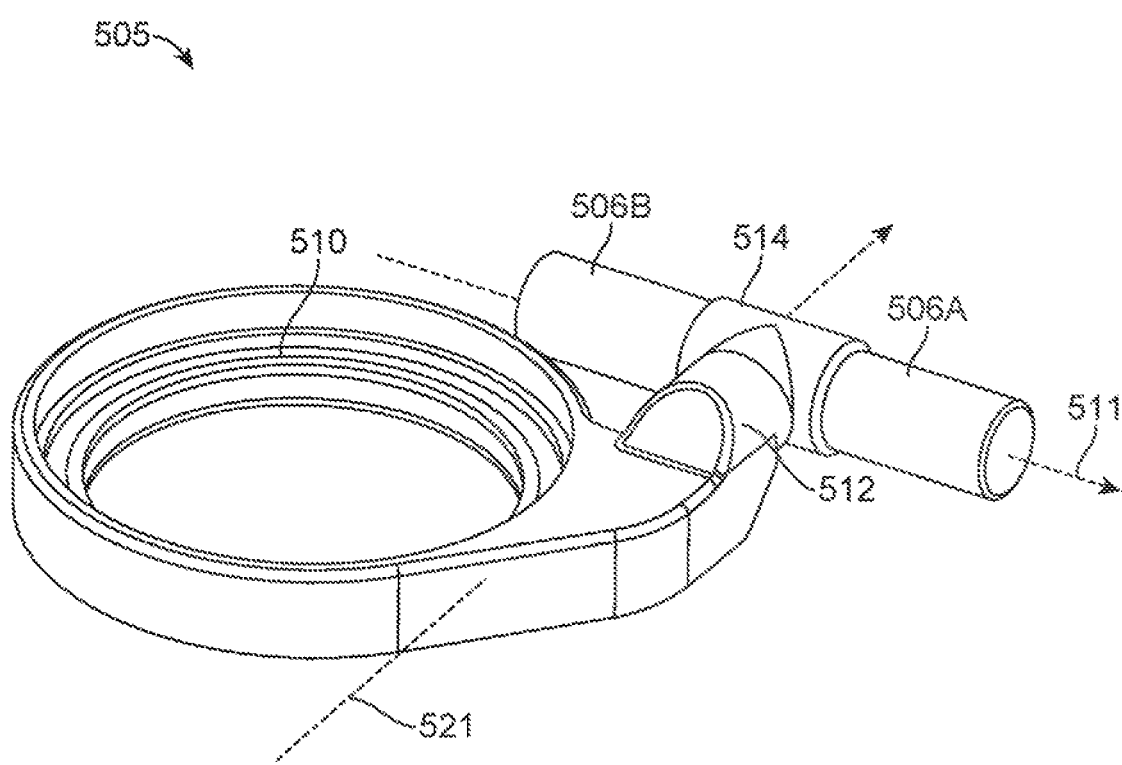
FIG. 5A is an isometric view of a column ring of the surgical robotics system according to one embodiment.

FIG. 5A is an isometric view of a column ring 505 of a surgical robotics system—for example, surgical robotics system 100, 400A, or 400B—according to one embodiment. The column ring 505 includes a column ring rail 510, arm mount pivot 512, arm mount base 514, and a set of arm mounts. The set of arm mounts includes one or more arm mounts. Specifically, the set of arm mounts in FIG. 5A includes a first arm mount 506A and a second arm mount 506B. Generally, each arm mount of the set of arm mounts and the arm mount base 514 are cylindrically shaped.

The first arm mount 506A and the second arm mount 506B are movably coupled the arm mount base 514. The first arm mount 506A and the second arm 506B mount may rotate—together or independently—about the axis 511 concentric to the arm mount base 514. For example, the surgical robotics system 400B rotates the first arm mount 506A and the second arm mount 506B using a motor or other means of actuation (not shown) inside the arm mount base 514 or arm mounts. In some embodiments, the first arm mount 506A and the second arm mount 506B rotate at predetermined increments, e.g., increments of 15 degrees.

The arm mount base 514 is coupled to the arm mount pivot 512. The arm mount pivot 512 uses a motor or other means of actuation (not shown) inside the arm mount pivot 512 to rotate the arm mount base 514 about the axis 521 orthogonal to the axis 511. The arm mount pivot 512 is coupled to, and stationary relative to, the column ring rail 510. Rotating the arm mount base 514 is advantageous because robotic arms (and arm mounts) coupled to the arm mount base 514 may be reoriented in response to rotation of the table 401B. Accordingly, robotic arms coupled to the arm mounts of the arm mount base 514 have greater access to a patient lying on the table 401B.

Figure 5B:
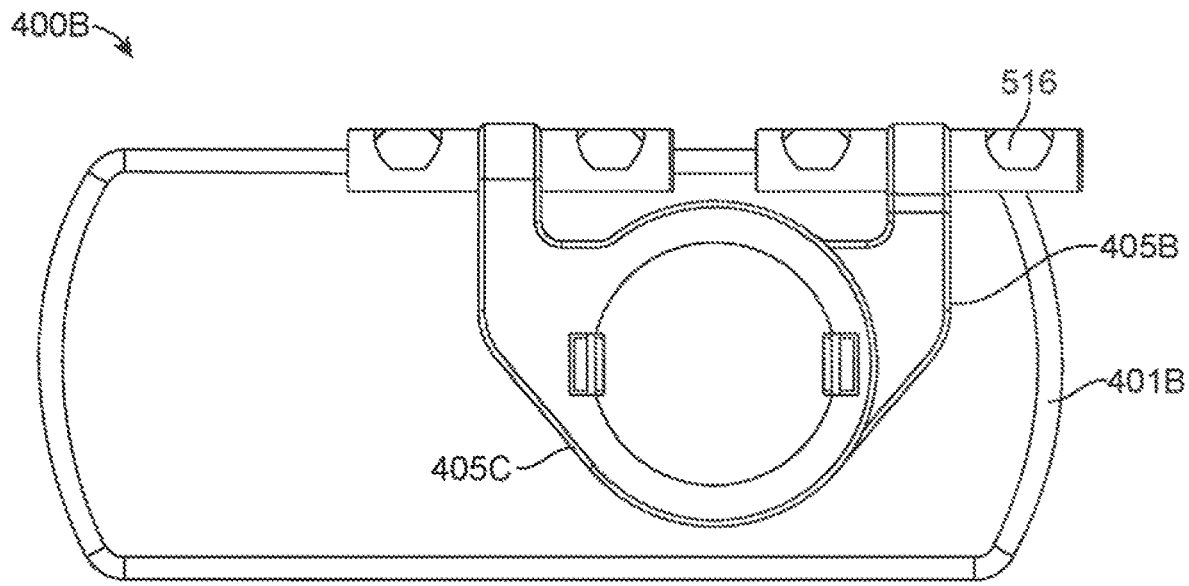
FIG. 5B is a bottom view of a set of column rings underneath a table according to one embodiment.

FIG. 5B is a bottom view of the set of column rings underneath the table 401B of FIG. 4B according to one embodiment. The set of column rings includes the first column ring 405B and the second column ring 405C. Note that FIG. 5B shows the first column ring 405B and the second column ring 405C aligned such that the arm mounts are on the same side of the table 401B, while FIG. 4B shows the first column ring 405B and the second column ring 405C positioned such that the arm mounts are on opposite sides of the table 401B. The surgical robotics system 400B may rotate the column rings 405B and 405C to position the arm mounts in other configurations. For example, two arm mounts are positioned on one side of the table 401B and two arm mounts are positioned on an opposite side of the table 401B. By rotating column rings independently from each other around the column, the surgical robotics system 400B may configure the arm mounts—and thus, robotic arms mounted to the arm mounts—in a greater number of possible positions. Due to this configurability, the surgical robotics system 400B accommodates a variety of surgical procedures because the robotic arms can access any area (e.g., upper body, core body, or lower body) of the body of a patient lying on the table 401B. In some embodiments, each arm mount of the column rings include a notch 516 which facilitates the attachment of a robotic arm to the arm mount.

Figure 5C:
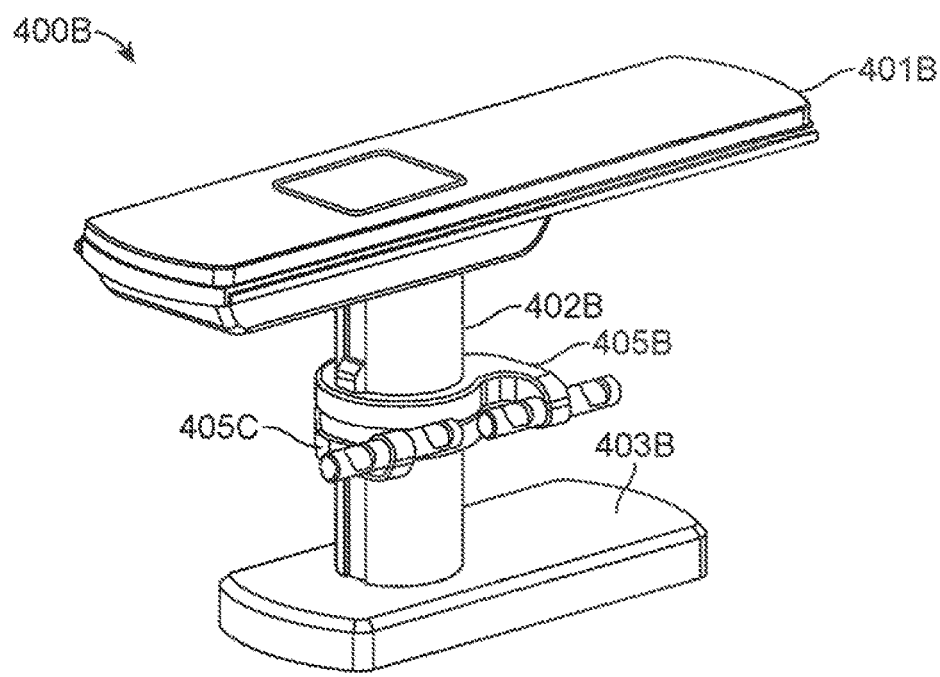
FIG. 5C is an isometric view of the set of column rings mounted to a column according to one embodiment.

FIG. 5C is an isometric view of the set of column rings mounted to the column 402B of FIG. 4B according to one embodiment. Similarly to FIG. 5B, FIG. 5C shows all the arm mounts aligned on the same side of the surgical robotics system 400B.

Figure 5D:
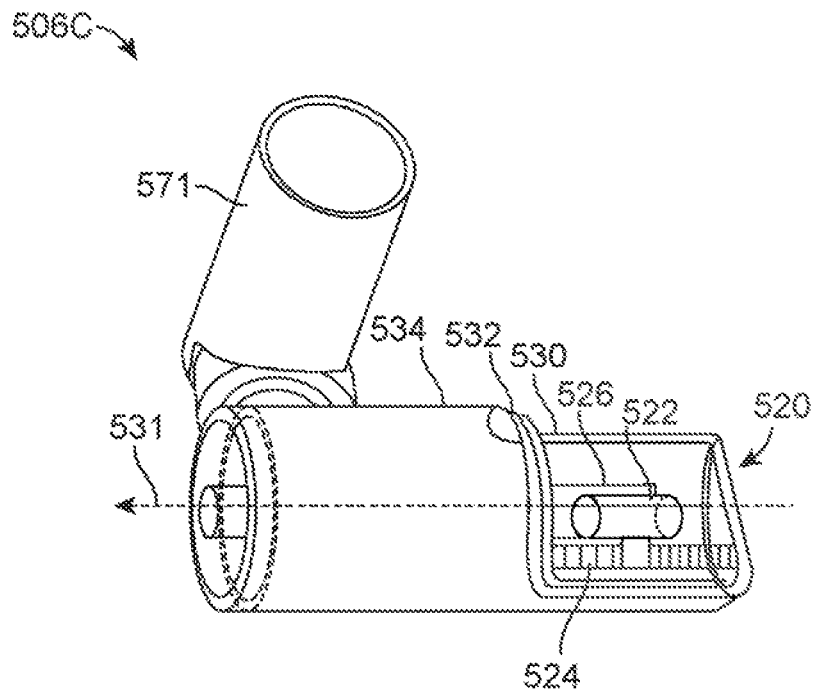
FIG. 5D is an isometric cutaway view of an arm mount of a column ring according to one embodiment.

FIG. 5D is an isometric cutaway view of an arm mount 506C of a column ring according to one embodiment. The arm mount 506C includes an arm mount telescoping mechanism 520 and a set of arm mount segments. The arm mount telescoping mechanism 520 includes an arm mount telescoping motor 522, arm mount telescoping lead screw 524, and arm mount telescoping rail 526. Generally, the set of arm mount segments includes one or more arm mount segments. Specifically, the set of arm mount segments in FIG. 5D includes a lower arm mount segment 530, middle arm mount segment 532, and upper arm mount segment 534. A robotic arm segment 571 (e.g., of the robotic arm 470B in FIG. 4B) is coupled to the upper arm mount segment 534. The middle arm mount segment 532 and the upper arm mount segment 534 are movably coupled to the lower arm mount segment 530. The lower arm mount segment 530 is coupled to an arm mount base (e.g., arm mount base 514 in FIG. 5A).

The surgical robotics system 400B translates the arm mount 506C along an axis 531 using the arm mount telescoping mechanism 520. In FIG. 5D, the axis 531 is in a horizontal orientation, though it should be noted that, in other embodiments, the axis 531 is in a vertical or any other orientation. The arm mount telescoping motor 522 is coupled to the arm mount telescoping rail 526. The arm mount telescoping rail 526 is engaged with the arm mount telescoping lead screw 524. The arm mount telescoping lead screw 524 is stationary relative to the lower arm mount segment 530. Output rotation of the arm mount telescoping motor 522 causes the arm mount telescoping rail 526 to translate along the vertical axis 531. Translation of the arm mount 506C is advantageous because, if the arm mount 506C is extended, a robotic arm mounted to the arm mount 506C may have greater access to a patient lying on the table 401B during a surgical procedure.

Figure 5E:
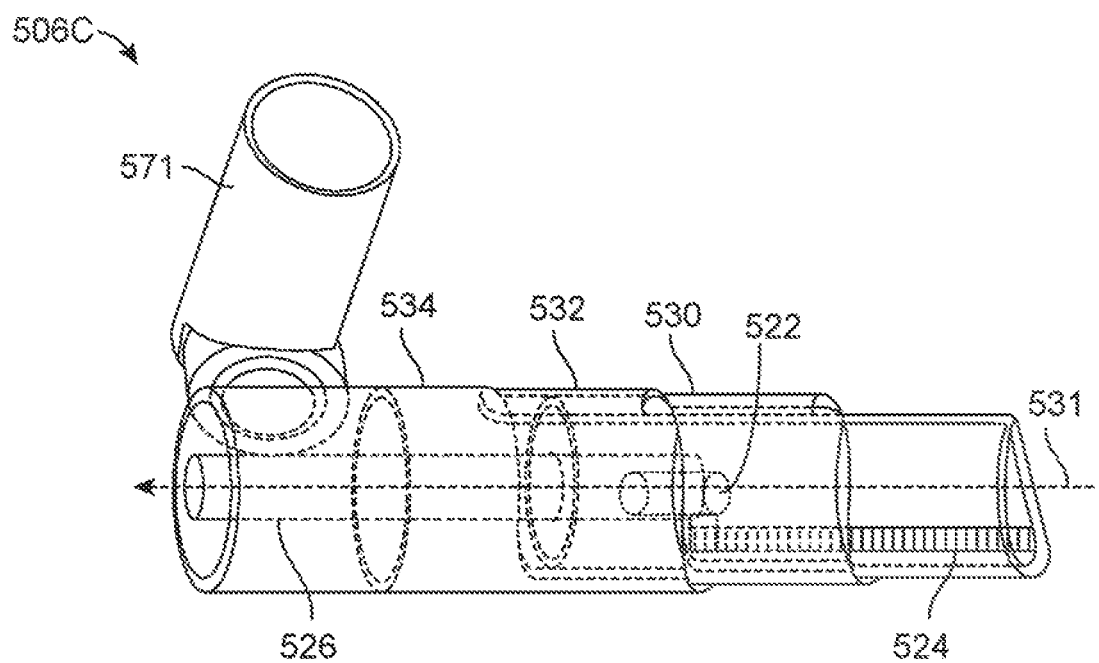
FIG. 5E is an isometric cutaway view of the arm mount in a telescoped configuration according to one embodiment.

FIG. 5E is an isometric cutaway view of the arm mount 506C in a telescoped configuration according to one embodiment. In the telescoped configuration, the upper arm mount segment 534 and the middle arm mount segment 532 extend in the positive axis 531 direction to facilitate extension of the arm mount 506C.

Alternative views and embodiments of the column ring 505 including the above-mentioned components are further illustrated and described at least in U.S. Provisional Application No. 62/162,486 filed May 15, 2015 and U.S. Provisional Application No. 62/162,467 filed May 15, 2015.

VI. Robotic Arm

Figure 6A:
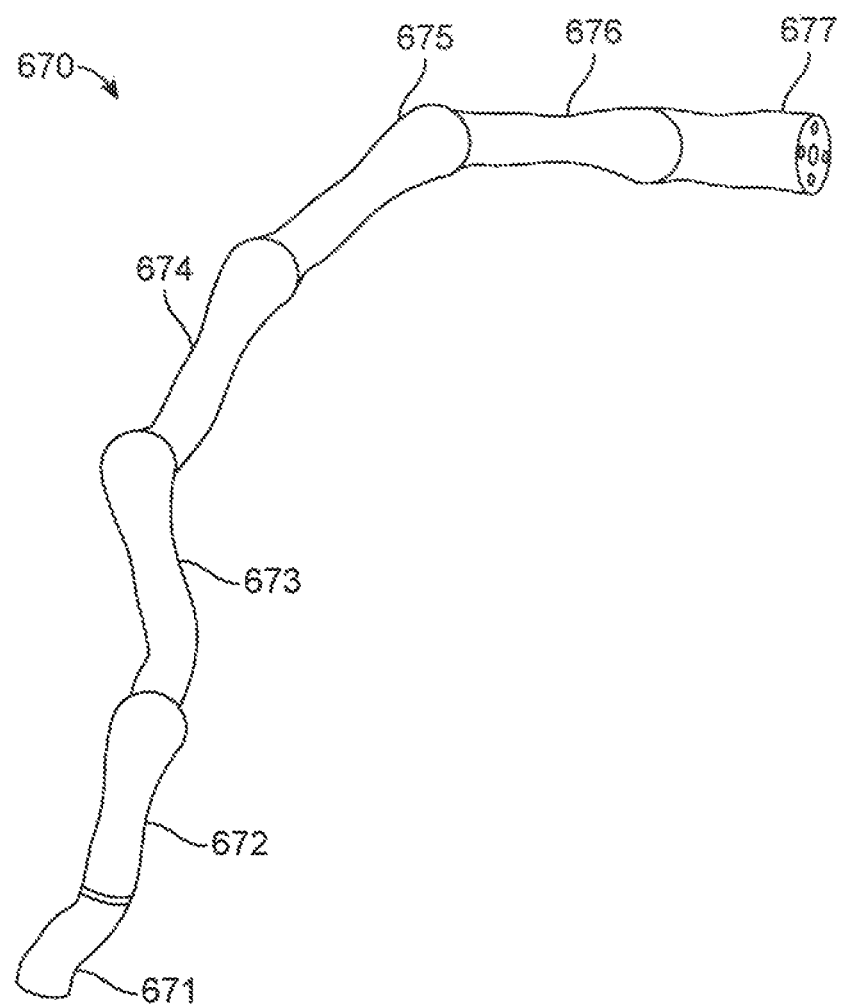
FIG. 6A is an isometric view of a robotic arm of the surgical robotics system according to one embodiment.

FIG. 6A is an isometric view of a robotic arm 670 of a surgical robotics system—for example, surgical robotics system 100, 400A, or 400B—according to one embodiment. Generally, the robotic arm 670 includes a set of robotic arm segments such as robotic arm segments 671, 672, 673, 674, 675, 676, and 677. Each arm segment is movably coupled to at least one other arm segment at an arm segment joint. In particular, the first arm segment 671 is movably coupled to the second arm segment 672, the second arm segment 672 is movably coupled to the third arm segment 673, and so forth. The first arm segment 671 is movably coupled to an arm mount (e.g., arm mount 506A in FIG. 5A). The seventh arm segment 677 (or the last arm segment of a set of arm segments including a number of arm segments different than seven), is coupled to a surgical instrument. The seventh arm segment 677 may also include mechanisms to hold a surgical instrument such as a clamp or robotic fingers. The robotic arm 670 uses electrical and mechanical components, such as motors, gears, and sensors, inside the robotic arm segments to rotate the arm segments at the arm segment joints.

The robotic arm 670 receives control signals from a robotic arm control system, for example, housed in the column 402B in FIG. 4B. In some embodiments, the robotic arm 670 receives control signals from a robotic arm control system located outside of the column 402B or separate from the surgical robotics system 400B. Generally, the robotic arm 670 may include sensors that provide sensor data to the robotic arm control system. Specifically, pressure sensors provide force feedback signals and encoders or potentiometers provide measurements of rotation of arm segments. The robotic arm control system uses the sensor data to generate the control signals provided to the robotic arm 670. Since each arm segment may rotate with respect to another adjacent segment, each arm segment provides an additional degree of freedom to the mechanical system of the robotic arm 670. By rotating the robotic arm segments, the surgical robotics system 400B positions a surgical instrument coupled to the robotic arm 670 such that the surgical instrument has access to a patient undergoing a surgical procedure. Configurations of robotic arms of the surgical robotics system 400B are further described with reference to FIGS. 7A-F in Section VII. System Orientations for Performing Surgical Procedures.

Figure 6B:
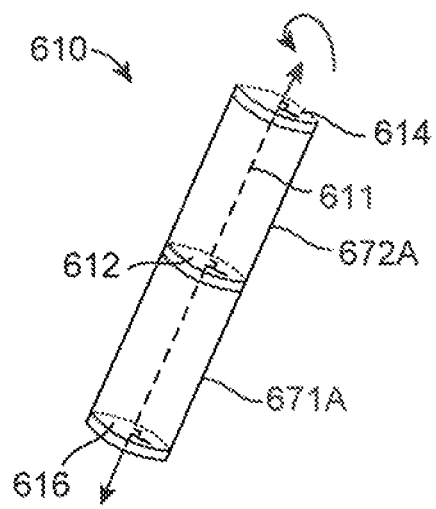
FIG. 6B is an isometric view of an arm segment joint of the robotic arm according to one embodiment.

FIG. 6B is an isometric view of an arm segment joint 610 of the robotic arm 670 according to one embodiment. The first arm segment 671A and the second arm segment 672A are embodiments of any of the arm segments in FIG. 6A. The arm segments 671A and 672A are cylindrically shaped and joined at the plane 612. The first arm segment 671A rotates relative to the second arm segment 672A about an axis 611 perpendicular to the plane 612. Further, the axis 611 is perpendicular to the plane 614 of the second arm segment 672A and perpendicular to the plane 616 of the first arm segment 671A. That is, the axis 611 is longitudinal relative to the arm segments 671A and 672A.

Figure 6C:
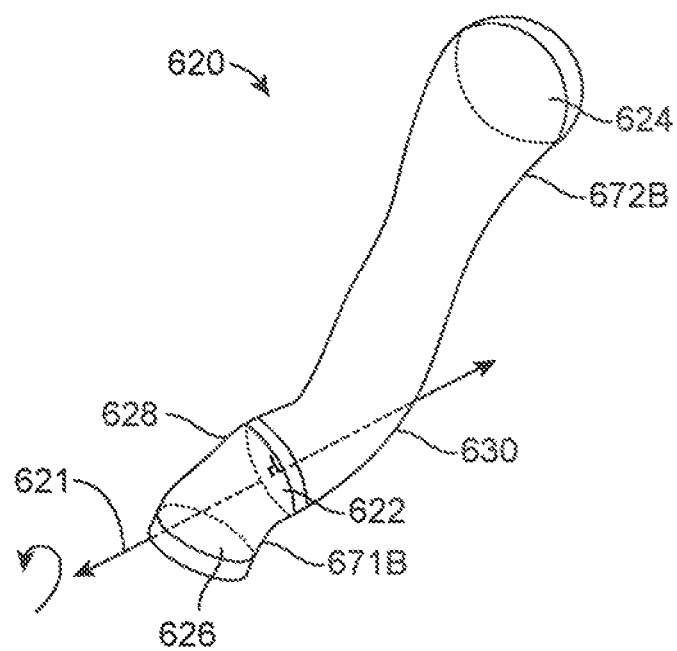
FIG. 6C is an isometric view of another arm segment joint of the robotic arm according to one embodiment.

FIG. 6C is an isometric view of another arm segment joint 620 of the robotic arm 670 according to one embodiment. The arm segments 671B and 672B are joined at the plane 622. Unlike the cylindrically shaped arm segments shown in FIG. 6B, the arm segments 671B and 672B each include a curved section 628 and 630, respectively. The first arm segment 671B rotates relative to the second arm segment 672B about an axis 621 perpendicular to the plane 622. The axis 621 is not perpendicular to the plane 624 of the arm segment 672B and not perpendicular to the plane 626 of the arm segment 671B. In some embodiments, the axis of rotation is perpendicular to a plane of one arm segment, but not perpendicular to a plane of the other arm segment of an arm segment joint.

Alternative views and embodiments of the robotic arm 670 including the above-mentioned components are further illustrated and described at least in U.S. Provisional Application No. 62/162,486 filed May 15, 2015 and U.S. Provisional Application No. 62/162,467 filed May 15, 2015.

VII. System Orientations for Performing Surgical Procedures

The surgical robotics system 400B in FIG. 4B performs a variety of surgical procedures using column-mounted robotic arms of the set of robotic arms. The surgical robotics system 400B configures the column-mounted robotic arms to access portions of a patient lying on the table 401B before, during, and/or after a surgical procedure. The column-mounted robotic arms access portions near the groin of the patient for surgical procedures such as ureteroscopy, percutaneous nephrolithotomy (PCNL), colonoscopy, and fluoroscopy. The column-mounted robotic arms to access portions near the core (e.g., abdomen) area the patient for surgical procedures such as prostatectomy, colectomy, cholecystectomy, and inguinal hernia. The column-mounted robotic arms to access portions near the head of the patient for surgical procedures such as bronchoscopy, endoscopic retrograde cholangiopancreatography (ERCP).

The surgical robotics system 400B automatically reconfigures the column-mounted robotic arms, column rings, column, and table to perform different surgical procedures. The features of each subsystem and component of the surgical robotics system 400B enable the same set of robotics arms to access a large working volume, and multiple working volumes (based on the configuration), to perform a variety of surgical procedures on the patient. In particular, as mentioned above, the robotic arms may be configured in a first configuration to access the patients' groin area, in a second configuration to access the patients' abdomen area, and in a third configuration to access the patients' head area, in addition to other possible configurations. The degrees of freedom provided by the arm segments of the robotic arms, column rings, column, and table contribute to the wide range of configurations. The surgical robotics system 400B includes a computer system that stores computer program instructions, for example within a non-transitory computer-readable storage medium such as a persistent magnetic storage drive, solid state drive, etc. When executed by a processor of the computer system, the instructions cause the components of the surgical robotics system 400B to automatically reconfigure without the need for intervention, or with minimal intervention, from a user, e.g., a physician. For example, based on the instructions, the computer system sends an electronic control signal to motors of the robotics arms. In response to receiving the control signal, the motors rotate arm segments of the robotics arms into a certain position. The physician or another user may design a configuration of the surgical robotics system by creating the instructions and providing the instructions to the computer system. For example, the instructions are uploaded to a database of the computer system. The automatic configurability of the surgical robotics system 400B is an advantage because the automatic configurability saves resources. Specifically, the surgical robotics system 400B reduces the amount of time taken by users to setup the surgical robotics system 400B for a surgical procedure. Further, by using the surgical robotics system 400B for a variety of surgical procedures, users reduce the amount of surgical equipment that they need to purchase, maintain, store, and learn to operate.

Alternative views and embodiments of use cases of the surgical robotics system 400B with column-mounted robotic arms including the above-mentioned components are further illustrated and described at least in U.S. Provisional Application No. 62/162,486 filed May 15, 2015 and U.S. Provisional Application No. 62/162,467 filed May 15, 2015.

VII. A. Lower Body Surgery

Figure 7A:
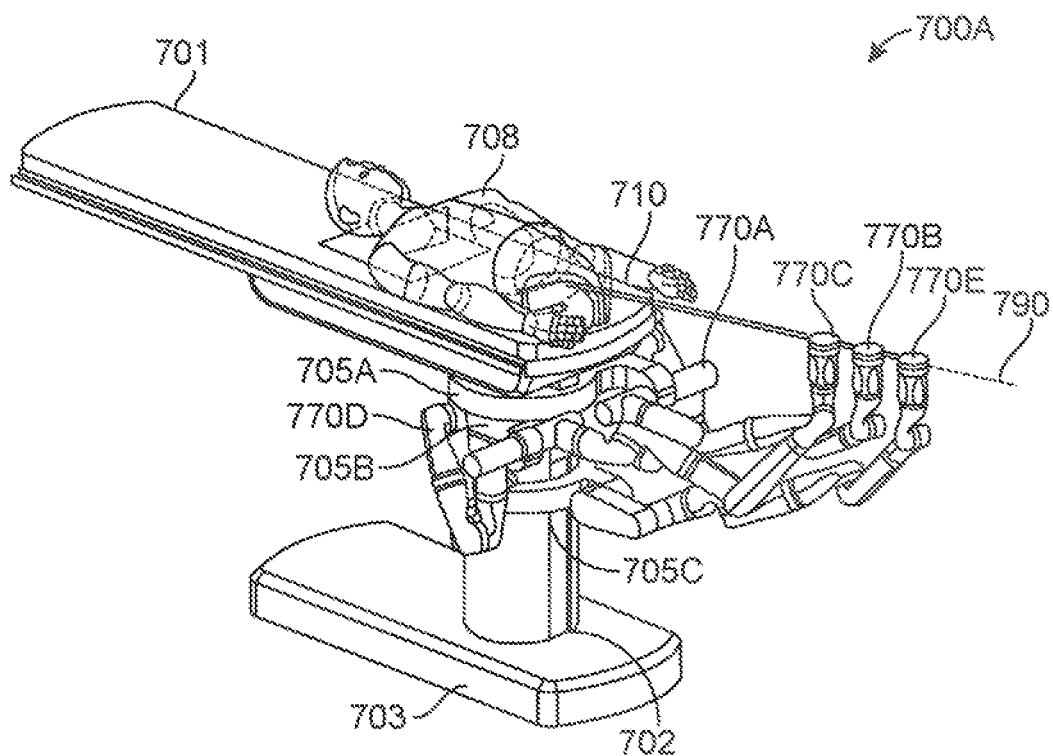
FIG. 7A is an isometric view of a surgical robotics system with column-mounted arms configured to access the lower body area of a patient according to one embodiment.

FIG. 7A is an isometric view of a surgical robotics system 700A with column-mounted arms configured to access the lower body area of a patient 708 according to one embodiment. The surgical robotics system 700A is an embodiment of—though includes more components than—the surgical robotics system 400B in FIG. 4B. Specifically, the surgical robotics system 700A includes a set of robotic arms (including five robotic arms in total) and a set of three column rings. A first robotic arm 770A and a second robotic arm 770B are coupled to a first column ring 705A. A third robotic arm 770C and a fourth robotic arm 770D are coupled to a second column ring 705B. A fifth robotic arm 770E is coupled to a third column ring 705C. FIG. 7A shows a wireframe of the patient 708 lying on the table 701 undergoing a surgical procedure, e.g., ureteroscopy, requiring access to the lower body area of the patient 708. Legs of the patient 708 are not shown as to not obscure portions of the surgical robotics system 700A.

The surgical robotics system 700A configures the set of robotic arms to perform a surgical procedure on the lower body area of the patient 708. Specifically, the surgical robotics system 700A configures the set of robotic arms to manipulate a surgical instrument 710. FIG. 7A shows the set of robotic arms inserting the surgical instrument 710 along a virtual rail 790 into the groin area of the patient 708. Generally, a virtual rail 790 is a co-axial trajectory along which the set of robotic arms translates a surgical instrument (typically a telescoping instrument). The second robotic arm 770B, the third robotic arm 770C, and the fifth robotic arm 770E are coupled, e.g., holding, the surgical instrument 710. The first robotic arm 770A and the fourth robotic arm 770D are stowed to the sides of the surgical robotics system because they are not necessarily required to for the surgical procedure—or at least part of the surgical procedure—shown in FIG. 7A. The robotic arms are configured such that they manipulate the surgical instrument 710 from a distance away from the patient 708. This is advantageous, for example, because there is often limited space available closer toward the patient's body or there is a sterile boundary around the patient 708. Further, there may also be a sterile drape around surgical equipment. During a surgical procedure, only sterile objects are allowed pass the sterile boundary. Thus, the surgical robotics system 700A may still use robotic arms that are positioned outside of the sterile boundary and that are covered with sterilized drapes to perform a surgical procedure.

In one embodiment, the surgical robotics system 700A configures the set of robotic arms to perform an endoscopy surgical procedure on the patient 708. The set of robotic arms hold an endoscope, e.g., the surgical instrument 710. The set of robotic arms insert the endoscope into the patient's body via an opening in the groin area of the patient 708. The endoscope is a flexible, slender, and tubular instrument with optical components such as a camera and optical cable. The optical components collect data representing images of portions inside the patient's body. A user of the surgical robotics system 700A uses the data to assist with performing the endoscopy.

Figure 7B:
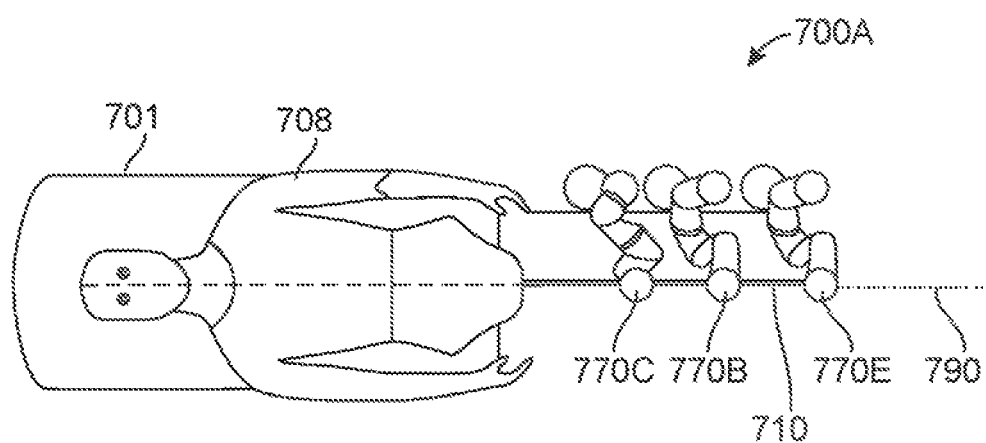
FIG. 7B is a top view of the surgical robotics system with column-mounted arms configured to access the lower body area of the patient according to one embodiment.

FIG. 7B is a top view of the surgical robotics system 700A with column-mounted arms configured to access the lower body area of the patient 708 according to one embodiment.

Figure 7C:
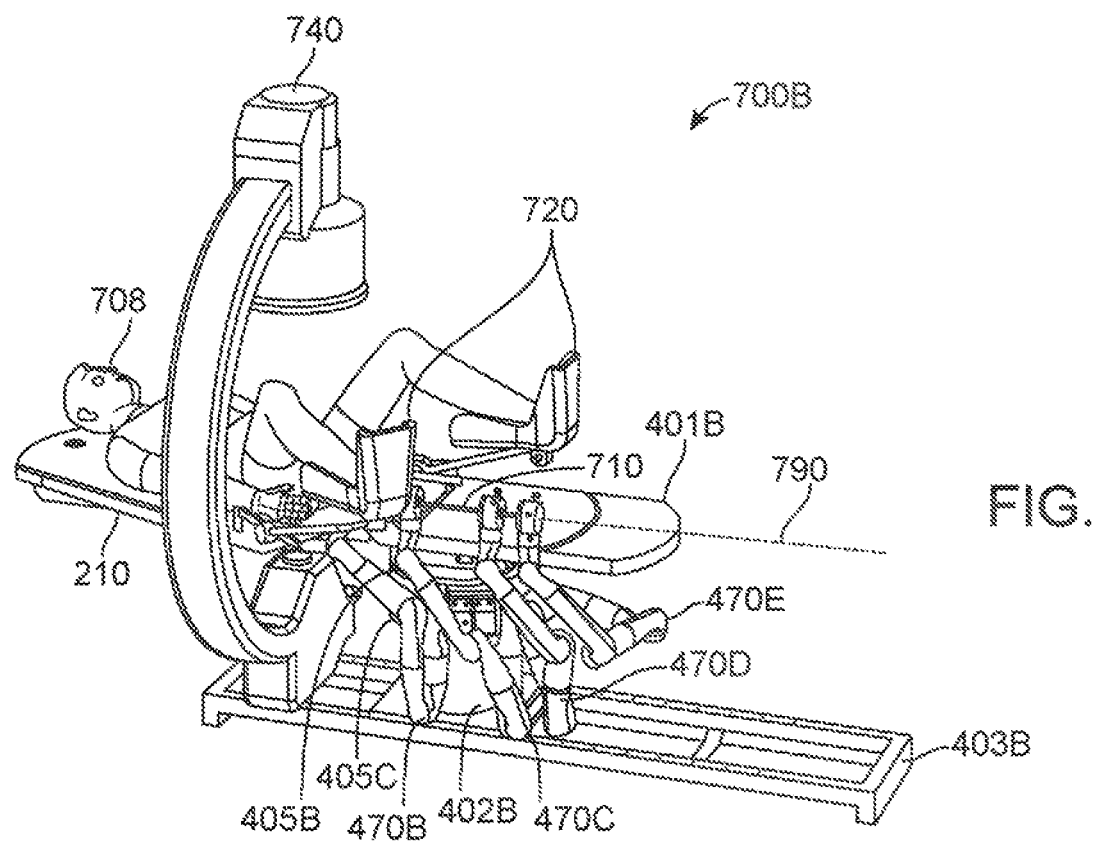
FIG. 7C is an isometric view of an imaging device and a surgical robotics system with column-mounted arms configured to access the lower body area of a patient according to one embodiment.

FIG. 7C is an isometric view of an imaging device 740 and a surgical robotics system 700B with column-mounted arms configured to access the lower body area of a patient 708 according to one embodiment. The surgical robotics system 700B is an embodiment of the surgical robotics system 400B in FIG. 4B. The surgical robotics system 700B includes a pair of stirrups 720 that support the legs of the patient 708, and thus exposing the groin area of the patient 708. Generally, the imaging device 740 captures images of body parts or other objects inside a patient 708. The imaging device 740 may be a C-arm, also referred to as a mobile C-arm, which is often used for fluoroscopy type surgical procedures, or another type of imaging device. A C-arm includes a generator, detector, and imaging system (not shown). The generator is coupled to the bottom end of the C-arm and faces upward toward the patient 708. The detector is coupled to the top end of the C-arm and faces downward toward the patient 708. The generator emits X-ray waves toward the patient 708. The X-ray waves penetrate the patient 708 and are received by the detector. Based on the received X-ray waves, the imaging system 740 generates the images of body parts or other objects inside the patient 708. The swivel segment 210 of the table 401B is rotated laterally such that the groin area of the patient 708 is aligned in between the generator and detector of the C-arm imaging device 740. The C-arm is a physically large device with a footprint that needs to be stationed underneath the patient. In particular, the generator of the C-arm needs to be underneath the operative area of the patient, e.g., the abdomen area. In typical surgical beds mounted to a column, the column interferes with the positioning of the C-arm generator, e.g., because the column is also underneath the operative area. In contrast, due to the configurability of the swivel segment 210, the surgical robotics system 700B may configure the table 401B such that the C-arm, the robotic arms, and a user (e.g., physician) have a sufficient range of access to perform a surgical procedure on a working area the patient's body. In one example use case, the table 401B is translated laterally along a longitudinal axis of the table 401B such that the robotic arms can access the groin or lower abdomen area of a patient on the table 401B. In another example use case, by rotating the swivel segment 210 away from the column 402B, the generator of the C-arm 740 may be positioned underneath the groin area of the patient 708. The swivel segment 210—with a patient lying on the swivel segment 210—may be rotated at least to 45 degrees relative to a longitudinal axis of the table 401B without tipping over the surgical robotics system. In particular, the surgical robotics system does not tip because the center of mass of the surgical robotics system (e.g., the center of mass of the combined, at least, table, bed, and base) is positioned above a footprint of the base. Outrigger casters, further described with reference to FIGS. 8G-J in Section VIII. Base, may provide further stability to prevent the surgical robotics system from tipping over when a swivel segment is rotated away from the table.

The surgical robotics system 700B uses a set of column-mounted robotic arms to manipulate a surgical instrument 710. Each of the robotic arms is coupled to, e.g., holding, the surgical instrument 710. The surgical robotics system 700B uses the robotic arms to insert the surgical instrument 710 into the groin area of the patient along a virtual rail 790.

Figure 7D:
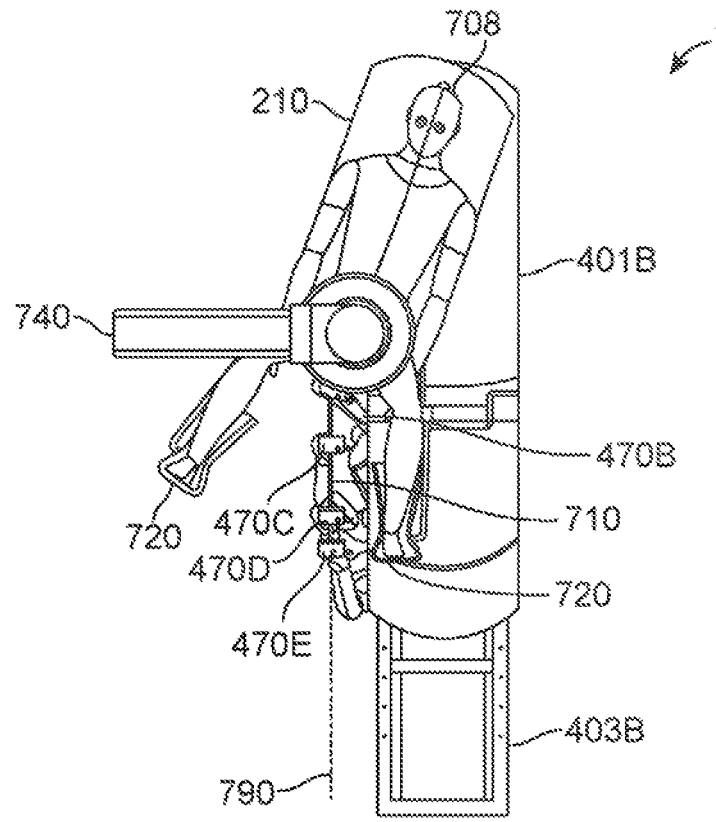
FIG. 7D is a top view of the imaging device and the surgical robotics system with column-mounted arms configured to access the lower body area of the patient according to one embodiment.

FIG. 7D is a top view of the imaging device 740 and the surgical robotics system 700B with column-mounted arms configured to access the lower body area of the patient 708 according to one embodiment.

VII. B. Core Body Surgery

Figure 7E:
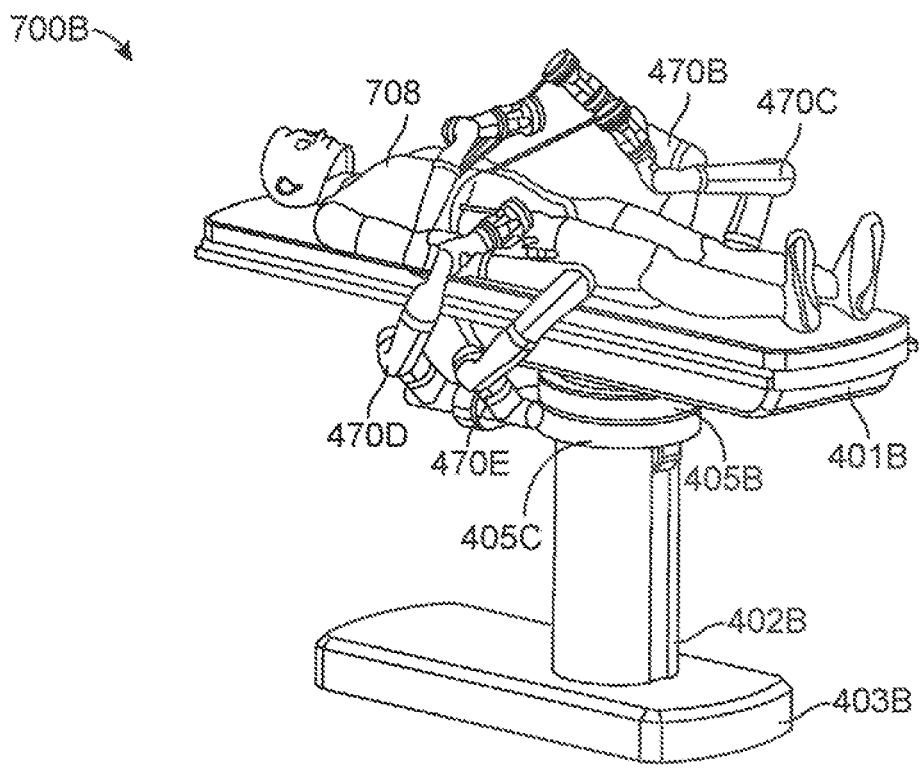
FIG. 7E is an isometric view of the surgical robotics system with column-mounted arms configured to access the core body area of a patient according to one embodiment.

FIG. 7E is an isometric view of the surgical robotics system 700B (or 400B) with column-mounted arms configured to access the core body area of a patient 708 according to one embodiment. The surgical robotics system 700B has been reconfigured from the configuration shown in FIG. 7C-D where the robotic arms access the lower body area of the patient 708. In embodiments where the table includes a swivel segment 210, the swivel segment 210 of the table is rotated in-line with the rest of the table. The patient 708 lying on the table 401B is undergoing a surgical procedure, e.g., prostatectomy or laparoscopy, requiring access to the core body area of the patient 708. Each robotic arm is manipulating a surgical instrument to perform the surgical procedure. The surgical robotics system 700B raises the column rings 405B and 405C toward the table 401B so that the robotic arms have greater access the patient 708. Further, the surgical robotics system 700B rotates the column rings such that two of the robotic arms extend from one side of the table 401B and the other two robotic arms extend from the opposite side of the 401B. Thus, the robotic arms are less likely to interfere with each other (e.g., a robotic arm blocking the motion of another robotic arm) during the surgical procedure.

VII. C. Upper Body Surgery

Figure 7F:
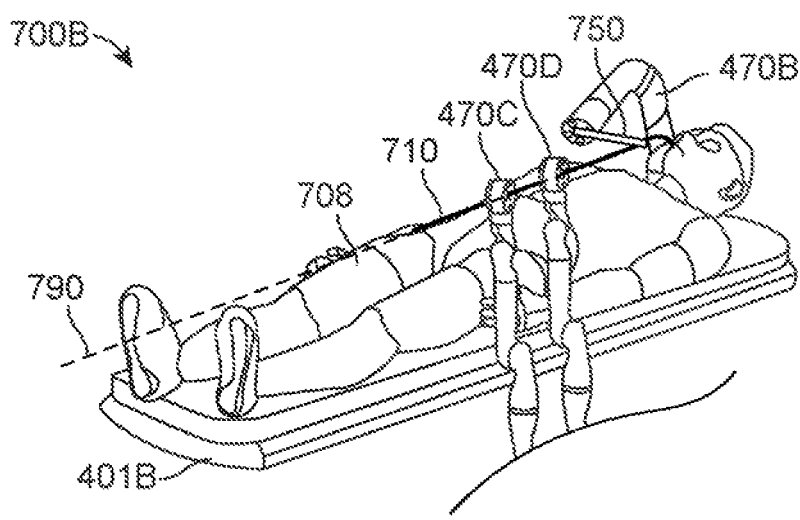
FIG. 7F is an isometric view of the surgical robotics system with column-mounted arms configured to access the upper body area of a patient according to one embodiment.

FIG. 7F is an isometric view of the surgical robotics system 700B (or 400B) with column-mounted arms configured to access the upper body area of a patient 708 according to one embodiment. The surgical robotics system 700B has been reconfigured from the configuration shown in FIG. 7E where the robotic arms access the core body area of the patient 708. In embodiments where the table includes a swivel segment 210, the swivel segment 210 of the table is rotated in-line with the rest of the table. The patient 708 lying on the table 401B is undergoing a surgical procedure, e.g., bronchoscopy, requiring access to the upper body area of the patient 708, specifically the head of the patient 708. The robotic arm 470C and the robotic arm 470D are inserting a surgical instrument 710D, e.g., a bronchoscope, into the mouth of the patient 708 along a virtual rail 790. The robotic arm 470B is coupled to, e.g., holding, an introducer 750. The introducer 750 is a surgical instrument that directs the bronchoscope into the mouth of the patient 708. Specifically, the trajectory of the bronchoscope along the virtual rail 790 begins parallel to the patient 708. The introducer 750 changes the angle of the virtual rail 790 just before the bronchoscope enters the mouth. The robotic arm 470E (not shown in FIG. 7F) is not used for the surgical procedure, and thus is stowed away.

VIII. Base

Figure 8A:
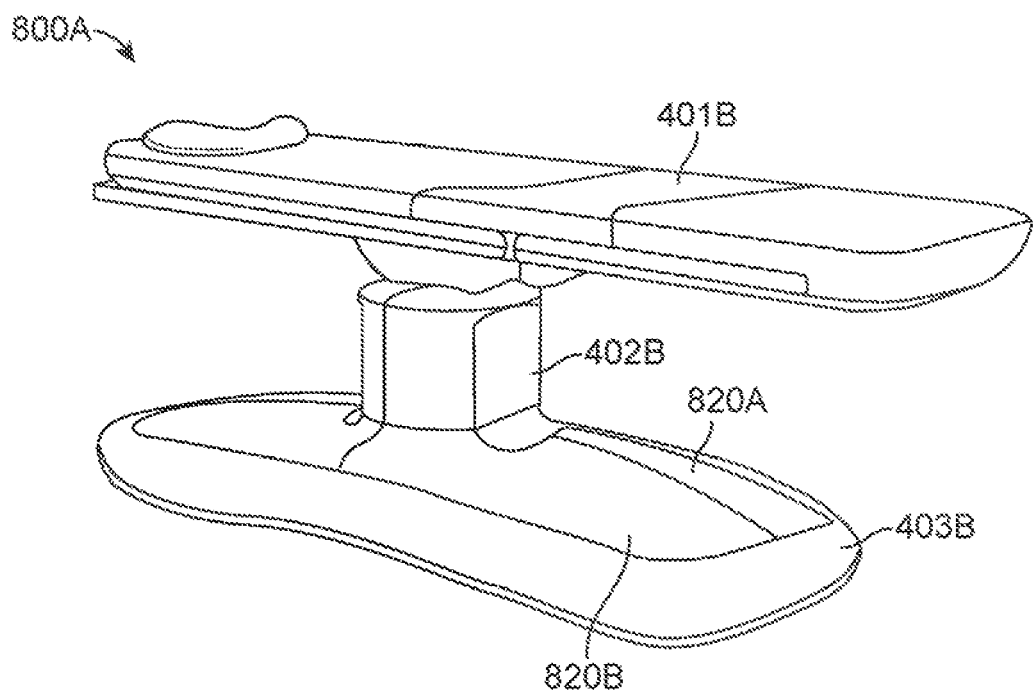
FIG. 8A is an isometric view of a base of a surgical robotics system according to one embodiment.

FIG. 8A is an isometric view of a base 403A of a surgical robotics system 800A according to one embodiment. The surgical robotics system 800A is an embodiment of the surgical robotics system 400B in FIG. 4B. The surgical robotics system 800A stores column-mounted robotic arms and/or column rings (not shown) inside the base 403B when the robotic arms are not in use. The base 403B includes a first panel 820A and a second panel 820B that cover stored robotic arms. The first panel 820A and the second panel 820B are advantageous because they prevent waste materials from de-sterilizing or otherwise contaminating stored robotic arms.

Figure 8B:
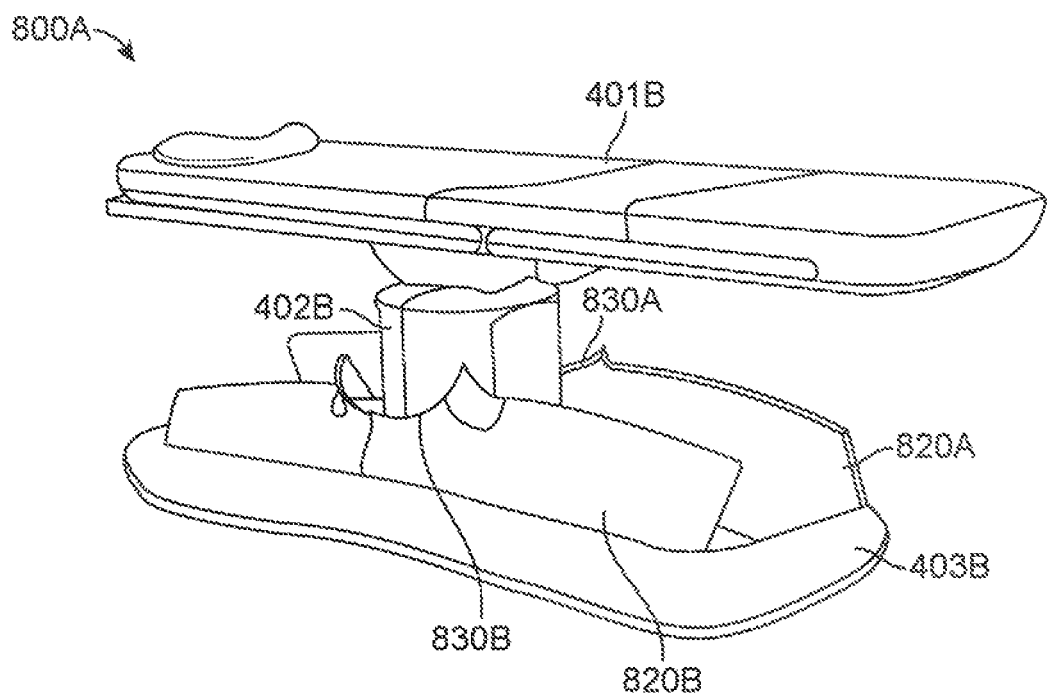
FIG. 8B is an isometric view of open panels of the base according to one embodiment.

FIG. 8B is an isometric view of open panels of the base 403B according to one embodiment. The first panel 820A and the second panel 820B pivot away from the column 802A such that column-mounted robotic arms have access to inside the base 403B. The first panel 820A includes a cutout 830A and the second panel 820B includes a cutout 830B. The cutouts 830A and 830B conform to the shape of the column 402B such that the panels 820A and 820B form a seal around the column 402B when closed. The surgical robotics system 800A may automatically open and close the first panel 820A and the second panel 820B using motors or other means of actuation. A user of the surgical robotics system 800A may also manually open and close the first panel 820A and the second panel 820B.

Figure 8C:
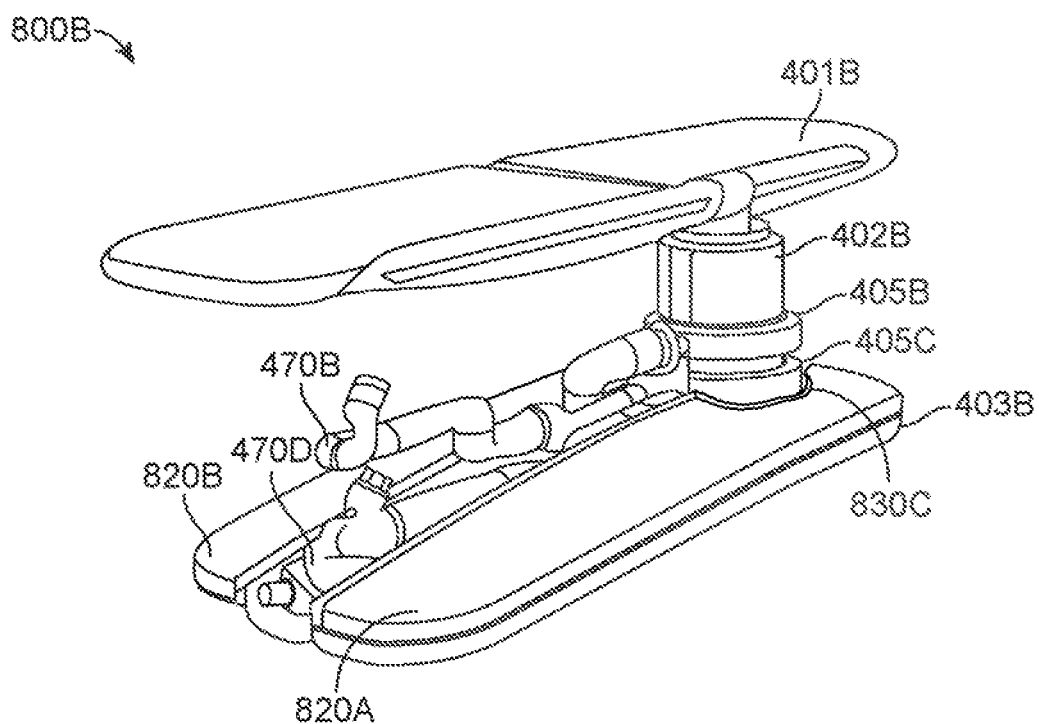
FIG. 8C is an isometric view of robotic arms stowed inside a base of a surgical robotics system according to one embodiment.

FIG. 8C is an isometric view of a robotic arm stowed inside a base 403B of a surgical robotics system 800B according to one embodiment. The surgical robotics system 800B is an embodiment of the surgical robotics system 400B in FIG. 4B. The surgical robotics system 800B stores column-mounted robotic arms 470B and 470D and column rings 405B and 405C inside the base 403B when the robotic arms are not in use. The base 403B includes a first panel 820A and a second panel 820B that cover stored robotic arms and column rings. The first panel 820A includes a cutout 830C. The second panel 820B also includes a cutout (not shown due to being obscured by other components). The cutouts conform to the shape of the column 402B such that the panels 820A and 820B form a seal around the column 402B when closed.

The first panel 820A and a second panel 820B translate laterally to provide access for the robotic arms and column rings into the base 403B. FIG. 8C shows the first panel 820A and a second panel 820B translated to form an opening. The opening may be large enough to provide access for a robotic arm, but not too large as to still provide protection to the robotic arms even when the panels are open. The robotic arm 470D and column ring 405C are stowed inside the base 403B. The robotic arm 470B and column ring 405B are outside the base 403B, though they may also be stowed inside the base 403B. The surgical robotics system 800B may automatically open and close the first panel 820A and the second panel 820B using motors or other means of actuation. A user of the surgical robotics system 800B may also manually open and close the first panel 820A and the second panel 820B.

Figure 8D:
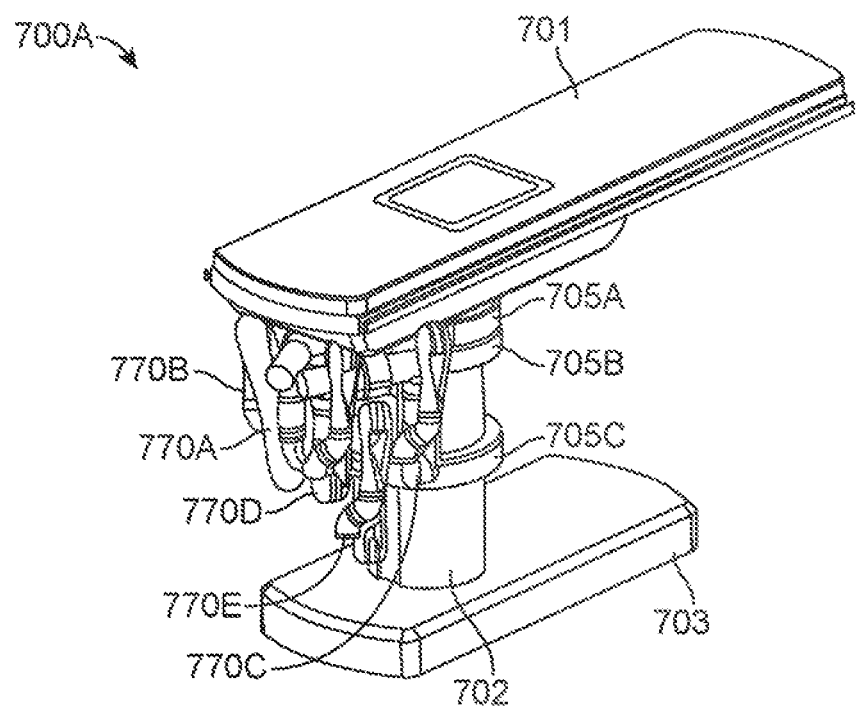
FIG. 8D is an isometric view of robotic arms stowed underneath a table of a surgical robotics system according to one embodiment.

FIG. 8D is an isometric view of robotic arms stowed underneath the table 701 of the surgical robotics system 700A according to one embodiment. Specifically, the arm segments of each robotic arm rotate such that the robotic arm is in a compact configuration for stowage. The surgical robotics system 700A raises the first column ring 705A and the second column ring 705B, and lowers the third column ring 705C toward the center of the column 702. This way, the robotic arms have enough space in the stowed configuration without interfering with each other. In one embodiment, the column 702 includes covers (e.g., similar to panels 820A and 820B) over the robotics arms to protect the robotic arms from contamination or damage.

Figure 8E:
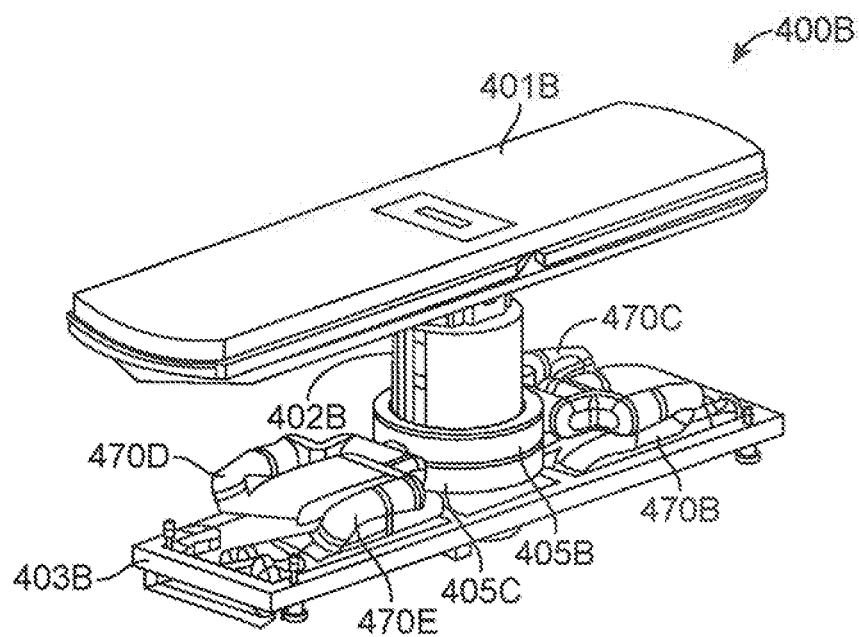
FIG. 8E is an isometric view of robotic arms stowed above a base of a surgical robotics system according to one embodiment.

FIG. 8E is an isometric view of robotic arms stowed above the base 403B of the surgical robotics system 400B according to one embodiment. The robotic arms 470B, 470C, 470D, and 470E are in a stowed configuration. Specifically, the arm segments of each robotic arm rotate such that the robotic arm is in a compact configuration for stowage. The surgical robotics system 400B lowers the first column ring 405B and the second column ring 405C along the column 402B such that the stowed robotic arms rest on the base 403B and are away from the table 401B. A cover (not shown) such as a drape or panel may be used to cover the stowed robotic arms for protection from de-sterilization or other contamination.

Figure 8F:
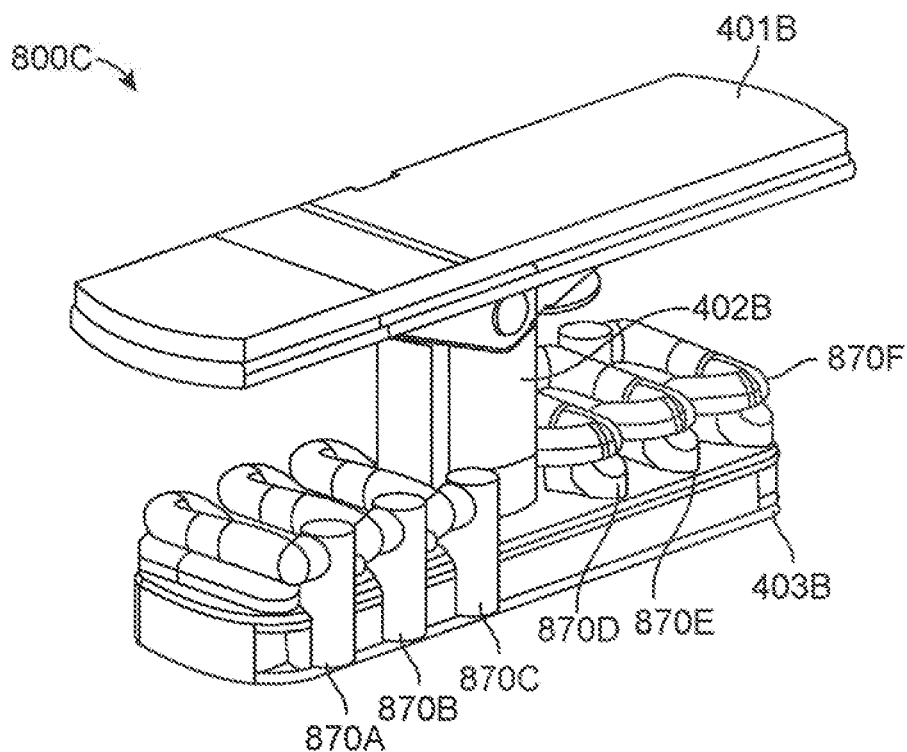
FIG. 8F is another isometric view of robotic arms stowed above a base of a surgical robotics system according to one embodiment.

FIG. 8F is another isometric view of robotic arms stowed above the base 403B of the surgical robotics system 800C according to one embodiment. The robotic arms are rail-mounted instead of column-mounted. Rail-mounted robotic arms are further described with reference to FIGS. 9A-B and FIGS. 10A-D in Section IX. Rail-Mounted Robotic Arms and Section X. Rails, respectively. The surgical robotics system 800C is an embodiment of the surgical robotics system 900B further described with reference to FIG. 9B in Section IX. Rail-Mounted Robotic Arms. The robotic arms 870C, 870D, 870E, 870F, 870G, and 870H are in a stowed configuration.

Figure 8G:
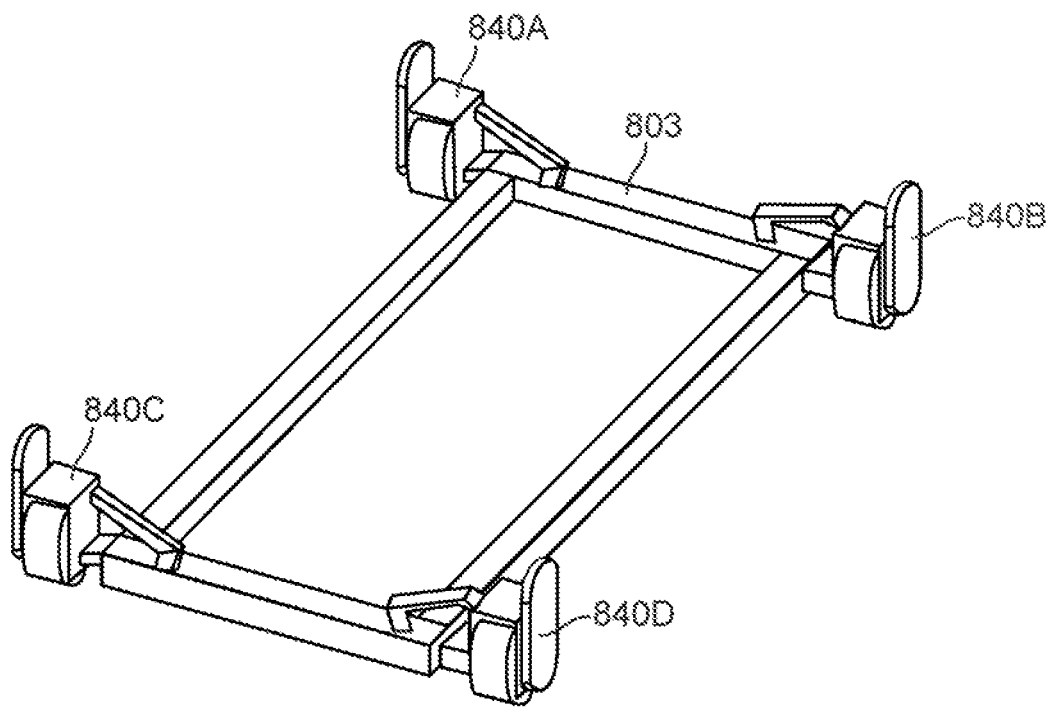
FIG. 8G is an isometric view of outrigger casters on a base of a surgical robotics system according to one embodiment.

FIG. 8G is an isometric view of outrigger casters on a base 803 of a surgical robotics system according to one embodiment. The base 803 shown in FIG. 8G includes four outrigger casters 840A, 840B, 840C, and 840D, each substantially the same as each other and positioned at a different corner of the base 803, though it should be noted that, in other embodiments, a base may include any number of outrigger casters positioned in other locations on the base. The outrigger casters 840A, 840B, 840C, and 840D are each in a mobile configuration, i.e., the caster wheel physically contacts the ground. Thus, a user of the surgical robotics system may transport the surgical robotics system using the caster wheels, e.g., to a storage area when the surgical robotics system is not in use.

Figure 8H:
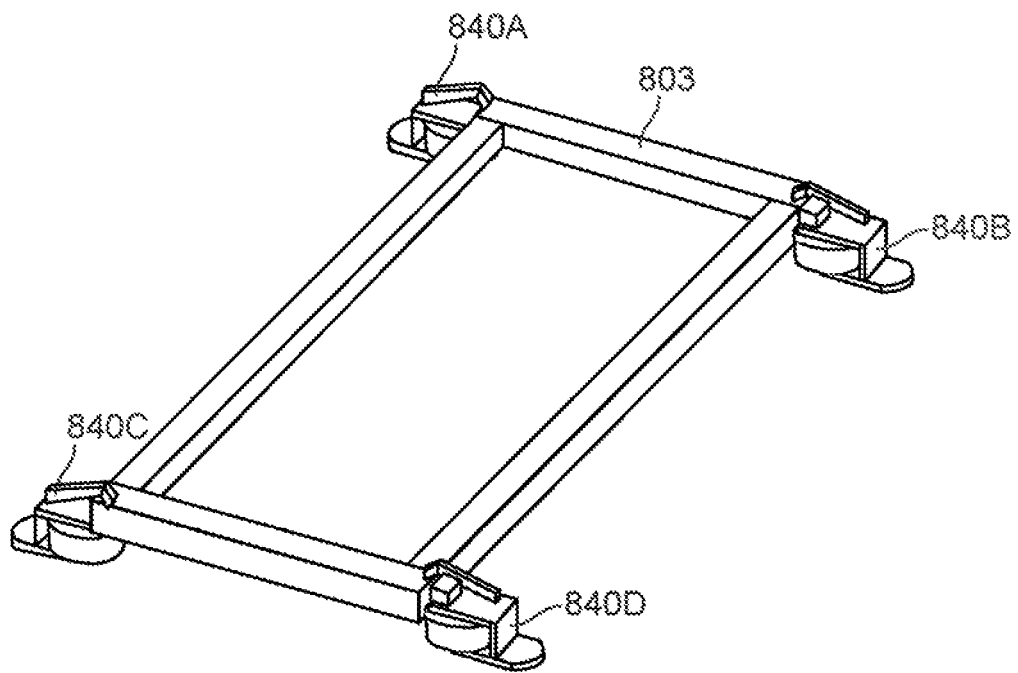
FIG. 8H is another isometric view of the outrigger casters on the base of the surgical robotics system according to one embodiment.

FIG. 8H is another isometric view of the outrigger casters 840A, 840B, 840C, and 840D on the base 803 of the surgical robotics system according to one embodiment. The outrigger casters 840A, 840B, 840C, and 840D are each in a stationary configuration, i.e., the outrigger caster is rotated such that the caster wheel does not physically contact the ground. Thus, the surgical robotics system may be stabilized and immobilized during a surgical procedure.

Figure 8I:
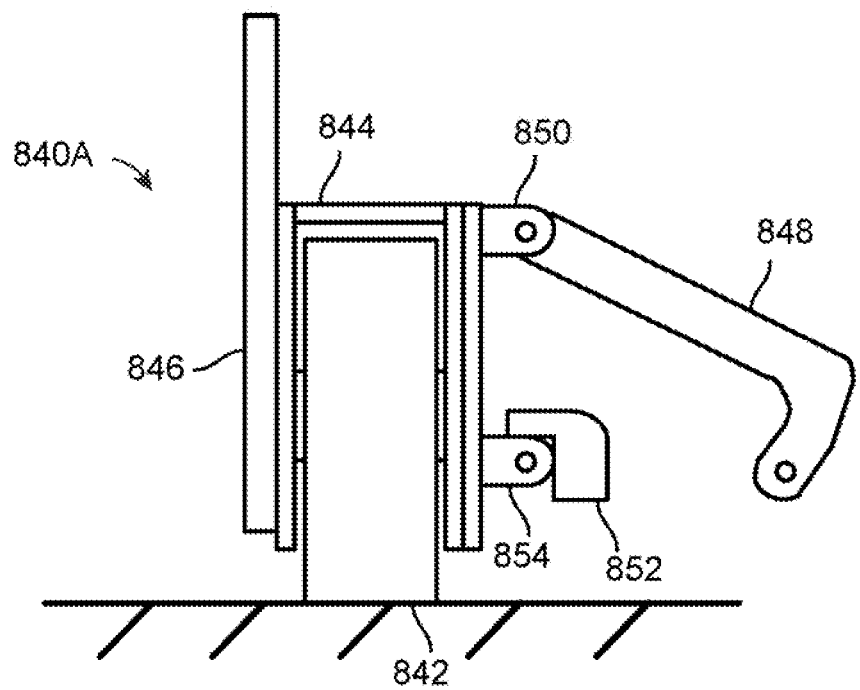
FIG. 8I is a side view of an outrigger caster in a mobile configuration according to one embodiment.

FIG. 8I is a side view of the outrigger caster 840A in a mobile configuration according to one embodiment. The outrigger caster 840A includes a caster wheel 842 movably coupled to an outrigger mount 844. The outrigger mount 844 is coupled to a foot 846. The first linkage 848 is movably coupled to the outrigger mount 844 by the first hinge 850. The second linkage 852 is movably coupled to the outrigger mount 844 by the second hinge 854. In the mobile configuration, the caster wheel 842 may rotate to move the outrigger caster 840 along the ground.

Figure 8J:
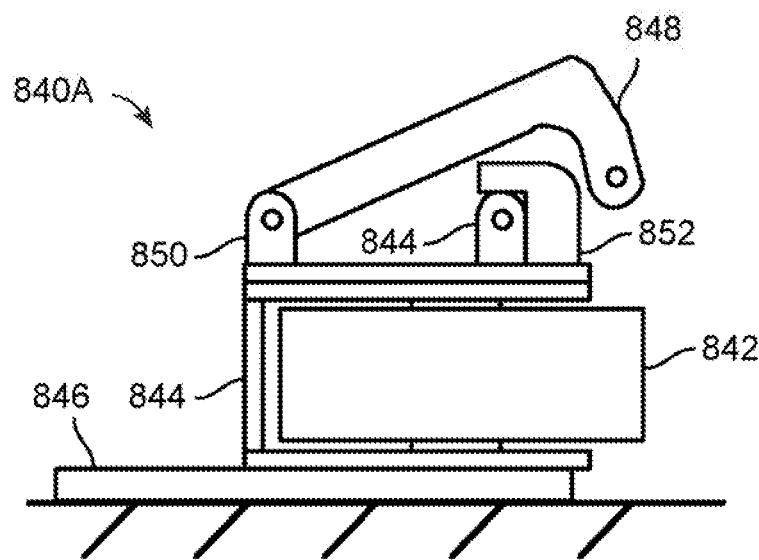
FIG. 8J is a side view of the outrigger caster in a stationary configuration according to one embodiment.

FIG. 8J is a side view of the outrigger caster 840A in a stationary configuration according to one embodiment. In the stationary configuration, the caster wheel 842 may freely rotate, but the caster wheel 842 does not move the outrigger caster 840A because the caster wheel 842 is not physically in contact with the ground. The surgical robotics system (or a user) rotates the outrigger caster 840A, e.g., 90 degrees, to change the outrigger caster 840A from the mobile configuration to the stationary configuration. Thus, the foot 846 now physically contacts the ground, and helps prevent the surgical robotics system from moving. The foot 846 may have a larger footprint relative to the caster wheel 842 to provide additional stability on the ground. The linkages 848 and 852 are positioned such that they do not interfere with the rotational path of the outrigger caster 840A. Combining the caster wheel 842 and the foot 846 in the outrigger caster 840A is advantageous, e.g., because the outrigger caster 840A allows the surgical robotics system to change between the mobile and stationary configurations using a compact mechanism, compared to having separate mechanisms for casters and stabilization. Further, in use cases of surgical robotics systems including swivel segments that rotate a patient lying on the swivel segment away from a corresponding table (e.g., as illustrated in FIGS. 7C-D), the feet of outrigger casters (in the stationary configuration) help prevent the surgical robotics system from tipping over due to the center of mass of the patient extending beyond the table base.

Alternative views and embodiments of the base 403B including the above-mentioned components are further illustrated and described at least in U.S. Provisional Application No. 62/203,530 filed Aug. 11, 2015.

IX. Rail-Mounted Robotic Arms

Figure 9A:
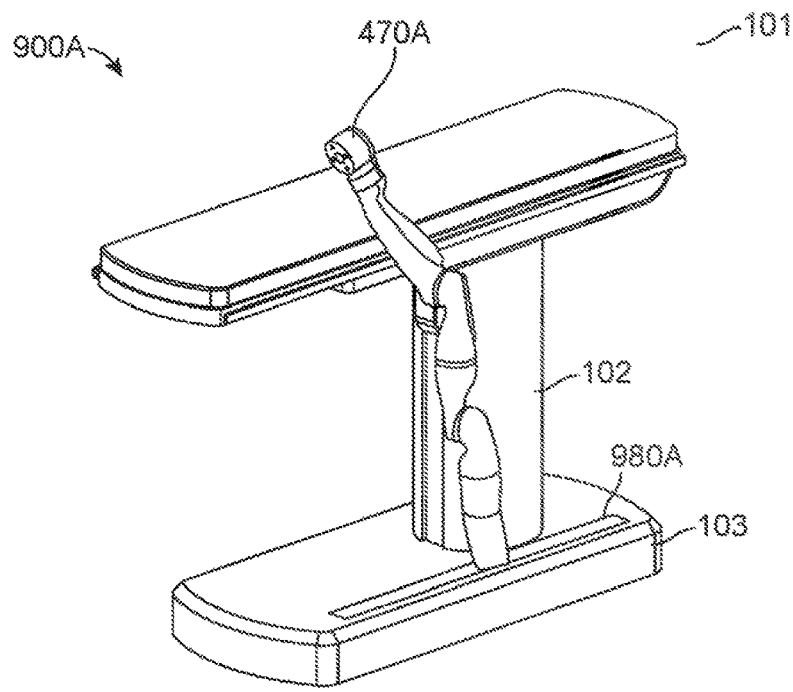
FIG. 9A is an isometric view of a surgical robotics system with a rail-mounted robotic arm according to one embodiment.

FIG. 9A is an isometric view of a surgical robotics system 900A with a rail-mounted robotic arm according to one embodiment. The surgical robotics system 900A includes a set of robotic arms (including at least arm 470A) and a set of base rails (including at least base rail 980A). The robotic arm 470A is coupled to the base rail 980A. Base rails are further described with respect to FIGS. 10A-D in Section X. Rails below. The base rail 980A is movably coupled to the base 103. Thus, the robotic arm 470A may be referred to as a rail-mounted robotic arm 470A.

Figure 9B:
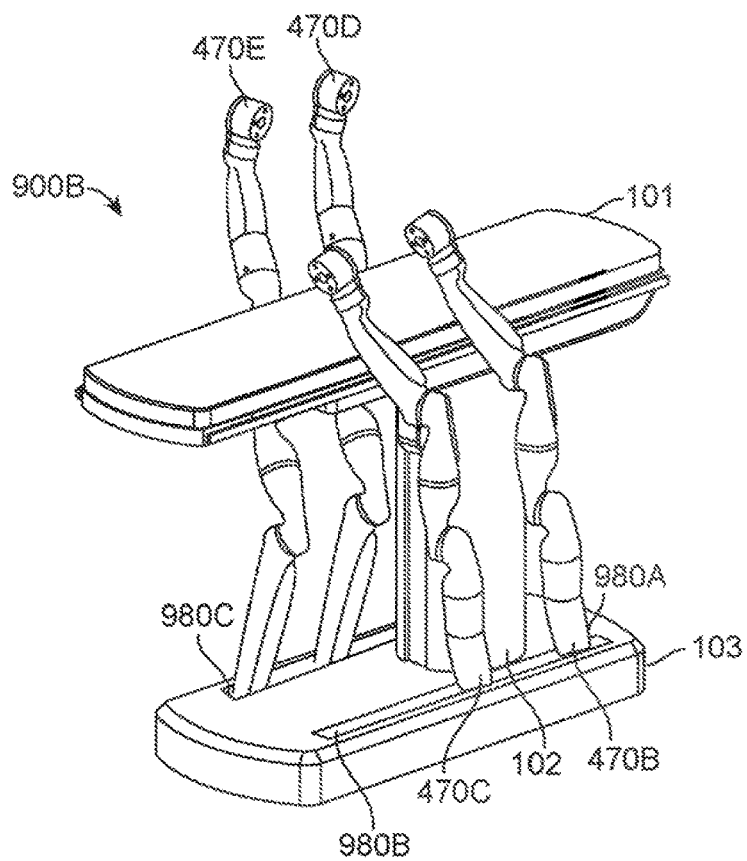
FIG. 9B is an isometric view of a surgical robotics system with rail-mounted robotic arms according to one embodiment.

FIG. 9B is an isometric view of a surgical robotics system 900B with rail-mounted robotic arms according to one embodiment. The surgical robotics system 900B includes robotic arms 470B, 470C, 470D, and 470E each coupled to a first base rail 980B or a second base rail 980C. The first base rail 980B and the second base rail 980C are movably coupled to the base 103.

In other embodiments, the surgical robotics system 900B may include additional or fewer robotic arms and/or base rails. Further, the robotic arms may be coupled to base rails in various configurations. For example, three robotic arms may be coupled to a base rail. Additionally, the surgical robotics system 900B may include three base rails each coupled to a robotic arm.

The surgical robotics system 900B may translate robotic arms mounted to a base rail by translating the base rails relative to the base 103. Base rails may translate beyond the starting footprint of the base 103, which allows the robotic arms to operate in a larger volume of space. Further, the surgical robotics system 900B may translate robotic arms mounted to a base rail independently from each other by translating the robotic arms relative to the base rail. This is advantageous, for example, because the surgical robotics system 900B may position the robotic arms in different configurations to perform a variety of surgical procedures.

Alternative views and embodiments of the surgical robotics system 900B with rail-mounted robotic arms including the above-mentioned components are further illustrated and described at least in U.S. Provisional Application No. 62/193,604 filed Jul. 17, 2015 and U.S. Provisional Application No. 62/201,518 filed Aug. 5, 2015.

X. Rails

Figure 10A:
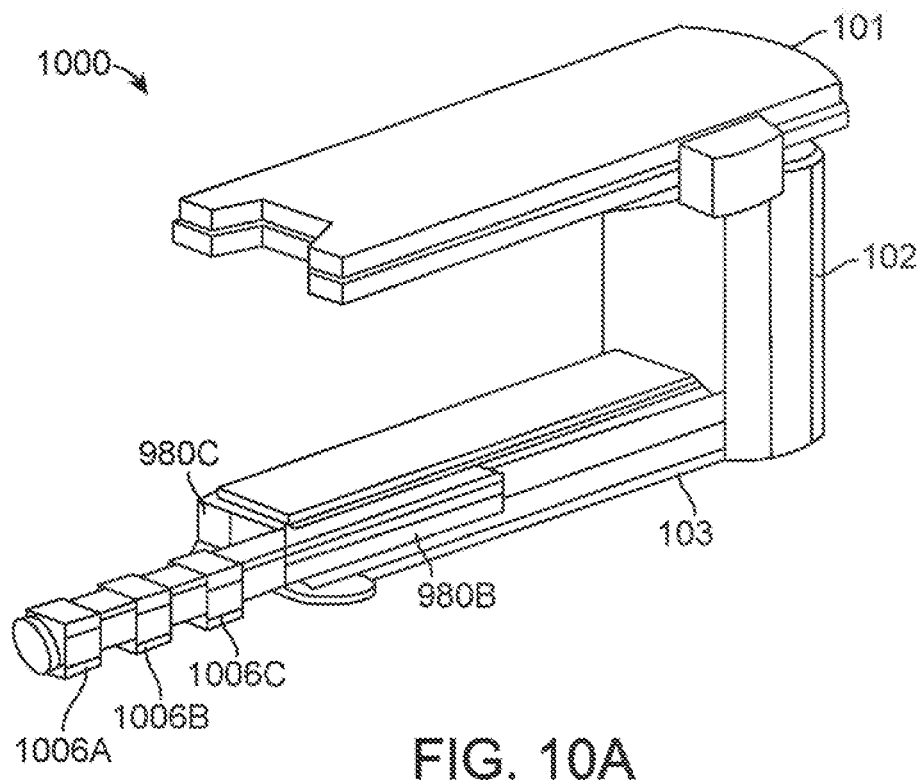
FIG. 10A is an isometric view of base rails of a surgical robotics system according to one embodiment.

FIG. 10A is an isometric view of base rails of a surgical robotics system 1000 according to one embodiment. A base rail includes a set of one or more arm mounts each movably coupled to the base rail. Further, each arm mount is an embodiment of the arm mount 506A or 506B previously described with reference to FIG. 5A in Section V. Column Ring. Specifically, the base rail 980B includes arm mounts 1006A, 1006B, and 1006C.

Figure 10B:
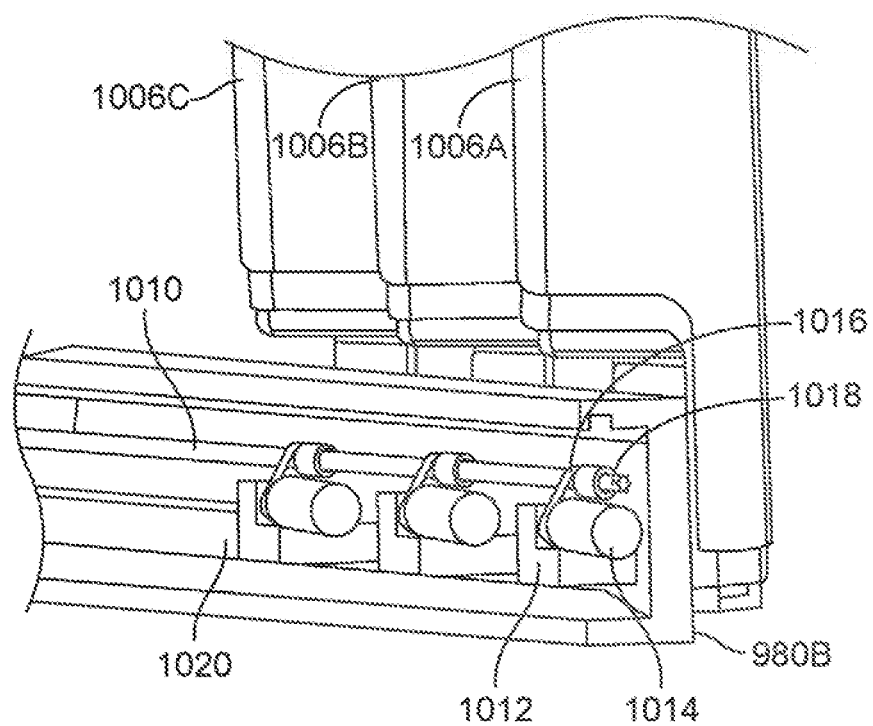
FIG. 10B is an isometric view of arm mounts on the base rail according to one embodiment.

FIG. 10B is an isometric view of arm mounts on the base rail 980B according to one embodiment. The arm mounts 1006A, 1006B, and 1006C each include a belt and pinion assembly. Specifically, the belt and pinion assembly of arm mount 1006A includes a bracket 1012, motor 1014, belt 1016, and pinion 1018. The belt and pinion assemblies of arm mount 1006B and 1006C are constructed similarly.

The surgical robotics system 1000 translates arm mounts—and thus, robotic arms mounted to the arm mounts—along base rails using the belt and pinion assemblies. Specifically, the arm mount 1006A is movably coupled to a channel 1020 of the base rail 980B by the bracket 1012. The bracket 1012 is coupled to motor 1014, belt 1016, and pinion 1018. The motor 1014 is coupled to the pinion 1018 by the belt 1016. Thus, output rotation of the motor 1014 causes the pinion 1018 to rotate. The pinion 1018 is engaged with a rail lead screw 1010 of the base rail 980B. Rotation of the pinion 1018 causes the arm mount 1006A to translate along the base rail 980B parallel to the rail lead screw 1010.

Figure 10C:
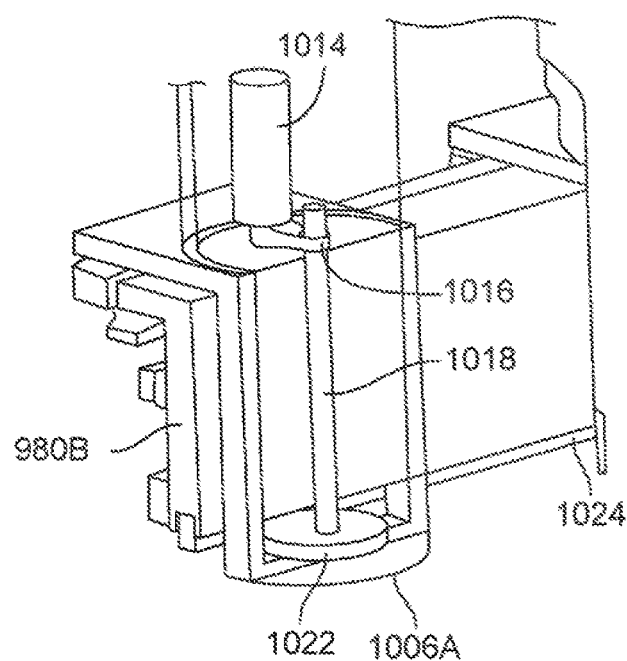
FIG. 10C is an isometric cutaway view of an arm mount on the base rail according to one embodiment.

FIG. 10C is an isometric cutaway view of an arm mount 1006A on the base rail 980B according to one embodiment. The arm mount 1006A includes a belt and pinion assembly. Specifically, the belt and pinion assembly includes a motor 1014, belt 1016, pinion 1018, and bearing 1022. The surgical robotics system 1000 translates the arm mount 1006A—and thus, a robotic arm mounted to the arm mount 1006A—along the base rail 980B using the belt and pinion assembly. The motor 1014 is coupled to the pinion 1018 by the belt 1016. Thus, output rotation of the motor 1014 causes the pinion 1018 to rotate. The pinion 1018 is coupled to the bearing 1022. In some embodiments, the bearing 1022 forms a rack and pinion assembly with the base rail 980B. Specifically, the bearing 1022 is a gear (i.e., the pinion) and is engaged with a rack 1024 of the base rail 980B. Rotation of the pinion 1018 causes the bearing 1022 to translate along the base rail 980B parallel to the rack 1024. Thus, the arm mount 1006A also translates along the base rail 980B.

Figure 10D:
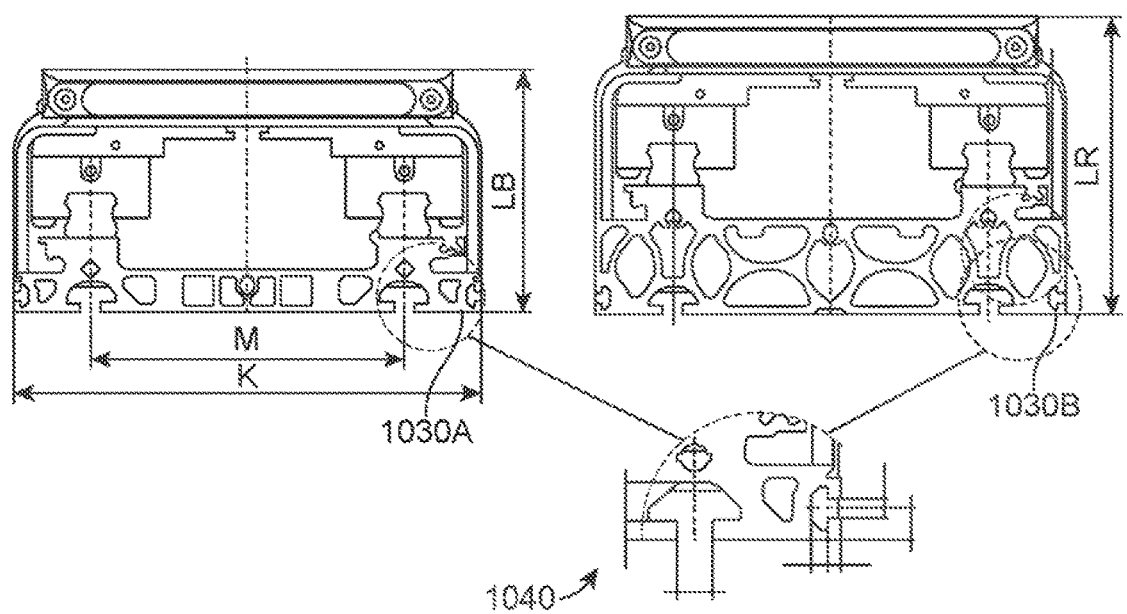
FIG. 10D is cross-sectional views of the base rail according to one embodiment.

FIG. 10D is cross-sectional views of the base rail 980B according to one embodiment. The cross-sectional view 1000A shows a basic profile of an embodiment of the base rail 980B. The cross-sectional view 1000B shows a reinforced profile of an embodiment of the base rail 980B. The lower segment 1030B of the reinforced profile is larger in size than the lower segment 1030A of the basic profile. Thus, the reinforced profile is an advantage, for example, because it enables the base rail 980B to withstand greater loads relative to the basic profile. Both the basic and the reinforced profiles have a T-slot attachment 1040, which engages with a corresponding T-slot on a base of a surgical robotics system.

Alternative views and embodiments of the base rails 980A, 980B, and 980C including the above-mentioned components are further illustrated and described at least in U.S. Provisional Application No. 62/193,604 filed Jul. 17, 2015 and U.S. Provisional Application No. 62/201,518 filed Aug. 5, 2015.

XI. Alternate Configurations

XI. A. Hybrid Configuration

Figure 11:
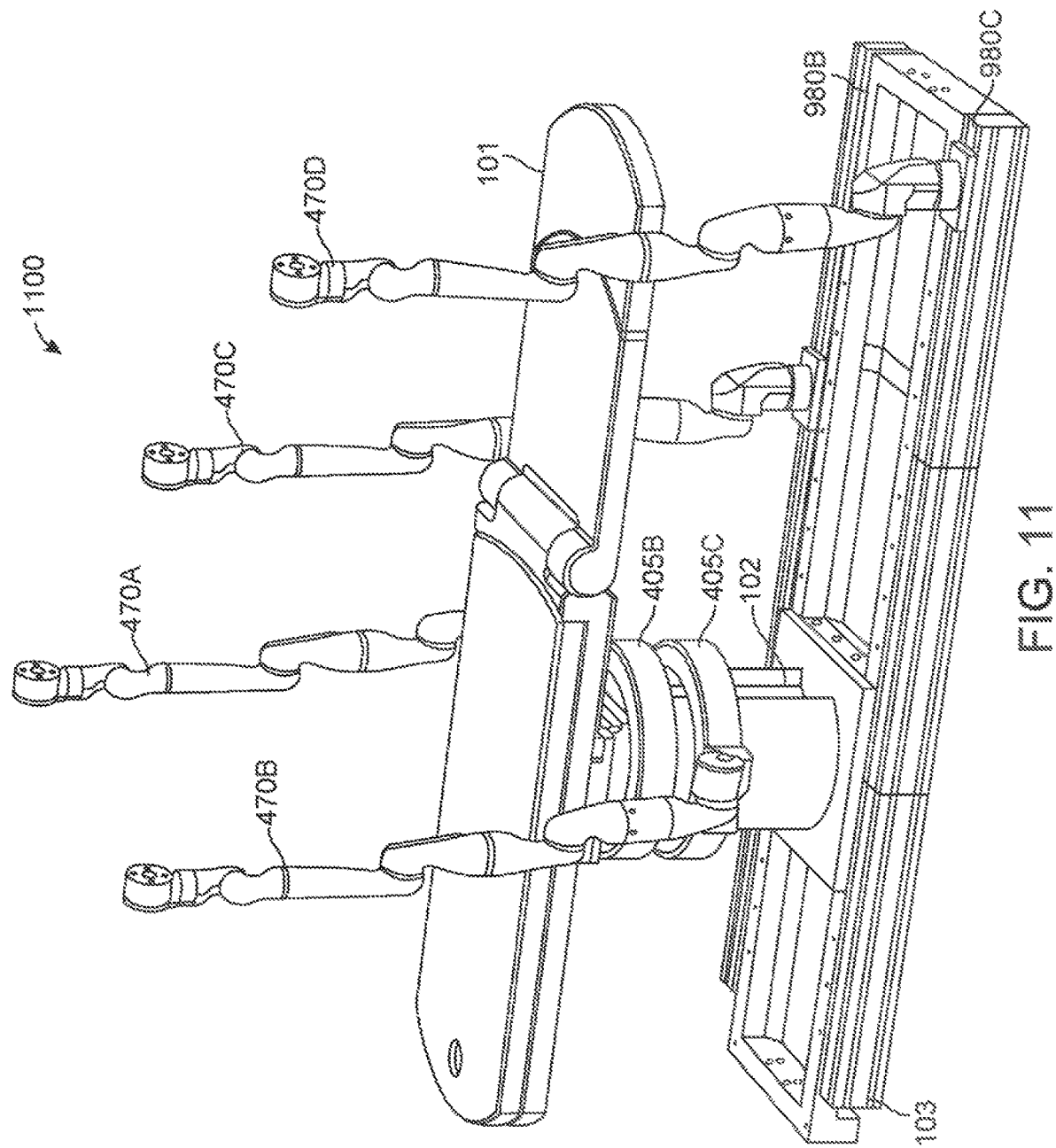
FIG. 11 is an isometric view of a surgical robotics system with column-mounted robotics arms and rail-mounted robotic arms according to one embodiment.

FIG. 11 is an isometric view of a surgical robotics system 1100 with column-mounted robotics arms and rail-mounted robotic arms according to one embodiment. Due to the hybrid configuration including both column-mounted robotics arms and rail-mounted robotic arms, the surgical robotics system 1100 may configure the robotic arms in a greater number of (or different types of) positions compared to surgical robotics systems with column-mounted robotics arms only or rail-mounted robotic arms only. Further, the surgical robotics system 1100 takes advantage of the rotational motion of robotic arms using the column rings as well as translational motion of the robotic arms using the base rails.

XI. B. Cart-Based Robotic Arm Column

Figure 12:
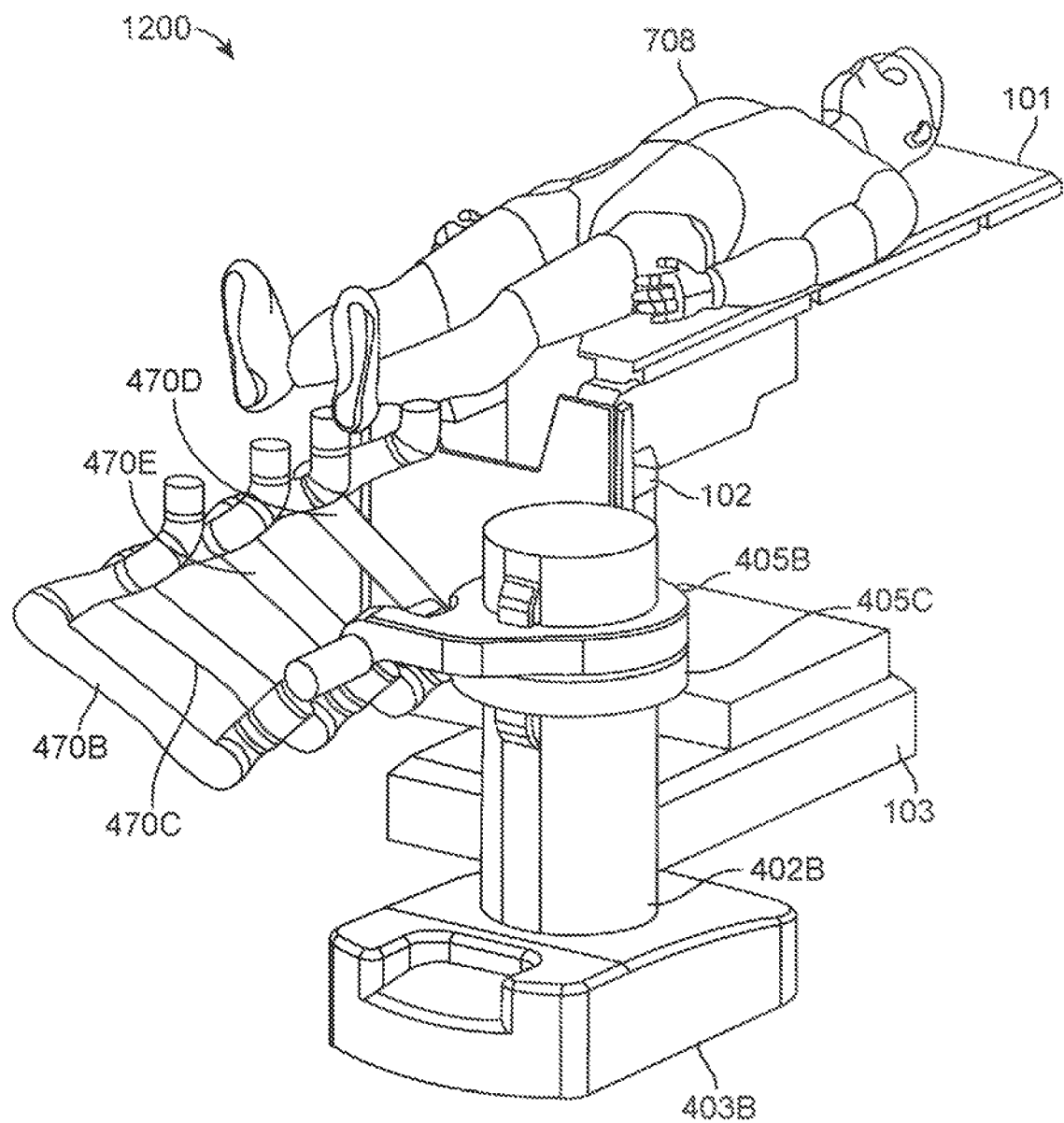
FIG. 12 is an isometric view of a surgical robotics system with column-mounted robotics arms on a platform separate from a table and a base of the surgical robotics system according to one embodiment.

FIG. 12 is an isometric view of a surgical robotics system 1200 with column-mounted robotics arms on a column 402B and base 403B separate, e.g., as a free standing cart, from a table 101, column 102, and base 103 of the surgical robotics system 1200 according to one embodiment. The surgical robotics system 1200 configures the robotic arms to access the lower body area of patient 708 lying on the table 101. In one embodiment, mounting the robotic arms on a cart including the column 402B separate from the column 102 coupled to the table 101 with the patient is advantageous. For example, because the surgical robotics system 1200 may configure the robotic arms to a greater number of (or different types of) positions compared to surgical robotics systems with robotics arms mounted to the same column as the table, which are limited at least in the angles where the table extends past the column 102. Further, the cart may include outrigger casters (e.g., previously described with reference to FIGS. 8G-J in Section VIII. Base) that allow users to more easily transport the robotic arms or keep the cart stationary. Mounting the robotic arms separately can also reduce the number of components and complexity of the column coupled to the table with the patient.

Alternative views and embodiments of the surgical robotics system 1100, the surgical robotics system 1200, and other surgical robotics systems including the above-mentioned components are further illustrated and described at least in U.S. Provisional Application No. 62/162,486 filed May 15, 2015, U.S. Provisional Application No. 62/162,467 filed May 15, 2015, U.S. Provisional Application No. 62/193,604 filed Jul. 17, 2015, U.S. Provisional Application No. 62/201,518 filed Aug. 5, 2015, U.S. Provisional Application No. 62/203,530 filed Aug. 11, 2015, and U.S. Provisional Application No. 62/235,394 filed Sep. 30, 2015.

XII. Adjustable Arm Supports

Robotic surgical systems can include adjustable arm supports as described in this section for supporting one or more robotic arms. The adjustable arm supports can be configured to attach to, for example, either a table, a column support of the table, or a base of the table to deploy the adjustable arm supports and robotic arms from a position below the table. In some embodiments, the adjustable arm supports can be attached to a bed (or table) or a cart positioned adjacent to a bed. In some examples, the adjustable arm supports include a bar, track, or rail on which one or more robotic arms are mounted. In some embodiments, the adjustable arm supports include at least four degrees of freedom that allow for adjustment of the position of the bar, track, or rail. One (or more) of the degrees of freedom can allow the adjustable arm supports to be adjusted vertically relative to the table. These and other features of the adjustable arm supports will be described in detail with reference to the examples of FIGS. 13A-21.

Figure 13A:
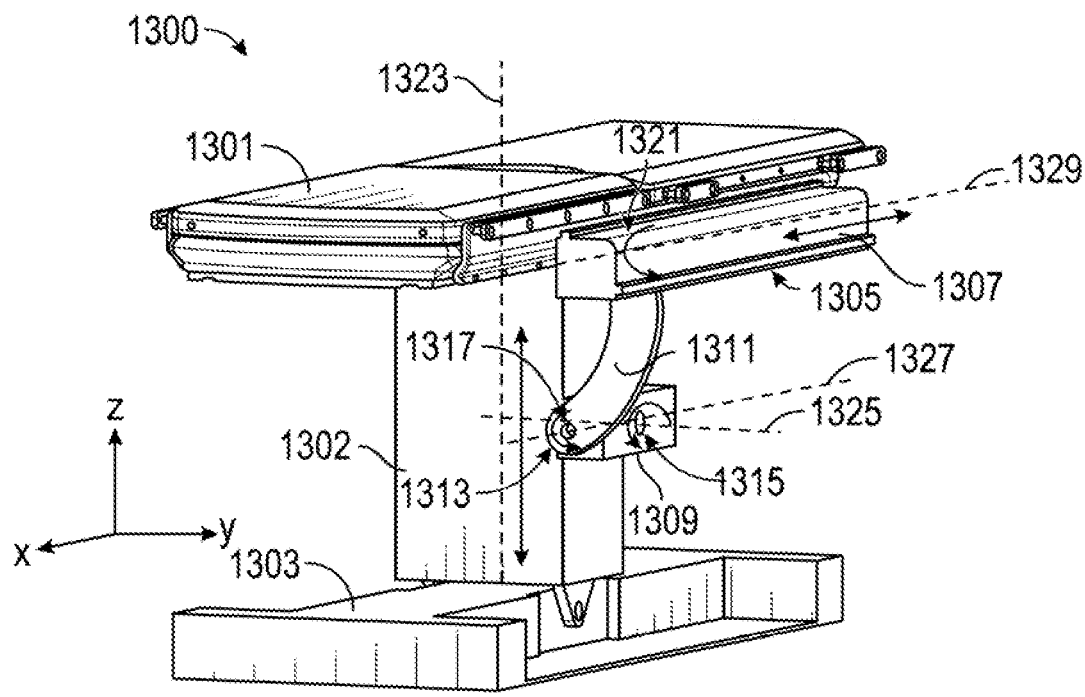
FIG. 13A is an isometric view of a surgical robotics system with an adjustable arm support according to one embodiment.
Figure 13B:
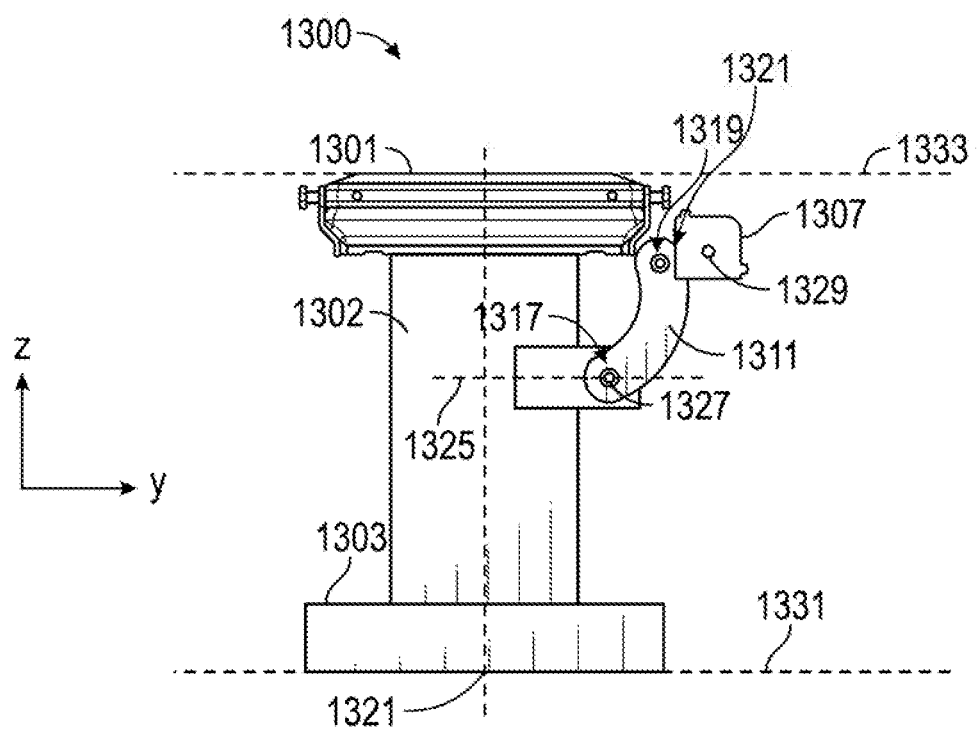
FIG. 13B is an end view of the surgical robotics system with an adjustable arm support of FIG. 13A.

FIGS. 13A and 13B are isometric and end views, respectively, of a surgical robotics system 1300 that includes an adjustable arm support 1305 according to one embodiment. The adjustable arm support 1305 can be configured to support one or more robotic arms (see, for example, FIGS. 14A-15B) relative to a table 1301. As will be described in greater detail below, the adjustable arm support 1305 can be configured so that it can move relative to the table 1301 to adjust and/or vary the position of the adjustable arm support 1305 and/or any robotic arms mounted to the adjustable arm support 1305 relative to the table 1301. For example, the adjustable arm support 1305 may include one or more degrees of freedom to allow adjustment of the adjustable arm support 1305 relative to the table 1301. Although the system 1300 illustrated in FIGS. 13A and 13B includes only a single adjustable arm support 1305, in some embodiments, systems can include multiple adjustable arm supports (see, e.g., system 1400 of FIG. 14A, which includes two adjustable arm supports 1305A, 1305B).

Surgical robotics systems including adjustable arm supports 1305 as described in this section can be designed to address one or more issues of known surgical robotics systems. For example, one issue with some surgical robotics systems is that they may be bulky, occupying large amounts of room space. This is often because large and elaborate support structures have been necessary to position robotic arms to perform robotic surgical procedures. Some surgical robotics systems include robotic arm support structures that support a plurality of robotic arms above a table that supports a patient during the robotic surgical procedure. For example, common surgical robotics systems include support structures that suspend one or more robotic arms over a table. These support structures are quite large and bulky because, for example, they must extend over and above the table.

Another issue with some surgical robotics systems is that they can be overly cumbersome. Due to, for example, the large and bulky support structures required by some surgical robotics systems as described above, these systems are not easily moved, which can be disadvantageous. Before and after surgery, it can be desirable to quickly and smoothly clear the robotic arms from a surgical area to provide easy access for loading a patient onto or removing a patient from the table. This has proven to be difficult with some surgical robotics systems because of the large and bulky support structures and the cumbersome nature of these systems. Some surgical robotics systems are not easily stored or moved.

Further, some surgical robotics systems have limited flexibility or versatility. That is, some surgical robotics systems are designed for a particular surgical procedure, and accordingly, do not work well for other types of surgical procedures. For example, a surgical robotics system that is configured for laparoscopic surgery may not work well for endoscopic surgery, or vice versa. In some instances, this is because the robotic arms used during the procedures need to be positioned in different locations relative the patient and/or table during different types of surgical procedures, and the support structures of conventional surgical robotics systems are not capable of accommodating the different positions of the robotic arms. Further, as mentioned above, some surgical robotics systems include support structures that suspend one or more robotic arms above the patient and table. It may be difficult to perform certain medical procedures with robotic arms mounted in this position.

Finally, some surgical robotics systems include robotic arms that are fixedly mounted to their corresponding support structures, and/or support structures themselves that are fixedly mounted or positioned. These systems may rely on articulation of the robotic arms alone to adjust the position of the robotic arms and/or surgical tools mounted thereto. Because the arms and/or supports are fixed in position, this can greatly limit the overall flexibility of these systems. The fixed nature of the robotic arms and/or supports of some systems may further limit the ability of these systems to avoid collisions between the arms and/or other objects (e.g., the patient, the table, other equipment, etc.) during surgery.

The system 1300 of FIGS. 13A and 13B, including the adjustable arm support 1305, as well as the other systems described in this section, can be configured to address (e.g., reduce or eliminate) one or more of the issues associated with some surgical robotics systems discussed above. For example, the systems described herein can be less bulky than some systems. The systems described herein can occupy less physical space than some systems. The systems described herein can be less cumbersome than some systems. For example, the systems described herein can be readily mobile and/or can be configured to store the arm supports and robotic arms quickly and easily to allow convenient access to the patient and/or table. The systems described herein can be highly flexible and configured for use in a wide variety of surgical procedures. For example, in some embodiments, the systems are configured for both laparoscopic and endoscopic procedures. The systems described herein can be configured to reduce collisions between the various robotic arms and other objects in the operating room.

In some embodiments, one or more of these advantages can be achieved by inclusion of one or more adjustable arm supports 1305 as described herein. As mentioned above, the adjustable arm supports 1305 can be configured so as to be able to move relative to the table 1301 to adjust and/or vary the position of the adjustable arm support 1305 and/or any robotic arms mounted to the adjustable arm support 1305 relative to the table 1301. For example, the adjustable arm supports 1305 can be capable of being stowed (for example, below the table 1301) and subsequently elevated for use. In some embodiments, the adjustable arm supports 1305 can be stowed in or near a base that supports the table 1301. In some embodiments, the adjustable arm supports 1305 can be stowed in one or more recesses formed along a central longitudinal axis of the base. In other embodiments, the adjustable arm supports 1305 can be stowed in one or more recesses offset from a central longitudinal axis of the base. Upon elevation, the adjustable arm supports 1305 can be positioned near the patient, but below the table 1301 (e.g., below the upper surface of the table 1301). In other embodiments, the arm supports 1305 can be raised above the table 1301 (e.g., above the upper surface of the table). Such a configuration can be useful, for example, when an adjustable arm support is positioned behind a patient lying on his side.

In some embodiments, the adjustable arm support 1305 is attached to the bed with a support structure that provides several degrees of freedom (e.g., lift, lateral translation, tilt, etc.). In the illustrated embodiment of FIGS. 13A and 13B, the arm support 1305 is configured with four degrees of freedom, which are illustrated with arrows in FIG. 13A. A first degree of freedom allows for adjustment of the adjustable arm support in the z-direction ("Z-lift"). For example, as will be described below, the adjustable arm support 1305 can include a carriage 1309 configured to move up or down along or relative to a column 1302 supporting the table 1301. A second degree of freedom can allow the adjustable arm support 1305 to tilt. For example, the adjustable arm support 1305 can include a rotary joint, which can, for example, permit the arm support 1305 to be aligned with a bed in a Trendelenburg position. A third degree of freedom can allow the adjustable arm support to pivot up as shown. As will be described below, this degree of freedom can be used to adjust a distance between the side of the table 1301 and the adjustable arm support 1305. A fourth degree of freedom can permit translation of the adjustable arm support 1305 along a longitudinal length of the table. Arm supports 1305 that include one or more of these degrees of freedom can address one or more of the issues associated with some systems noted above by providing a highly positionable support to which various robotic arms can be attached. The adjustable arm support 1305 can allow for adjustment of the position of the robotic arms relative to, for example, the table 1301. In some embodiments, these degrees of freedom can be controlled serially, in which one movement is performed after another. In other embodiments, different degrees of freedom can be controlled in parallel. For example, in some embodiments, one or more linear actuators can provide both Z-lift and tilt.

These degrees of freedom, as well as other features of the adjustable arm support 1305, will now be described in greater detail with reference to FIGS. 13A and 13B, which are isometric and end views, respectively, of the surgical robotics system 1300, which includes the adjustable arm support 1305 according to one embodiment. In the illustrated embodiment, the system 1300 includes the table 1301. In some embodiments, the table 1301 may be similar to the tables described above. In the illustrated embodiment, the table 1301 is supported by a column 1302, which is mounted to a base 1303. The base 1303 can be configured to rest on a support surface, such as a floor. Thus, the base 1303 and the column 1302 support the table 1301 relative to the support surface. FIG. 13B, illustrates a support surface plane 1331. In some embodiments, the table 1301 can be supported by one or more supports, wherein one of the supports comprises the column 1302. For example, the table 1301 can be supported by a Stewart mechanism comprising a plurality of parallel actuators.

The system 1300 can also include the adjustable arm support 1305. In the illustrated embodiment, the adjustable arm support 1305 is mounted to the column 1302. In other embodiments, the adjustable arm support 1305 can be mounted to the table 1301 or the base 1303. As mentioned above, the adjustable arm support 1305 is configured so that the position of the adjustable arm support 1305 can be adjusted relative to the table 1301. In some embodiments, the position of the adjustable arm support 1305 can also be adjusted relative to the column 1302 and/or base 1303.

The adjustable arm support 1305 can include a carriage 1309, a bar or rail connector 1311, and a bar or rail 1307. The bar or rail 1307 can comprise a proximal portion and a distal portion. One or more robotic arms can be mounted to the rail 1307, as shown, for example, in FIGS. 14A-15B. For example, in some embodiments, one, two, three, or more robotic arms can be mounted to the rail 1307. Further, in some embodiments, the robotic arms that are mounted to the rail can be configured to move (e.g., translate) along the rail 1307, such that the position of the robotic arms on the rail 1307 can be adjusted relative to one another, thereby reducing the risk of collision between the robotic arms. This will be described in greater detail below. In the illustrated embodiment, the rail 1307 is connected to the bar or rail connector 1311. The bar or rail connector 1311 is connected to the carriage 1309. The carriage is connected to the column 1302. Other arrangements are possible.

The column 1302 can extend along a first axis 1323. In some embodiments, the first axis 1323 is parallel to the z-axis as illustrated. In some embodiments, the first axis 1323 is a vertical axis. For example, the first axis 1323 can be perpendicular to the support surface or floor on which the system 1300 rests.

The carriage 1309 can be attached to the column 1302 by a first joint 1313. The first joint 1313 can be configured to allow the carriage 1309 (and accordingly the adjustable arm support 1305) to move relative to the column 1302. In some embodiments, the first joint 1313 is configured to allow the carriage 1309 to move along the column 1302 (for example, up and down along the column 1302). In some embodiment, the first joint 1313 is configured to allow the carriage 1309 to move along the first axis 1323 (for example, back and forth along the first axis 1323). The first joint 1313 can comprise a linear or prismatic joint. The first joint 1313 can comprise a powered joint, such as a motorized or hydraulic joint. The first joint 1313 can be configured to provide the first degree of freedom ("Z-lift") for the adjustable arm support 1305.

The adjustable arm support 1305 can include a second joint 1315 as shown. The second joint 1315 can be configured to provide the second degree of freedom (tilt) for the adjustable arm support 1305. The second joint 1315 can be configured to allow the adjustable arm support 1305 to rotate around a second axis 1325 that is different than the first axis 1323. In some embodiments, the second axis 1325 is perpendicular to the first axis 1323. In some embodiments, the second axis 1325 need not be perpendicular relative to the first axis 1323. For example, in some embodiments, the second axis 1325 is at an acute angle to the first axis 1323. In some embodiments, the second axis 1325 extends in the y-direction. In some embodiments, the second axis 1325 may lie in a plane that is parallel to the support surface or floor on which the system 1300 rests. The second joint 1315 can comprise a rotational joint. The second joint 1315 can comprise a powered joint, such as a motorized or hydraulic joint.

In the illustrated embodiment, the second joint 1315 is formed between the carriage 1309 and the column 1302, such that the carriage 1309 can rotate about the second axis 1325 relative to the column 1302. In other embodiments, the second joint 1315 can be positioned in other locations. For example, the second joint 1315 can be positioned between the carriage 1309 and the rail connector 1311, or between the rail connector 1311 and the rail 1307.

As noted above, the second joint 1315 can be configured to allow the adjustable arm support 1305 to rotate about the second axis 1325 to allow for the second degree of freedom (tilt) for the adjustable arm support 1305. As will be described in greater detail with reference to FIG. 16 below, rotating the adjustable arm support 1305 about the second axis 1325 can allow adjustment of a tilt angle of the adjustable arm support 1305. That is, an angle of tilt of the rail 1307 can be adjusted by rotating the adjustable arm support 1305 about the second axis 1325 (see FIG. 16).

The adjustable arm support 1305 can include a third joint 1317 as shown. The third joint 1317 can be configured to provide the third degree of freedom (pivot up) for the adjustable arm support 1305. The third joint 1317 can be configured as a rotational joint to allow the rail connector 1311 to rotate around a third axis 1327 that is different from the first axis 1323 and the second axis 1325. In some embodiments, the third axis 1327 can be perpendicular to the second axis 1325. In other embodiments, the third axis 1327 need not be parallel to the second axis 1325. For example, the third axis 1327 can be at an acute angle relative to the second axis 1325. In some embodiments, the third axis 1327 extends in the x-direction. In some embodiments, the third axis 1327 may lie in a plane that is parallel to the support surface or floor on which the system 1300 rests. The third axis 1327 may lie in the same plane or a different plane than the second axis 1325. When the adjustable arm support 1305 is positioned as shown in FIGS. 13A and 13B, the third axis 1327 can be perpendicular to the first axis 1323; however, as the adjustable arm support 1305 is rotated about the second joint 1315, the angle between the first axis 1323 and the third axis 1327 can vary. In some embodiments, the third axis 1327 can be parallel to the rail 1307.

When configured as a rotational joint, the third joint 1317 can allow the rail connector 1311 to rotate around the third axis 1327. As the rail connector 1311 rotates around the third axis 1327, a distance (for example, measured along the y-direction) between an edge of the table 1301 and the rail 1307 can be adjusted. For example, the distance between the edge of the table 1301 and the rail 1307 would increase as the rail connector 1311 is rotated downward from the position shown in FIG. 13B. Thus, the third joint 1317 can be configured to provide a degree of freedom that allows adjustment of the positioning of the rail 1307 along the y-direction. Further, when configured as a rotational joint, the third joint 1317 can also allow additional adjustment of the position of the rail 1307 along the z-direction. For example, the height of the rail 1307 (along the z-direction) would decrease as the rail connector 1311 is rotated downward from the position shown in FIG. 13B. In some embodiments, the third joint 1317 can allow the rail 1307 to pivot upwards in a "biceps curl" type fashion from a stowed position to an elevated position.

As best seen in FIG. 13B, in the illustrated embodiment, the third joint 1317 is positioned on a first end of the rail connector 1311 that connects the rail connector 1311 to the carriage. An additional joint 1319 can be included at a second end of the rail connector 1311 that connects the rail connector 1311 to the rail 1307. In some embodiments, the position of the third joint 1317 and the additional joint 1319 can be reversed. In some embodiments, the additional joint 1319 is mechanically constrained to the third joint 1317 such that the third joint 1317 and the additional joint 1319 rotate together. For example, the third joint 1317 and the additional joint 1319 can be mechanically constrained via a four-bar linkage. Other methods for mechanical constraint are also possible. Mechanical constraint between the third joint 1317 and the additional joint 1319 can be configured to maintain an orientation of the rail 1307 as the rail connector 1311 is rotated about the third axis 1327. For example, mechanical constraint between the third joint 1317 and the additional joint 1319 can be configured such that, as the rail connector 1311 rotates, an upper surface of the rail 1307 (to which one or more robotic arms can be mounted) continue to face in the same direction. In the illustrated example of FIGS. 13A and 13B, the upper face of the rail 1307 is facing upwards (in the z-direction). Mechanical constraint between the third joint 1317 and the additional joint 1319 can be configured such that the upper face of the rail 1307 remains facing upwards (in the z-direction) as the rail connector 1311 rotates. In some embodiments, mechanical constraint can be replaced with a software-defined constrained. For example, each of the third joint 1317 and the additional joint 1319 can be a powered joint, and software can be used to constrain rotation of each joint together.

In some embodiments, the third joint 1317 can comprise a linear joint or prismatic joint (in place of the rotation joint described above and illustrated in the figures) configured to allow linear displacement of the rail 1307 toward and away from the column 1302 (for example, along the y-direction).

The third joint 1317 can comprise a powered joint. In some embodiments, the third joint 1317 can comprise a motorized or hydraulic joint.

The adjustable arm support 1305 can include a fourth joint 1321 as shown. The fourth joint 1321 can be configured to provide the fourth degree of freedom (translation) for the adjustable arm support 1305. For example, the fourth joint 1321 can be configured to allow the rail 1307 to translate back and forth relative to, for example, the table 1301, the column 1302, the carriage 1309, and/or the rail connector 1311. The rail 1307 can extend along a fourth axis 1329. The fourth joint 1321 can be configured to allow the rail 1307 to translate along the fourth axis 1329. In some embodiments, the fourth axis 1329 can be parallel to third axis 1327. In other embodiments, the fourth axis 1329 can be at a non-parallel (e.g., acute angle) to third axis 1327. In some embodiments, the fourth axis 1329 can be perpendicular to the second axis 1325. In other embodiments, the fourth axis 1329 can be at a non-perpendicular angle (e.g., acute angle) to the second axis 1325. When the adjustable arm support 1305 is positioned as shown in FIGS. 13A and 13B, the fourth axis 1329 can be perpendicular to the first axis 1323; however, as the adjustable arm support 1305 is rotated about the second joint 1315, the angle between the first axis 1323 and the fourth axis 1329 can vary.

The fourth joint 1321 can comprise a linear or prismatic joint. The fourth joint 1321 can comprise a powered joint, such as a motorized or hydraulic joint. In the illustrated embodiment, the fourth joint 1321 is positioned between the bar or rail connector 1311 and the rail 1307.

As will be described in greater detail below with reference to FIGS. 15A and 15B, translation of the rail 1307 can be configured to provide increased longitudinal reach (for example, along the x-direction) for the system 1300. This may improve the flexibility of the system 1300, allowing the system 1300 to be used in a wider variety of surgical procedures.

In some embodiments, the adjustable arm support 1305 is configured to allow for variable positioning of the rail 1307 relative to the table 1301. In some embodiments, the position of the rail 1307 remains below a table support surface plane 1333 that is parallel with an upper surface of the table 1301. This may be advantageous as it may improve the ability to maintain a sterile field above the table support surface plane 1333 during a medical procedure. In the operating environment, medical personal may desire to maintain a sterile field above the surface of the table. As such, there may be heightened requirements or stricter procedures for equipment that is positioned above the surface of the table. For example, equipment positioned above the surface of the table may need to be draped. As such, it may be desirable, and some medical personal may prefer, that the arm support is maintained below the surface of the table. In some instances, when the arm support is maintained below the surface of the table, it may not need to be draped. In other embodiments, however, the adjustable arm support 1305 can adjust the position of the rail 1307 such that it is positioned above the table support surface plane 1333.

In some embodiments, the adjustable arm support 1305 is attached to the base 1303, the column 1302, or the table 1301 at a position below the table support surface plane 1333. As will be described below with reference to FIGS.

18A and 18B, this may advantageously permit the adjustable arm support 1305 (and any attached robotic arms) to be moved to a stowed configuration in which the adjustable arm support 1305 (and any attached robotic arms) are stowed below the table 1301 (see FIG. 18B). This may advantageously make the system 1300 less bulky and/or less cumbersome when compared to previously known surgical robotics systems.

Movement of the arm support 1305 (for example, movement of one or more of the first, second, third, or fourth joints 1313, 1315, 1317, 1321) may be controlled and/or commanded in several ways. For example, the system 1300 can include a controller (e.g., a pendant) either on the bed (patient side) or a surgeon console. As another example, buttons (or other actuation mechanisms) could be included on one or more of the components of the adjustable arm support 1305 (or on one or more of the connected robotic arms). As another example, movement of the adjustable arm support 1305 can be provided automatically by system software, for example, for adjustment within the robot's null space (while maintaining the tooltip position commanded by the surgeon). Additionally, movement of the adjustable arm support 1305 can be provided automatically by system software during setup, deployment, draping, or other workflow steps when tools are not inserted into the patient. Other examples are also possible.

FIGS. 13A and 13B illustrate an embodiment that includes one adjustable arm support 1305. As noted previously, some systems can include more than one adjustable arm support 1305, each supporting one or more robotic arms. In such systems, each adjustable arm support can be configured as described above. Further, in such systems, each adjustable arm support can be controlled independently.

Figure 14A:
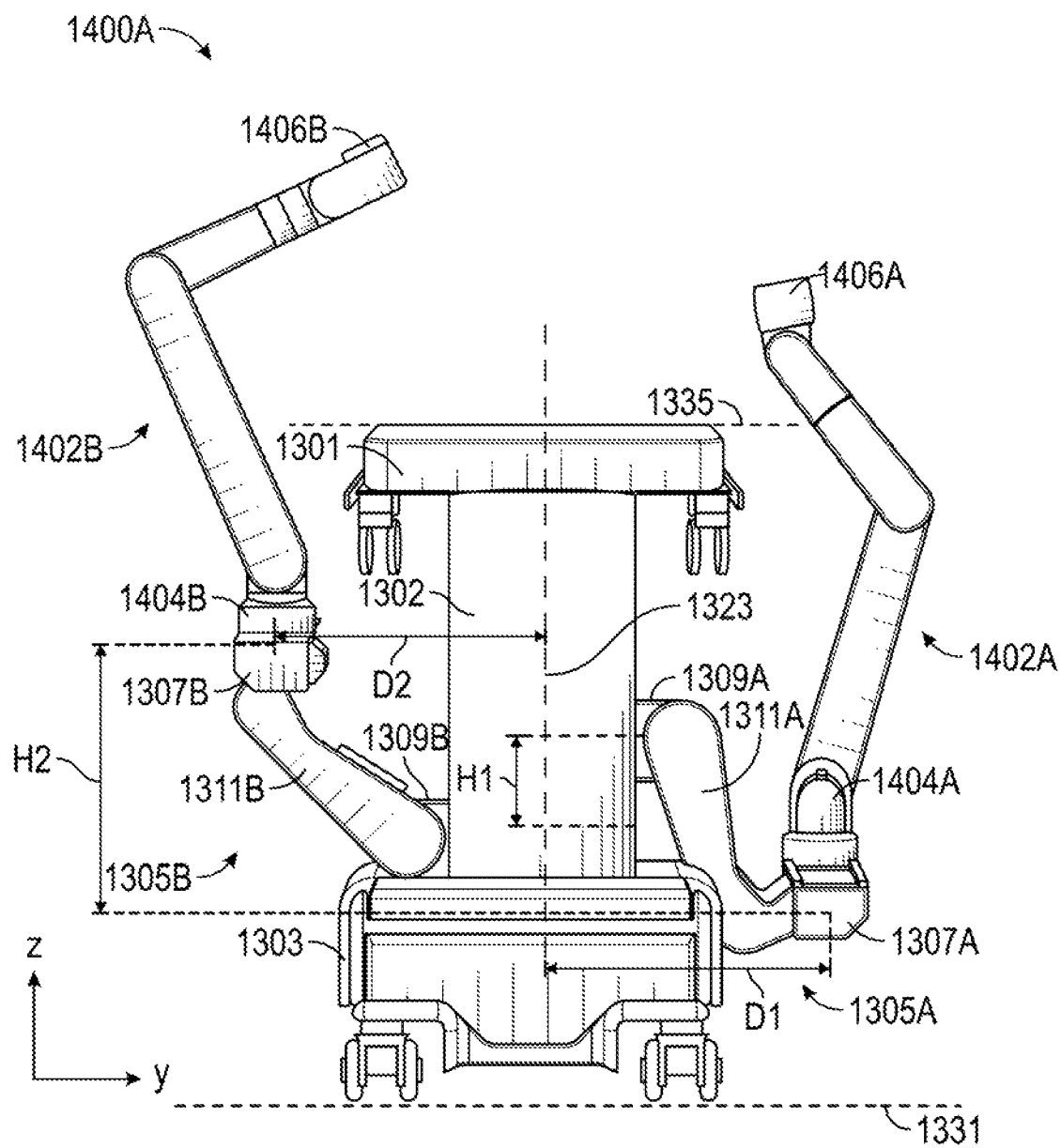
FIG. 14A is an end view of a surgical robotics system with two adjustable arm supports mounted on opposite sides of a table according to one embodiment.

FIG. 14A is an end view of a surgical robotics system 1400A with two adjustable arm supports 1305A, 1305B mounted on opposite sides of the table 1301 according to one embodiment. Each of the adjustable arm supports 1305A, 1305B can be configured as described above. In the illustrated embodiment, a first adjustable arm support 1305A is positioned on a first side of the table 1301 (e.g., the right side as shown in the figure), and a second adjustable arm support 1305B is positioned on a second side of the table 1301 (e.g., the left side as shown in the figure). The second side can be opposite the first side.

Further, a first robotic arm 1402A is illustrated attached to the bar or rail 1307A of the first adjustable arm support 1305A, and a second robotic arm 1402B is illustrated attached to the bar or rail 1307B of the second adjustable arm support 1305B. As illustrated, the first robotic arm 1402A includes a base 1404A attached to the rail 1307A. The distal end of the first robotic arm 1402A includes an instrument drive mechanism 1406A. The instrument drive mechanism 1406A can be configured to attach to one or more robotic medical instruments or tools. Similarly, the second robotic arm 1402B includes a base 1404B attached to the rail 1307B. The distal end of the second robotic arm 1402B includes an instrument drive mechanism 1406B. The instrument drive mechanism 1406B can be configured to attach to one or more robotic medical instruments or tools. Example robotic arms configured for use with the adjustable arm supports 1305 are described below in greater detail in Section XIII (see FIG. 21).

FIG. 14A illustrates that the adjustable arm supports 1305A, 1305B can be independently controlled and positioned. As illustrated, the first adjustable arm support 1305A is positioned at a first height along the first axis 1323, and the second adjustable arm support 1305B is positioned at a second height along the first axis 1323. In some embodiments, the second height can be different and independent from the first height. In other embodiments, the second height can be substantially equivalent to the first height.

In the embodiment in FIG. 14A, the carriage 1309A of the first adjustable arm support 1305A is positioned at a first height along the first axis 1323, and the carriage 1309B of the second adjustable arm support 1305B is positioned at a second height along the first axis 1323 different than the first height. Thus, a height difference H1 can exist between the carriages 1309A, 1309B of the first and second adjustable arm supports 1305A, 1305B. In other embodiments, the carriages 1309A, 1309B of the first and second adjustable arm supports 1305A, 1305B can be positioned at the same height.

Further, FIG. 14A illustrates the position of the bar or rail connectors 1311A, 1311B of the first and second adjustable arm supports 1305A, 1305B, which can also be independently adjusted to have different orientations. For example, as illustrated, the rail connector 1311A of the first adjustable arm support 1305A is rotated downwardly, and the rail connector 1311B of the second adjustable arm support 1305B is rotated upwardly. A height difference H2 can exist between the rails 1307A, 1307B of the first and second adjustable arm supports 1305A, 1305B, as illustrated. Further, in this position, each of the rail connectors 1311A, 1311B, of the first and second adjustable arm supports 1305A, 1305B is positioned at a different distance from the first axis 1323. For example, the rail connector 1311A of the first adjustable arm support 1305A is positioned at a first distance D1 from the first axis 1323, and the rail connector 1311B of the second adjustable arm support 1305B is positioned at a second distance D2 from the first axis 1323. This distance D1 can be different than the distance D2. In some embodiments, the rail connectors 1311A, 1311B, of the first and second adjustable arm supports 1305A, 1305B can be rotated to the same degree and/or the distance D1 can be equal to the distance D2.

Figure 14B:
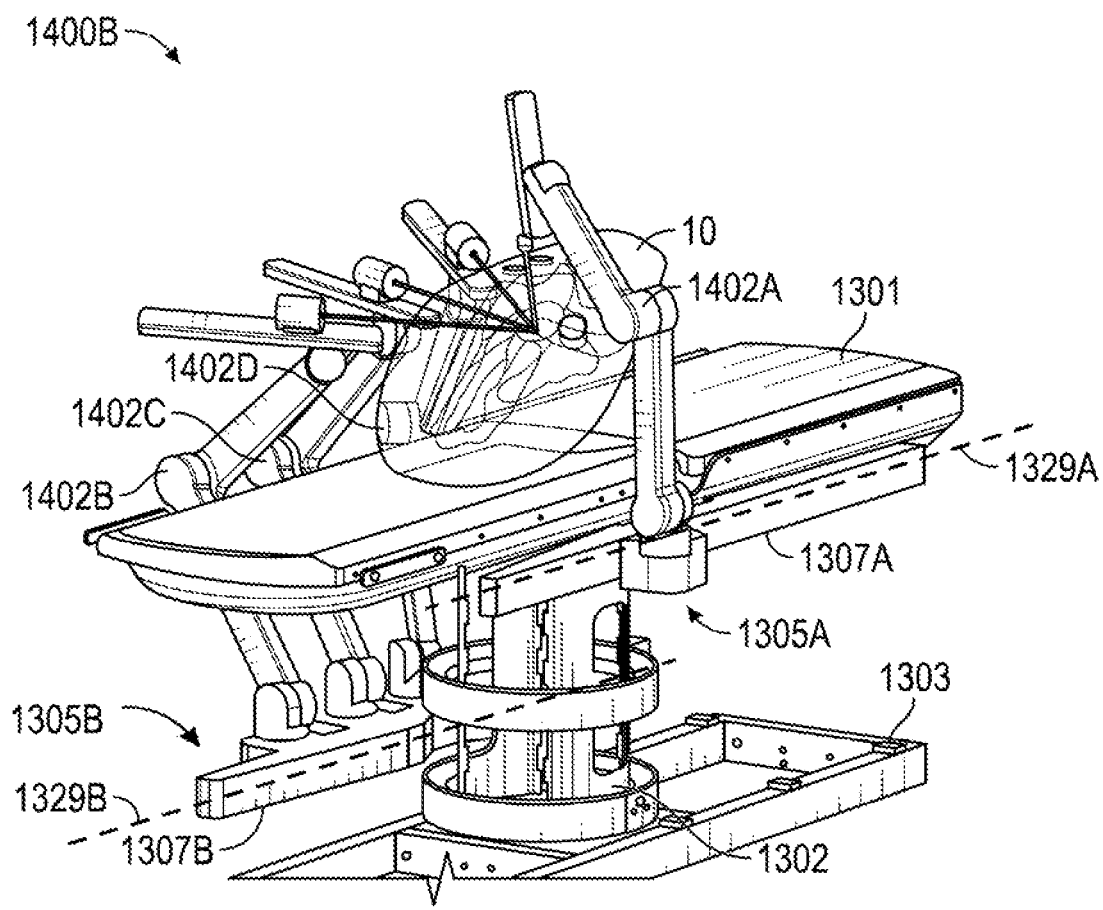
FIG. 14B is an isometric view of a surgical robotics system with two adjustable arm supports and a plurality of robotic arms configured for a laparoscopic procedure according to one embodiment.
Figure 14C:
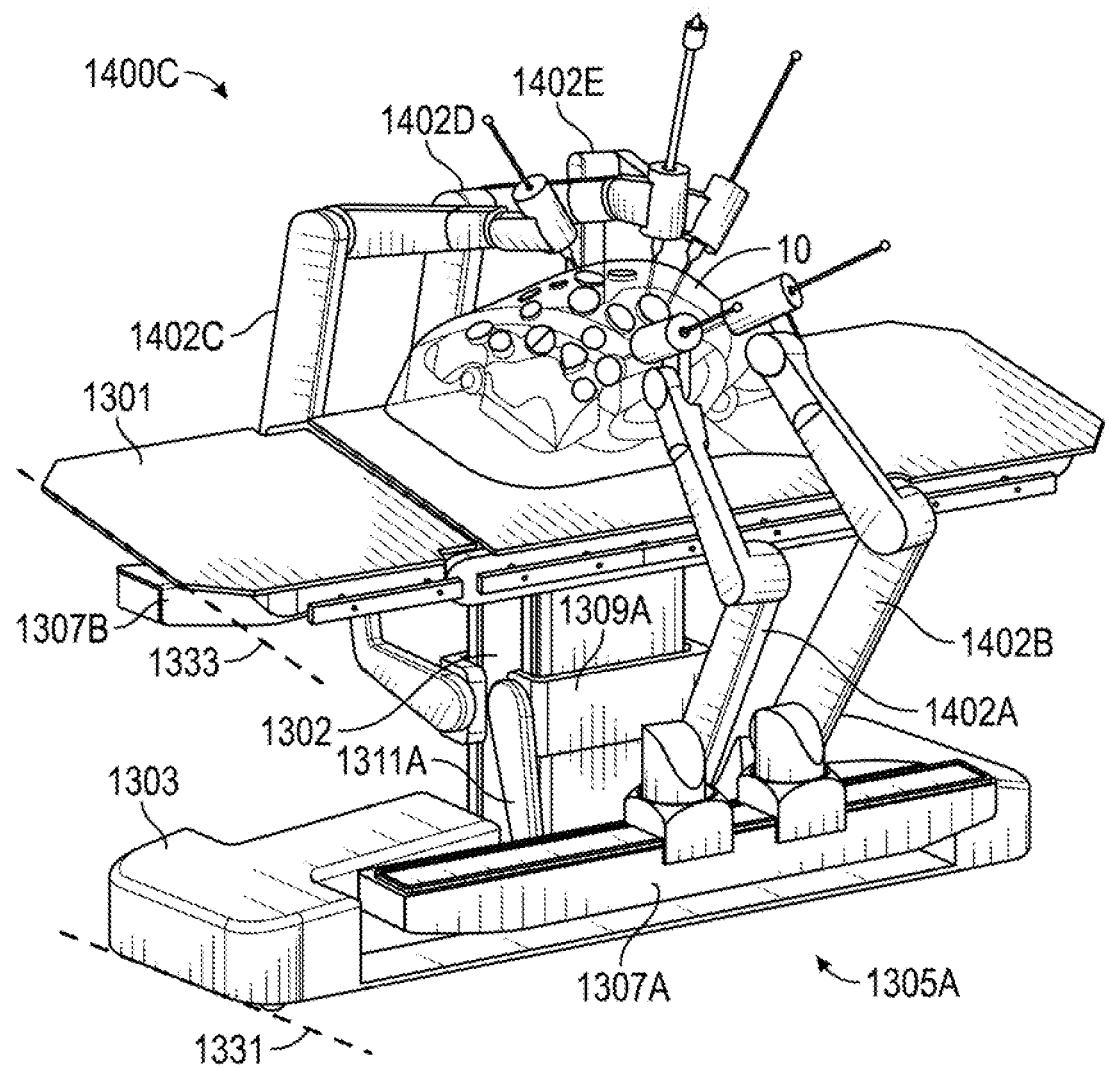
FIG. 14C is an isometric view of a surgical robotics system with two adjustable arm supports and a plurality of robotic arms configured for a laparoscopic procedure according to one embodiment.

FIG. 14A illustrates that the adjustable arm supports 1305A, 1305B can each be positioned or adjusted independently to provide different positions at which the robotic arms attached thereto are supported. FIG. 14A illustrates only one example among many. The adjustable arm supports 1305 can have continuous movement (e.g., vertical or longitudinal) and can be stopped at any point as desired by a surgeon or clinician. This can be beneficial, for example, in creating a height differential between the arm supports, which can be advantageous for certain types of surgeries, such as when one set of robotic arms needs to reach low and the other needs to reach over a patient. For example, as shown in FIG. 14A, the second adjustable arm support 1305B with attached robotic arm 1402B is raised higher than the first adjustable arm support 1305A with attached robotic arm 1402A. This position may be especially helpful when the patient is on its side (e.g., lateral decubitus), such as in a nephrectomy procedure, although one skilled in the art will appreciate that a differential can be beneficial in other procedures as well. FIGS. 14B and 14C provide additional examples.

FIG. 14B is an isometric view of a surgical robotics system 1400B with two adjustable arm supports 1305A, 1305B and a plurality of robotic arms 1402A, 1402B, 1402C, 1402D configured for a laparoscopic procedure according to one embodiment. In the illustrated embodiment, a first adjustable arm support 1305A supports a first robotic arm 1402A, and a second adjustable arm support 1305B supports a second robotic arm 1402B, a third robotic arm 1402C, and a fourth robotic arm 1402D.

The first robotic arm 1402A can be configured to translate back and forth along the rail 1307A of the first adjustable arm support 1305A. That is, the first robotic arm 1402A can be configured to translate along the fourth axis 1329A. This can allow for adjustment of the first robotic arm 1402A relative to the rail 1307A. Similarly, the second robotic arm 1402B, the third robotic arm 1402C, and the fourth robotic arm 1402D can each be configured to translate back and forth along the rail 1307B of the second adjustable arm support 1305B. That is, the second robotic arm 1402B, the third robotic arm 1402C, and the fourth robotic arm 1402D can be configured to translate along the fourth axis 1329B of the second adjustable arm support 1305B. This can allow for adjustment of the second robotic arm 1402B, the third robotic arm 1402C, and the fourth robotic arm 1402D relative to the rail 1307B. Further, each of the second robotic arm 1402B, the third robotic arm 1402C, and the fourth robotic arm 1402D can be independently moved along the rail 1307B such that the spacing between each of the second robotic arm 1402B, the third robotic arm 1402C, and the fourth robotic arm 1402D can be adjusted. Among other things, FIG. 14B illustrates that in some embodiments, the position of each robotic arm 1402 along the corresponding rail 1307 of the corresponding arm support 1305 can be independently controlled and adjusted.

Further, FIG. 14B illustrates another example of a height differential between the first and second arm supports 1305A, 1305B. In the illustrated embodiment, a patient 10 is positioned on his or her side during a laparoscopic procedure. The first adjustable arm support 1305A is positioned in a high position (but below the surface of the table 1301) such that the first robotic arm 1402A can reach over the patient 10. As illustrated, the second adjustable arm support 1305B is positioned at a lower position such that the second robotic arm 1402B, the third robotic arm 1402C, and the fourth robotic arm 1402D can access an anterior side of the patient.

In some embodiments, one or more of the robotic arms 1402A, 1402B, 1402C, 1402D can operate laparoscopic surgical instruments or tools, and one or more of the other of the 1402A, 1402B, 1402C, 1402D can operate a camera laparoscopically inserted into the patient. In some embodiments, the one or more laparoscopic surgical instruments and the camera can be sized and configured to extend through one or more laparoscopic ports in a patient.

FIG. 14C is an isometric view of a surgical robotics system 1400C with two adjustable arm supports 1305A, 1305B and a plurality of robotic arms 1402A, 1402B, 1402C, 1402D, 1402E configured for a laparoscopic procedure according to one embodiment. In the illustrated embodiment, a first adjustable arm support 1305A supports a first robotic arm 1402A and a second robotic arm 1402B, and a second adjustable arm support 1305B supports a third robotic arm 1402C, a fourth robotic arm 1402D, and a fifth robotic arm 1402E.

In the illustrated embodiment, the table 1301 supporting the patient 10 is positioned at an angle relative to the floor. That is, rather than being parallel, as illustrated for example, in FIG. 14B, a table surface plane 1333 is angled with respect to a support surface plane 1331. The first adjustable arm support 1305A, positioned on the lower side of the table 1301, can be positioned in a low position such that the first robotic arm 1402A and the second robotic arm 1402B can access the patient 10. As illustrated, the second adjustable arm support 1305B is positioned at a higher position (which may be lower than the table support surface 1333) such that the third robotic arm 1402C, the fourth robotic arm 1402D, and the fifth robotic arm 1402E can reach over and access the patient 10.

Figure 15A:
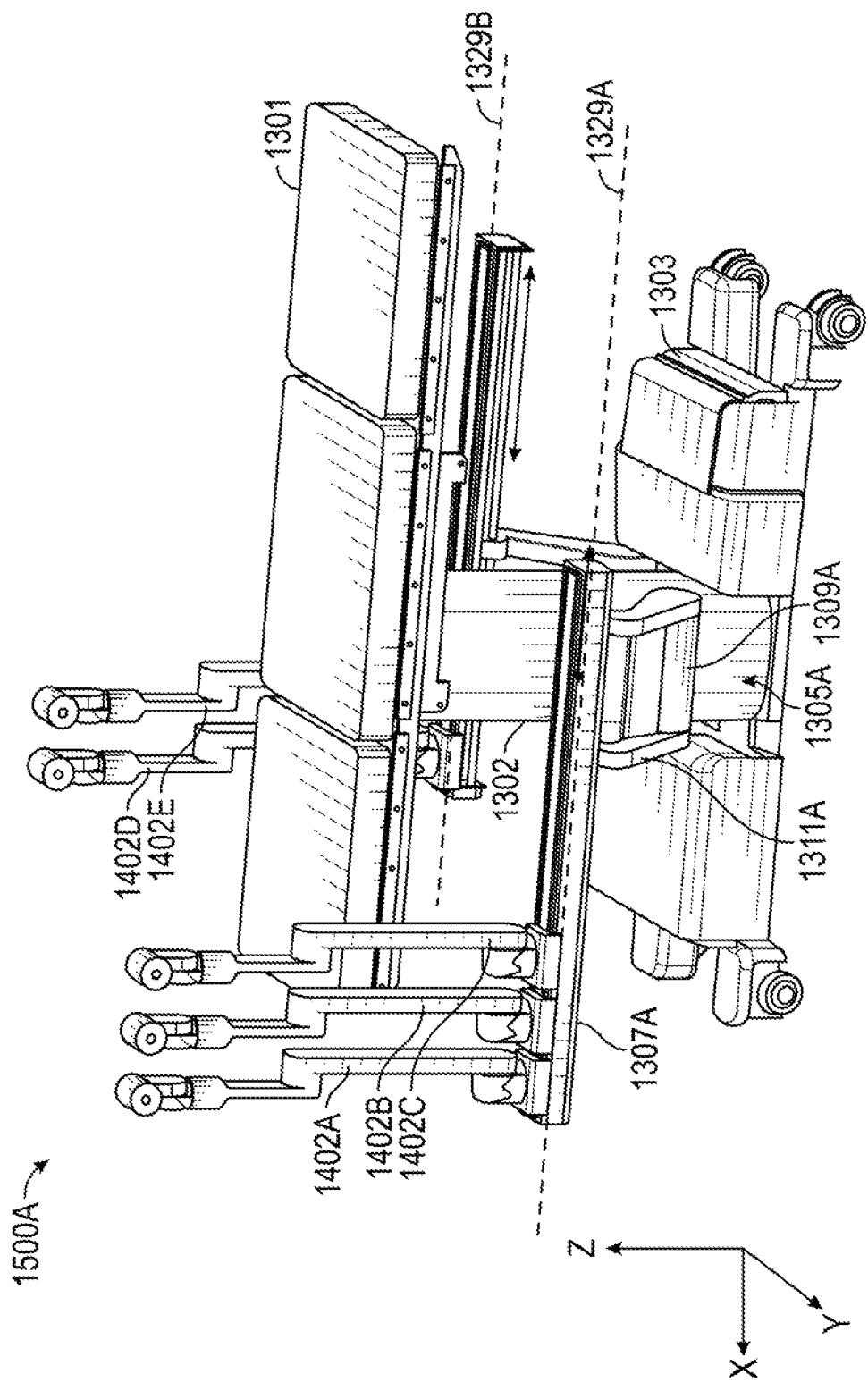
FIG. 15A is an isometric view of a surgical robotics systems with two adjustable arm supports that are configured to translate to adjust the position of the adjustable arm supports according to one embodiment.

FIG. 15A is an isometric view of a surgical robotics systems with two adjustable arm supports 1305A, 1305B that are configured to translate to adjust the position of the adjustable arm supports 1305A, 1305B according to one embodiment. As described previously, the adjustable arm support 1305 can include a fourth joint 1321 configured to allow the rail 1307 to translate along the fourth axis 1329 relative to the base 1301, column 1302, table 1301, carriage 1309, and/or rail connector 1311. FIG. 15A illustrates that, in embodiments that include two adjustable arm supports 1305A, 1305B, the rail 1307A, 1307B of each adjustable arm support 1305A, 1305B can be translated along its corresponding axis 1329A, 1329B, independently of the other rail. For example, in FIG. 15A, the rail 1307A can translate back and forth along the axis 1329A, independently from the rail 1307B, which can also translate back and forth along the axis 1329B.

In other embodiments, rails 1307 are not configured to translate along the axis 1329. For example, in some embodiments, longer rails 1307 can be used in lieu of translating rails. In some embodiments, translation of the rails 1307 permits shorter rails 1307 to be used while still maintaining the overall versatility and flexibility of the system. In some embodiments, shorter rails 1307 (with or without translation) can improved the ability of system to be stowed below the table 1301 (see FIG. 18B).

Figure 15B:
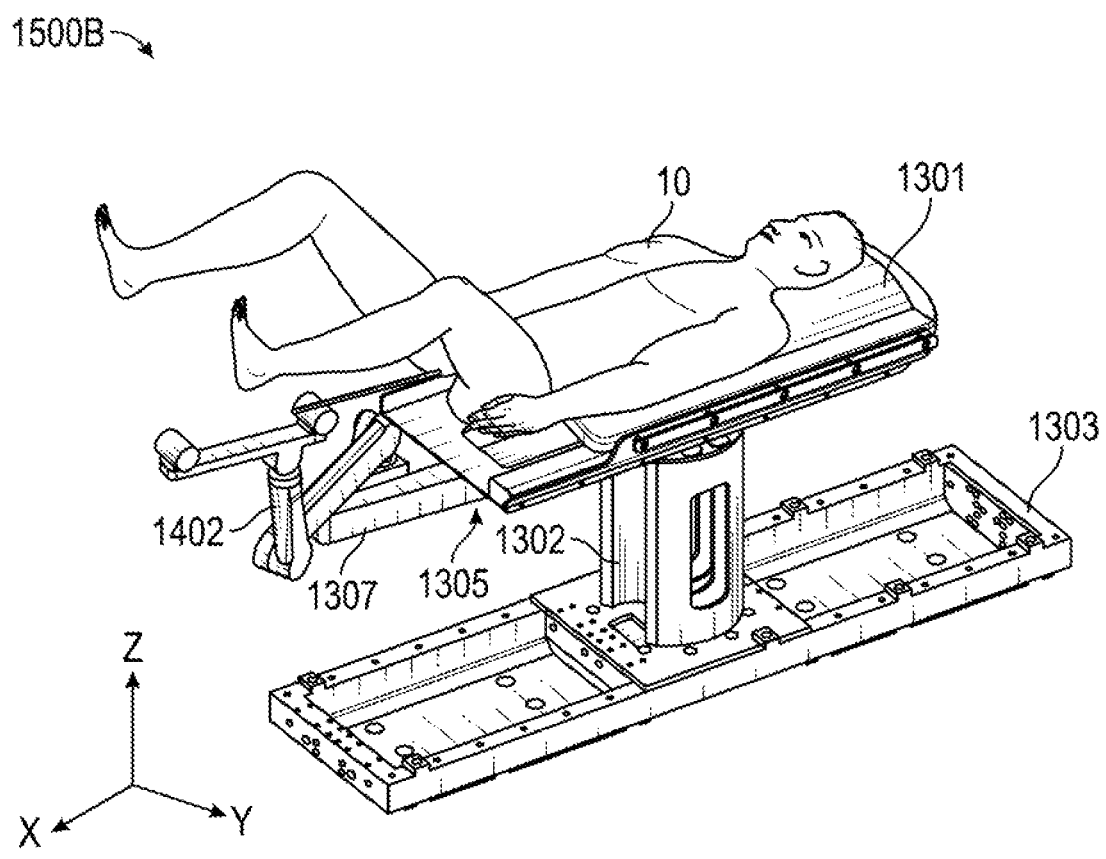
FIG. 15B is an isometric view of a surgical robotics system with an adjustable arm support and robotic arm configured for an endoscopic procedure according to one embodiment.

FIG. 15B is an isometric view of a surgical robotics system 1500B with an adjustable arm support 1305 and robotic arm 1402 configured for an endoscopic procedure according to one embodiment. FIG. 15B illustrates that, in some embodiments, a system including an adjustable arm support 1305 can be configured to provide a long longitudinal range of motion that can be useful, for example, in an endoscopic procedure, such as a ureteroscopy, wherein an endoscope is inserted into the patient through the groin area. For example, as shown in FIG. 15B, the rail 1307 can be translated all the way toward the foot of the table 1301. From there, the arm 1402 can further extend longitudinally to position an instrument between the legs of the patient 10 for access to the groin area. Although only one robotic arm 1402 is illustrated in FIG. 15B, in other embodiments, multiple robotic arms, either mounted on the same adjustable arm support 1305 or an additional arm support 1305 can be configured for use in an endoscopic procedure. FIG. 15B provides only one example of an endoscopic procedure. Systems including adjustable arm supports 1305 can be used in other types of endoscopic procedures, such as bronchoscopy, for example.

Figure 16:
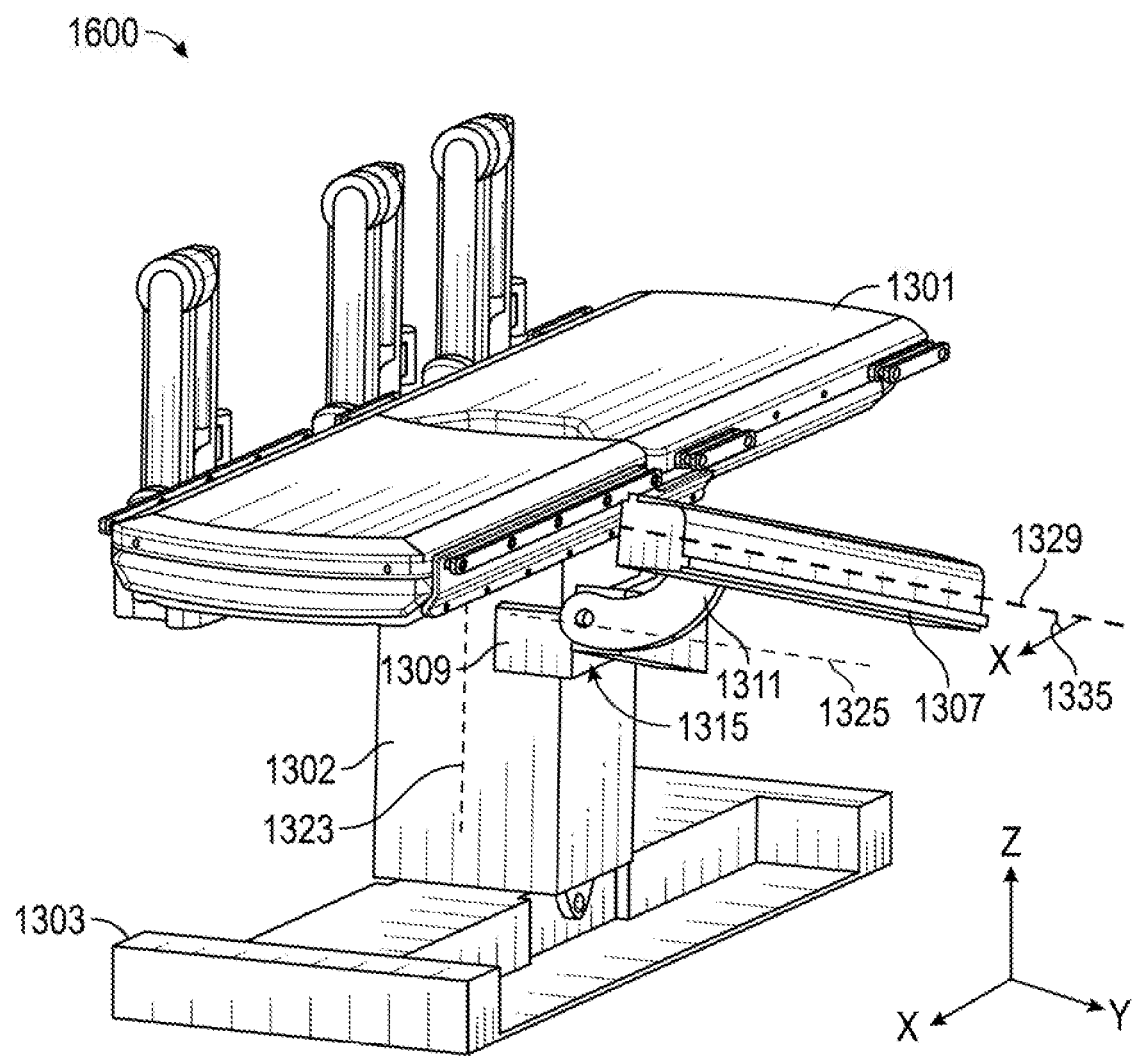
FIG. 16 is an isometric view of a surgical robotics system with an adjustable arm support configured with a rail capable of tilting according to one embodiment.

FIG. 16 is an isometric view of a surgical robotics system 1600 with an adjustable arm support 1305 configured with a rail 1307 capable of tilting according to one embodiment. As discussed previously, an arm support can include a second joint 1315 configured to allow the arm support 1305 to tilt. In the illustrated embodiment of FIG. 16, the second joint 1315 is positioned between the carriage 1309 and the rail connector 1311, although, as discussed previously, other positions for the second joint 1315 are possible. The second joint 1315 can be rotational joint configured to rotate or provide adjustment of the arm support 1305 about the second axis 1325. As shown in FIG. 16, by rotating or providing adjustment of the arm support 1305 about the second axis 1325, a tilt angle 1335 of the axis 1329 can be adjusted. The tilt angle 1335 can be measured between, for example, the axis 1329 (of the rail 1307) and the x-axis, the support surface plane 1331, or the table surface plane 1333.

In some embodiments, the second joint 1315 permits tilting of the rail relative to the table 1301. In some embodiments, the table 1301 can also pivot or tilt (for example to a Trendelenburg position), and the second joint 1315 can allow the adjustable arm support 1305 to follow the pivoting or tilting of the table 1301. This can allow surgical arms 1402 to remain in position a relative to the patient 10 and/or table 1301 as the table 1301 pivots or tilts. This may be advantageous as a surgeon or clinician may desire to pivot or tilt the table 1301 intraoperatively. In some embodiments, the second joint 1315 pivots or tilts to allow the rail 1307 to remain parallel with the table 1301 as the table tilts. In some embodiments, the rail 1307 need not remain parallel with the table 1301.

Figure 17A:
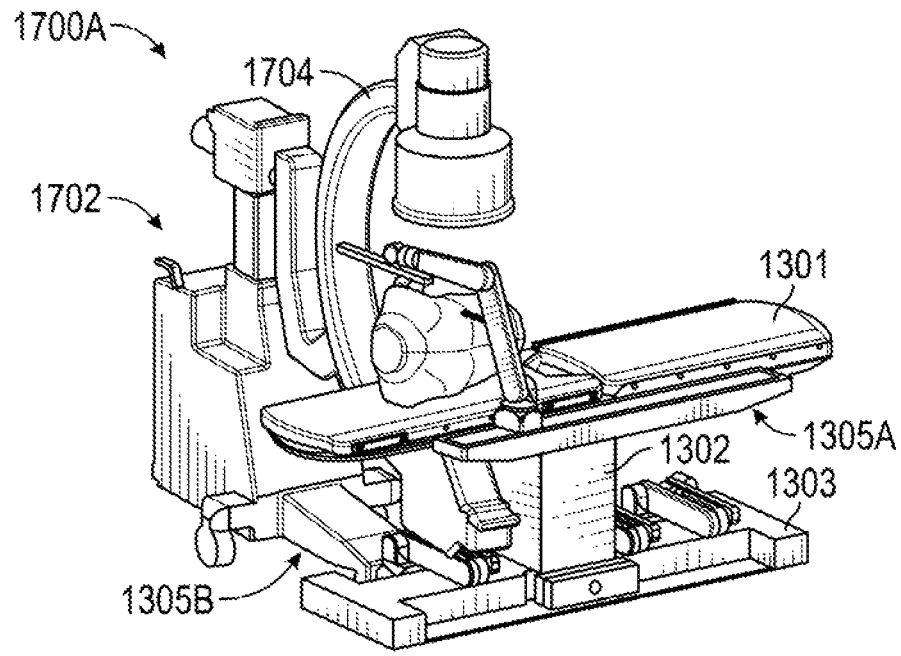
FIG. 17A is an isometric view of a surgical robotics system with adjustable arm supports positioned to allow access for a C-arm of a medical imaging device according to one embodiment.
Figure 17B:
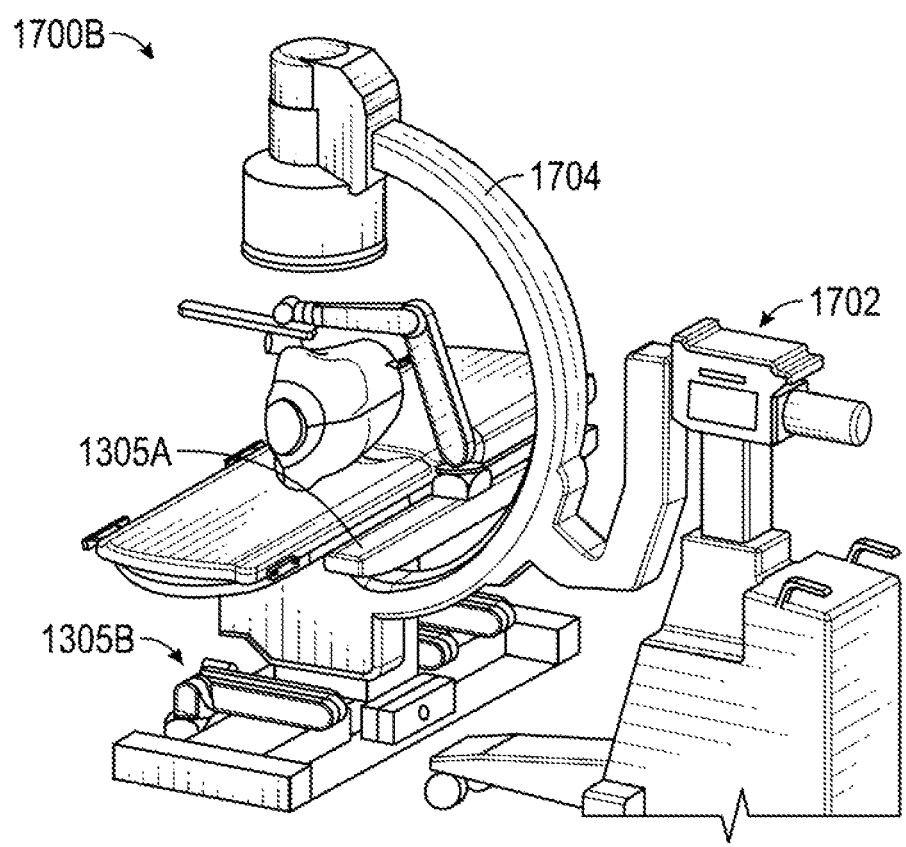
FIG. 17B is an isometric view of the surgical robotics system of FIG. 17A with the adjustable arm supports positioned to allow access for the C-arm of the medical imaging device according to another embodiment.

FIGS. 17A and 17B illustrate that systems including adjustable arm supports 1305 may provide improved access for medical imaging devices. As described above, the position of the adjustable arm support 1305 can be adjusted so as to allow access to or accommodate a medical imaging device, such as a C-arm. In addition to providing improved access for medical imaging devices, the adjustable arm supports also provide improved access for clinicians.

FIG. 17A is an isometric view of a surgical robotics system 1700A with adjustable arm supports 1305A, 1305B positioned to allow access for a C-arm 1704 of a medical imaging device 1702 according to one embodiment. As shown, the second adjustable arm support 1305B is positioned near the floor, so as to be positioned below the C-arm 1704 of the medical imaging device. The first adjustable arm support 1305A is positioned near the table 1301 such that the robotic arm can access the patient.

FIG. 17B is an isometric view of the surgical robotics system 1700B with the adjustable arm supports 1305A, 1305B positioned to allow access for the C-arm 1704 of the medical imaging device 1702 according to another embodiment. In the illustrated embodiment, the first adjustable arm support 1305A is positioned near the table 1301, such that the C-arm 1704 partially surrounds the first adjustable arm support 1305A.

The adjustability of the adjustable arm supports 1305 can advantageously allow the systems to work with will other types of medical imaging devices as well.

Figure 18A:
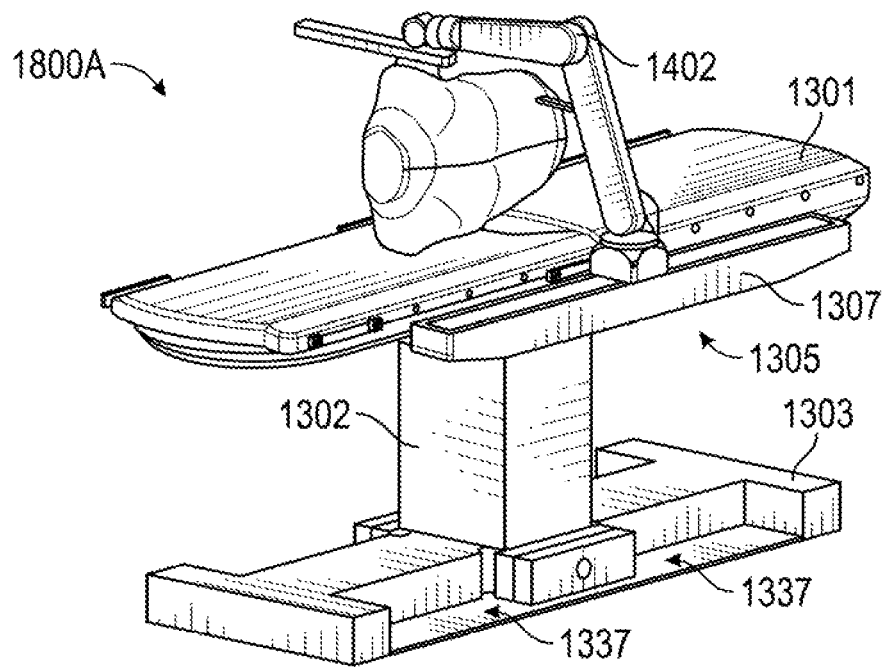
FIG. 18A is an isometric view of a surgical robotics system with adjustable arm supports positioned in a deployed configuration according to one embodiment.
Figure 18B:
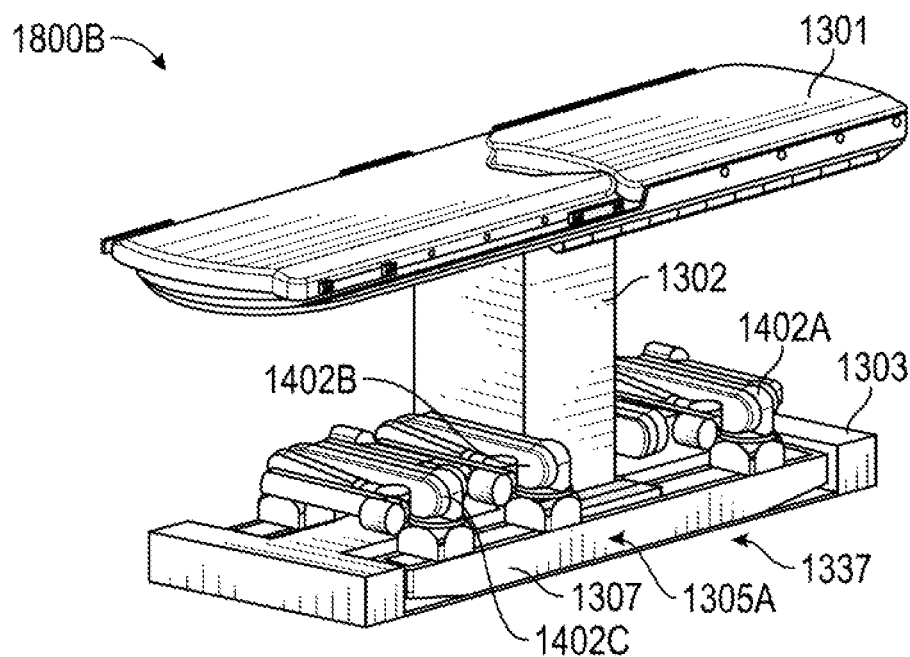
FIG. 18B is an isometric view of a surgical robotics system with adjustable arm supports positioned in a stowed configuration according to one embodiment.

FIGS. 18A and 18B illustrate that systems including adjustable arm supports 1305 can be configured to allow the adjustable arm supports 1305 and corresponding robotic arms 1402 to stow conveniently below the table 1301. This may advantageously provide that the systems are less bulky and cumbersome than some surgical robotics systems. The adjustable arm supports 1305 can transition between a stowed configuration (FIG. 18B) and a deployed configuration (FIG. 18A).

FIG. 18A is an isometric view of a surgical robotics system 1800A with an adjustable arm support 1305 positioned in a deployed configuration according to one embodiment. As shown, the adjustable arm support 1305 has been adjusted such that the rail 1307 is positioned adjacent to a side of the table 1301, and a robotic arm 1402 has been deployed so as to access the patient 10. FIG. 18A also illustrates that the base 1303 can include a recess 1337. The recess 1337 can be configured to receive the arm support 1305 in the stowed configuration, as shown for example, in FIG. 18B.

FIG. 18B is an isometric view of a surgical robotics system 1800B with adjustable arm supports 1305A, 1305B positioned in a stowed configuration according to one embodiment. As shown, bar or rails 1307A, 1307B of each arm support are received into recesses 1337 in the base 1303. In some embodiments, the robotic arms 1402A, 1402B, 1402C can fold over the arm supports 1305A, 1305B as shown. A stowed configuration, for example, with the arm supports 1305A, 1305B stored in recesses 1337 below the table 1301, as shown in FIG. 18B, can advantageously make the system less bulky and cumbersome. In other embodiments, both the arm supports and robotic arms can be stored into recesses in the base 1303. While embodiments described herein illustrate an arm support in a low position relative to the table, in other embodiments, adjustable arm supports can be provided from an elevated or suspended position above the table. These adjustable arm supports in a suspended position can have attributes similar to those that are positioned lower, including independent adjustability, height differential relative to one another, tilt, and longitudinal translation.

In some embodiments, systems including adjustable arm supports 1305 can be configured to be mobile. For example, in some embodiments, the base 1303 can include wheels to allow the system to be easily repositioned (see, e.g., FIG. 14A). For example, the system could have a separate transport cart that lifts it off the floor and moves it. In some embodiments, the system is not permanently affixed in the operating room.

Figure 19:
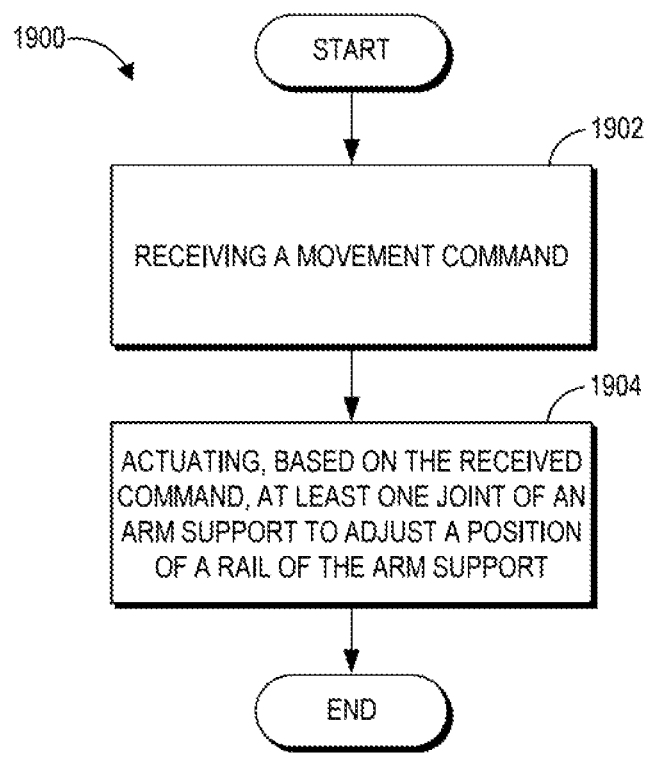
FIG. 19 is a flow chart illustrating a method for operating a surgical robotics system with adjustable arm supports according to one embodiment.

FIG. 19 is a flow chart illustrating a method 1900 for operating a surgical robotics system with adjustable arm supports according to one embodiment. For example, the method 1900 can be used to operate any of the systems described above with reference to FIGS. 13A-18B. In some embodiments, the method 1900 can be stored as computer readable instructions stored in a memory. A processor can access the memory and execute the computer readable instructions to perform the method 1900.

The method 1900 begins at block 1902 which involves receiving a command. In some embodiments, the command is received from a physician, nurse, physician assistant, surgeon staff, etc. The command may relate to the positioning of at least one of a first robotic arm, a medical instrument coupled to an end effector of the robotic first arm, and/or an arm support coupled to a base of the first robotic arm. In some embodiments, the command may be a command to stow or deploy the system.

In some embodiments, a first command actuates the at least one joint to adjust the position of the arm support along a vertical axis of the column, a second command actuates a second joint for pivoting up the arm support, a third command actuates a third joint for tilting the arm support and a fourth command causes longitudinal translation of the arm support.

At block 1904, the method 1900 involves actuating at least one joint of an adjustable arm support to adjust a position of a bar or rail of the arm support based on the received command. For example, the method 1900 may actuate one or more of the first joint, the second joint, the third joint, and/or the fourth joint. This may cause the arm support to move in one or more of its degrees of freedom.

The method 1900 may further include raising the arm support, the first robotic arm, and the second robotic arm from a stowed position below the table; positioning the arm support, the first robotic arm and the second robotic arm adjacent the table; adjusting a position of the arm support relative to the table via at least one of the first command, second command, third command, or fourth command, and adjusting a position of the first robotic arm relative to the second robotic arm along the rail of the support joint in preparation for a surgical procedure. In some embodiments, the arm support is positioned below an upper surface of the table.

In some embodiments, the method 1900 is executed by a controller for executing one or more commands based on a kinematics model, wherein the one or more commands control the positioning of one or more of the first robotic arm, the medical instrument coupled to an end effector of the robotic first arm; and an arm support coupled to a base of the first robotic arm and to a column supporting a patient-support table, wherein the arm support comprises at least one joint and a rail configured to support the first robotic arm.

Figure 20:
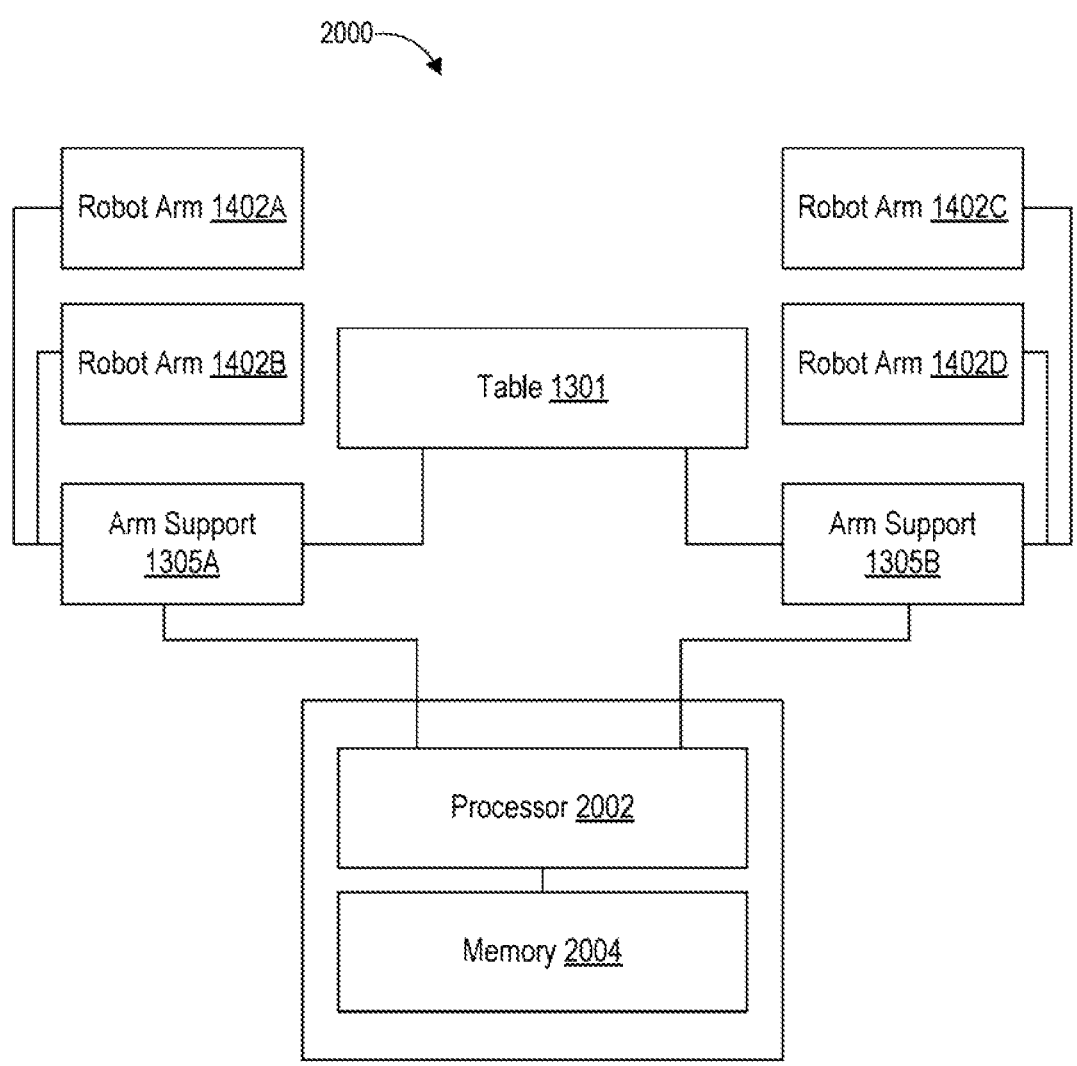
FIG. 20 is a block diagram of a surgical robotics system with adjustable arm supports according to one embodiment.

FIG. 20 is a block diagram of a surgical robotics system 2000 with adjustable arm supports 1305A, 1305B according to one embodiment. As shown, the system 2000 includes a processor 2002 in communication with a memory 2004. The processor 2002 and memory 2004 can be configured to execute, for example, the method 1900 described above.

The system also includes the table 1301. In the illustrated embodiments, two adjustable arm supports 1305A, 1305B are coupled to the table 1301. The adjustable arm supports 1305A, 1305B can be coupled to the table 1301, a column 1302 supporting a table, or a base 1303 supporting the column. Each of the adjustable arm supports 1305A, 1305B is in communication with the processor 2002 such that the process can adjust the position of the adjustable arm supports 1305A, 1305B.

In the illustrated embodiment, a set of robotic arms is attached to each of the adjustable arm supports 1305A, 1305B. For example, robotic arms 1402A, 1402B are coupled to adjustable arm support 1305A, and robotic arms 1402C, 1402D are coupled to adjustable arm support 1305B. In other embodiments, other numbers of robotic arms (e.g., one, three, four, etc.) can be coupled to each arm support 1305A, 1305B. Example robotic arms are described in section XIII below. In some embodiments, as the arm supports support multiple robotic arms, the stiffness of the arm supports can be increased. This increased stiffness provides an added benefit of stability when used with multiple arms, as this can reduce the shaking of the robotic arms during a surgical process.

In some embodiments, the processor 2002 is configured to execute instructions stored in the memory 2004 to adjust a position of the bar or rail along the first axis in response to receiving a command. The command can comprise a command to adjust a position of a robotic medical tool coupled to a robotic arm coupled to the arm support. In some embodiments, the processor 2002 is further configured to execute the instructions to cause the system to at least adjust a position of a rail or the arm supports 1305A, 1305B in response to a physician selected procedure. In some embodiments, the processor 2002 is further configured to execute the instructions to cause the system 2000 to at least adjust a position of the rail to avoid a collision between the robotic arm and at least one of: the table, a patient, an additional robotic arm, and a medical imaging device. The system 2000 may further be configured to avoid collision with other items in the environment of the system, such as, pendants, stirrups, things that clip onto the bed rail, a nurse, etc.). In addition to collision avoidance, the processor 2002 can further be configured to adjust the position of the arm supports 1305A, 1305B to optimize pose or improve manipulability of the robotic arms 1402A, 1402B, 1402C, 1402D.

XIII. Robot Arms Associated with Adjustable Arm Supports

The adjustable arm supports described above can be configured to mount to the table, the column, or the base, and are adjustable (moveable in various degrees of freedom) to support robotic arms positioned on the adjustable arm supports. As the adjustable arm supports can be configured to mount below the surface of the table in accordance with some embodiments, it can be advantageous to employ certain types of robotic arms with the adjustable arm supports. In particular, robot arms that have increased movement and flexibility may be desirable, as the robot arms may have to "work up" from a lower position and avoid collisions (e.g., with the table). This section outlines certain features of robotic arms configured for use with adjustable arm supports.

For example, in some embodiments, robotic arms configured for use with the adjustable arm supports differ from parallelogram remote center robotic arms. In one example, a robotic arm configured for use with the adjustable arm supports can comprise a shoulder with at least two degrees of freedom, an elbow with at least one degree of freedom, and a wrist with at least two degrees of freedom. The kinematics associated with such an arm allow the arm base to be positioned arbitrarily relative to the workspace, allowing for setups that would be challenging for a parallelogram remote center robot mounted alongside a bed.

Further, in some embodiments, a robotic arm configured for use with the adjustable arm supports may include a semi-spherical or spherical wrist configured with at least three degrees of freedom. Such a wrist can allow the robotic arm to roll its wrist joint such that an instrument drive mechanism positioned at the distal end of the robotic arm can be below the arm wrist. This can enable procedures where target workspaces are far above ports.

Some surgical robotic arms include a mechanically constrained remote center with no redundant degrees of freedom (e.g., parallelogram robotic arms). That is, for any remote center position, the distance to the base is mechanically constrained. Robotic arms coming from below the bed, as is the case with robotic arm mounted on the adjustable arm supports described above, can be limited by their mount structures and cannot reach the optimal configurations to make parallelogram robot arms excel. To address this issue, robotic arms configured for use with the adjustable arm supports described above can include one or more redundant degrees of freedom. The redundant degrees of freedom can allow the arms to be jogged within their null space without moving the tool tip, allowing for intraoperative collision avoidance that is not possible previously known surgical robotic arms.

Figure 21:
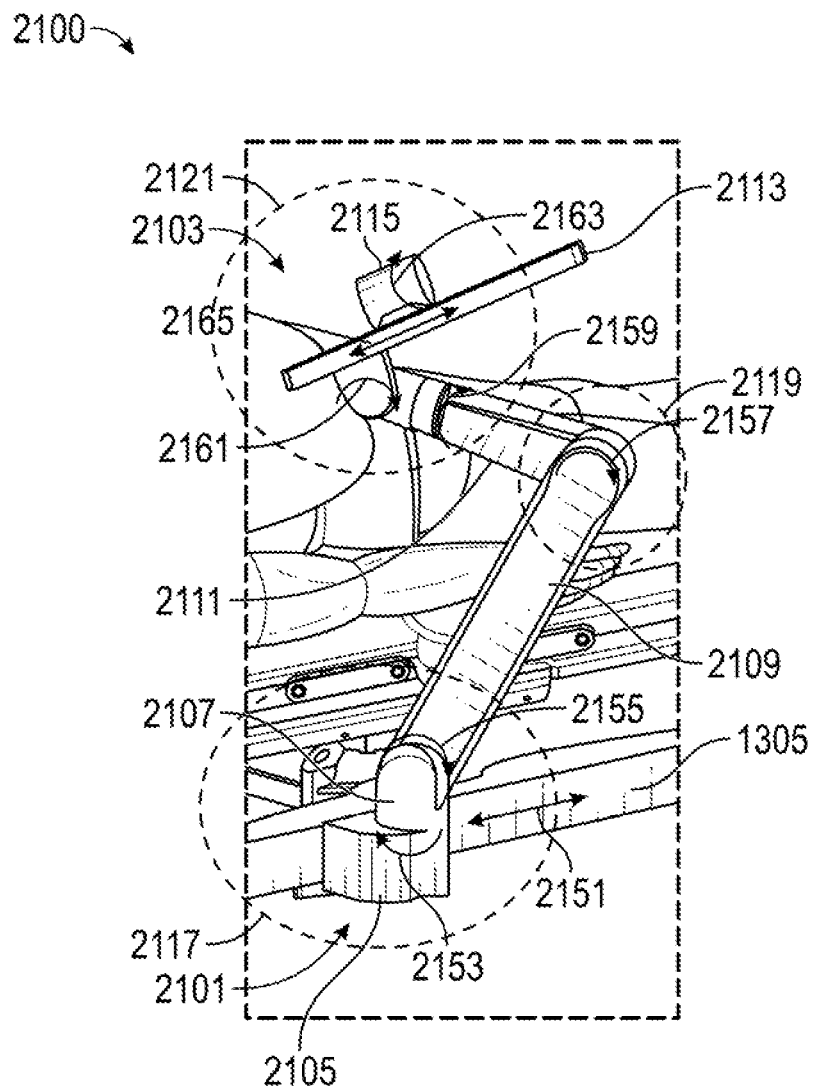
FIG. 21 is an isometric view of a robotic arm according to one embodiment.

FIG. 21 is an isometric view of a robotic arm 2100, according to one embodiment, which may be configured to provide one or more of the features or advantages described above. The robotic arm 2100 can be configured for use with the adjustable arm support(s) 1305 described above. The robotic arm 2100 may comprise a plurality of components arranged serially. The components can be connected by one or more joints (e.g., motorized or hydraulic joints) configured to allow movement or articulation of the robotic arm 2100. As illustrated, for some embodiments, the joints can be grouped into the shoulder 2117, the elbow 2119, and the wrist 2121.

In the illustrated example, the shoulder 2117 includes three joints, the elbow 2119 includes one joint, and the wrist 2121 includes two joints. Stated another way, in some embodiments, one or more of the shoulder 2117, the elbow 2119, or the wrist 2121 can provide more than one degree of freedom for the robotic arm 2100. In the illustrated embodiment, the shoulder 2117 is configured to provide three degrees of freedom, the elbow 2119 is configured to provide one degree of freedom, and the wrist 2121 is configured to provide two degrees of freedom. In other embodiments, the shoulder 2117, the elbow 2119, or the wrist 2121 can be configured with other numbers of joints and/or to provide other numbers of degrees of freedom.

The shoulder 2117 can be located generally at a proximal portion 2101 of the robotic arm 2100. The wrist 2121 can be located generally at a distal portion 2103 of the robotic arm 2100. The elbow 2119 can be located generally between the proximal portion 2101 and the distal portion 2103. In some embodiments, the elbow 2119 is located between a proximal link 2109 and a distal link 2111. In some embodiments, the robotic arm 2100 can include other joints or regions of joints than those illustrated in FIG. 21. For example, the robotic arm 211 could include a second elbow (comprising one or more joints) between the elbow 2119 and the wrist 2121 and/or between the elbow 2110 and the shoulder 2117.

The shoulder 2117, elbow 2119, and wrist 2121 (and/or other joints or components of or associated with the robotic arm) can provide various degrees of freedom. For the illustrated embodiment, the degrees of freedom are illustrated with arrows. The arrows are intended to indicate the motions provided by each degree of freedom. The illustrated embodiment includes the following degrees of freedom. Not all degrees of freedom need be included in all embodiments, and in some embodiments, additional degrees of freedom can be included. The joints providing the various degrees of freedom can be powered joints, such as motorized joints or hydraulically powered joints, for example.

As illustrated, the robotic arm 2100 includes a degree of freedom permitting shoulder translation. The robotic arm 2100 can also include a degree of freedom permitting shoulder yaw. The robotic arm 2100 can also include a degree of freedom permitting shoulder pitch. The robotic arm 2100 can also include a degree of freedom permitting elbow pitch. The robotic arm 2100 can also include a degree of freedom permitting wrist yaw. The robotic arm 2100 can also include a degree of freedom permitting wrist pitch. The robotic arm 2100 can also include a degree of freedom permitting instrument driver roll. This degree of freedom can be configured allow an instrument attached to the instrument driver (or the instrument driver itself) to be rolled around its axis.

An insertion degree of freedom can also be associated with the robotic arm 2100. The insertion degree of freedom can be configured to permit insertion (or retraction) of the instrument (or tool) attached to an instrument driver mechanism 2115 along an axis of the instrument or an axis of the instrument driver 2115.

XIV. Motorized Arms for Adjustable Arm Supports

As described above, robotic systems can include adjustable arm supports for supporting and positioning robotic arms for use during robotic medical or surgical procedures. For example, FIG. 13A illustrates an example adjustable arm support 1305 that includes a bar or rail 1307 on which one or more robotic arms can be mounted. In this example, the bar or rail 1307 is coupled to a column 1302 of a table 1301 by a bar or rail connector 1311 and a carriage 1309 as described above. The adjustable arm support 1305 is adjustable in several degrees of freedom that allow the bar or rail 1307 of the adjustable arm support 1305 to be positioned at a large number of positions relative to the table 1301. As discussed above, the adjustable arm support 1305 may also be configured to transition to a stowed position, wherein the adjustable arm support 1305 and robotic arms mounted thereto are stowed below the surface of the table 1301 (for example, as shown in FIG. 18B).

This section provides further detail related to features and structures of a connector that connects the bar or rail of an adjustable arm support to the column of the table. For example, as will be described below, the connector can include a motorized arm that connects a rail or bar of the adjustable arm support to a column of the table. In some embodiments, the motorized arm may include, for example, the carriage and rail or bar connector described above. In some embodiments, the motorized arm may include, alternatively or additionally, one or more of the additional features described in this section with reference to FIGS. 22-36.

As will be described more fully below, the motorized arms can include one or more links that are configured to raise, lower, tilt, and/or otherwise position the arm supports (e.g., the bars or rails of the adjustable arm supports) that support the robotic arms. In some instances, the motorized arms can be considered base or set-up arms or joints because they can be designed and configured to position the arm supports prior to actuation of the robotic arms during a medical procedure. For example, in some instances, the motorized arms are configured to move the arm supports (and robotic arms mounted thereto) from a stowed position (e.g., FIG. 18B) to a set-up position (e.g., FIG. 18A). In some instances, in the set-up position, the motorized arms and arm supports may remain stationary while the robotic arms mounted on the arm supports move to perform the medical procedure. In some instances, the motorized arms and/or arm supports also move during the medical procedure. Accordingly, in some embodiments, the motorized arms are configured to raise, lower, and angulate the arm supports, and can move the attached robotic arms from a lower, stowed position into a raised position in preparation for surgery. In some embodiments, the motorized arms can enable clinicians or physicians to have better access to the head or foot of the patient, thereby enabling procedures such as urology and gastrointestinal (GI) procedures.

As described in this section and above, various embodiments for the motorized arms that support the arm supports are possible and some examples are provided below. For example, FIGS. 22-26 provide a first example, wherein the motorized arm comprises a single link. FIGS. 27-35B relate to a second example, wherein the motorized arm comprises a dual link design. These two examples, which are described in detail below, are provided by way of illustration and not limitation. Those of ordinary skill in the art will appreciate, upon consideration of this disclosure, that various features described in relation to the illustrated examples can be modified and combined in various ways. For example, features of the first illustrated example can be combined with features of the second illustrated example and vice versa.

XIV. (a) Single Link Motorized Arms

Figure 22:
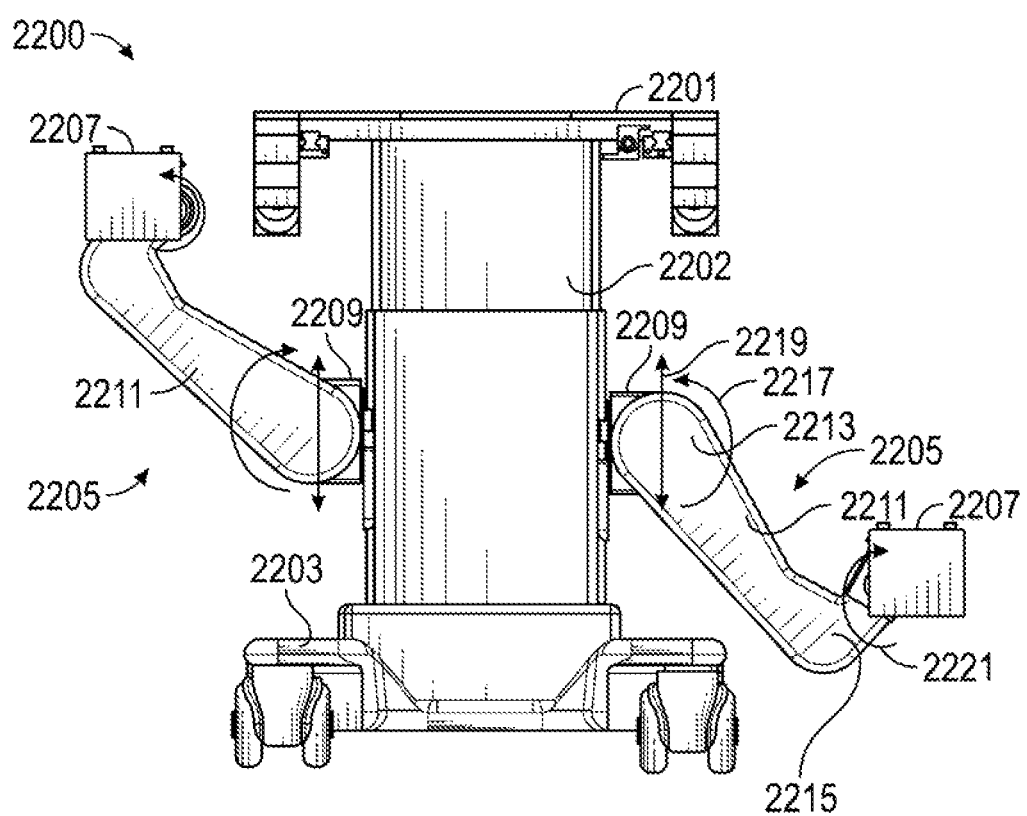
FIG. 22 is an end view of an embodiment of a robotic system that includes two single-link motorized arms for positioning arm supports.
Figure 24:
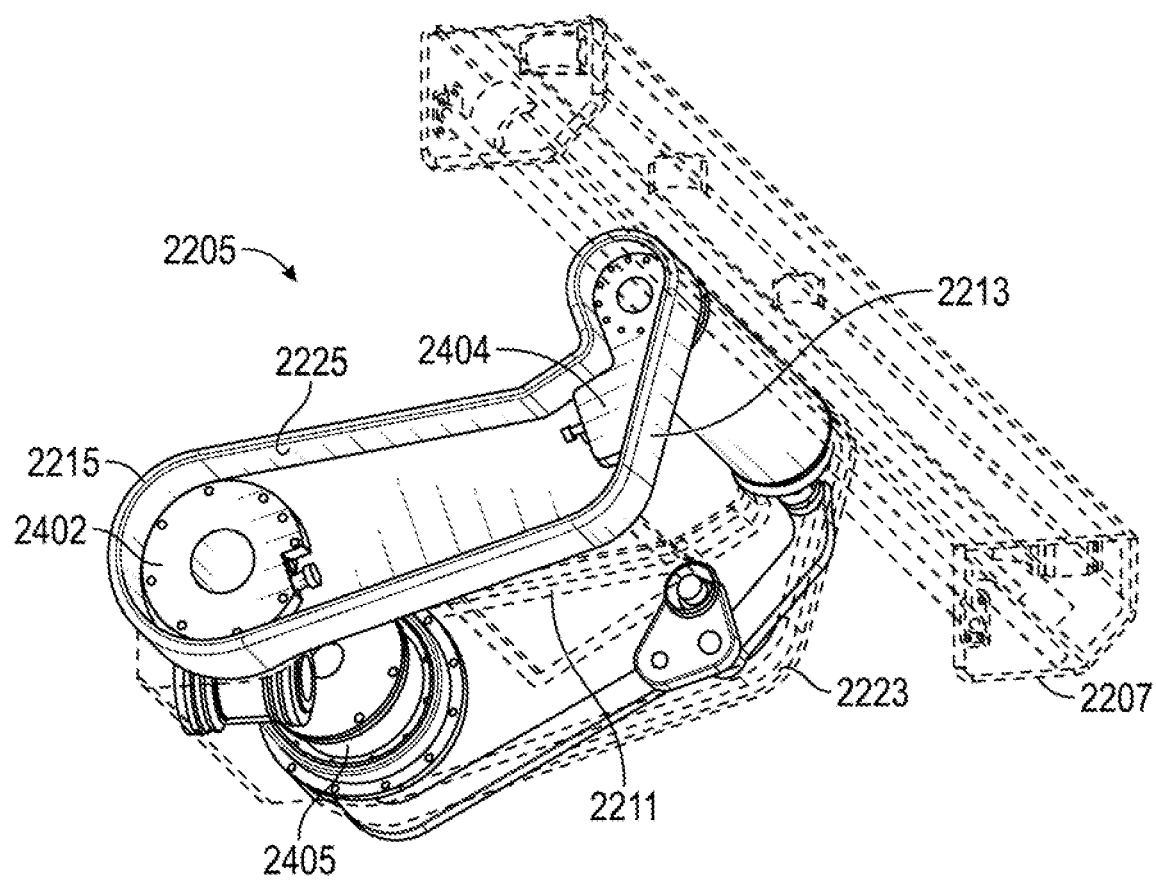
FIG. 24 is an isometric view of an embodiment of a motorized arm and an arm support.

FIG. 22 illustrates an end view of a medical robotic system 2200 that includes two motorized arms 2205 that position the robotic arm supports or rails 2207. In this example, each motorized arm 2205 comprises a single link 2211 that extends between a shoulder 2209 and an arm support 2207. The term "link" as used throughout this application can refer to any link and its associated structures that are kinematically associated with one or more degrees of freedom and/or joint movements. In some embodiments, a single "link" can comprise two or more structural pieces that a coupled together. For example, as shown in FIG. 24 (described in more detail below) the link 2211 comprises a first lateral side piece 2223 and a second lateral side piece 2225 that are structurally coupled together to form the single link 2211. The arm supports 2207 may comprise a bar or rail on which one or more robotic arms can be mounted as discussed above. As will be discussed below, the link 2211 can be configured to rotate about the shoulder 2209 in a sweeping or "bicep curl" type motion. This bicep curl type motion of the link 2211 in conjunction with the additional degrees of freedom of the motorized arm 2205 can advantageously provide a significant range of motion that can provide a high number of possible positions for the arm support 2207. For example, in some embodiments, the motorized arm comprises a significant range of motion to adequately achieve many or all positions required for robotic medical procedures or surgery, such as robotic laparoscopic surgery.

In the illustrated embodiment, the two motorized arms 2205 are positioned on opposite sides of a column 2202 that supports a table 2201 above a base 2203. That is, one motorized arm 2205 is positioned on a first lateral side of the column 2202 and the other motorized arm 2205 is positioned on a second lateral side of the column 2202 opposite the first lateral side. In this configuration, one motorized arm 2205 can be configured to position the connected arm support 2207 on the first lateral side of the table 2201 and the other motorized arm 2205 can be configured to position the connected arm support 2207 on the second lateral side of the table 2201. As illustrated in the example of FIG. 22, each motorized arm 2205 can be independently controllable and positionable, such that arm supports 2207 can be positioned at different positions on each side of the table 2201. While the two motorized arms 2205 can be independently controllable and positionable, they may comprise similar features. Thus, the following discussion will focus on one of the motorized arms 2205 with the understanding that the other motorized arm 2205 can be similar. In some embodiments, the robotic system 2200 includes only one motorized arm 2205. In some embodiments, the robotic system 2200 includes more than one motorized arm 2205. For example, the robotic system 2200 can include two motorized arms 2205 (as illustrated), three motorized arms 2205, four motorized arms 2205, etc.

A single link motorized arm 2205, for example, as illustrated in FIG. 22, may comprise one or more innovative features that allow it to perform effective bed-mounted robotic laparoscopic or endoscopic surgery (or other robotic medical procedures) while also stowing to a compact form within or proximal to the base 2203 to, for example, allow access for manual surgery. To be useable for a wide variety of medical procedures, the arm supports 2207 must be capable of being positioned in multiple positions or configurations relative to the table 2201. As noted previously, the motorized arm 2205 provides significant range of motion to adequately achieve these positions.

As noted above, the link 2211 of the motorized arm 2205 extends between the shoulder 2209 and the arm support 2207. The link 2211 can extend between a proximal end 2213 and a distal end 2215. The proximal end 2213 of the link 2211 can be coupled to the shoulder 2209. In some embodiments, the proximal end 2213 of the link 2211 is coupled to the shoulder 2209 with a rotational joint. The rotational joint that couples the proximal end 2213 of the link 2211 to the shoulder 2209 can provide a rotational degree of freedom 2217 as shown, which permits the link 2211 to rotate relative to the shoulder 2209. The rotational joint between the shoulder 2209 and the link 2211 may be configured to allow rotation about an axis that extends through the shoulder 2209 and the proximal end 2213 of the link 2211 and that is parallel to a longitudinal axis of the about the table 2201 so as to provide the rotational degree of freedom 2217.

In some embodiments, the rotational degree of freedom 2217 is configured to allow at least 120 degrees, at least 140 degrees, at least 150 degrees, at least 160 degrees, at least 170 degrees, at least 180 degrees of rotation, or more. The rotational degree of freedom 2217 can be measured from the fully lowered position, wherein the arm support 2207 is positioned proximal to the base 2203. In some embodiments, the link 2211 wraps around the column 2202, as discussed below) allowing additional rotation. In some embodiments, the rotational range can be as large as possible, while still avoiding collision with the table 2201 or other structures.

Such rotation can allow the link 2211 to rotate relative to the shoulder 2209 to deploy the arm support 2207 in the sweeping or bicep curl type motion discussed above. In some embodiments, the rotation of the joint between the link 2211 and shoulder 2209 allows the arm support 2207 to be placed laterally close or far away from the table 2201 or column 2202, but only at specific angles of rotation. Thus, in some embodiments, the motorized arm 2205 can include an additional degree of freedom 2219 that allows the height of the arm support 2207 to also be adjusted at various angles of rotation. This can effectively allow the user or the system to have vertical and lateral positional control of the arm support 2207 location relative to the table 2201, which advantageously allows for the flexible positioning of the arm support 2207 to accommodate different surgical or medical procedures, as well as to clear patient positioning accessories and accommodate various patient widths.

As illustrated in FIG. 22, the degree of freedom 2219 may comprise a translational degree of freedom 2219 along an axis that is parallel to the axis of the column 2202. This translational degree of freedom 2219 can be provided by the connection or joint of the shoulder 2209 to the column 2202. For example, the shoulder 2209 can be coupled to the column 2202 with a joint that translates vertically along the column 2202. The joint between the shoulder 2209 and the column 2202 can comprise a linear, sliding, or prismatic joint so as to allow for the translational degree of freedom 2219 for the motorized arm 2205. In some embodiments, this joint can be referred to as a "z-lift" mechanism because it translates along the z-axis. In some embodiments, the translational degree of freedom 2219 is configured translate along a length of the column 2202. In some embodiments, the translational degree of freedom 2219 is configured to allow translation along 30%, 40%, 50%, 60%, 70%, 80%, 90%, or more of the length of the column 2202. In some embodiments, the translational degree of freedom 2219 is configured to allow at least 20 cm, at least 30 cm, at least 40 cm, at least 50 cm or more of translation along the length of the column 2202.

In combination, the shoulder 2209, the link 2211, the rotational degree of freedom 2217 (provided by the rotational joint between the shoulder 2209 and the link 2211), and the translational degree of freedom 2219 (provided by the joint between the shoulder 2209 and the column 2202) can provide the motorized arm 2205 with a high range of motion that allows the arm support 2207 (positioned at the distal end 2215 of the link 2211) to be positioned at many horizontal and vertical distances relative to the table 2201. Specifically, rotation of the link 2211 about the shoulder 2209 (with the rotational degree of freedom 2219) can allow the arm support 2207 to be positioned at different horizontal and vertical distances relative to the table 2201, and translation of the shoulder 2209 along the column 2202 (with the translational degree of freedom 2219) can allow the arm support 2207 to be positioned at different vertical distances relative to the table 2201. In some embodiments, rotation of the link 2211 about the shoulder 2209 (with the rotational degree of freedom 2219) can allow the arm support 2207 to have a circular sweep about a pivot point at the shoulder 2209.

Figure 31:
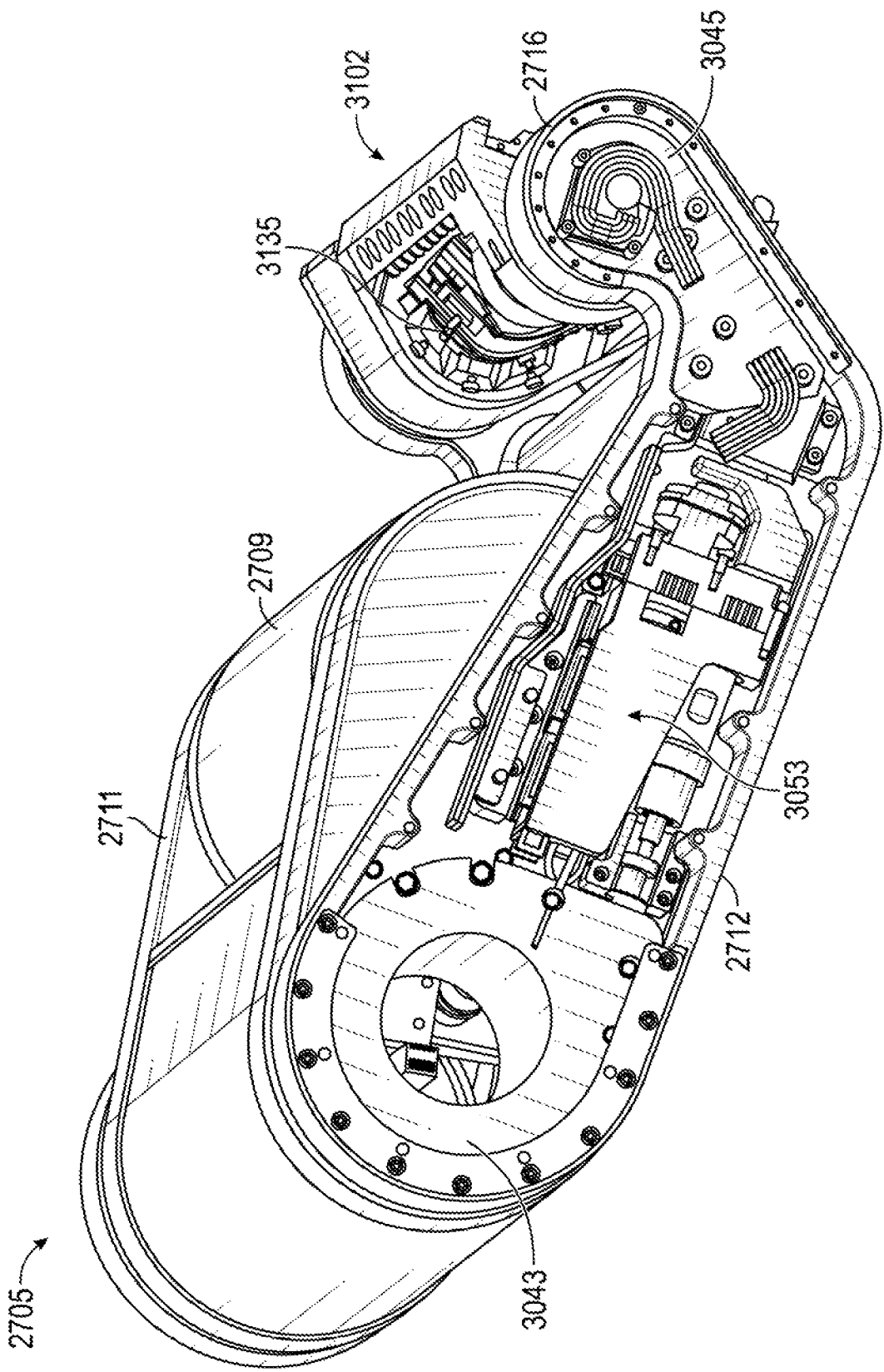
FIG. 31 is an isometric view of a dual-link motorized arm that includes an embodiment of an arm support linkage.
Figure 32:
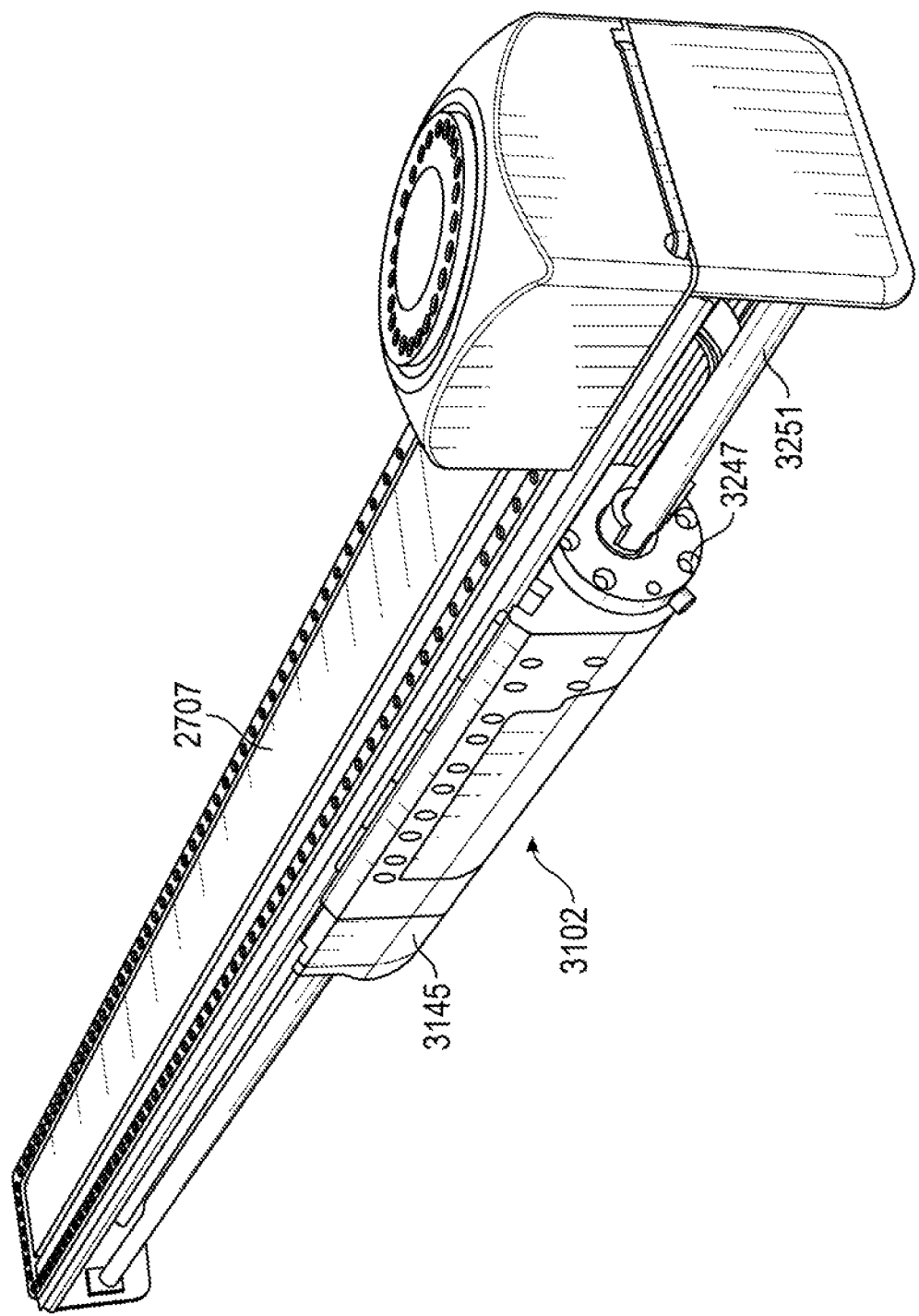
FIG. 32 is a perspective view of an embodiment of an arm support linkage and attached arm support.

As illustrated in FIG. 22, the distal end 2215 of the link 2211 can be coupled to the arm support 2207. In some embodiments, the distal end 2215 of the link 2211 can be coupled to the arm support 2207 with a rotational joint that provides a rotational degree of freedom 2221. The rotational degree of freedom 2221 can be configured to enable the motorized arm 2205 to tilt or rotate the arm support 2207 that supports the robotic arms. In some embodiments, an additional mechanism is provided at the distal end 2215 of the link 2211, thereby allowing the arm support 2207 to translate relative to the link 2211 (an example is shown in FIGS. 31-32, described below).

In some embodiments, the rotational degree of freedom 2221 can be constrained to the rotational degree of freedom 2217 so as to maintain an orientation of the arm support 2207 during rotation of the link 2211 about the shoulder 2209. For example, in some embodiments, it may be beneficial to maintain the arm support 2207 such that an upper surface of the arm support 2207 remains level (e.g., parallel to a surface of the table 2201 or the floor) regardless of the rotational position of the link 2211. An example mechanism for constraining the rotational degree of freedom 2221 to the rotational degree of freedom 2217 is shown in FIGS. 23A and 23B.

Figure 23A:
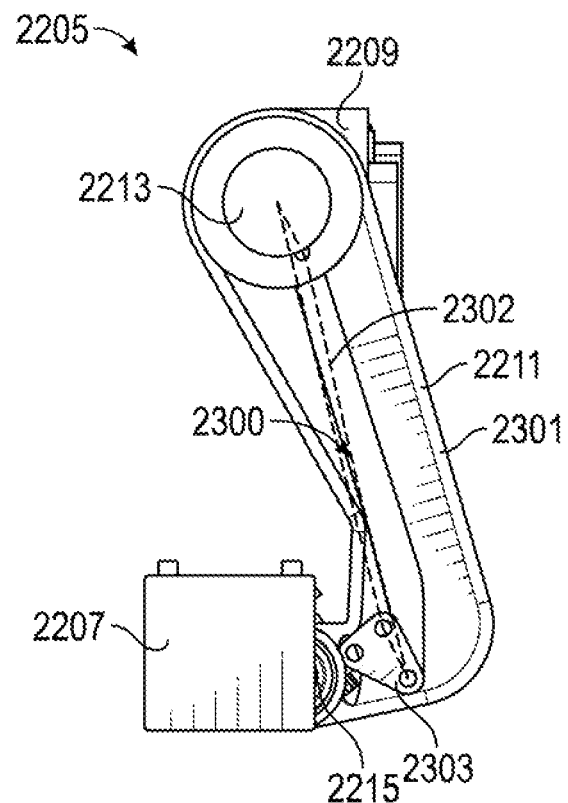
FIGS. 23A and 23B, illustrate an embodiment of a four-bar linkage in a motorized arm support for constraining the orientation of the arm support.
Figure 23B:
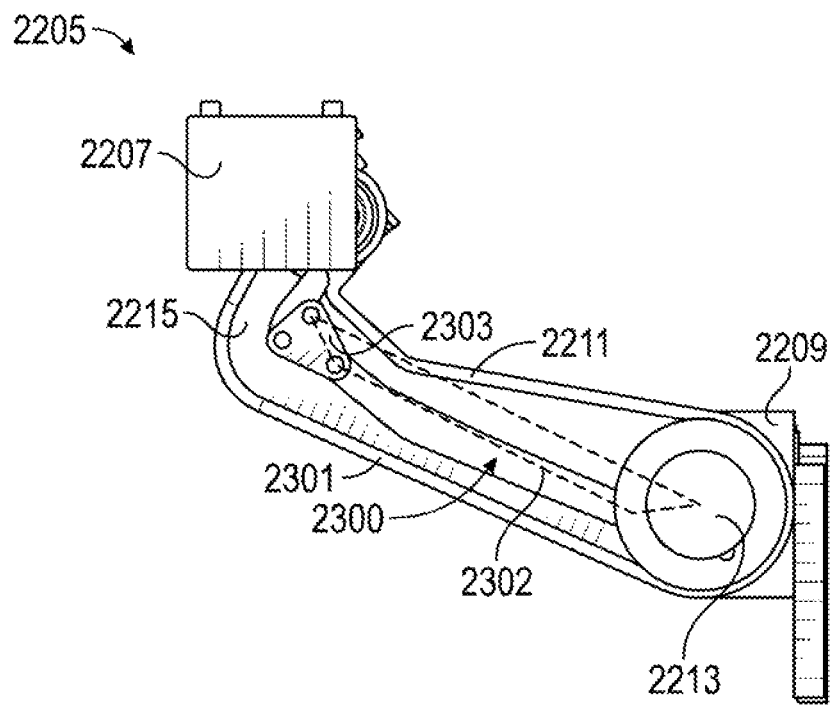

FIGS. 23A and 23B illustrate an embodiment of a motorized arm 2205 that includes a mechanism for constraining rotation of the arm support 2207 to rotation of link 2211 so as to maintain an orientation of the arm support 2207 during rotation of the link 2211. In the illustrated embodiment, the motorized arm support 2205 includes a four-bar linkage 2300 configured to constrain rotation of the arm support 2207 to rotation of link 2211 so as to maintain the arm support 2207 in a position wherein an upper surface of the arm support 2207 remains level or parallel with the floor or the table, regardless of how the link 2211 is rotated relative to the shoulder 2209. For example, in FIG. 23A, the link 2211 is rotated to a downward position, and the four-bar linkage 2300 maintains the arm support 2207 in a level position. In FIG. 23B, the link 2211 is rotated to a different position, an extended position, yet still the four-bar linkage 2300 maintains the arms support 2207 in a level position.

This can be advantageous as this can maintain the orientation of robotic arms attached to the arm support 2207 regardless of the position of the motorized arm 2205. Further, because the rotation of the arm support 2207 is constrained to the link 2211, the system need only control a single rotational degree of freedom. For example, rather than controlling both rotational degrees of freedom 2217, 2221, the system need only control the rotational degree of freedom 2217.

FIGS. 23A and 23B illustrate some internal features of the motorized arm 2205 to illustrate the four-bar linkage 2300. FIG. 23A shows the motorized arm 2205 in an example stowed position, while FIG. 23B shows the motorized arm 2205 in an example raised position. As illustrated in FIGS. 23A and 23B, the motorized arm 2205 can include an actuator positioned within the proximal end 2213 of the link 2211. In some embodiments, the actuator comprises a motor and a harmonic drive gearbox. Other types of actuators are also possible. The motorized arm 2205 also includes the four-bar linkage 2300, which can include a first link 2301 and a second link 2302 (which together form a primary linkage) and a secondary linkage 2303. The motor can be configured to drive the first link 2301, which may comprise the primary structure of the four-bar linkage 2300. For example, the motor may cause the first link 2301 to rotate relative to the shoulder 2209. The second link 2302 of the four-bar linkage 2300 can connect to a secondary linkage system 2302, which maintains the orientation of the arm support 2307. In FIGS. 23A and 23B, the four bars of the four-bar linkage 2300 are illustrated with dashed lines.

Other mechanisms for constraining the orientation of the arm support 2207 are also possible. For example, in some embodiments, a six-bar linkage can be used instead of the four-bar linkage 2300. In some embodiments, software may control a motor associated with the orientation of the arm support 2207 to constrain the orientation of the arm support 2207.

As shown in FIGS. 23A and 23B, in some embodiments, an actuator comprising a motor and a gearbox are positioned in the proximal end of the link 2211 to control rotation of the motorized arm 2205 (i.e., the sweep or bicep curl motion of the link 2211). In some embodiments, additional features may be incorporated to increase the stiffness of the motorized arm 2205 to allow for accurate robotic arm use. For example, in some embodiments, a high torsional stiffness brake can be added to the link 2211 at the proximal end 2213 and/or the distal ends 2213, as shown in FIG. 24.

Figure 23C:
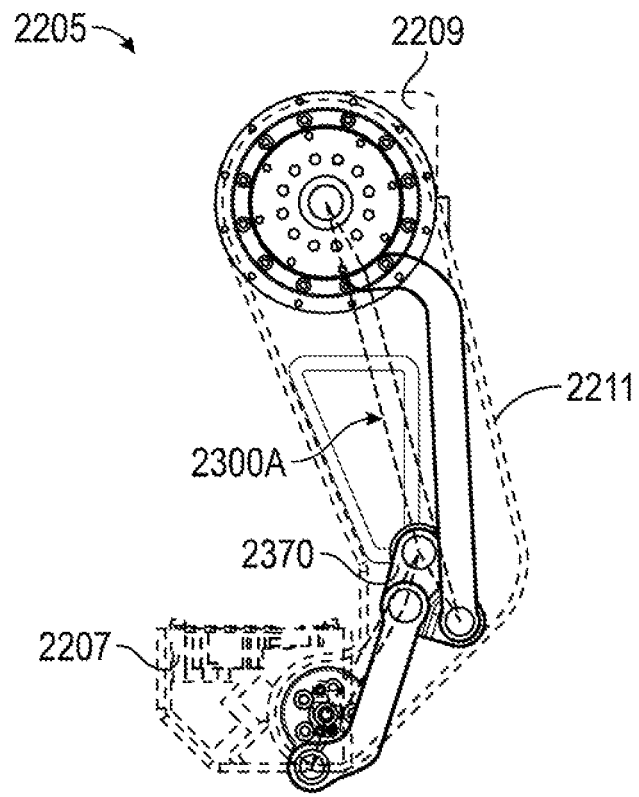
FIGS. 23C and 23D, illustrate an embodiment of a dual four-bar linkage in a motorized arm support for constraining the orientation of the arm support.
Figure 23D:
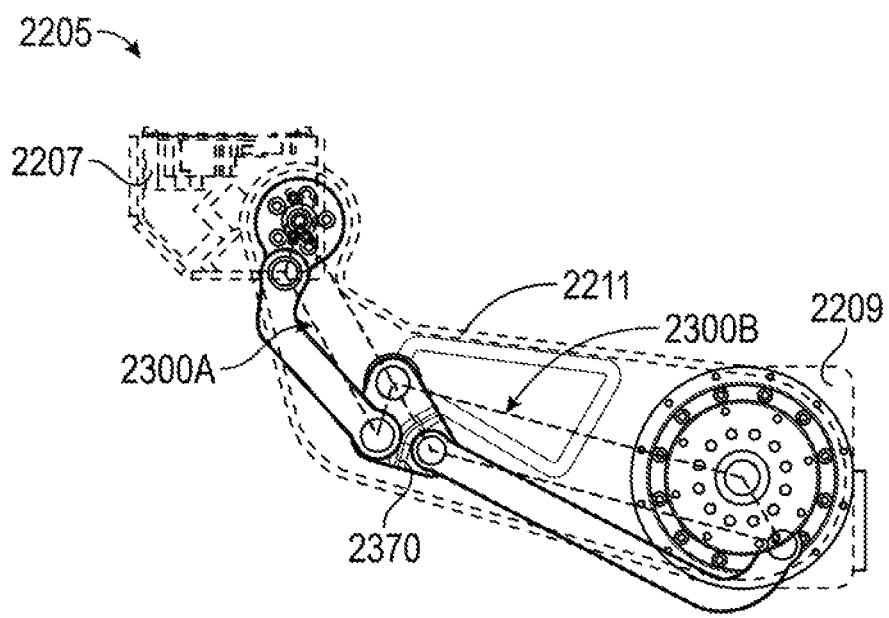

FIGS. 23C and 23D illustrate an additional embodiment of the link 2211 that includes dual four-bar linkages 2300A, 2300B. FIG. 23C shows the motorized arm 2205 in a stowed position, while FIG. 23C shows the motorized arm 2205 in a raised position. The dual four-bar linkages 2300A, 2300B can be configured to maintain the orientation of the arm support 2207 during rotation of the link 2211 relative to the shoulder 2209. In FIGS. 23C and 23D, the first four-bar linkage 2300A is illustrated in dashed lines, and the second four-bar linkage 2300B is illustrated in dot-dash lines. As illustrated, the first four-bar linkage 2300A and the second four-bar linkage 2300B can be connected via a plate 2370 such that motion of the second four-bar linkage 2300B is constrained to motion of the first four-bar linkage 2300A. In some embodiments, two four-bar linkages 2300A, 2300B can be used to reduce collisions with the link 2211.

FIG. 24 illustrates an isometric view of an embodiment of the motorized arm 2205 that includes a proximal torsional stiffness mechanism 2402 (illustrated as an arbor) and a distal tortional stiffness mechanism 2404 (illustrated as an arbor). The proximal torsional stiffness mechanism 2402 and the distal torsional stiffness mechanism 2405 can be configured to increase the stiffness of the motorized arm 2205. As shown in FIG. 24, in some embodiments, the link 2211 can include a first lateral side 2223 and an opposite second lateral side 2225. In some embodiments, an actuator 2405 including one or more of a motor, brake, sensor and/or gearbox can be positioned in the proximal end 2213 of the link 2211 at the first lateral side 2223. In some embodiments, the actuator 2405 can include a brake in the form of an electromagnetic brake. On the second lateral side 2225, the proximal end 2213 of the link 2211 can include the proximal torsional stiffness mechanism 2402. Thus, the actuator 2405 including a motor can be positioned on one lateral side and the proximal torsional stiffness mechanism 2402 can be positioned on the other lateral side of the link 2211. The proximal torsional stiffness mechanism 2402 can be a high torsional stiffness brake. In some embodiments, the proximal torsional stiffness mechanism 2402 can be part of a hydraulic arbor brake system. The proximal torsional stiffness mechanism 2402 can be configured to increase the stiffness of the motorized arm 2205 when actuated. For example, in some embodiments, the actuator 2405, including the motor, is used to rotate the link 2211 to a rotational position. The torsional stiffness mechanism brake 2402 can be disengaged before rotation of the link 2211. Once in position, the proximal torsional stiffness mechanism 2402 can be engaged to increase the stiffness of the motorized arm 2205. In some embodiments, the proximal torsional stiffness mechanism 2402 or braking system can be considered part of a hydraulic expansion arbor brake system as described further below (see, for example, FIGS. 30A, 30B, 33A, 33B, and 33C). The distal torsional stiffness mechanism 2404 can similarly be used to increase the torsional stiffness of the motorized arm 2205 at the joint between the link 2211 and the arm support 2207. Other types of brakes can also be used. For example, in some embodiments, one or both of the proximal torsional stiffness mechanism 2402 and the distal torsional stiffness mechanism 2404 can be an arbor (as described below); a spring engaged, electromagnetic tooth brake; or a spring engaged, hydraulic released tooth brake. In some embodiments, alternatively or additionally, a higher stiffness gearbox in the actuator 2405 (such as a cycloidal gearbox in place of the harmonic gearbox) could also be used to increase torsional stiffness.

FIG. 24 also illustrates that a second, or distal brake 2404 may be included in the distal end 2215 of the link 2211. In the illustrated embodiment, the distal brake 2404 can be included on the second lateral side 2225 of the link 2211. That is, in some embodiments, both the proximal and distal brakes 2402, 2404 are on the same lateral side of the link 2211. This need not be the case in all embodiments. For example, the distal brake 2404 can be included on the first lateral side 2223. The distal brake 2404 can operate in a manner similar to the proximal brake 2402. For example, the distal brake 2404 can be configured to increase the stiffness of the motorized arm 2205. In some embodiments, like the proximal brake 2402, the distal brake 2404 can be part of a hydraulic expansion arbor brake system as described further below. Other types of brakes can be used instead a hydraulic expansion arbor brake system, including a spring engaged, electromagnetic tooth brake system or a spring engaged, hydraulic released tooth brake system.

The motorized arm 2205 described herein with reference to FIGS. 22-24 can also be configured to provide unique advantages for compactly stowing the robotic arms that are attached to the patient platform. For example, the motorized arm 2205 can lower the arm supports 2207 (and attached robotic arms) to a position below the table 2201 and proximal to the base 2203 or the floor to stow the robotic arms. This can allow, for example, access to the patient for manual surgery, as well as access for additional systems (e.g., a fluoroscopic c-arm), to be provided near the patient platform. To facilitate stowage, in some embodiments, the motorized arm 2205 is configured such that the link 2211 wraps around the column 2202, thereby bringing the motorized arm 2205 as close to the column 2250 as possible so as to remain within the footprint of the table 2201. This can be advantageous from a clinical perspective as may not limit patient-side access when the robotic system is not in use. These features are shown, for example, in FIGS. 25A, 25B, and 26.

Figure 25A:
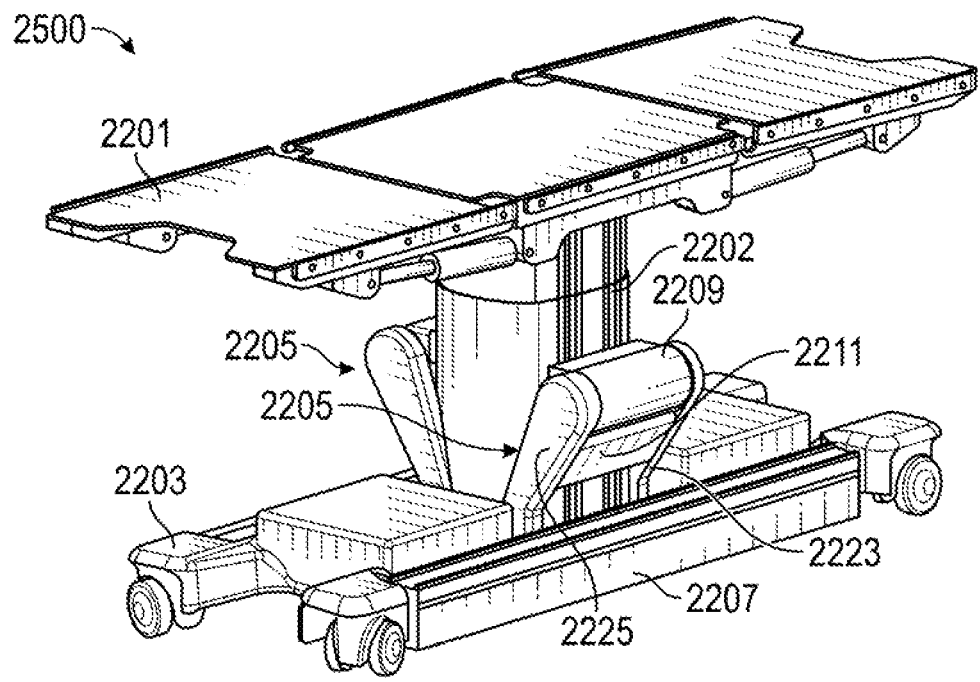
FIGS. 25A and 25B show perspective and end views, respectively, of an embodiment of a robotic system that includes two single-link motorized arms in a stowed configuration.
Figure 25B:
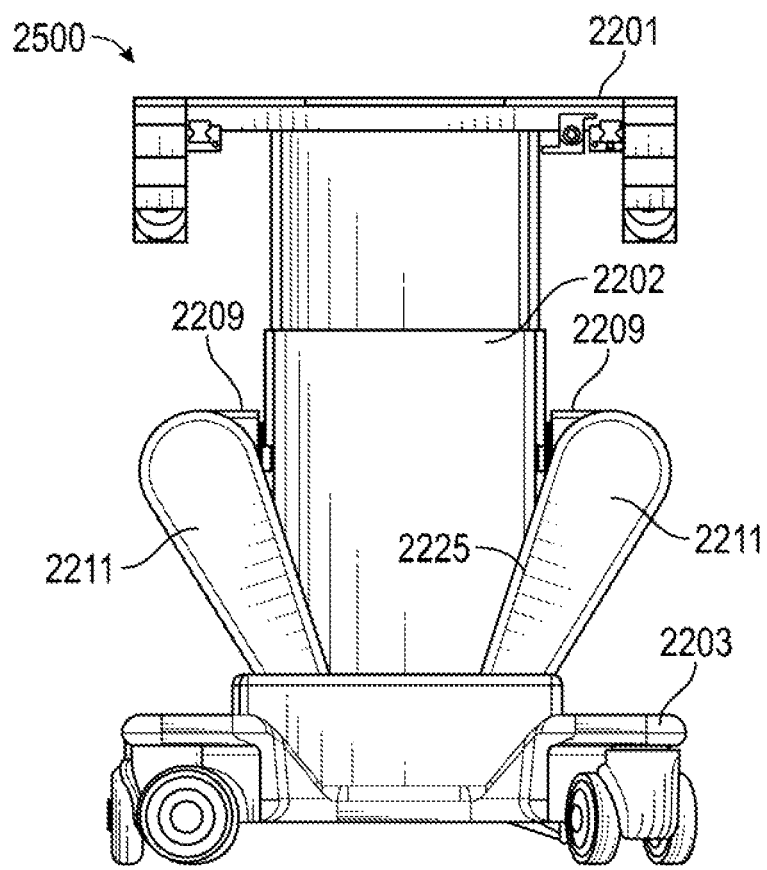

FIGS. 25A and 25B illustrate an isometric view and an end view, respectively, of a system 2500 including two motorized arms 2205 according to the present disclosure. In these embodiments, the motorized arms 2205 are illustrated in an example stowed configuration. As shown, the motorized arms 2205 are positioned such that the arm supports 2207 are stored below the table 2201, for example, in a position in or proximal to the base 2203. As shown in the illustrated embodiment of FIGS. 25A and 25B, the link 2211 wraps around the column 2202 in this position. For example, in this embodiment, the link 2211 includes a first lateral side 2223 and a second lateral side 2225 as mentioned above. For at least a portion of the link 2211 the first lateral side 2223 can be spaced apart from the second lateral side 2225. When in the stowed configuration, the column 2202 can extend between the first lateral side 2223 and a second lateral side 2225 such that the link 2211 wraps around the column 2202. This configuration may advantageously reduce the amount of space required to store the motorized arms 2205 when not in use.

Figure 26:
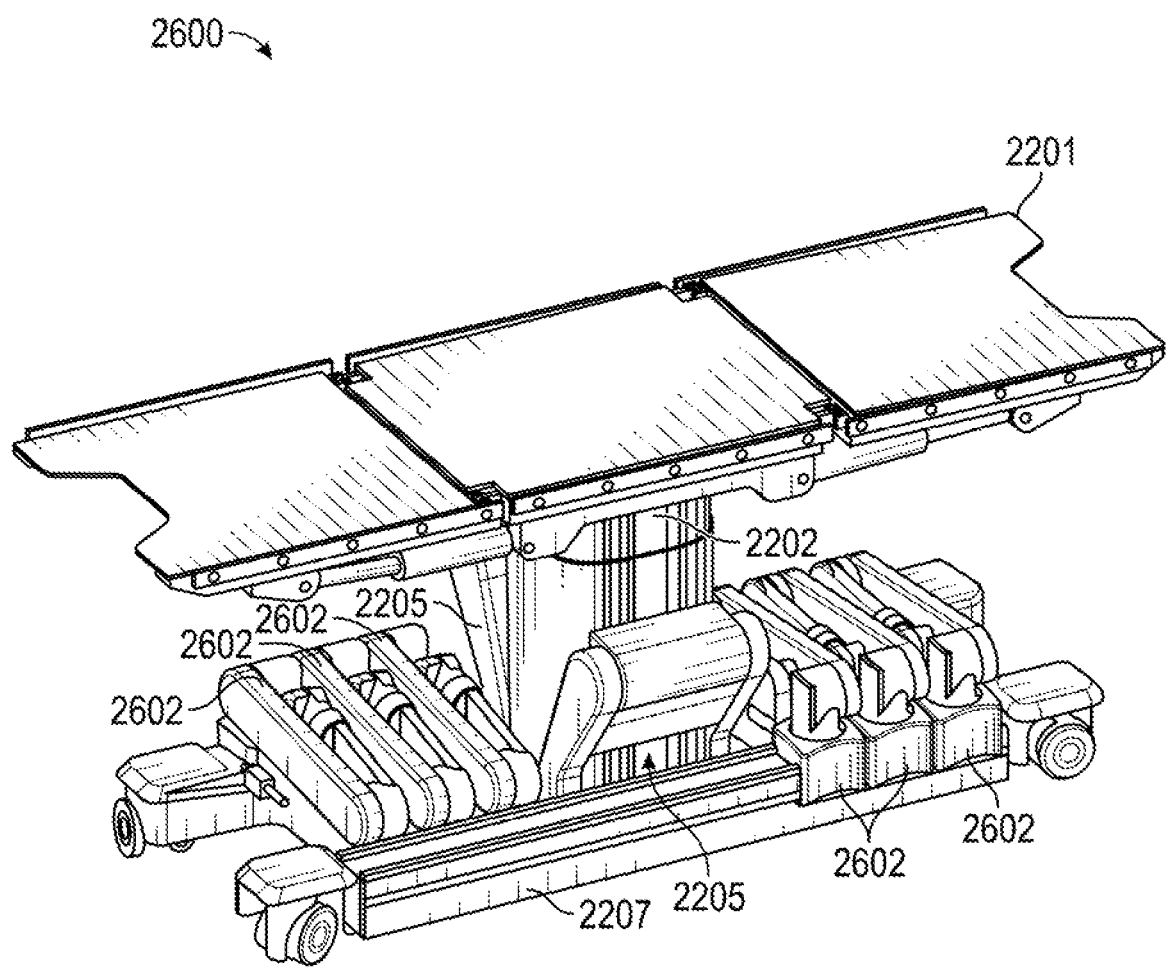
FIG. 26 is a perspective view of an embodiment of a robotic system that includes two single-link motorized arms and six robotic arms in a stowed configuration.

FIG. 26 illustrates a system 2600 including two motorized arms 2205 and six robotic arms 2602 in the stowed configuration. As illustrated, each arm support 2207 may support three robotic arms 2602. When in the stowed configuration, the robotic arms 2602 associated with each arm support 2207 can be folded below the table 2201 as shown in the present embodiment. FIG. 26 illustrates that the system 2600, including two motorized arms 2205 and six robotic arms 2602, can have a compact size when in the stowed configuration. In some embodiments, other numbers of robotic arms 2602 can be used. For example, the system 2600 may include one, two, three, four, five, six, seven, eight, or more robotic arms 2602.

An advantage of the motorized arm 2205 as illustrated in FIGS. 22-26 can include, in some embodiments, only one rotational degree of freedom being needed to transition from a compact stowed position to a fully deployed procedural position. This can facilitate compact packaging. For example, in some embodiments, transitioning between a stowed position and a deployed position comprises rotating the link 2211 about the shoulder 2209 using the rotational degree of freedom 2217. In some embodiments, an additional, translational degree of freedom 2219 may also be actuated to transition between the stowed position and the deployed position. Further, in some embodiments, the orientation of the arm support 2207 is constrained (e.g., via the four-bar linkage 2300 of FIGS. 23A and 23B) so as to eliminate the need to have a separate actuator at the distal end 2215 of the link 2211 to maintain the orientation of the arm support 2207.

XIV. (b) Dual Link Motorized Arms

Figure 27:
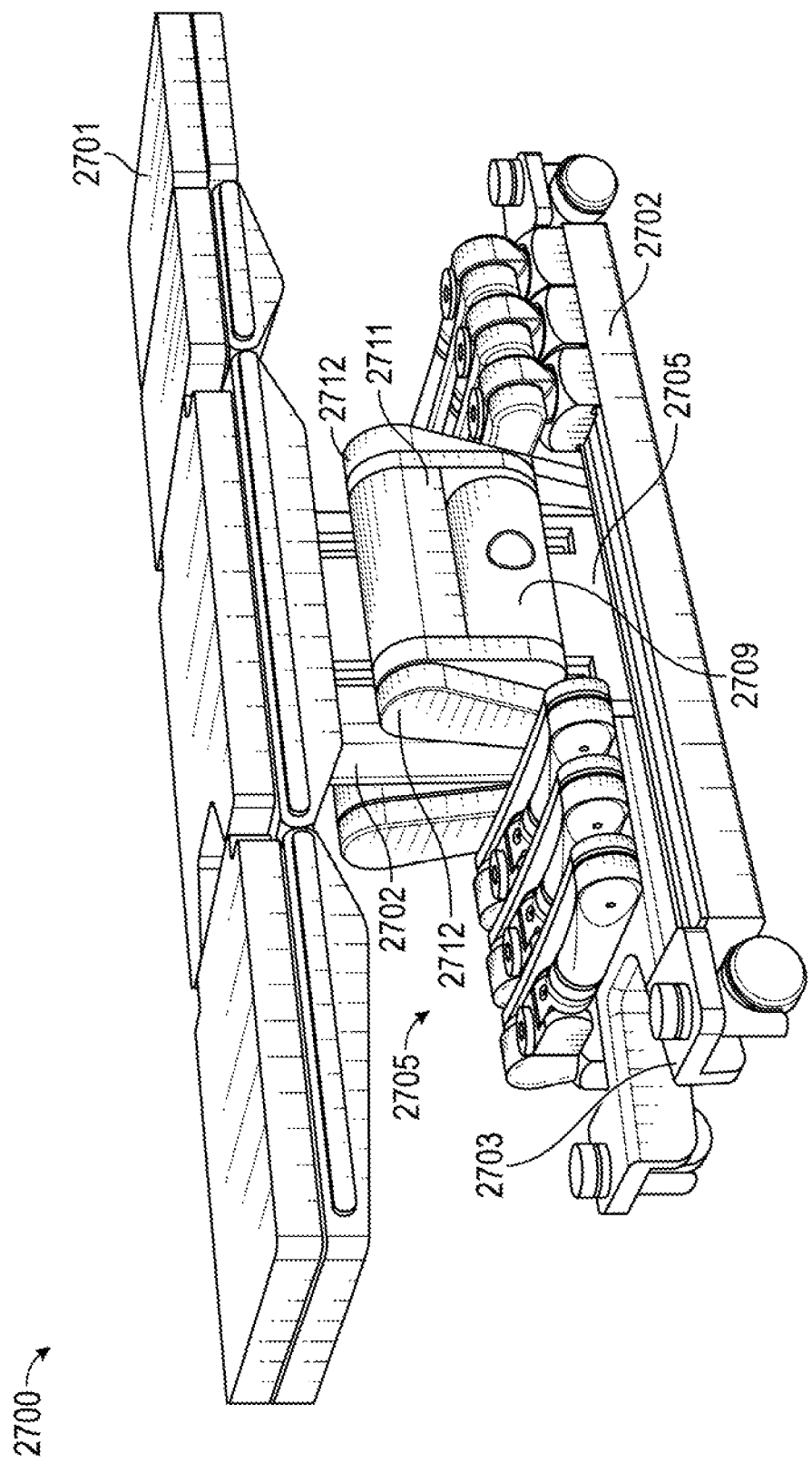
FIG. 27 is a perspective view of an embodiment of a robotic system that includes two dual-link motorized arms and six robotic arms in a stowed configuration.

FIG. 27 illustrates a perspective view of a medical robotic system 2700 that includes two motorized arms 2705. In this example, each motorized arm 2705 comprises a dual-link configuration that includes a first link 2711 and a second link 2712. As shown, the first link 2711 is connected to a shoulder 2709. The shoulder 2709 can be connected to a column 2702 as previously described. The column 2702 extends between a table 2701 and a base 2703. The first link 2711 is also connected to the second link 2712. The second link 2712 is connected to an arm support 2707. The arm support 2707 may comprise a bar or rail on which one or more robotic arms can be mounted as discussed above (e.g., bar or rail 1307). In contrast with the single link design of the motorized arm 2205 of FIGS. 22-26, the dual-link design of the motorized arm 2705 of FIG. 27 includes the first link 2211 and the second link 2212 extending between the shoulder 2709 and the arm support 2707. As will be described in more detail below, the second link 2212 can be configured to rotate relative to the first link 2211 to provide an additional rotational degree of freedom for the motorized arm 2705. This additional degree of freedom can allow for increased clinical workspace and reach above the table 2701, thereby providing greater flexibility for positioning the arm supports 2707 and the attached robotic arms. Further, in some embodiments, with the additional rotational degree of freedom between the first link 2711 and the second link 2712, the motorized arm 2705 may be less likely to contact the side of the table 2701.

In the illustrated embodiment, the two motorized arms 2705 are positioned on opposite sides of the column 2702 that supports the table 2701 above the base 2703. In some embodiments, each motorized arm 2705 can be independently controllable and positionable, such that arm supports 2707 can be positioned at different positions on each side of the table 2701. While the two motorized arms 2705 can be independently controllable and positionable, they may comprise similar features. Thus, this discussion will focus on one of the motorized arms 2705 with the understanding that the other motorized arm 2705 can be similar. In some embodiments, the robotic system 2700 includes only one motorized arm 2705. In some embodiments, the robotic system 2700 includes more than one motorized arm 2705. For example, the robotic system 2700 can include two motorized arms 2705 (as illustrated), three motorized arms 2705, four motorized arms 2705, etc. Further, in the illustrated embodiment of FIG. 27, each motorized arm 2705 and arm support 2707 supports three robotic arms. Other numbers of robotic arms may be used in other embodiments.

FIG. 27 further illustrates that, similar to the systems discussed above, the motorized arms 2705 of the robotic medical system 2700 can be configured to be stored in a compact space below the table 2701. For example, the motorized arms 2705 can be configured to move the arm supports 2707 to a position in or proximal to the base 2703 as shown. As will be discussed more fully below, the motorized arms 2705 can be configured to move from this stowed configuration (as shown, for example, in FIG. 27) to a range of deployed positions that enable the robotic arms to be employed during robotic surgical or medical procedures.

Figure 28A:
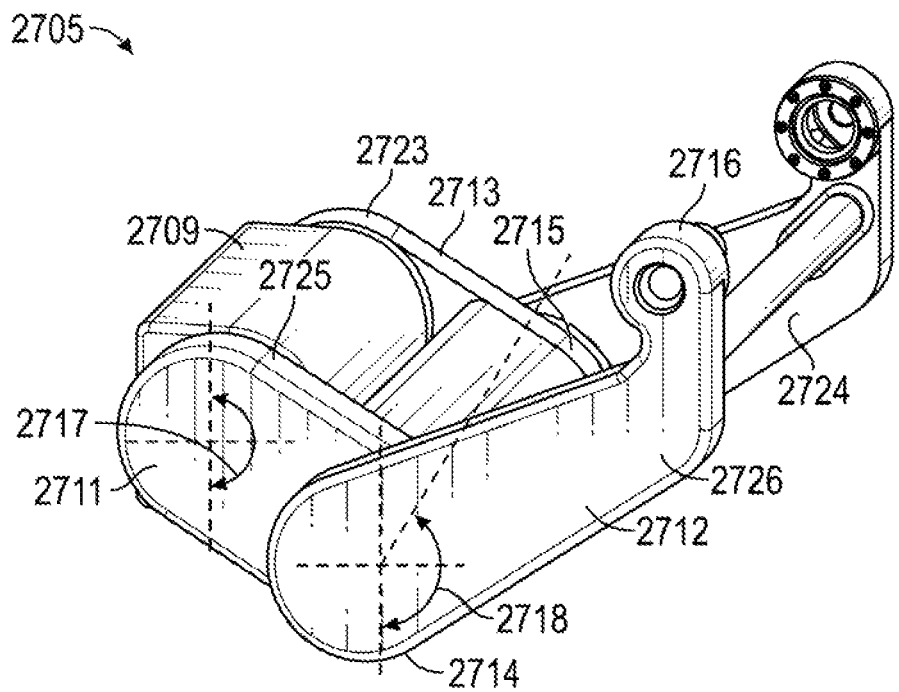
FIGS. 28A and 28B illustrate perspective views of an embodiment of a dual-link motorized arm in extended and stowed configurations, respectively.
Figure 28B:
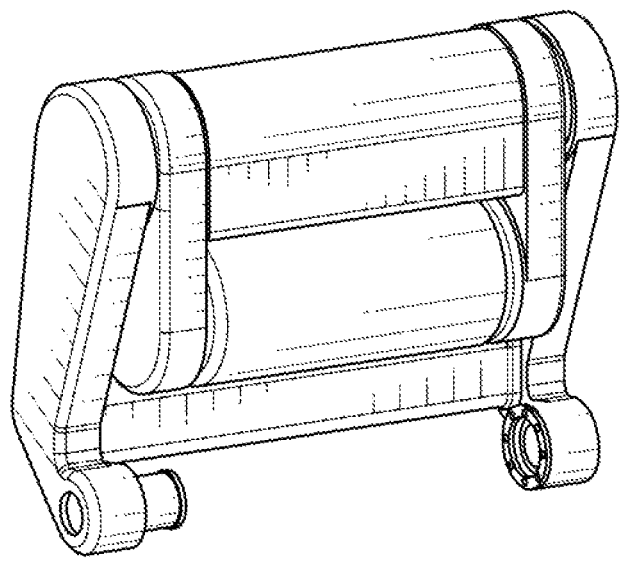

FIGS. 28A and 28B illustrate an embodiment of the motorized arm 2705 alone. FIG. 28A illustrates the motorized arm 2705 in an example deployed position, and FIG. 28B illustrates the motorized arm 2705 in an example stowed position. As shown in FIGS. 28A and 28B, the motorized arm 2705 comprises the shoulder 2709, the first link 2711, and the second link 2712. Although not illustrated in FIGS. 28A and 28B, the second link 2712 is further configured to connect to the arm support 2707, as shown in FIG. 27 and as will be described in more detail below with reference to FIGS. 31 and 32. The shoulder 2709 may be similar to the shoulder 2209 described previously with reference to FIGS. 22-26. For example, the shoulder 2709 may be coupled to the column 2702 with a joint that allows the shoulder 2709 to translate along the column 2702, for example, in a z-lift motion as described above.

The first link 2711 extends between a proximal end 2713 and a distal end 2715. As illustrated in FIGS. 28A and 28B, the proximal end 2713 can be connected to the shoulder 2709 by a rotational joint. The rotational joint between the proximal end 2713 of the first link 2711 and the shoulder 2709 can be configured to permit the first link 2711 to rotate relative to the shoulder 2709 with a first rotational degree of freedom 2717. In some embodiments, the first rotational degree of freedom 2717 allows for 180 degrees of rotation for the first link 2711, although this need not be the case in all embodiments. For example, in some embodiments, the first rotational degree of freedom 2717 allows for greater than or less than 180 degrees of rotation for the first link 2711. In some embodiments, the first rotational degree of freedom 2717 allows the first link 2711 to move relative to the shoulder 2709 in a bicep curl or sweeping motion.

As illustrated in FIGS. 28A and 28B, the first link 2711 may comprise a first lateral side 2723 and a second lateral side 2725. As shown, the first lateral side 2723 may be separated from the second lateral side 2725 to create a space therebetween. The shoulder 2709 can be positioned between the first lateral side 2723 and the second lateral side 2725 of the first link 2711. That is, the first lateral side 2723 can be connected to a first lateral side of the shoulder 2709 and the second lateral side 2725 can be connected to a second lateral side of the shoulder 2709. This configuration can advantageously allow the first link 2711 to rotate relative to the shoulder 2709 over a large range of motion (e.g., 180 degrees) without the first link 2711 coming into contact with the shoulder 2709.

The second link 2712 also extends between a proximal end 2714 and a distal end 2716. As illustrated in FIGS. 28A and 28B, the proximal end 2714 of the second link 2712 can be connected to the distal end 2715 of the first link 2711 by a rotational joint. The rotational joint between the proximal end 2714 of the second link 2712 and the distal end 2715 of the first link 2711 can be configured to permit the second link 2712 to rotate relative to the first link 2711 with a second rotational degree of freedom 2718. In some embodiments, the second rotational degree of freedom 2718 allows for 150 degrees of rotation for the second link 2712 relative to the first link 2711, although this need not be the case in all embodiments. For example, in some embodiments, the second rotational degree of freedom 2718 allows for greater than or less than 150 degrees of rotation for the second link 2712 relative to the first link 2711. In some embodiments, the second rotational degree of freedom 2718 allows the second link 2712 to move relative to the first link 2711 in a bicep curl or sweeping motion.

Similar to the first link 2711, the second link 2712 may also comprise a first lateral side 2724 and a second lateral side 2726. As shown, the first lateral side 2724 may be separated from the second lateral side 2726 to create a space therebetween. The first link 2711 can be positioned between the first lateral side 2724 and the second lateral side 2726 of the second link 2712. That is, the first lateral side 2724 of the second link 2712 can be connected to a first lateral side 2723 of the first link 2711 and the second lateral side 2726 of the second link 2712 can be connected to the second lateral side 2725 of the first link 2711. This configuration can advantageously allow the second link 2712 to rotate relative to the first link 2711 over a large range of motion (e.g., 150 degrees) without the second link 2712 coming into contact with the first link 2711. This configuration can also allow the motorized arm 2705 to fold to a small, compact size in the stowed configuration, as shown, for example, in FIGS. 27 and 28B.

The distal end 2716 of the second link 2712 can be configured to connect to an arm support 2707 (not illustrated in FIGS. 28A and 28B) configured as a rail or bar for supporting one or more robotic arms. Features of the distal end 2716 of the second link 2712 will be described in more detail below with reference to FIGS. 31 and 32.

Because the motorized arm 2705 includes two links 2711, 2712 that are each configured to rotate with their own rotational degree of freedom 2717, 2718, the motorized arm 2705 is capable of moving an attached arm support to an even wider range of positions to facilitate robotic medical procedures. In some embodiments, for example, inclusion of the second link 2712 and additional rotational degree of freedom 2718 enables the motorized arm 2705 to reach around the table 2701 and next to the patient.

Figure 29:
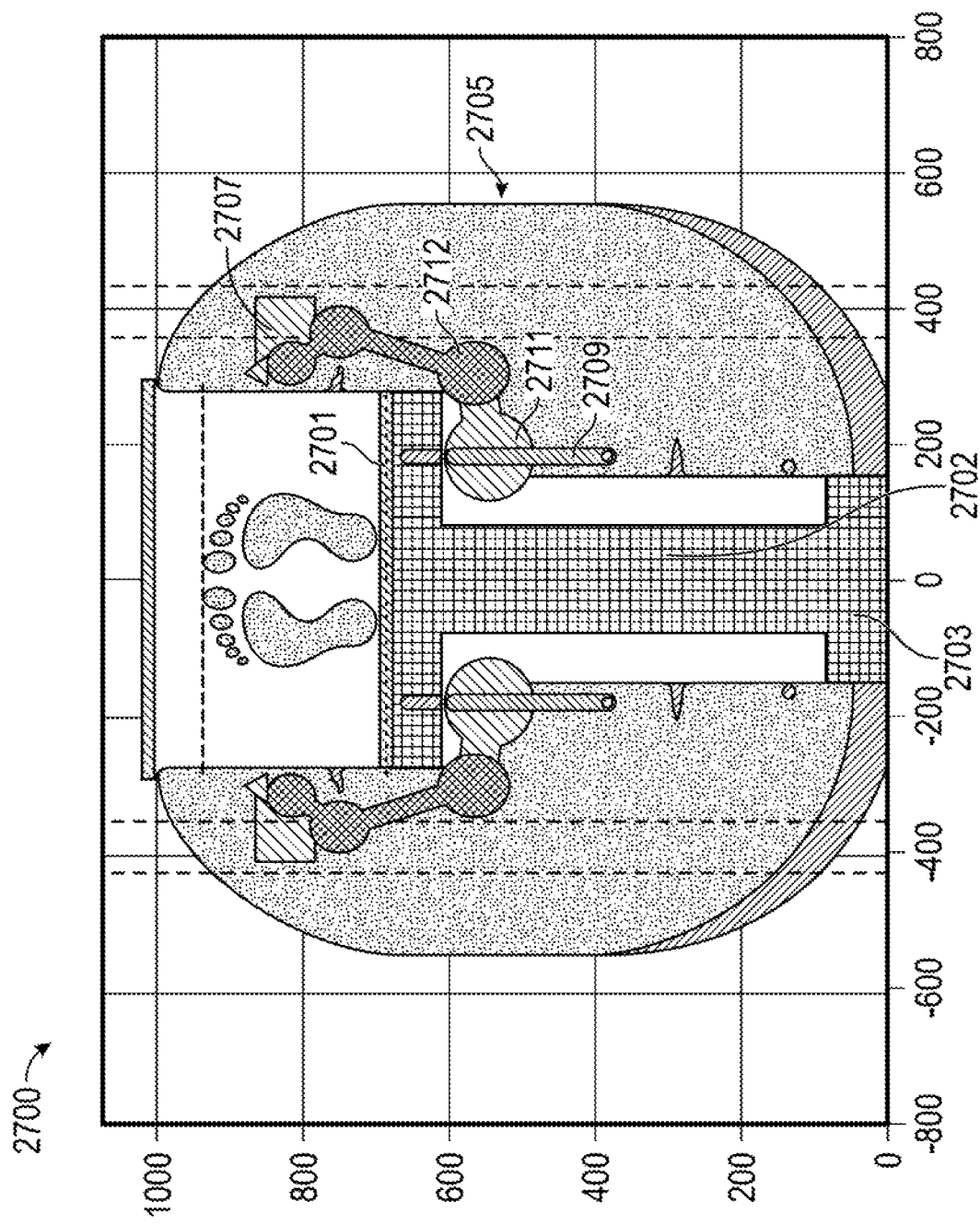
FIG. 29 schematically illustrates the different positions at which arm supports can be positioned using a dual-link motorized arm, according to one embodiment.

FIG. 29 schematically illustrates the different positions at which the motorized arms 2705 can position the arm supports 2707 attached thereto according to one embodiment. In FIG. 29, the shaded area represents the area in which the arm supports 2707 can be positioned using the motorized arm 2705. As shown, the first link 2711, and the second link 2712 allow the arm supports 2707 to reach around the table 2701 to position the arm supports above the table 2701 proximal to the patient. Further, as illustrated by the shaded area of FIG. 29, it is apparent that the motorized arms 2705 can position the arm supports 2707 at a large number of different positions. Thus, the motorized arms 2705 can be suitable for providing a wide number of set up positions for the arm supports 2707.

The high number of possible positions for the arm supports 2707 achievable with the motorized arms 2705 (represented by the shaded area in FIG. 29) can be attributed to, in some embodiments, the ability of the shoulder 2709 to translate along the column 2702, the ability of the first link 2711 to rotate relative to the shoulder 2709, and the ability of the second link 2712 to rotate relative to the first link 2711.

Rotation of the first link 2711 relative to the shoulder 2709 can be driven by an actuator positioned within the first link 2711. The actuator can include one or more of a motor, brake, sensor, and/or gearbox. In some embodiments, the motor may be positioned within the shoulder 2709. Rotation of the second link 2712 relative to the first link 2711 can be driven by a motor positioned within the second link 2712. In some embodiments, the motor may be positioned within the first link 2711. Once the motorized arm 2705 has been rotated to the desired position, brakes may be engaged to stop rotation, hold the motorized arm 2705 in place, and increase the torsional stiffness of the motorized arm 2705. In some embodiments, the motorized arm may further include arbors positioned within the shoulder 2709, the first link 2711, and/or the second link 2712 that may also be engaged to further increase the torsional stiffness of the motorized arm 2705. These features of the motorized arm 2705 relating to the motors, brakes, and arbors will now be described in greater detail with reference to FIGS. 30A-36.

Figure 30A:
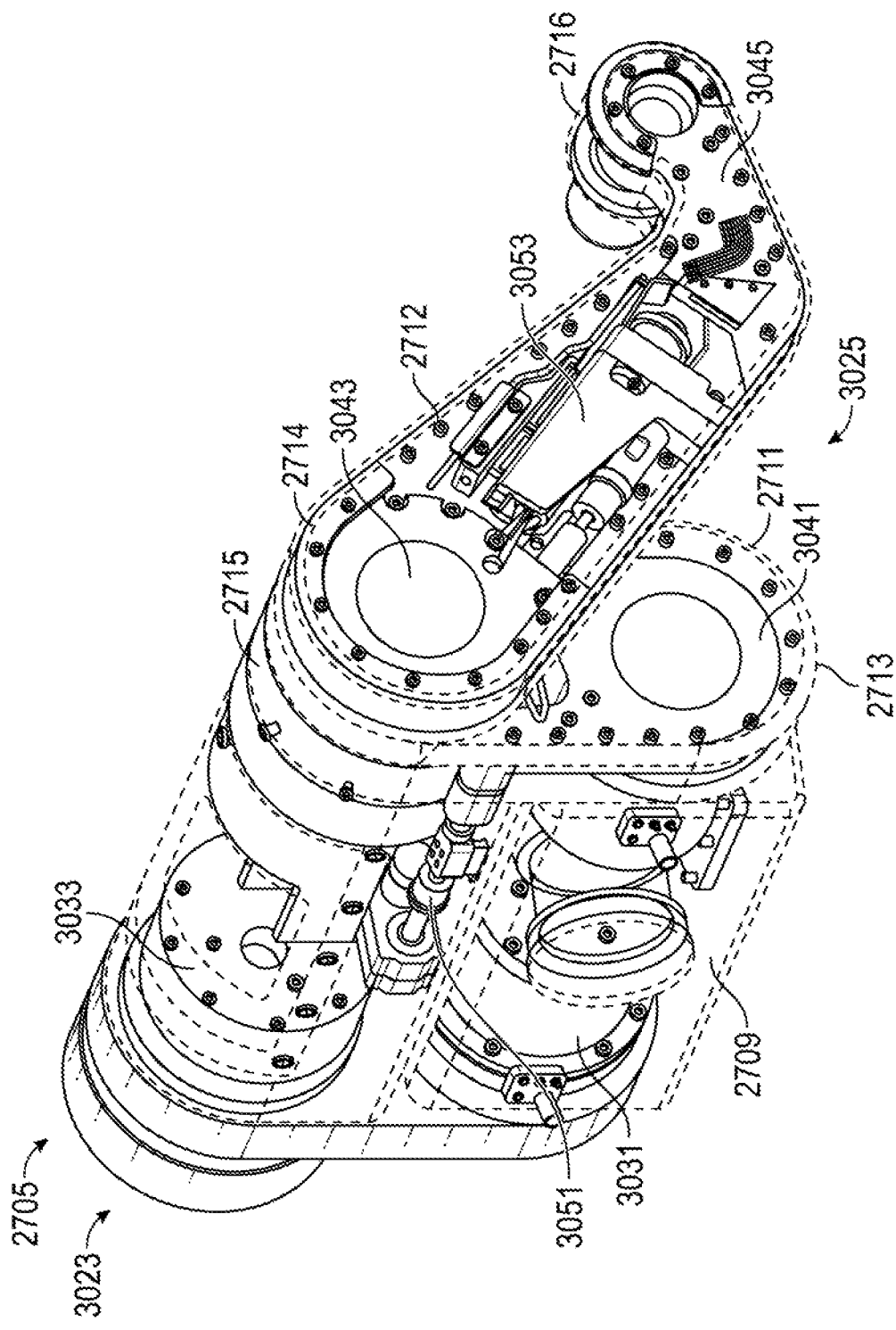
FIG. 30A is an isometric view of an embodiment of a dual-link motorized arm shown with transparent covers so as to visualize the motors and arbors within.
Figure 30B:
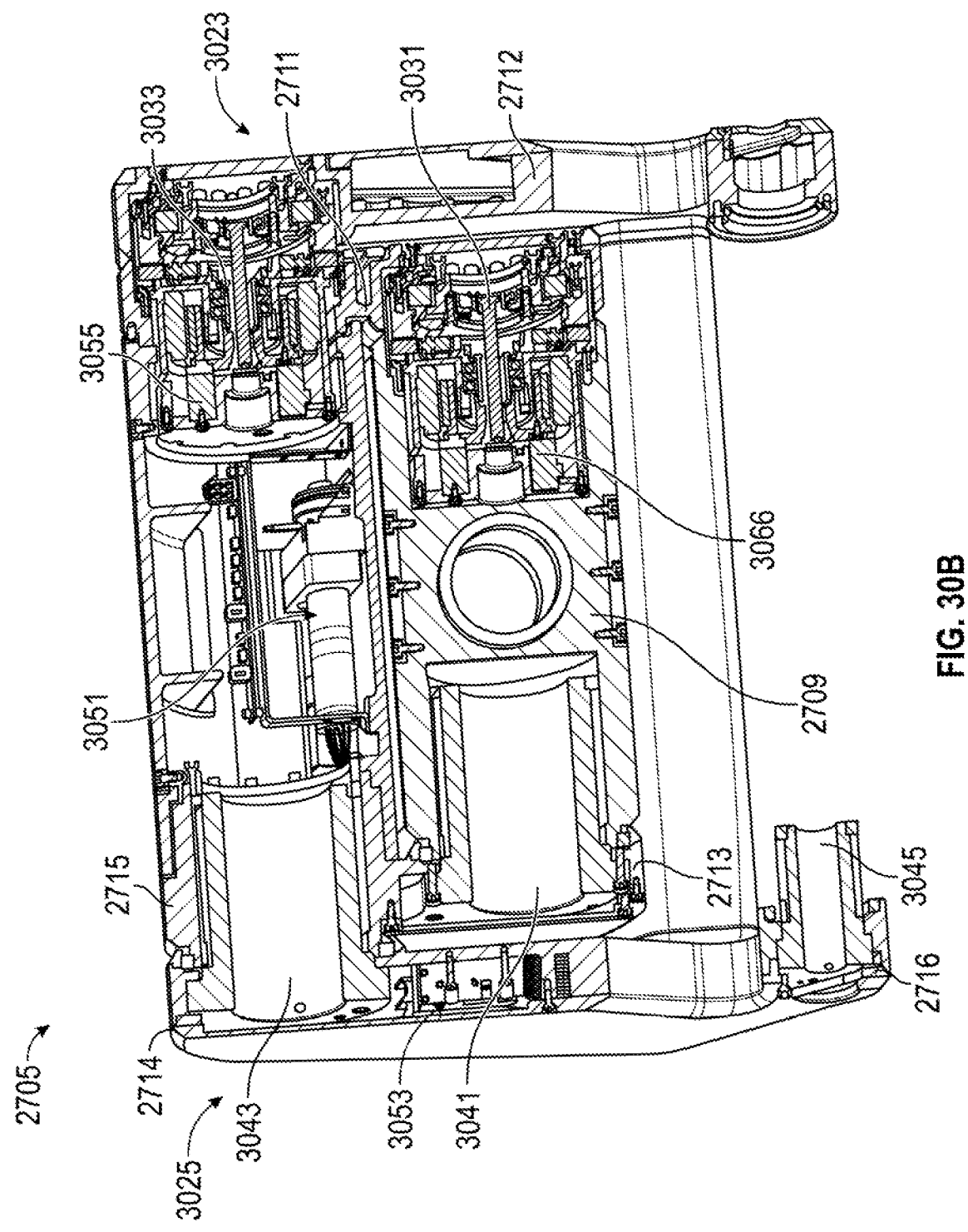
FIG. 30B is a cross-section view of an embodiment a dual-link motorized arm.

FIG. 30A is an isometric view of an embodiment of the motorized arm 2705. In FIG. 30A, portions of the covers of the shoulder 2709, the first link 2711, and the second link 2712 are illustrated as transparent so that internal components of motorized arm 2705 can be seen. FIG. 30B is a cross-sectional view of the motorized arm 2705 and further illustrates the internal components thereof. In particular, the positions of a first motor 3031, a second motor 3033, a first arbor 3041, a second arbor 3043, and a third arbor 3045 are illustrated according to one embodiment in FIGS. 30A and 30B.

The first actuator 3031, which can include a motor, can be configured to provide the first rotational degree of freedom 2717 (see FIG. 28A). For example, the first actuator 3031 including the motor can be configured to drive rotation of the first link 2711 relative to the shoulder 2709. As illustrated in FIGS. 30A and 30B, the first actuator 3031 including the motor can be positioned in the proximal end 2713 of the first link 2711. This need not be the case in all embodiments. For example, the first actuator 3031 including the motor can be positioned in the shoulder 2709. The first actuator 3031 including the motor can be considered a joint actuation mechanism because it can be configured to actuate the joint between the shoulder 2709 and the first link 2711. In some embodiments, the first actuator 3031 including the motor further comprises a harmonic drive or a harmonic gearbox. In some embodiments, other types of actuators including electric motors or other mechanisms entirely (e.g., hydraulic mechanisms) can be used as the joint actuation mechanism. The first actuator 3031 can also comprise a brake 3055. In some embodiments, the brake 3055 is built into the actuator 3031 or positioned adjacent to the actuator 3031. The brake can be engaged to limit or prevent rotation of the first link 2711 relative to the shoulder 2709.

The second actuator 3033, which can include a motor, can be configured to provide the second rotational degree of freedom 2718 (see FIG. 28B). For example, the second actuator 3033 including the motor can be configured to drive rotation of the second link 2712 relative to the first link 2711. As illustrated in FIGS. 30A and 30B, the second actuator 3033 can be positioned in the proximal end 2714 of the second link 2712. This need not be the case in all embodiments. For example, the second actuator 3033 can be positioned in the distal end 2715 of the first link 2711. Similar to the first actuator 3031, the second actuator 3033 can be considered a joint actuation mechanism because it can be configured to actuate the joint the first link 2711 and the second link 2712. In some embodiments, the second actuator 3033 comprises a harmonic drive or a harmonic gearbox. In some embodiments, other types of electric motors or other mechanisms entirely (e.g., hydraulic mechanisms) can be used as the joint actuation mechanism. The second actuator 3033 can also comprise a brake 3066. In some embodiments, the brake 3066 is built into the actuator 3033 or positioned adjacent to the actuator 3033. The brake 3066 can be engaged to limit or prevent rotation of the second link 2712 relative to the first link 2711.

In some embodiments, one or more stiffeners or brakes in the form of arbors 3041, 3043, 3045 (e.g., hydraulic expansion arbors) can further be included to increase the torsional stiffness of the motorized arm 2705. For example, the first actuator 3031 and the second actuator 3033 (and corresponding brakes) may provide low stiffness or rigidity. This can, in some instances, lead to instability of the motorized arm 2705. In the illustrated embodiment, the motorized arm 2705 includes the arbors 3041, 3043, 3045 to improve torsional stiffness in each of the joints. The arbors 3041, 3043, 3045 are shown alone in FIGS. 33A, 33B, and 33C, respectively. In general, each arbor 3041, 3043, 3045 can be configured for expansion (e.g., radial expansion) with an arbor actuation mechanism. Upon expansion, the arbors 3041, 3043, 3045 are tightly fit within the surrounding structure, thereby increasing torsional stiffness and reducing the instability of the joints. As will be described in more detail below, the arbor actuation mechanisms can be configured to function by driving a ball screw to push on a hydraulic piston until it hits a hardstop. When the piston is compressed, pressure within the arbor is increased causing the arbor to expand and the joint is engaged at peak stiffness.

As shown in FIGS. 30A and 30B, the first arbor 3041 can be positioned within the proximal end 2713 of the first link 2711. This need not be the case in all embodiments. For example, in some embodiments, the first arbor 3041 can be positioned within the shoulder 2709. The first arbor 3041 can be configured to increase the rigidity or torsional stiffness of the joint between the shoulder 2709 and the first link 2711. Accordingly, the first arbor 3041 can be considered a first torsional stiffness mechanism. In the illustrated embodiment, the first arbor 3041 is a hydraulic arbor, although other types of arbors or other torsional stiffness mechanisms can also be used. The first arbor 3041 is shown alone in FIG. 33A. The motorized arm 2705 includes a first arbor actuation mechanism 3051 configured to actuate the first arbor 3041. In the illustrated embodiment, the first arbor actuation mechanism 3051 is positioned within the first link 2711 between the first and second lateral sides 3023, 3025. The first arbor actuation mechanism 3051 is described in more detail below with reference to FIGS. 34A and 34B.

The second arbor 3043 can be positioned within the proximal end 2714 of the second link 2712. This need not be the case in all embodiments. For example, in some embodiments, the second arbor 3043 can be positioned within distal end of the first link 2711. The second arbor 3043 can be configured to increase the rigidity or torsional stiffness of the joint between the first link 2711 and the second link 2712. Accordingly, the second arbor 3043 can be considered a second torsional stiffness mechanism. In the illustrated embodiment, the second arbor 3043 is a hydraulic arbor, although other types of arbors or other torsional stiffness mechanisms can also be used. The second arbor 3043 is shown alone in FIG. 33B. The motorized arm 2705 can include a second arbor actuation mechanism 3053 configured to actuate the second arbor 3043. In the illustrated embodiment, the second arbor actuation mechanism 3051 is positioned within the second link 2712 between the proximal and distal ends 2714, 2716. The second arbor actuation mechanism 3053 is described in more detail below with reference to FIGS. 35A and 35B.

As shown in FIGS. 30A and 30B, a third arbor 3045 can be provided at the distal end 2716 of the second link 2712. The third arbor 3045 can be configured to increase the rigidity or torsional stiffness of the joint between the second link 2712 and the arm support 2707. The second arbor 3045 can be considered a third torsional stiffness mechanism. In the illustrated embodiment, the third arbor 3045 is a hydraulic arbor, although other types of arbors or other torsional stiffness mechanisms can also be used. The third arbor 3045 is shown alone in FIG. 33C. In the illustrated embodiment, the second arbor actuation mechanism 3053 is configured to actuate the third arbor 3045 (in addition to the second arbor 3043). This can be advantageous as the single arbor actuation mechanism 3053 can be used to actuate both the second arbor 3043 and the third arbor 3045. This will be described in more detail below with reference to FIGS. 35A and 35B. In some embodiments, the third arbor 3045 is actuated by its own dedicated arbor actuation mechanism.

The motorized arm 2705 can include a first lateral side 3023 and a second lateral side 3025 indicated generally in FIGS. 30A and 30B. In some embodiments, the first actuator 3031 including a motor and the second actuator 3033 including a motor can each be positioned on the first lateral side 3023. For example, the first actuator 3031 can be positioned in the first lateral side 3023 of the first link 2711, and the second actuator 3033 can be positioned in the first lateral side 3032 of the second link 2712. In some embodiments, the first, second, and third arbors 3041, 3043, 3045 can be positioned on the second lateral side 3025 of the motorized arm. For example, the first arbor 3041 can be positioned in the second lateral side 3025 of the first link 2711 and the second arbor 3043 and the third arbor 3045 can be positioned in the second lateral side 3025 of the second link 2712.

Thus, in the illustrated embodiment, the first link 2711 includes the first actuator 3031 including a motor on the first lateral side 3023 and the first arbor 3041 on the second lateral side 3025. This may provide a space efficient configuration for packaging the first motor 3031 and the first arbor 3041. Further, in the illustrated embodiment, the second link 2712 includes the second actuator 3033 including a motor on the first lateral side 3023 and the second arbor 3043 and the third arbor 3045 on the second lateral side 3025. This may provide a space efficient configuration for packaging the second motor 3033, the second arbor 3043, and the third arbor 3045.

Other configurations are possible for the placement of the first actuator 3031 including a motor, the second actuator 3033 including a motor, the first arbor 3041, the second arbor 3043, and the third arbor 3045. For example, one or more these features can be moved from the first lateral side 3023 to the second lateral side 3025 or vice versa. In some embodiments, the first lateral side 3023 can include both motors and arbors and the second later side 3025 can include both motors and arbors.

FIG. 31 is an isometric view of an embodiment of the motorized arm 2705 and illustrates an embodiment of an arm support linkage 3102. The arm support linkage 3102 may comprise an assembly configured to engage and support the arm support 2707 (see FIG. 32). The arm support linkage 3102 may be configured to allow the arm support 2707 to rotate relative to the second link 2712. The arm support linkage 3102 may also be configured to allow the arm support 2707 to translate relative to the second link 2712, as will be described with reference to FIG. 32.

As shown in FIG. 31, the arm support linkage 3102 can be positioned between distal ends 2716 of the second link 2712. The arm support linkage 3102 can include an actuator 3135, which can include a motor, can be configured to drive rotation of the arm support linkage 3102 relative to the second link 2712. In other embodiments, the actuator 3135 may be provided in the distal end 2716 of the second link 2712. For example, the actuator 3135 may be positioned in the distal end 2716 on a lateral side of the link 2712 opposite the third arbor 3045. In some embodiments, the actuator 3135 can further comprise a harmonic drive or gearbox, although other joint actuation mechanisms can also be used. The actuator 3135 including a motor can be configured to drive rotation of the arm support linkage 3102 relative to the second link 2712 and the third arbor 3045 can be configured to engage the arm support linkage 3102 to provide increased rigidity or torsional stiffness for this joint when engaged.

FIG. 32 is a perspective view illustrating the arm support linkage 3102 attached to an embodiment of the arm support 2707. In addition to the motor 3145 for causing rotation of the arm support linkage 3102 (and the attached arm support 2707) relative to the second link 2712, the arm support linkage 3102 may also comprise a second motor 3247 configured to cause translation of the arm support 2707 relative to the arm support linkage 3102. For example, in some embodiments, the second motor 3247 is configured to allow the arm support 2707 to translate back and forth along an axis of the arm support 2707 relative to the arm support linkage 3102.

In the illustrated embodiment, the arm support 2707 comprises a ball screw 3251 that extends along the arm support 2707 and through the arm support linkage 3102. The ball screw 3251 can extend through a nut housing in the arm support linkage 3102. The nut housing can be rotated by the second motor 3247 to cause the arm support 2707 to translate relative to the arm support linkage 3102. Other mechanisms for causing translation of the arm support 2707 relative to the arm support linkage 3102 are also possible.

Figure 33A:
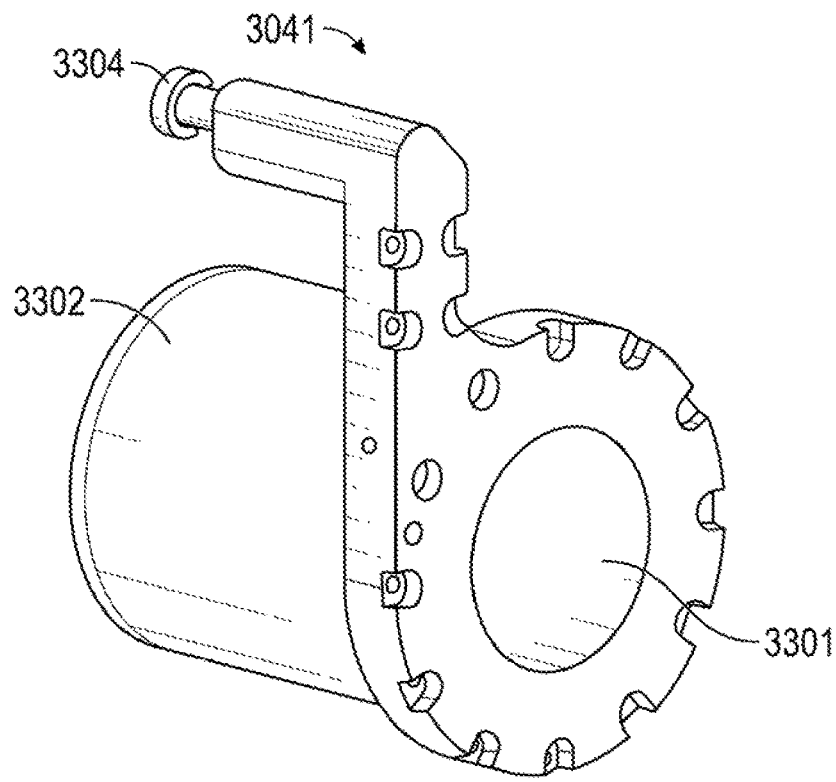
FIGS. 33A, 33B, and 33C illustrate views of various embodiments of arbors configured for use in a motorized arm.
Figure 33B:
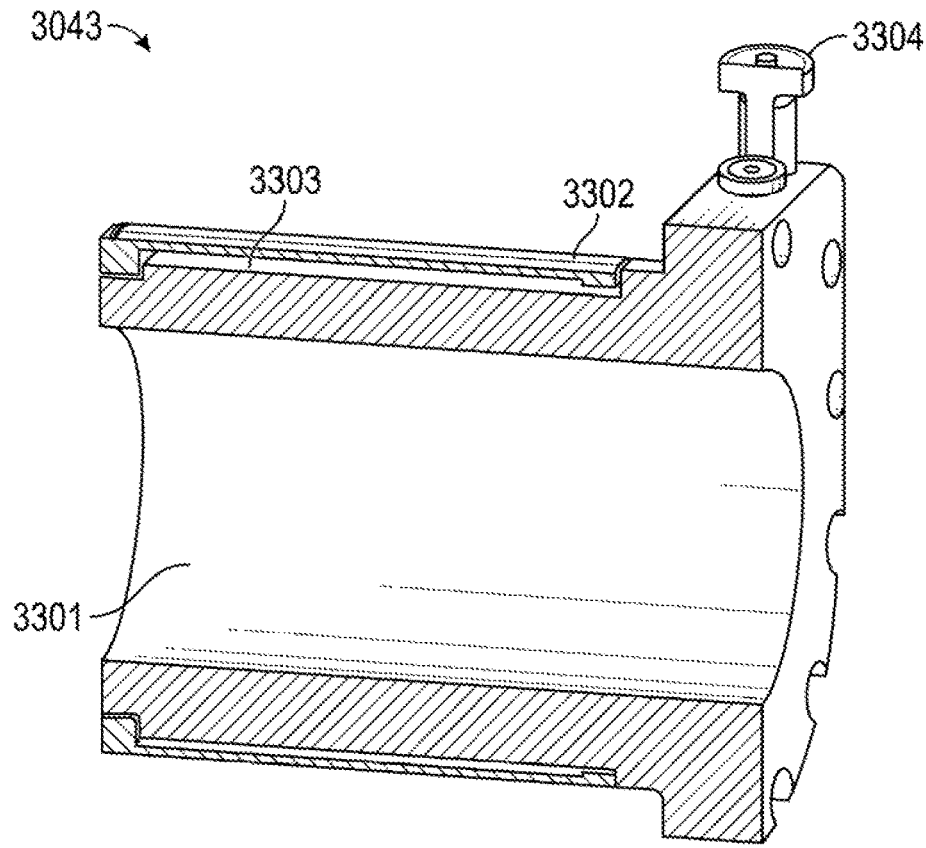
Figure 33C:
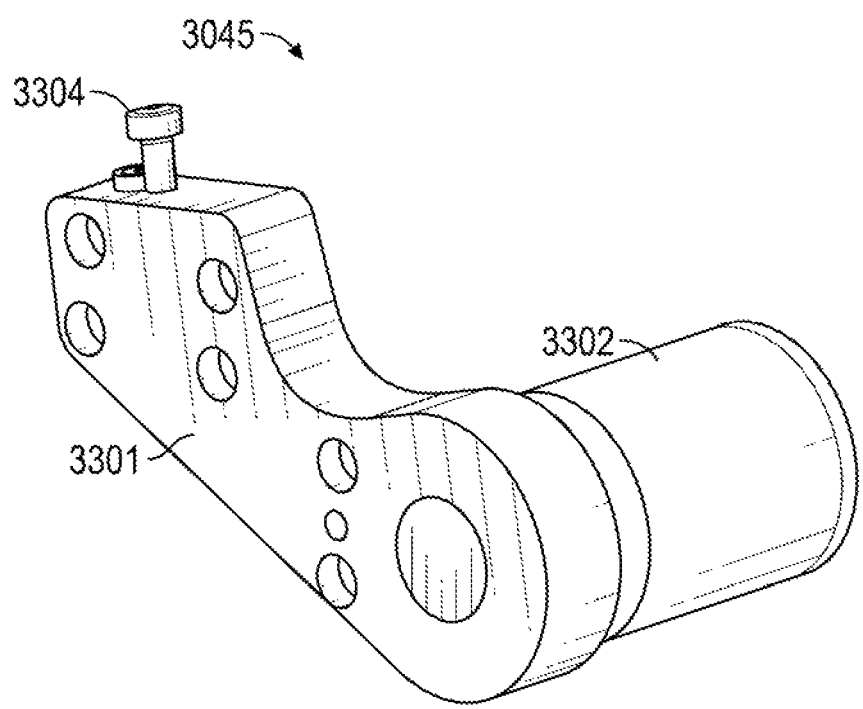

FIGS. 33A, 33B, and 33C provide views of the first arbor 3041, the second arbor 3043, and the third arbor 3045, respectively. Each arbor 3041, 3043, 3045 may comprise a main body 3301 and a thin wall 3302. The main body 3301 and the thin wall 3302 can be arranged to form a cavity 3303 therebetween as shown in the cross-sectional view of the second arbor 3043 of FIG. 33B. The cavity 3303 can be filled with a fluid, such as hydraulic fluid. Each arbor 3041, 3043, 3045 also comprises a piston 3304. The piston can be compressed to increase the pressure of the fluid within the cavity 3303. As the pressure within the cavity 3303 increases, the thin wall 3302 deflects outward causing the arbor 3041, 3043, 3045 to expand. As the arbor 3041, 3043, 3045 expands, it engages with corresponding structure of the joint in which is placed increasing the rigidity and torsional stiffness of the joint. Although the arbors 3041, 3043, 3045 are illustrated as hydraulic arbors, other types of arbors, or other torsional stiffness mechanisms may also be used.

Further, as shown in FIGS. 33A, 33B, and 33C, the shape of each arbor 3041, 3043, 3045 can be uniquely configured to fit within a certain portion of the motorized arm 2705. For example, the first arbor 3041 can be larger than the other two arbors 3041, 3043 because a larger arbor can be used at the joint between the shoulder 2709 and the first link 2711, as this arbor should be able to stabilize the weight of all portions of the motorized arm distal to it. In addition, the larger the arbor, the greater the torsional rigidity, and hence the desire to increase the size of the arbor to the extent possible within an available package. Similarly, the third arbor 3045 can be smaller than the other arbors 3041, 3043 for similar reasons. Additionally, the shape of each arbor 3041, 3043, 3045 can be configured so as to position the piston 3304 such that it can be actuated on by a corresponding arbor actuation mechanism as shown in FIGS. 34A and 34B (for the first arbor 3041) and FIGS. 35A and 35B (for the second and third arbors 3043, 3045).

Figure 34A:
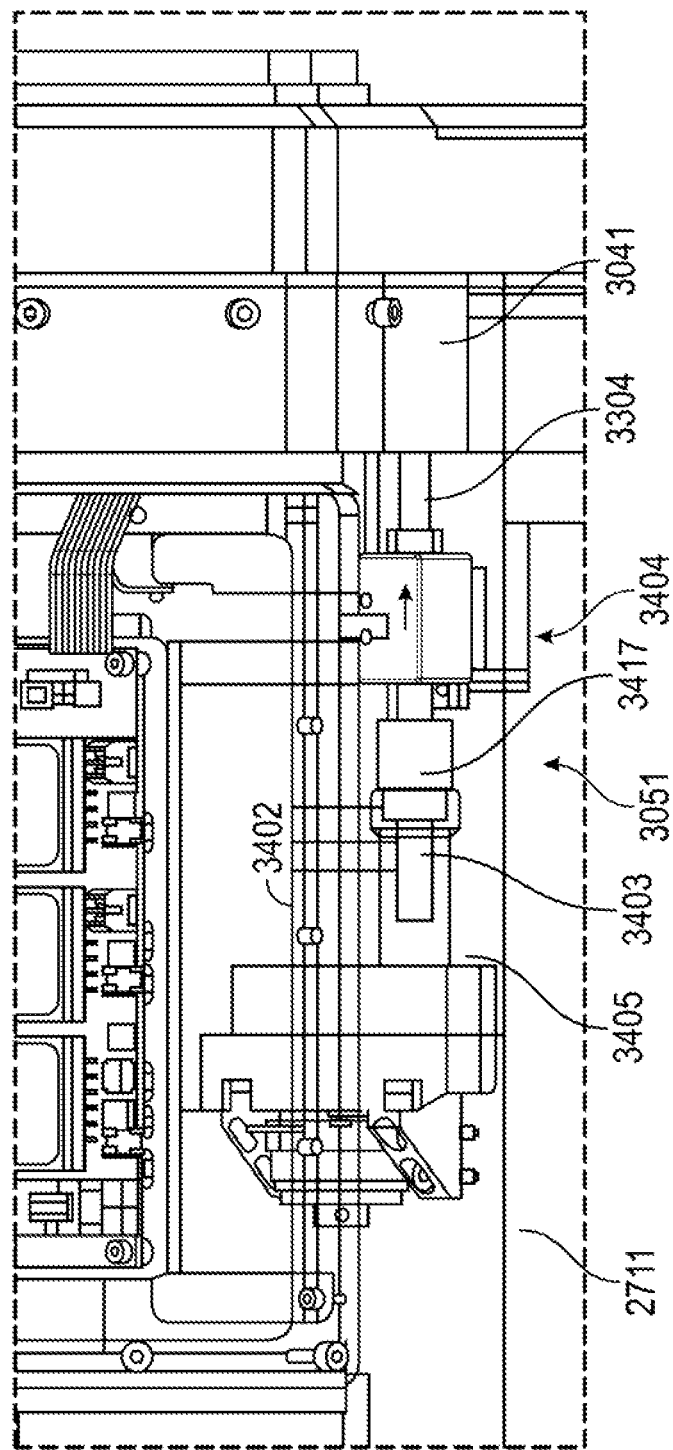
FIGS. 34A and 34B illustrate an embodiment of a first arbor actuation mechanism in unactuated and actuated states, respectively.
Figure 34B:
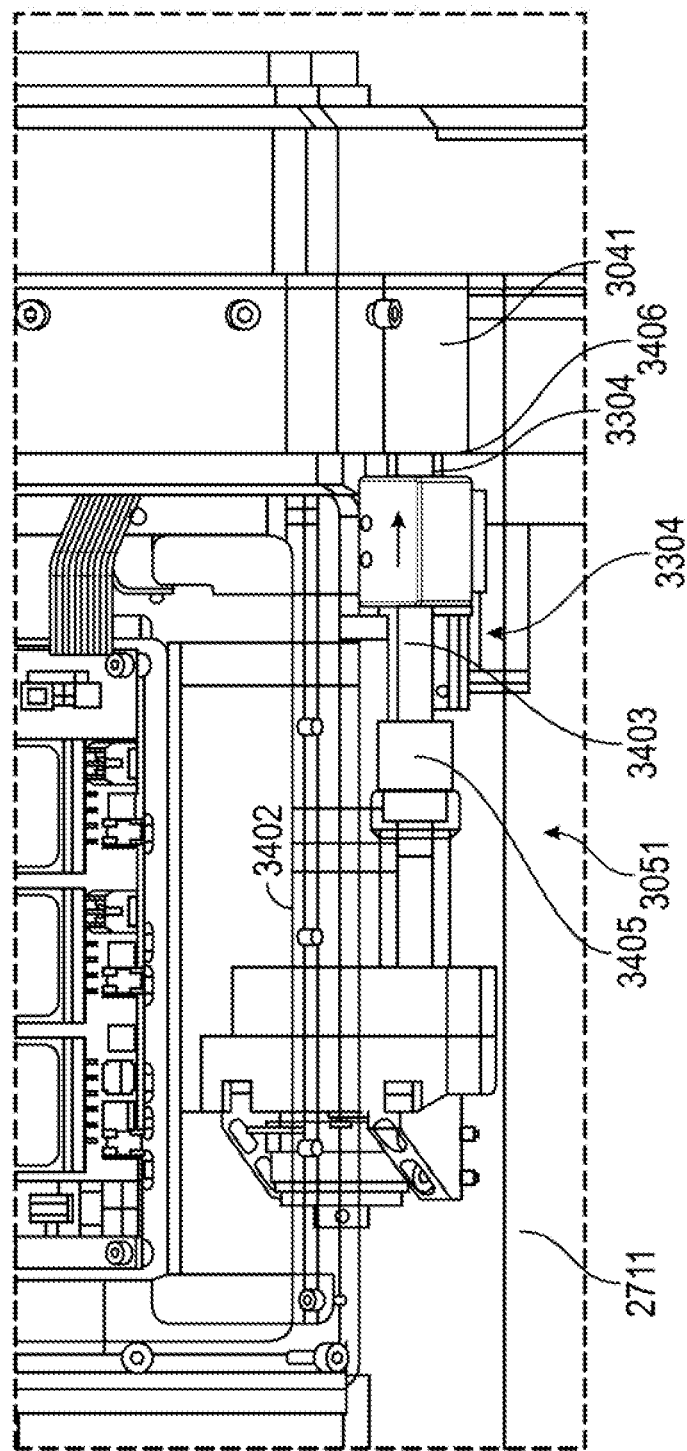

FIGS. 34A and 34B provide views of the first arbor actuation mechanism 3051 in unactuated and actuated positions, respectively. As illustrated in FIGS. 34A and 34B, the first arbor actuation mechanism 3051 may comprise a motor 3402 (not clearly visible), a ball screw 3403, a ball screw nut 3417, and an actuator 3404. The motor 3402 can be configured to rotate the ball screw nut 3417 to cause translation of the ball screw 3403 relative to the ball screw nut 3417. In some embodiments, the motor 3402 can be directly attached to the ball screw nut 3417. In some embodiments, the motor 3402 can be indirectly attached to the ball screw nut 3417 through one or more transmission linkages (such as a gear train). In the illustrated embodiment, the actuator 3404 comprises the motor 3402, the ball screw nut 3417, and the ball screw 3403. In some embodiments, the actuator 3404 may also comprise a gear train (indirectly liking the motor 3402 to the ball screw nut 3417) and/or a brake. A brake can be configured to brake to prevent the system from backdriving and disengaging the arbors. As noted above, the motor 3402 is configured to rotate to drive the ball screw 3403 to drive the actuator 3404 in and out. As shown in FIG. 34A, in the unactuated position, the ball screw 3403 is driven such that the actuator 3404 is pulled back from the piston 3304 allowing the pressure in the first arbor 3041 to decrease. As illustrated, in this configuration, the actuator 3404 may not apply a pressure to the piston 3304. A hardstop 3405 may be provided to limit travel of the ball screw 3403 in the direction away from the piston 3304.

Figure 35A:
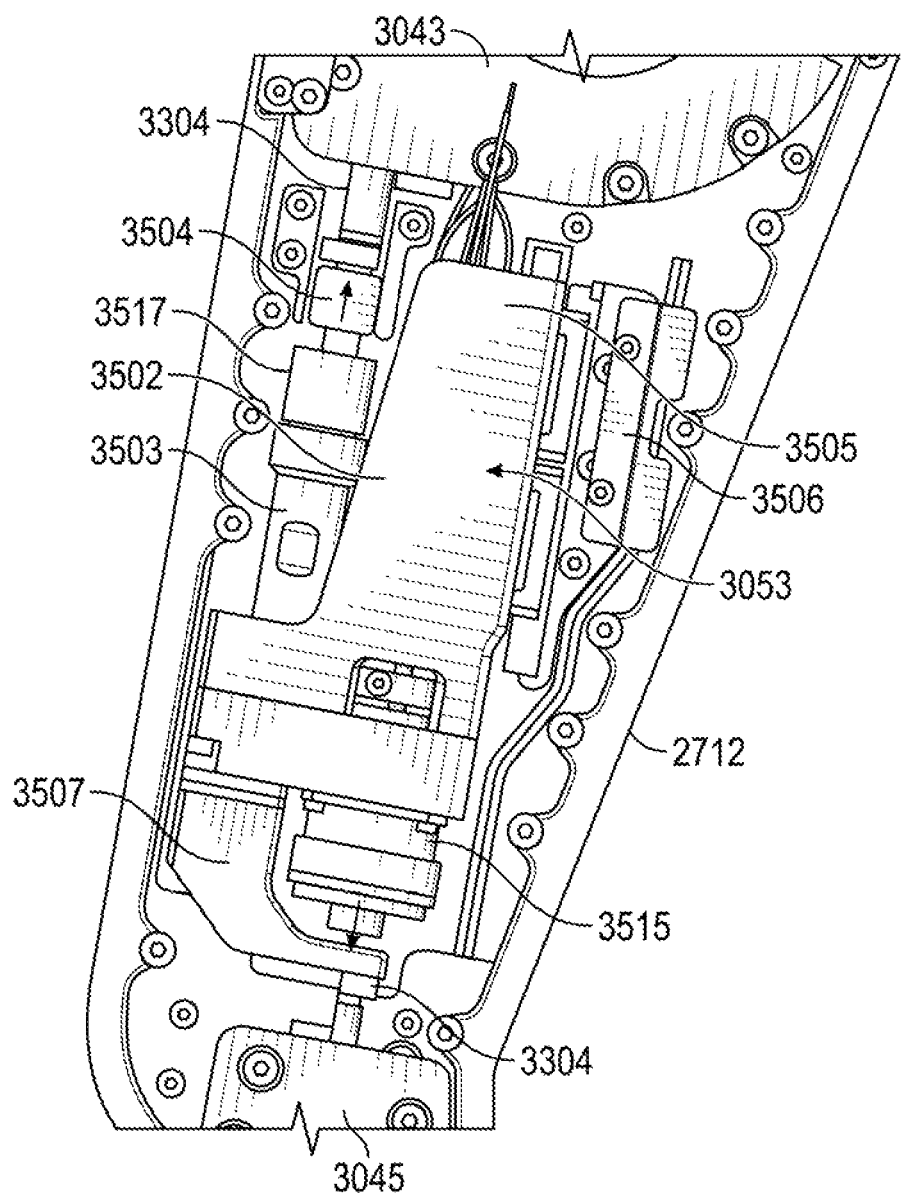
FIGS. 35A and 35B illustrate an embodiment of a second arbor actuation mechanism in unactuated and actuated states, respectively.
Figure 35B:
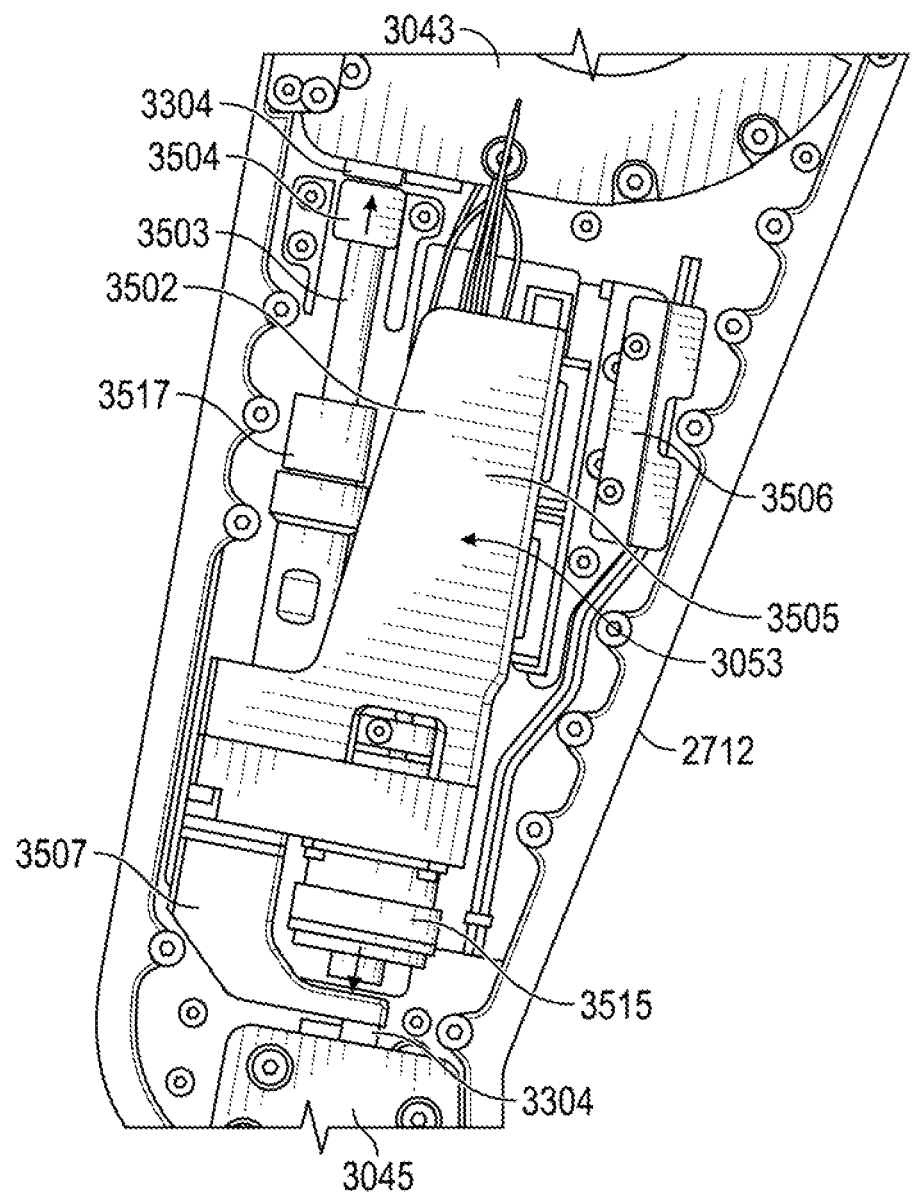

As illustrated in FIG. 35B, when the ball screw 3403 is driven in the opposite direction (toward the piston 3304), the actuator 3404 contacts and applies a force to the piston 3304. This force depresses the piston 3304 increasing the pressure in the first arbor 3041 and engaging the first arbor 3041 to increase the torsional stiffness of the joint. Contact between the head of the piston 3304 and the arbor 3041 may provide a hardstop 3406 that limits travel of the ball screw 3403 in the direction towards the piston 3304.

As shown in FIG. 34A, the ball screw 3403 may be configured for about 15.5 mm of travel, although this need not be the case in all embodiments. The ball screw 3404 may provide sufficient travel so as to depress the piston 3304 to engage the first arbor 3041. As shown in FIG. 34B, the first arbor actuation mechanism 3051 may be configured to provide a force of 700 N to the piston 3304 to engage the first arbor 3041. This need not be the case in all embodiments, and other forces may be used. Additionally, other mechanisms for actuating the arbor 3041 may also be used.

FIGS. 35A and 35B provide views of the second arbor actuation mechanism 3053 in unactuated and actuated positions, respectively. As mentioned above, in the illustrated embodiment, the second arbor actuation mechanism 3053 is configured to actuate both the second arbor 3043 and the third arbor 3045 with a single mechanism. Using a single mechanism to actuate both the second arbor 3043 and the third arbor 3045 can maximize space within the second link 2712 and simplify control of the motorized arm 2705.

As illustrated in FIGS. 35A and 35B, the second arbor actuation mechanism 3053 may comprise a motor 3502 (not clearly visible), a ball screw 3503, a ball screw nut 3517, a first actuator 3504, a housing 3505, glide rails 3506, and a second actuator 3507. As described above, the motor 3502 can be configured to rotate the ball screw nut 3517 to cause translation of the ball screw 3503 relative to the ball screw nut 3517. In some embodiments, the motor 3502 can be directly attached to the ball screw nut 3517. In some embodiments, the motor 3502 can be indirectly attached to the ball screw nut 3517 through one or more transmission linkages (such as a gear train). In this embodiment, the motor 3502 drives the ball screw 3503 to cause the first actuator 3504 to act on the piston 3304 of the second arbor 3043 in a manner that is similar to the first arbor actuation mechanism 3051 described above. However, the second arbor actuation mechanism 3053 further uses the housing 3505, glide rails 3506, and second actuator 3507 to simultaneously actuate the piston 3304 of the third arbor 3045. The housing 3505 is mounted on glide rails 3506 so that it can slide back and forth along the glide rails. The second actuator 3507 is attached to the housing 3505 so as to be able to contact the piston 3304 during at least a portion of the motion. When the motor 3502 drives the ball screw 3503 to cause the first actuator 3504 to act on the piston 3304 of the second arbor 3043, a reaction force causes the housing 3505 to slide along the glide rails 3506 causing the second actuator 3507 to act on the piston 3304 of the third arbor 3045. In this manner, the second arbor actuation mechanism 3053 can simultaneously actuate both the second arbor 3043 and the third arbor 3045.

Figure 36:
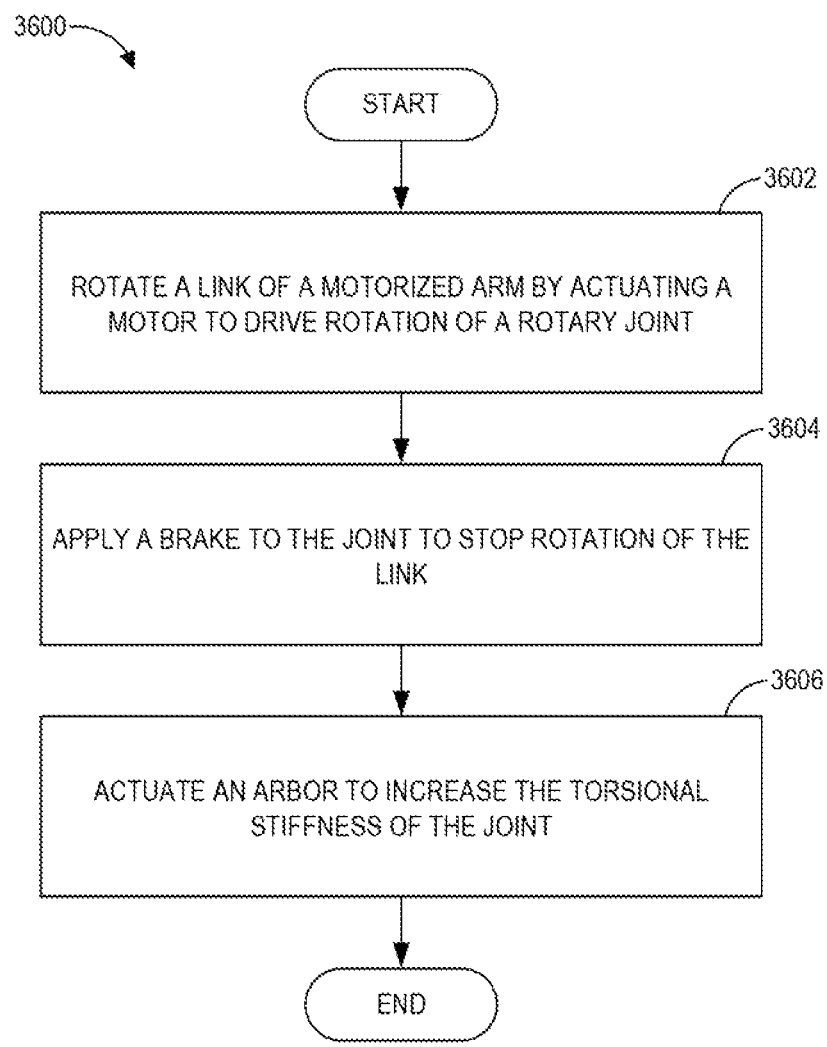
FIG. 36 is flowchart depicting a method for actuating a link of a motorized arm according to one embodiment.

As shown in FIG. 35A, the ball screw 3503 may be configured for about 15.5 mm of travel, although this need not be the case in all embodiments. The housing 3505 can be configured for about 10 mm of travel, although this need not be the case in all embodiments. As shown in FIG. 35B, the second arbor actuation mechanism 3053 may be configured to provide a force of 700 N to the pistons 3304 to engage the second arbor 3043 and the third arbor 3045. This need not be the case in all embodiments, and other forces may be used. Additionally, other mechanisms for actuating the second arbor 3043 and the third arbor 3045 may also be used. In some embodiments, the second arbor 3043 and the third arbor 3045 are actuated independently by dedicated arbor actuation mechanisms. In some embodiments, the second arbor actuation mechanism 3053 may also include a brake 3515. The brake 3515 can be configured to prevent the system from backdriving and disengaging the arbors FIG. 36 is a flowchart depicting a method 3600 for positioning a motorized arm of a robotic medical system. The method 3600 can begin at block 3602, at which a link of the motorized arm is rotated by actuating a motor to drive rotation of a rotary joint. In some embodiments, the motor comprises a harmonic drive or harmonic gearbox. The link can be, for example, a link of a single link motorized arm 2205 as shown in FIGS. 22-26, or a link of a dual link motorized arm 2705 as shown in FIGS. 27-35B. In some embodiments, the motorized arm is moved from a stowed position to a deployed position.

At block 3604, a brake is applied the joint to stop rotation of the link. The brake can be part of the motor or positioned in proximity to the motor. Finally, at block 3606, an arbor is actuated to increase a torsional stiffness of the rotary joint. In some embodiment, the arbor comprises a hydraulic arbor.

In some embodiments, the method 3600 further comprises translating the motorized arm in a vertical direction. In some embodiments, translating the motorized arm comprises translating a shoulder of the motorized arm along a column supporting a table of the robotic medical system. A proximal end of the link can be coupled to the shoulder.

In some embodiments, the method 3600 further comprises translating the arm support relative to the motorized arm. For example, in some embodiments, the arm support can extend along a longitudinal axis and the arm support can be configured to translate back and forth relative to the motorized arm along the longitudinal axis of the arm support. An example of such translation is described above with reference to FIGS. 31 and 32.

In some embodiments, the method 3600 further comprises performing a robotic medical procedure using at least one robotic arm positioned on adjustable arm support coupled to a distal end of the motorized arm. In some embodiments, the medical procedure is a robotic laparoscopic or robotic endoscopic procedure.

XV. Software

In some embodiments, one or more aspects of a system including adjustable arm supports and corresponding robotic arms can be controlled via software. For example, the system can be designed so that all actuations are robotically controlled by the system, and the system knows the position of all end effectors relative to the tabletop. This may provide a unique advantage that existing robotic surgery systems do not have. Further, this may allow for advantageous workflows including: adjusting the table top intraoperatively (e.g., tilt, Trendelenburg, height, flexure, etc.) while arms and arm positioning platforms move in sync; moving the robotic arms can move away from the operative field for draping or patient loading; after a clinician tells the system the type of procedure, the robotic arms can move to approximate positions near where ports are typically placed (Surgeons could modify and set port selection "presets" for how they like to do surgery); and performing "last mile" docking with cameras on the end effectors and vision targets on cannulas (other non-optical sensors around the end effector could provide similar functionality).

Further, some incarnations of robotic arm joints may require applying high forces to the arm to back-drive the motors and transmissions. This can be reduced with torque sensors in arm joints or a force sensor or joystick at the end effector to allow the robot to know where the clinician is trying to push it and move accordingly (admittance control) to lower back-drive forces felt at the output. Such back-drive regulation can be accomplished in software in some embodiments.

XVI. Additional Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

The invention claimed is:

1. A method for positioning a motorized arm of a robotic medical system, the method comprising:

rotating a link of the motorized arm by actuating an actuator to drive rotation of a rotary joint;

applying a brake to the rotary joint to stop rotation of the link; and actuating an arbor to increase a torsional stiffness of the rotary joint.

2. The method of claim 1, wherein the actuator comprises a gearbox.

3. The method of claim 2, wherein the arbor comprises a hydraulic arbor.

4. The method of claim 1, comprising translating the motorized arm in a vertical direction.

5. The method of claim 4, wherein translating the motorized arm comprises translating a shoulder of the motorized arm along a column supporting a table of the robotic medical system, wherein a proximal end of the link is coupled to the shoulder.

6. The method of claim 1, further comprising:

performing a robotic medical procedure using at least one robotic arm positioned on an adjustable arm support coupled to a distal end of the motorized arm.

7. The method of claim 6, further comprising translating the adjustable arm support along an axis of the adjustable arm support relative to the motorized arm.

* * * * *